(12) United States Patent
Hedrick et al.

(10) Patent No.: US 7,470,537 B2
(45) Date of Patent: Dec. 30, 2008

(54) ADIPOSE-DERIVED STEM CELLS AND LATTICES

(76) Inventors: Marc H. Hedrick, 5147 Valjean Ave., Encino, CA (US) 91346; Adam J. Katz, 503 Broadleaf Way, Charlottesville, VA (US) 22911; Ramón Llull, Placa Hostels, 10-A Santa Maria, Mallorca, Balearic Isles (ES) E-7320; J. William Futrell, 1 Sweetwater La., Pittsburgh, PA (US) 15238; Prosper Benhaim, 16260 Dickens St., Encino, CA (US) 91436; Hermann Peter Lorenz, 3900 Christian Dr., Belmont, CA (US) 94002; Min Zhu, 3175 S. Sepulveda Blvd., Apt. 309, Los Angeles, CA (US) 90034

(*) Notice: Subject to any disclaimer, the term of this patent is extended or adjusted under 35 U.S.C. 154(b) by 400 days.

(21) Appl. No.: 10/740,315

(22) Filed: Dec. 17, 2003

(65) Prior Publication Data

US 2005/0153441 A1 Jul. 14, 2005

Related U.S. Application Data

(63) Continuation of application No. 09/952,522, filed on Sep. 10, 2001, now abandoned, which is a continuation-in-part of application No. 09/936,665, filed as application No. PCT/US00/06232 on Mar. 10, 2000, now Pat. No. 6,777,231.

(60) Provisional application No. 60/162,462, filed on Oct. 29, 1999, provisional application No. 60/123,711, filed on Mar. 10, 1999.

(51) Int. Cl.
*C12N 5/00* (2006.01)
(52) U.S. Cl. .................................................. 435/325
(58) Field of Classification Search ........................ None
See application file for complete search history.

(56) References Cited

U.S. PATENT DOCUMENTS

| | | | |
|---|---|---|---|
| 4,438,032 A | 3/1984 | Golde et al. | |
| 5,226,914 A | 7/1993 | Caplan et al. | |
| 5,336,616 A * | 8/1994 | Livesey et al. | 435/395 |
| 5,486,359 A | 1/1996 | Caplan et al. | |
| 5,591,625 A | 1/1997 | Gerson et al. | |
| 5,624,840 A * | 4/1997 | Naughton et al. | 435/395 |
| 5,688,531 A | 11/1997 | Benayahu et al. | |
| 5,728,739 A | 3/1998 | Ailhaud et al. | |
| 5,736,396 A | 4/1998 | Bruder et al. | |
| 5,786,207 A | 7/1998 | Katz et al. | |
| 5,811,094 A | 9/1998 | Caplan et al. | |
| 5,817,050 A | 10/1998 | Klein | |
| 5,827,735 A | 10/1998 | Young et al. | |
| 5,827,740 A | 10/1998 | Pittenger | |
| 5,827,897 A | 10/1998 | Ailhaud et al. | |
| 5,854,292 A | 12/1998 | Ailhaud et al. | |
| 5,906,934 A | 5/1999 | Grande et al. | |
| 5,908,784 A | 6/1999 | Johnstone et al. | |
| 5,937,863 A * | 8/1999 | Knowlton | 128/898 |
| 6,200,606 B1 | 3/2001 | Peterson et al. | |
| 6,261,549 B1 * | 7/2001 | Fernandez et al. | 424/85.1 |
| 6,391,297 B1 | 5/2002 | Halvorsen | |
| 6,429,013 B1 | 8/2002 | Halvorsen et al. | |
| 6,555,374 B1 | 4/2003 | Gimble et al. | |
| 6,777,231 B1 | 8/2004 | Katz et al. | |
| 6,852,533 B1 * | 2/2005 | Rafii et al. | 435/372 |
| 7,266,457 B1 * | 9/2007 | Hickman | 702/19 |
| 2001/0033834 A1 | 10/2001 | Wilkison et al. | |
| 2002/0076400 A1 | 6/2002 | Katz et al. | |
| 2002/0119126 A1 | 8/2002 | Halvorsen | |
| 2003/0082152 A1 | 5/2003 | Hedrick et al. | |
| 2003/0161817 A1 * | 8/2003 | Young et al. | 424/93.21 |
| 2003/0211602 A1 * | 11/2003 | Atala | 435/366 |
| 2004/0067218 A1 | 4/2004 | Casteilla et al. | |
| 2004/0171146 A1 | 9/2004 | Katz et al. | |
| 2005/0076396 A1 | 4/2005 | Katz et al. | |
| 2005/0153442 A1 | 7/2005 | Katz et al. | |
| 2005/0282275 A1 | 12/2005 | Katz et al. | |

FOREIGN PATENT DOCUMENTS

| | | |
|---|---|---|
| WO | WO97/18299 | 5/1997 |
| WO | WO 97/26326 | 7/1997 |
| WO | WO97/39104 | 10/1997 |
| WO | WO97/40137 | 10/1997 |
| WO | WO97/41208 | 11/1997 |
| WO | WO 98/04682 | 2/1998 |

(Continued)

OTHER PUBLICATIONS

WO 0104268A1, Simmons et al Intl Publictaion date Jan. 18, 2001.*

(Continued)

*Primary Examiner*—Celine X Qian
(74) *Attorney, Agent, or Firm*—Mandel & Adriano

(57) ABSTRACT

The present invention provides adipose-derived stem cells (ADSCs), adipose-derived stem cell-enriched fractions (ADSC-EF) and adipose-derived lattices, alone and combined with the ADSCs of the invention. In one aspect, the present invention provides an ADSC substantially free of adipocytes and red blood cells and clonal populations of connective tissue stem cells. The ADSCs can be employed, alone or within biologically-compatible compositions, to generate differentiated tissues and structures, both in vivo and in vitro. Additionally, the ADSCs can be expanded and cultured to produce molecules such as hormones, and to provide conditioned culture media for supporting the growth and expansion of other cell populations. In another aspect, the present invention provides an adipose-derived lattice substantially devoid of cells, which includes extracellular matrix material from adipose tissue. The lattice can be used as a substrate to facilitate the growth and differentiation of cells, whether in vivo or in vitro, into anlagen or even mature tissues or structures.

3 Claims, 45 Drawing Sheets

FOREIGN PATENT DOCUMENTS

| WO | WO98/20731 | 5/1998 |
| --- | --- | --- |
| WO | WO98/32333 | 7/1998 |
| WO | WO98/51317 | 11/1998 |
| WO | WO99/01145 | 1/1999 |
| WO | WO 99/02654 | 1/1999 |
| WO | WO99/03973 | 1/1999 |
| WO | WO99/11789 | 3/1999 |
| WO | WO 99/28444 | 6/1999 |
| WO | WO 99/43286 | 9/1999 |
| WO | WO 99/56759 | 11/1999 |
| WO | WO 00/50048 | 8/2000 |
| WO | WO 00/53795 | 9/2000 |
| WO | WO 01/21767 | 3/2001 |
| WO | WO 01/62901 A2 | 8/2001 |

OTHER PUBLICATIONS

Considine, et al., "Paracrine stimulation of preadipocyte-enriched cell cultures by mature adipocytes," *American Journal of Physiology* 1996 270(5) E895-E899 (Exhibit 6).

Dani, et al., "Differentiation of embryonic stem cells into adipocytes in vitro," *J. Cell Sci.* 1997 110, 1279-1285 (Exhibit 7).

Entenmann, et al., "Relationship between replication and differentiation cultured human adipocyte precursor cells," *American Phys. Soc.* 1996 270,C1011-C1016 (Exhibit 8).

Eslami Varzaneh, et al., "Extracellular Matrix Components Secreted by Microvascular Endothelial Cells Stimulate Preadipocyte Differentiation In Vitro, " *Metabolism* 1994 43 (7), 906-912 (Exhibit 9).

Hauner, et al., "Endothelin-1 Inhibits the Adipose Differentiation of Cultured Human Adipocyte Precursor Cells," *Metabolism* 1994 43(2) pp. 227-232 (Exhibit 10).

Hausman, et al., "The Influence of Extracellular Matrix Substrata on Preadipocyte Development in Serum-Free Cultures of Stromal-Vascular Cells," *J. Anim.Sci.* 1996 74(9), 2117-2128 (Exhibit 11).

Hui-Ling et al., "Increased expression of G in mouse embryo stem cells promotes terminal differentiation to adipocytes," *American Physiological Society* 1993 265(6), C1729-C1735 (Exhibit 12).

Marko, et al., "Isolation of a Preadipocyte Cell Line from Rat Bone Marrow and Differentiation to Adipocytes," *Endocrinology* 1995 136(10), 4582-4588 (Exhibit 13).

Shillabeer, et al., "A novel method for studying preadipocyte differentiation *in vitro*," *Intl. J. Obesity* 1996 20(Supp. 3), S77-S83 (Exhibit 14).

Sorisky et al., "From preadipocyte to Adipocyte: Differentiation-Directed Signals of Insulin from the Cell Surface to the Nucleus," *Critical Review in Clinical Laboratory Sciences* 1999 36(1), 1-34 (Exhibit 15).

Vassaux, et al., "Proliferation and differentiation of Rat Adipose Precursor Cells in Chemically Defined Medium: Differential Action of Anti-Adipogenic Agents," *Journal of Cellular Physiology* 1994 161(2), 249-256 (Exhibit 16).

Wabitsch, et al., "Biological Effects of Human Growth Hormone in Rat Adipocyte Precursor Cells and Newly Differentiated Adipocytes in primary Culture," *Metabolism* 1996 vol. 45,No. 1 pp. 34-42 (Exhibit 17).

Young et al., "Mesenchymal Stem Cells Reside Within the Connective Tissues of Many Organs," *Developmental Dynamics* 1995 202(2), 137-144 (Exhibit 18).

Bennett, JH, et al., 1991 *J. Cell Sci.* "Adipocytic cells cultured from marrow have osteogenic potential," 99(Pt1):131-139 (Exhibit 26).

Beresford, et al., 1986 *Endo.* "1,25- Dihydroxyvitamin $D_3$ and Human Bone-Derived Cells *in Vitro*: Effects on Alkaline Phosphatase, Type I Collagen and Proliferation," 119:1776-1785 (Exhibit 27).

Bjornson, et al., 1999 *Science* "Turning Brain into Blood: A Hematopoetic Fate Adopted by Adult Neural Stem Cells in Vivo," 283:534-537 (Exhibit 28).

Bruder, et al., 1997 J. Cell Biochem. "Growth Kinetics, Self-Renewal, and the Osteogenic Potential of Purified Human Mesenchymal Stem Cells During Extensive Subcultivation and Following Cryopreservation," 64:278-294 (Exhibit 29).

Butler-Browne et al., 1990 *Anat. Embryol. (Berl)* "Myosin heavy and light chain expression during human skeletal muscle development and precocious muscle maturation induced by thyroid hormone," 181:513-522 (Exhibit 30).

Cheng S-L., et al., 1994 *Endo* "Differentiation of Human Bone Marrow Osteogenic Stromal Cells *in Vitro*: Induction of the Osteoblast Phenotype by Dexamethasone," 134: 277-286 (Exhibit 31).

Chyun, et al., 1987 *Endo.* "Cortisol Decreases Bone Formation by Inhibiting Periosteal Cell Proliferation," 114:477-480 (Exhibit 32).

Conget, PA and JJ Minguell 1999 *J. Cell Physiol* "Phenotypical and Functional Properties of Human Bone Marrow Mesenchymal Progenitor Cells," 181:67-73 (Exhibit 33).

Cooper, et al., 1999 *J. Endocrinol.* "Glucocorticoid activity, inactivity and the osteoblast," 163:159-164 (Exhibit 34).

Denker, A.E., et al., 1995 *Differentiation* "Formation of cartilage-like spheroids by micromass cultures of murine C3H101/2 cells upon treatment with transforming growth factor-β1," 59:25-34 (Exhibit 35).

Denker, et al., 1999 *Differentiation* "Chondrogenic differentiation of murine C3H10T1/2 multipotential mesenchymal cells: I. Stimulation by bone morphogenetic protein-2 in high-density micromass cultures," 64:67-76 (Exhibit 36).

Dimri, et, al., 1995 *Proc. Natl. Acad. Sci. USA* "A biomarker that identifies a senescent human cells in culture and in aging skin *in vivo*," 92: 9363-9367 (Exhibit 37).

Ducy, et, al., 1997 *Cell* "Osf2/Cbfa1: A Transcriptional Activator of Osteoblast Differentiation,"89:747-754 (Exhibit 38).

Ferrari G., et al., 1998 *Science* "Muscle Regeneration by Bone Marrow-Derived Myogenic Progenitors," 279: 1528-1530 (Exhibit 39).

Frederikson and McKay 1988 *J. Neurosci.* "Proliferation and Differentiation of Rat Neuroepithelial Precursor Cells *in vivo*, " 8:1144-1151 (Exhibit 40).

Fridman, et al., 1992 *Int. J. Cancer* "Malignant Transformation of NIH-3T3 Cells After Subcutaneous co-Injection With A Reconstituted Basement Membrane (Matrigel)," 51(5), 740-44 (Exhibit 41).

Grigoradis A., et al., 1988 *J. Cell Biol.* "Differentiation of Muscle, Fat, Cartilage, and Bone from Progenitor Cells Presnt in a Bone-derived Clonal Cell Population: Effect of Dexamethasone,"106: 2139-2151(Exhibit 42).

Guerriero, V and JR Florini 1980 *Endocrinology* "Dexamethasone Effects on Myoblast Proliferation and differentiation," 106:1198-1202(Exhibit 43).

Hall, BK 1981 "Intracellular and extracellular control of differentiation of cartilage and bone," Histochem. J. 13:599-614(Exhibit 44).

Jaiswal, et al., 1997 "Osteogenic Differentiation of Purified, Culture-Expanded Human Mesenchymal Stem Cells In Vitro," J. Cell Biochem. 64:295-312(Exhibit 45).

Johnstone B., et al., 1998 "*In Vitro* Chondrogenesis of Bone Marrow-Derived Mesenchymal Progenitor Cells," Exp. Cell Res. 238: 265-272(Exhibit 46).

Kania, et al., 1990 "The *Drosophila* segmentation gene *runt* encodes a novel nuclear regulatory protein that is also expressed in the developing nervous system," Genes Dev. 4:1701-1713(Exhibit 47).

Kehlen, A. et al., 2000 *J. Cell Biochem.* "Increased Lymphocytic Aminopeptidase N/CD13 Promoter Activity After Cell-Cells Contact," 80:115-123(Exhibit 48).

Kosher, RA, et al., 1986 *J. Cell Biol.* "Collagen Gene Expression During Limb Cartilage Differentiation," 102:1151-1156(Exhibit 49).

Kuri-Harcuch, W. et al., 1984, *Differentiation* "Extracellular matrix production by mouse 3T3-F442A cells during adipose differentiation in culture," 28(Exhibit 50).

Lanier, L.L. et al, 1991 *J. Immunol.* "Molecular and Functional Analysis of Human Natural Killer Cell-Associated Neural Cells Adhesion Molecule (N-Cam/CD56),"146:4421-4426(Exhibit 51).

Lawson-Smith, M.J. and McGeachie, J.K. 1998 *J. Anat.* "The identification of myogenic cells in skeletal muscle, with emphasis on the use of tritiated thymidine autoradiography and desmin antibodies," 192:161-171 (Exhibit 52).

Leboy, et al., 1991 *J. Cell Physiol.* "Dexamethasone Induction of Osteoblast mRNAs in Rat Marrow Stromal Cell Cultures," 146:370-378 (Exhibit 53).

Lendahl, et al., 1990 *Cell* "CNS Stem Cells Express a New Class of Intermediate Filament Protein," 60:585-595 (Exhibit 54).

Lenoir, N. 2000 *Science* "Europe Confronts The Embryonic Stem Cell Research Challenge," 287:1425-1427 (Exhibit 55).
Lumelsky, N., et al. 2001 *Science* "Differentiation of Embryonic Stem Cells to Insulin-Secreting Structures Similar to Pancreatic Islets," 292:1389-1394. (Exhibit 56).
Lynch, et al., 1995, *Exp. Cell. Res.* "The Influence of Type I Collagen on the Development and Maintenance of the Osteoblast Phenotype in Primary and Passaged Rat Calvarial Osteoblasts: Modification of Expression of Genes Supporting Cell Growth, Adhesion, and Extracellular Matrix Mineralization," 216:35-45 (Exhibit 57).
Malaval, et al., 1994 *J. Cell. Physiol.* "Cellular Expression of Bone-Related Proteins During In Vitro Ostegenesis in Rat Bone Marrow Stromal Cell Culture," 158:555-572 (Exhibit 58).
Manduca, et al., 1992 *Eur. J. Cell Biol.* "Chondrogenic differentiation in chick embryo osteoblast cultures," 57:193-201 (Exhibit 59).
Martin, et al., 1999 *Exp. Cell Res.* "Mammalian Chondrocytes Expanded in the Presence of Fibroblast Growth Factor 2 Maintain the Ability to Differentiate and Regenerate Three-Dimensional Cartilaginous Tissue," 253:681-688 (Exhibit 60).
Megeney, et al., 1996 *Genes Dev.* "MyoD is required for myogenic stem cell function in adult skeletal muscle," 10:1173-1183 (Exhibit 61).
Molkentin and Olson 1996 *Curr. Opin. Genet. Dev.* "Defining the regulatory networks for muscle development," 6:445-453 (Exhibit 62).
Mundlos, et al., 1997 *Cell* "Mutation Involving the Transcription Factor CBFA12 Casue Cleidocranial Dysplasia," 89:773-779 (Exhibit 63).
Nehls, A. and D Drenckhahn 1991 *J. Cell Biol.* "Heterogeneity of Microvascular Pericytes for Smooth Muscle Type Alpha-Actin," 113:147-154 (Exhibit 64).
Owen, TA, et al., 1990 *J. Cell Physiol.* "Progressive Development of the Rat Osteoblast Phenotype in Vitro: Reciprocal Relationships in Expression of Genes Associated with Osteoblast Proliferation and Differentiation During Formation of the Bone Extracellular Matrix," 143:420-430 (Exhibit 65).
Paul S.R., et al., 1991 *Blood* "Stromal Cell-Associated Hematopoiesis: Immortalization and Characterization of Primate Bone Marrow-Derived Stromal Cell Line," 77: 1723-33 (Exhibit 66).
Pittenger M.F., et al.,.1999 *Science* "Multilineage Potential of Adult Human Mesenchymal Stem Cells," 284: 143-147 (Exhibit 67).
Prockop D.J. 1997 *Science* "Marrow Stromal Cells as Stem Cells for Nonhematopoietic Tissues," 276: 71-74 (Exhibit 68).
Rando, et al., 1995 *Exp. Cell Res.* "The Fate of Myoblasts Following Transportation into Mature Muscle," 220:383-389 (Exhibit 69).
Saalbach, A., et al., 1997 *Cell and Tiss. Res.* "The Fibroblast-specific MAb AS02: a novel tool for detection and elimination of human fibroblasts," 290:593-599 (Exhibit 70).
Sanchez-Ramos, et al., 2000 "Adult Bone Marrow Stromal Cells Differentiate into Neural Cells in *Vitro*," Exp. Neurol. 164:247-256 (Exhibit 71).
Seale and Rudnicki 2000 *Dev. Biol.* "A New Look at the Origin, Function, and "Stem-Cell" Status of Muscle Satellite Cells," 218:115-124 (Exhibit 72).
Shukunami, C., et al., 1998 *Exp. Cell Res.* "Sequential Progression of the Differentiation Program by Bone Morphogenetic Protein-2 in Chondrogenic Cell Line ATDC5," 241:1-11 (Exhibit 73).
Shukunami C., et. al., 1996 *Journ. Of Cell Bio.* "Chondrogenic Differentiation of Clonal Mouse Embryonic Cell Line ATDC5 In Vitro: Differentiation-dependent Gene Expression of Parathyroid Hormone (PTH)/PTH-related Peptide Receptor," 133:2:457-468 (Exhibit 74).
Silberstein, L., et al., 1986 *Cell* "Developmental Progression of Myosin Gene Expression in Cultured Muscle Cells," 46:1075-1081 (Exhibit 75).
Suga, S., et al., 1996, "*Eur. J. Cell Biol.* "Intracellular localization of antigens recognized by anti-vimentin monoclonal antibodies (mAbs): Cross-reactivities of anti-vimentin mAbs with other cellular components 70:84-91 (Exhibit 76).
Tacchetti, C, et al., 1992 *Exp Cell Res.* "Condensation in Chondrogenic Differentiation," 200:26-33 (Exhibit 77).

Tapscott, et al., 1988 *Science* "MyoD1: A Nuclear Phosphoprotein Requiring a Myc Homology Region to Convert Fibroblasts to Myoblasts," 242:405-411 (Exhibit 78).
Thronell, et al., 1984 *J. Neurol. Sci.* "Development of Fiber Types in Human Fetal Muscle," 66:107-115 (Exhibit 79).
Totonoz, et al., 1995 *Nucl. Acid Res* "mPPARγ2: tissue-specific regulator of an adipocyte enhancer," (Exhibit 80).
Tsonis and Goetinck 1990 *Exp. Cell Res.* "Cell Density Dependent Effect of a Tumor Promoter on Proliferataion and Chondrogenesis of Limb Bud Mesenchymal Cells," 190:247-253 (Exhibit 81).
von der Mark, et al., 1977 *Nature* "Relationship between cell shape and type of collagen synthesised as chondrocytes lose their cartilage phenotype in culture," 267:531-532 (Exhibit 82).
Vukicevic et al., 1992 *Exp. Cell Res* "Identification of Multiple Active Growth factors in Basement Membrane Matrigel Suggests Caution in Interpretation of Cellular Activity Related to Extracellular Matrix Components,", 202(1), 1-8 (Exhibit 83).
Weintraub, et al., 1991 *Science* "The myoD Gene Family: Nodal Point During Specification of the Muscle Cell Lineage," 251:761-766 (Exhibit 84).
Woodbury, et al., 2000 *J. Neurosci. Res. Science* "Adult Rat and Human Bone Marrow Stromal cells Differentiate Into Neurons," 61:364-370 (Exhibit 85).
Young, 2000 *Science* "A Time for Restraint," 287:1424. (Exhibit 86).
Zalin, RJ 1987 *Exp. Cell Res.* "The Role of Hormones and Prostanoids in the *in Vitro* Proliferation and differentiation of Human Myoblasts," 172:265-281. (Exhibit 87).
Ankrom, Michael A., "Age-related changes in human oestrogen receptor function and levels in osteoblasts," *Biochem J.* 333:787-794. (Exhibit 88).
Aso, Hisashi, et al., "A Preadipocyte Clonal Line from bovine Intramuscular Adipose Tissue: Nonexpression of GLUT-4 protein during Adipocyte Differentiation," *Biochem. Biophys. Res. Commun.* 213:369-375. (Exhibit 89).
Bernlohr, David A. et al., "Tissue Specific Expression of p422 protein, A putative Lipid Carrier, In Mouse Adipocytes," *Biochem. Biophys. Res. Comun.* 1985 132:850-855. (Exhibit 90).
Cheifetz, S. et al., "Endoglin Is a Component of the Transforming Growth Factor-β Receptor System in Human Endothelial Cells," *J. Biol. Chem.*, 1992 267:19027-19030. (Exhibit 91).
Chen, Theresa L. et al., "1α25-Dihydroxyvitamin $D_3$ Receptors in Cultured Rat osteoblast-like Cells," *J. Biol. Chem.* 1983 258:4350-4355. (Exhibit 92).
Enomoto, Hirayuki et al., "Cbfal Is a Positive Regulatory Factor in Chondrocyte Maturation," *J. Biol. Chem.* 2000 275:8695-8702. (Exhibit 93).
Herman, Ira M. and Patricia D'Amore, "Microvascular Pericytes Contain Muscle and Nonmuscle Actins," *J. Cell Biol.* 1985 101:43-52. (Exhibit 94).
Lucas, Paul A. et al., "Mesenchymal Stem Cells From Granulation Tissue," *J. Cell Biochem.*, 1993 17E:122, R212 (Exhibit 95).
Majeska, Robert J. and Gideon A. Rodan, "The Effect of 1,25(OH)$_2$D$_3$ on Alkaline Phosphates in Osteoblastic Osteosarcoma Cells," *J. Biol. Chem.* 1982 257:3362-3365. (Exhibit 96).
Periasamy, Muthu et al., "Regulation of myosin heavy-chain gene expression during sleletal-muscle hypertrophy," *Biochem. J.* 1989 257:691-698. (Exhibit 97).
Poliard, a. et al., "Controlled Conversion of an Immortalized Mesodermal progenitor Cell Towards osteogenic, Chondrogenic, or Adipogenic Pathways," *J. Cell Biol.* 1995 130;1461-1472. (Exhibit 98).
Price, Paul A. et al., "Matrix GLA Protein, A New γ-Carboxyglutamic Acid-Containing Protein Which is Associated With The Organic Matrix of Bone," *Biochem. Biophys. Res. Commun.*, 1983 117:765-771. (Exhibit 99).
Rando, Thomas A. and Helen M. Blau, "Primary Mouse Myoblast Purification, Characterization, and Transplantation for Cell-mediated Gene Therapy," *J. Cell Biol* 1994 125:1275-1287. (Exhibit 100).
Weiner, Francis R. et al., "Regulation of collagen Gene Expression in 3T3-L1 Cells. Efects of Adipocyte Differentiation and Tumor necrosis Factor α," *Biochem* 1989 28:4094-4099. (Exhibit 101).
Williams, Irene H. and S. Efthimios Polakis, "Differentiation of 3T3-L1 Fibroblasts to Adipocytes The Effect Of Indomethacin, Prostaglandin $E_1$ And Cyclic AMP On The Process of Differentiation," *Biochem. Biophys. Res. Commun.* 1977 77:175-186. (Exhibit 102).

Wise, Leigh S. and Howard Green, "Participation of One Isozyme of Cytosolic Glycerophosphate Dehydrogenase in the Adipose Conversion of 3T3 Cells," *J. Biol. Chem.* 1979 254:273-275. (Exhibit 103).

Yoon, Kyonggeun et al., "Characterization of the Rat osteocalcin Gene: Stimulation of Prometer activity by 1,25-Dihydroxyvitamin $D_3$," *Biochem.* 1988 27:8521-8526. (Exhibit 104).

Bastard, J. P. et al., "A Mini-Liposuction Technique Adapted to the Study of Human Adipocyte Glucose Transport System," *Diabetologia*, 36(Suppl. 1):A135, 1993 (Exhibit 120).

Caplan, Arnold I., "The Mesengenic Process," *Clinics in Plastic Surgery*, 21:429-35, 1994 (Exhibit 121).

Crandall, David L. et al., "Identification of Estrogen Receptor β RNA in Human Breast and Abdominal Subcutaneous Adipose Tissue," *Biochemical and Biophysical Research Communications*, 248:523-6, 1998 (Exhibit 122).

Hauner, Hans et al., "Promoting Effect of Glucocorticoids on the Differentiation of Human Adipocyte Precursor Cells Cultured in a Chemically Defined Medium," *Journal of Clinical Investigation*, 84:1663-70, 1989 (Exhibit 123).

Hauner H. et al., "Glucocorticoids and Insulin Promote the Differentiation of Human Adipocyte Precursor Cells into Fat Cells," *Journal of Clinical Endocrinology and Metabolism*, 64:832-5, 1987 (Exhibit 124).

Johnson, P. R. et al., "Uncontrolled adipocyte proliferation is not the primary lesion in the genetically-obese Zucker rat," *International Journal of Obesity*, 5:563-70, 1981 (Exhibit 125).

Killinger, D. W. et al., "Influence of Adipose Tissue Distribution on the Biological Activity of Androgens," *Annals New York Academy of Sciences*, 595:199-211, 1990 (Exhibit 126).

Killinger, Donald W. et al., "The Relationship Between Aromatase Activity and Body Fat Distribution," *Steroids*, 50:61-72, 1987 (Exhibit 127).

Lafontan, M. et al., "Réflexions sur une nouvelle approche de chirurgie plastique réparatrice: la réimplantation de fragments de tissu adipeux prélevés par liposuccion," *Ann. Chir. Plast/ Esthet.*, 34:77-81, 1989 (Exhibit 128).

Lam, Anson and Ronald Moy, "The Potential for Fat Transplantation," *J. Dermatol. Surg. Oncol.*, 18:432-4, 1992 (Exhibit 129).

Lecouer, L. and J. P. Ouhayoun, "*In vitro* induction of osteogenic differentiation from non-osteogenic mesenchymal cells," *Biomaterials*, 18:989-93, 1997 (Exhibit 130).

Loncar, D., "Ultrastructural analysis of differentiation of rat endoderm *in vitro*. Adipose vascular-srtromal cells induce endoderm differentiation, which in turn induces differentiation of the vascular-stromal cells into chondrocytes," *J. Submicrosc. Cytol. Pathol.*, 24:509-19, 1992 (Exhibit 131).

Novakofski, Jan E., "Primary Cell Culture of Adipose Tissue," *Biology of the Adipocyte: Research Approaches*, Van Nostrand Reinhold Company, NY, 1987 160-97 (Exhibit 132).

Pedersen, S. B. et al., "Identification of oestrogen receptors and oestrogen receptor mRNA in human adipose tissue," *European Journal of Clinical Investigation*, 26:262-9, 1996 (Exhibit 133).

Pettersson, Per et al., "Adipocyte Precursor Cells in Obese and Nonobese Humans," *Metabolism*, 34:808-12, 1985 (Exhibit 134).

Ramsay, T. G. et al., "Pre-Adipocyte Proliferation and Differentiation in Response to Hormone Supplementation of Decapitated Fetal Pig Sera," *J. Anim. Sci.*, 64:735-44, 1987 (Exhibit 135).

Rubens, F. D. et al., "Tissue Factor Expression by Cells Used for Sodding of Prosthetic Vascular Grafts," *Journal of Surgical Research*, 72:22-8, 1997 (Exhibit 136).

Smahel, J., "Aspiration lipectomy and adipose tissue injection: pathophysiologic commentary," *European Journal of Plastic Surgery*, 14:126-31, 1991 (Exhibit 137).

Springhorn, Jeremy P. et al., "Human Capillary Endothelial Cells from Abdominal Wall Adipose Tissue: Isolation Using an Anti-Pecam Antibody," *In Vitro Cellular & Developmental Biology-Animal*, 31:473-81, 1995 (Exhibit 138).

Tavassoli, Mehdi, "In Vivo Development of Adipose Tissue Following Implantation of Lipid-Depleted Cultured Adipocyte," *Experimental Cell Research*, 137:55-62, 1982 (Exhibit 139).

Williams, John T. et al., "Cells Isolated from Adult Human Skeletal Muscle Capable of Differentiating into Multiple Mesodermal Phenotypes," *The American Surgeon*, 65:22-6, 1999 (Exhibit 140).

Williams, Stuart K. et al., "Liposuction-derived human fat used for vascular graft sodding contains endothelial cells and not mesothelial cells as the major cell type," *Journal of Vascular Surgery*, 19:916-23, 1994 (Exhibit 141).

Wlodarski, Krzysztof H., "Section III. Basic Science and Pathology. Properties and Origin of Osteoblasts," *Clinical Orthopaedics and Related Research*, 252:276-93, 1990 (Exhibit 142).

Ahrens, Patricia Buckley et al., "Stage-Related Capacity for Limb Chondrogenesis in Cell Culture," *Developmental Biology*, 1977, 60:69-82 (Exhibit 143).

Alameddine, Hala S. et al., "Regeneration of Skeletal Muscle Fibers from Autologous Satellite Cells Multiplied In Vitro. An Experimental Model for Testing Cultured Cell Myogenicity," *Muscle & Nerve*, 1989, 12:544-55 (Exhibit 144).

Angele, P. et al., "Engineering of Osteochondral Tissue with Bone Marrow Mesenchymal Progenitor Cells in a Derivatized Hyaluronan-Gelatin Composite Sponge," *Tissue Engineering*, 1999, 5:545-53 (Exhibit 145).

Bailey, A. J. et al., "Age-Related Changes in the Biochemical Properties of Human Cancellous Bone Collagen: Relationship to Bone Strength," *Calcified Tissue International*, 1999. 65:203-10 (Exhibit 146).

Barghorn, A. et al., "α-Smooth Muscle Actin Distribution in the Pulmonary Vasculature Comparing Hypoplastic and Normal Fetal Lungs," *Pediatric Pathology & Laboratory Medicine*, 1998, 18:5-22 (Exhibit 147).

Baylink, David J., "Glucocorticoid-Induced Osteoporosis," *The New England Journal of Medicine*, 1983, 309:306-8 (Exhibit 148).

Becerra, José et al., "Demineralized Bone Matrix Mediates Differentiation of Bone Marrow Stromal Cells In Vitro: Effect of Age of Cell Donor," *Journal of Bone and Mineral Research*, 1996, 11:1703-14 (Exhibit 149).

Beiser, Ian H. and Irvin O. Kanat, "Subchondral Bone Drilling: A Treatment for Cartilage Defects," *Journal of Foot Surgery*, 1990, 29:595-601 (Exhibit 150).

Breen, Ellen C. et al., "TGFβ Alters Growth and Differentiation Related Gene Expression in Proliferating Osteoblasts In Vitro, Preventing Development of the Mature Bone Phenotype," *Journal of Cellular Physiology*, 1994, 160:323-35 (Exhibit 151).

Bruder, Scott P. et al., "Bone Regeneration by Implantation of Purified, Culture-Expanded Human Mesenchymal Stem Cells," *Journal of Orthopaedic Research*, 1998, 16:155-62 (Exhibit 152).

Butnariu-Ephrat, Miriam et al., "Resurfacing of Goat Articular Cartilage by Chondrocytes Derived From Bone Marrow," *Clinical Orthopaedics and Related Research*, 1996, 330:234-43 (Exhibit 153).

Campion, Dennis R., "The Muscle Satellite Cell: A Review," *Internationals Review of Cytology*, 1984, 87:225-51 (Exhibit 154).

Caplan, Arnold I., "Mesenchymal Stem Cells," *Journal of Orthopaedic Research*, 1991, 9:641-50 (Exhibit 155).

Caplan, Arnold I., "The Mesengenic Process," *Clinics in Plastic Surgery*, 1994, 21:429-35 (Exhibit 156).

Carranza-Bencano, A. et al., "Comparative Study of the Reconstruction of Articular Cartilage Defects with Free Costal Perichondrial Grafts and Free Tibial Periosteal Grafts: An Experimental Study on Rabbits," *Calcified Tissue International*, 1999, 65:402-7 (Exhibit 157).

Chen, Xiaoli et al., "Differentiation-dependent expression of obese (ob) gene by preadipocytes and adipocytes in primary cultures of porcine stromal-vascular cells," *Biochemica et Biophysica Acta*, 1997, 1359:136-42 (Exhibit 158).

Chimal-Monroy, Jesús and Lino Díaz de León, "Expression of N-cadherin, N-CAM, fibronectin tenascin is stimulated by TGF-β1, β2, β3 and β5 during the formation of precartilage condensations," *The International Journal of Developmental Biology*, 1999, 43:59-67 (Exhibit 159).

Deng, Weiwen et al., "In Vitro Differentiation of Human Marrow Stromal Cells into Early Progenitors of Neural Cells by Conditions That Increase Intracellular Cyclic AMP," *Biochemical and Biophysical Research Communications*, 2001, 282:148-52 (Exhibit 160).

Dennis, James E. et al., "A Quadripotential Mesenchymal Progenitor Cell Isolated from the Marrow of an Adult Mouse," *Journal of Bone and Mineral Research*, 1999, 14:700-9 (Exhibit 161).

Dias, Peter et al., "The Molecular Basis of Skeletal Muscle Differentiation," *Seminars in Diagnostic Pathology*, 1994, 11:3-14 (Exhibit 162).

Diefenderfer, David L. and Carl T. Brighton, "Microvascular Pericytes Express Aggrecan Message Which is Regulated by BMP-2," *Biochemical and Biophysical Research Communications*, 2000, 269:172-8 (Exhibit 163).

Eisenberg, Shlomo, "High density lipoprotein metabolism," *Journal of Lipid Research*, 1984, 25:1017-58 (Exhibit 164).

Fajas, Lluis, et al., "Transcriptional control of adipogenesis," *Current Opinion In Cell Biology*, 1998, 10:165-73 (Exhibit 165).

Farndale, Richard W. et al., "Improved quantitation and discrimination of sulphated glycosaminoglycans by use of dimethylene blue," *Biochimica et Biophysica Acta*, 1986, 883:173-7 (Exhibit 166).

Fülöp, Csaba et al., "Expression of Alternatively Spliced Epidermal Growth Factor-like Domains in Aggrecans of Different Species," *The Journal of Biological Chemistry*, 1993, 268:17377-83 (Exhibit 167).

Glowacki, J., "Influence of Age on Human Marrow," *Calcified Tissue International*, 1995, 56(Supp. 1):S50-1 (Exhibit 168).

Grigoriadis, Agamemnon E. et al., "Analysis of chondroprogenitor frequency and cartilage differentiation in a novel family of clonal chondrogenic rat cell lines," *Differentiation*, 1996, 60:299-307 (Exhibit 169).

Hardingham, Tim et al., "Studies on the Synthesis, Secretion and Assembly of Proteoglycan Aggregates by Chondrocytes," *Matrices and Cell Differentiation*, 1984, 151:17-29 (Exhibit 170).

Haynesworth, S. E. et al., "Cell Surface Antigen on Human Marrow-Derived Mesenchymal Cells are Detected by Monoclonal Antibodies," *Bone*, 1992, 13:69-80 (Exhibit 171).

Huss, Ralf, "Isolation of Primary and Immortalized CD34 Hematopoietic and Mesenchymal Stem Cells from Various Sources," *Stem Cells*, 2000, 18:1-9 (Exhibit 172).

Iwasaki, Motoki et al., "Regulation of Proliferation and Osteochondrogenic Differentiation of Periosteum-Derived Cells by Transforming Growth Factor-β and Basic Fibroblast Growth Factor," *Journal of Bone and Joint Surgery*, 1995, 77A:543-54 (Exhibit 173).

Katz, Adam J. et al., "Emerging Approaches to the Tissue Engineering of Fat," *Clinics in Plastic Surgery*, 1999, 26:587-603 (Exhibit 174).

Kirsch, Thorsten and Klaus von der Mark, "Remodeling of collagen types I, II and X and calcification of human fetal cartilage," *Bone and Mineral*, 1992, 18:107-17 (Exhibit 175).

Kosher, Robert A. and Michael Solursh, "Widespread Distribution of Type II Collagen during Embryonic Chick Development," *Developmental Biology*, 1989, 131:558-66 (Exhibit 176).

Lazarus, Hillard M. et al., "Human Bone Marrow-Derived Mesenchymal (Stromal) Progenitor Cells (MPCs) Cannot Be Recovered from Peripheral Blood Progenitor Cell Collections," *Journal of Hematotherapy*, 1997, 6:447-55 (Exhibit 177).

Leboy, Phoebe S. et al., "Ascorbic Acid Induces Alkaline Phosphates, Type X Collagen, and Calcium Deposition in Cultured Chick Chondrocytes," *The Journal of Biological Chemistry*, 1989, 264:17281-6 (Exhibit 178).

Lee, Yun-Shain and Cheng-Ming Chuong, "Adhesion Molecules in Skeletogenesis: I. Transient Expression of Neural Cell Adhesion Molecules (NCAM) in Osteoblasts During Endochondral and Intramembranous Ossification," *Journal of Bone and Mineral Research*, 1992, 7:1435-46 (Exhibit 179).

Lennon, Donald P. et al., "Human and Animal Mesenchymal Progenitor Cells from Bone Marrow: Identification of Serum for Optimal Selection and Proliferation," *In Vitro Cell. Dev. Biol.—Animal*, 1996, 32:602-11 (Exhibit 180).

Lev, Robert and S. S. Spicer, "Specific Staining of Sulphate Groups with Alcian Blue at Low pH," *J. Histochem. Cytochem.*, 1964, 12:309-10 (Exhibit 181).

Long, Michael W. et al., "Age-Related Phenotypic Alterations in Populations of Purified Human Bone Precursor Cells," *The Journals of Gerontology*, 1999, 54A:B54-62 (Exhibit 182).

Lucas, P. A. et al., "Isolation of Putative Mesenchymal Stem Cells from Rat Embryonic and Adult Skeletal Muscle," *In Vitro Cell Dev. Biol.*, 1992, 28:154A (Exhibit 183).

MacDougald, Ormond A. and M. Daniel Lane, "Transcriptional Regulation of Gene Expression During Adipocyte Differentiation," *Annu. Rev. Biochem.*, 1995, 64:345-73 (Exhibit 184).

Mullen, Richard J. et al., "NeuN, a neuronal specific nuclear protein in vertebrates," *Development*, 1992, 116:201-11 (Exhibit 185).

Nagle, R. B. et al., "Factor VII-Associated Antigen in Human Lymphatic Endothelium," *Lymphology*, 1987, 20:20-4 (Exhibit 186).

Nakahara, H. et al., "Bone and Cartilage Formation in Diffusion Chambers by Subcultured Cells Derived from the Periosteum," *Bone*, 1990, 11:181-8 (Exhibit 187).

Nakano, Hirotaka et al., "RT-PCR Suggests Human Skeletal Muscle Origin of Alveolar Soft-Part Sarcoma," *Oncology*, 2000, 58:319-23 (Exhibit 188).

O'Driscoll, Shawn W., "Current Concepts Review: The Healing and Regeneration of Articular Cartilage," *Journal of Bone and Joint Surgery*, 1998, 80A:1795-812 (Exhibit 189).

Olson, E. N. et al., "Know Your Neighbors: Three Phenotypes in Null Mutants of the Myogenic bHLH Gene MRF4," *Cell*, 1996, 85:1-4 (Exhibit 190).

Pairault, Jacques and Howard Green, "A study of the adipose conversion of suspended 3T3 cells by using glycerophosphate dehydrogenase as differentiation marker," *Proc. Natl. Acad. Sci. USA*, 1979, 76:5138-42 (Exhibit 191).

Park, S. R. et al., "Interconversion Potential of Clone Human Marrow Adipocytes In Vitro," *Bone*, 1999, 24:549-54 (Exhibit 192).

Pettersson, Per et al., "Cells in Human Adipose Tissue Developing into Adipocytes," *Acta Med Scand*, 1984, 215:447-51 (Exhibit 193).

Pierelli, Luca et al., "CD34+/CD105+ cells are enriched in primitive circulating progenitors residing in the G0 phase of the cell cycle and contain all bone marrow and cord blood $CD34+/CD38^{low/-}$ precursors," *British Journal of Haematology*, 2000, 108:610-20 (Exhibit 194).

Price, Paul A., "GLA-Containing Proteins of Bone," *Connective Tissue Research*, 1989, 21:51-60 (Exhibit 195).

Price, Paul A. and Sharon A. Baukol, "1,25-Dihydroxyvitamin $D_3$ Increases Synthesis of the Vitamin K-dependent Bone Protein by Osteosarcoma Cells," *The Journal of Biological Chemistry*, 1980, 255:11660-3 (Exhibit 196).

Probst, M. et al., "Homologous bladder augmentation in dog with the bladder acellular matrix graft," *BJU International*, 2000, 85:362-71 (Exhibit 197).

Richardson, J. B. et al., "Repair of human articular cartilage after implantation of autologous chondrocytes," *The Journal of Bone and Joint Surgery*, 1999, 81:1064-8 (Exhibit 198).

Rickard, David J. et al., "Isolation and Characterization of Osteoblast Precursor Cells from Human Bone Marrow," *Journal of Bone and Mineral Research*, 1996, 11:312-24 (Exhibit 199).

Sarnat, Harvey B. et al., "Neuronal nuclear antigen (NeuN): a marker of neuronal maturation in the early human fetal nervous system," *Brain & Development*, 1998, 20:88-94 (Exhibit 200).

Scott, Douglas M. et al., "Collagen Synthesis in Cultured Osteoblast-like Cells," *Archives of Biochemistry and Biophysics*, 1980, 201:384-91 (Exhibit 201).

Shalhoub, Victoria et al., "Downregulation of Cell Growth and Cell Cycle Regulated Genes during Chick Osteoblast Differentiation with the Reciprocal Expression of Histone Gene Variants," *Biochemistry*, 1989, 28:5318-22 (Exhibit 202).

Siffert, Robert S., "The Role of Alkaline Phosphatase in Osteogenesis," *The Journal of Experimental Medicine*, 1951, 93:415-26 (Exhibit 203).

Syrjälä, M. et al., "A flow cytometric assay of CD34-positive cell populations in the bone marrow," *British Journal of Haematology*, 1994, 88:679-84 (Exhibit 204).

Tacchetti, C. et al., "In Vitro Morphogenesis of Chick Embryo Hypertrophic Cartilage," *The Journal of Cell Biology*, 1987, 105:999-1006 (Exhibit 205).

Tontonoz, Peter et al., "mPPARγ2: tissue-specific regulator of an adipocyte enhancer," *Genes & Development*, 1994, 8:1224-34 (Exhibit 206).

Trayhurn, P. and Margaret Ashwell, "Control of white and brown adipose tissues by the autonomic nervous system," *The Proceedings of the Nutrition Society*, 1987, 46:135-42 (Exhibit 207).

Vandenburgh, Herman H. and Patricia Karlisch, "Longitudinal Growth of Skeletal Myotubes In Vitro in a New Horizontal Mechanical Cell Stimulator," *In Vitro Cellular & Developmental Biology*, 1989, 25:607-16 (Exhibit 208).

Wakitani, Shigeyuki et al., "Mesenchymal Cell-Based Repair of Large, Full-Thickness Defects of Articular Cartilage," *The Journal of Bone and Joint Surgery*, 1994, 76A:579-92 (Exhibit 209).

Wakitani, Shigeyuki et al., "Myogenic Cells Derived from Rat Bone Marrow Mesenchymal Stem Cells Exposed to 5-Azacytidine," *Muscle & Nerve*, 1995, 18:1417-26 (Exhibit 210).

Weintraub, Harold et al. "Tissue-specific gene activation by MyoD: determination of specificity by cis-acting repression elements," *Genes & Development*, 1994, 8:2203-11 (Exhibit 211).

Yoo, Jung U. and Brian Johnstone, "The Role of Osteochondral Progenitor Cells in Fracture Repair," *Clinical Orthopaedics and Related Research*, 1998, 355S:S73-81 (Exhibit 212).

Young, Henry E. et al., "Human Pluripotent and Progenitor Cells Display Cell Surface Cluster Differentiation Markers CD10, CD13, CD56, and MHC Class-I $_{(44385)}$," *Proc. Soc. Exp. Biol. Med.*, 1999, 221:63-71 (Exhibit 213).

Zezulak, Kathleen M. and Howard Green, "Specificity of Gene Expression in Adipocytes," *Molecular and Cellular Biology*, 1985, 5:419-21 (Exhibit 214).

Zohar, R. et al., "Analysis of intracellular osteopontin as a marker of osteoblastic cell differentiation and mesenchymal cell migration," *European Journal of Oral Sciences*, 1998, 106(Supp. 1):401-7 (Exhibit 215).

Zuk, Patricia Z. et al., "Multilineage Cells from Human Adipose Tissue: Implication for Cell-Based Therapies," *Tissue Engineering*, 2001, 7:211-28 (Exhibit 216).

Boskey, et al., 1985, "The Effect of Osteocalcin on *In Vitro* Lipid-Induced Hydroxyapatite Formation and Seeded Hydroxyapatite Growth," *Calc. Tiss. Int.* 37:75. (Exhibit 217).

Fortier, Lisa, et al., 2000, "Isolation and chondrocytic differentiation of equine bone marrow-derived mesenchymal stem cells," *Am. J. Vet. Res.* 59:1182-1187. (Exhibit 218).

Huibregtse, Barbara, et al., 1998, "Effect of Age and Sampling Site on the Chondro-Osteogenic Potential of Rabbit Marrow-derived Mesenchymal Progenitor Cells," *Journal of Orthopaedic Research.* 18:18-24. (Exhibit 219).

Linsenmayer, Thomas et al., 1998, "Type X Collagen: A Hypertrophic Cartilage-Specific Molecule," *Pathol. Immunopathol.* 7:14-19. (Exhibit 220).

Nakajima, I. et al., 1998, "Adipose tissue extracellar matrix: newly organized by adipocytes during differentiation," *Differentiation* 63:193-200. (Exhibit 221).

Zvaifler, et al., 2000, "Mesenchymal precursor cells in the blood of normal individuals," *Arthritis Res.* 2:477-488. (Exhibit 222).

Bond et al., 1999, "Human Subcutaneous preadipocytes Differentiate Into osteoblasts," *FSEB Journal* 13:600A (Exhibit 225).

Smith et al., 2000, "Mesenchymal Stem Cells Derived From Bone Marrow And Human Adipose Tissue Exhibit Multilineage Potential," *Journal of Investigative Medicine*, 95A. (Exhibit 226).

Stashower et al., 1999, "Stromal progenitor cells present within liposuction and reduction abdominoplasty fat for autologous transfer to aged skin," *Dermatologic Surgery*, 25:12:945-949. (Exhibit 227).

Strutt et al., 1996, "Growth and differentiation of human adipose stromal cells in culture," *methods in Molecular Medicine: Human Cell Culture Protools*, 41-51. (Exhibit 228).

Tavassoli et al., 1981, "The Nature of Fibroblasts Derived From Adipose Tissue In-Vitro," *Clinical Research*, 29:5:871A. (Exhibit 229).

Van et al., 1978, "Complete Differentiation of Adipocyte Precursors," *Cell Tissue*, 195:317-329. (Exhibit 230).

Soda, et al., 1983, "Adipocyte stem cell: A brief review," *Int. J. of Cell Cloning*, 1:79-84. (Exhibit 234).

Ailhaud, et al., 1983, "Hormonal requirements for growth and differentiation of OB17 preadipocyte cells in vitro," *Diabete & Metabolisme*, vol. 9:125-133. (Exhibit 237).

Ailhaud, et al., 1985, "Lipoprotiene lipase et differenciation adipocytaire," *Reprod. Nutr. Develop.*, vol. 25:153-158. (Exhibit 238).

Zuk, Patricia A. et al., "Human Adipose Tissue Is A Source Of Multipotent Stem Cells," *Molecular Biology of the Cell*, 2002, 13:4279-4295. (Exhibit 239).

Gimble, Jeffrey M. et al., "Adipose tissue-derived therapeutics," *Expert Opin. Biol.*, 2003, 3(5)705-713. . (Exhibit 240).

Safford, Kristine M. et al., "Neurogenic differentiation of murine and human adipose-derived stromal cells," *Biochemical and Biophysical Research Communications*, 2002, 371-379. (Exhibit 241).

Compliant For Correction Of Inventorship Under 35 U.S.C.§§ 1 and 256 dated Oct. 29, 2004 (Exhibit 243).

Answer To Compliant For Correction of Inventorship Under 35 U.S.C. §256 and Demand For Jury Trial dated Jan. 5, 2005 (Exhibit 244).

Ng, C.W. et al., "Dif ferences in Growth *in vitro* of Adipose Cells From Normal and Obese Patients," *Nature*, 1971, 231:445 (Exhibit 245).

Poznanski, W. J. et al., "Human Fat Cell Precursors: Morphologic and Metabolic Differentiation in Culture," *Laboratory Investigation*, 1973, 29:570-6 (Exhibit 246).

Friedenstein, Alexander J., et al., "Fibroblast Precursor s in Normal and Irradiated Mouse Hematopoietic Organs," *Exp. Hemat.*, 1976, 4:267-74 (Exhibit 247).

Van, Robin L. R. et al., "Cyt ological and Enxymological Characterization of Adult Human Adipocyte Precursors in Culture," *The Journal of Clinical Investigation*, 1976, 58:699-704 (Exhibit 248).

Green, Howard and Olaniyi Kehinde, "Formation of Norm ally Differentiated Subcutaneous Fat Pads by an Established Preadipose Cell Line," *J. Cell. Physiol.*, 1979, 101:169-72 (Exhibit 249).

Roncari, Daniel A. K. et al., "Exaggerated Replication in Culture of Adipocyte Precursors From Massively Obese Persons," *Metabolism*, 1981, 30:425-7 (Exhibit 250).

Van, Robin L. R. and Daniel A. K. Roncari, "Complete dif ferentiation in vivo of implanted cultured adipocyte precursors from adult rats," *Cell Tissue Res*, 1982, 225:557-66 (Exhibit 251).

Fried, Susan K. and John G. Kral, "Sex Differences in Re gional Distribution of Fat Cell Size and Lipoprotein Lipase Activity in Morbidly Obese Patients," *International Journal of Obesity*, 1987, 11:129-40 (Exhibit 252).

Hausman, G. J. and G. B. Thomas, "Structural and Histochemical Aspects of Perirena l Adipose Tissue in Fetal Pigs: Relationships Between Stromal-Vascular Characteristics and Fat Cell Concentration and Enzyme Activity," *Journal of Morphology*, 1986, 190:271-83 (Exhibit 253).

Deslex, Sylviane et al., "Dev elopment of a Chemically Defined Serum-free Medium for Differentiation of Rat Adipose Precursor Cells," *Experimental Cell Research*, 1987, 168:15-30 (Exhibit 254).

Lau, D. C. W. et al., "Release of Mitogenic Factors by Cu ltured Preadipocytes from Massively Obese Human Subjects," *J. Clin. Invest.*, 1987, 79:632-6 (Exhibit 255).

Silverman, K. J. et al., "Angi ogenic Activity of Adipose Tissue," *Biochemical and Biophysical Research Communications*, 1988, 153:347-52 (Exhibit 256).

Hauner, H. et al., "Dif ferentiation of Adipocyte Precursor Cells from Obese and Nonobese Adult Women and from Different Adipose Tissue Sites," *Horm. Metab. Res. Suppl.*, 1989, 19:35-9 (Exhibit 257).

Bruder, Scott P. et al., "Oste ochondral differentiation and the emergence of stage-specific osteogenic cell-surface molecules by bone marrow cells in diffusion chambers," *Bone and Mineral*, 1990, 11:141-51 (Exhibit 258).

Dobson, Deborah E. et al., "1-Butyryl-Glycerol: A Novel Angiogenesis Factor Secreted by Differentiating Adipocytes," *Cell*, 1990, 61:223-30 (Exhibit 259).

Lau, David C. W. et al., "Influence of Paracrine Factors on Preadipocyte Replication and Differentiation," *International Journal of Obesity*, 1990, 14(Suppl. 3):193-201 (Exhibit 260).

Hauner, Hans and Gero Entenmann, "Regional variation of adipose differentiatio n in cultured stromal-vascular cells from the abdominal and femoral adipose tissue of obese women," *International Journal of Obesity*, 1991, 15:121-6 (Exhibit 261).

Claffey, Kevin P. et al., "Vascular Endothelial Growth Factor," *The Journal of Biological Chemistry*, 1992, 267:16317-22 (Exhibit 262).

Eppley, Barry L. et al., "Autologous Facial Fat Transplantation: Improved Graft Maintenance by Microbead Bioactivation," *J Oral Macillofac Surg*, 1992, 50:477-82 (Exhibit 263).

Folkman, Judah and Yuen Shing, "Control of Angiogenesis by Heparin and Other Sulfated Polysaccharides," *Heparin and Related Polysaccharides*, 1992, D. A. Lane et al. (eds.), Plenum Press, New York, NY, pp. 355-364 (Exhibit 264).

Ibrahimi, Azeddine et al., "Essential Role of Collagens for Terminal Differentiation of Preadipocytes," *Biochemical and Biophysical Research Communications*, 1992, 187:1314-22 (Exhibit 265).

Teichert-Kuliszewska, Krystyna et al., "Augmented Production of Heparin-binding Mitogenic Proteins by Preadipocytes from Massively Obese Persons," *J. Clin. Invest.*, 1992, 90:1226-31 (Exhibit 266).

Zocchi, Michele, "Ultrasonic Liposculpturing," *Aesthetic Plastic Surgery*, 1992, 16:287-98 (Exhibit 267).

Fried, Susan K. et al., "Lipoprotein Lipase Regulation by Insulin and Glucocorticoid in Subcutaneous and Omental Adipose Tissues of Obese Women and Men," *J. Clin. Invest.*, 1993, 92:2191-8 (Exhibit 268).

Petruschke, Th. and H. Hauner, "Tumor Necrosis Factor-$\alpha$ Prevents the Differentiation of Human Adipocyte Precursor Cells and Causes Delipidation of Newly Developed Fat Cells," *Journal of Clinical Endocrinology and Metabolism*, 1993, 76:742-7 (Exhibit 269).

Bruder, Scott P. et al., "Mesenchymal Stem Cells in Bone Development, Bone Repair, and Skeletal Regeneration Therapy," *Journal of Cellular Biochemistry*, 1994, 56:283-94 (Exhibit 270).

Butterwith, S. C., "Molecular Events in Adipocyte Development," *Pharmac. Ther.*, 1994, 61:399-411 (Exhibit 271).

Kim, Nam W. et al., "Specific Association of Human Telomerase Activity with Immortal Cells and Cancer," *Science*, 1994, 266:2011-5 (Exhibit 272).

Tontonoz, Peter et al., "Adipocyte-specific transcription factor ARF6 is a heterodimeric complex of two nuclear hormone receptors, PPAR$\gamma$ and RXR$\alpha$," *Nucleic Acids Research*, 1994, 22:5628-34 (Exhibit 273).

van de Venter, Maryna et al., "Catecholamine Stimulated Lipolysis in Differentiated Human Preadipocytes in a Serum-Free, Defined Medium," *Journal of Cellular Biochemistry*, 1994, 54:1-10 (Exhibit 274).

Coleman, Sydney R., "Long-Term Survival of Fat Transplants: Controlled Demonstrations," *Aesthetic Plastic Surgery*, 1995, 19:421-5 (Exhibit 275).

Hauner, H. et al., "Effects of epidermal growth factor (EGF), platelet-derived growth factor (PDGF) and fibroblast growth factor (FGF) on human adipocyte development and function," *European Journal of Clinical Investigation*, 1995, 25:90-6 (Exhibit 276).

Kliewer, Steven A. et al., "A Prostaglandin $J_2$ Metabolite Binds Peroxisome Proliferator-Activator Receptor $\gamma$ and Promotes Adipocyte Differentiation," *Cell*, 1995, 83:813-9 (Exhibit 277).

Moore, John H. et al., "Viability of Fat Obtained by Syringe Suction Lipectomy: Effects of Local Anesthesia with Lidocaine," *Aesthetic Plastic Surgery*, 1995, 19:335-9 (Exhibit 278).

Schor, A. M. et al., "Pericyte Differentiation," *Clinical Orthopaedics and Related Research*, 1995, 313:81-91 (Exhibit 279).

Zhu, Yijun et al., "Structural organization of mouse peroxisome proliferator-activated receptor $\gamma$ (mPPAR$\gamma$) gene: Alternative promoter use and different splicing yield two mPPAR$\gamma$ isoforms," *Proceedings of the National Academy of Sciences USA*, 1995, 92:7921-5 (Exhibit 280).

Ashkenas, John et al., "The Extracellular Matrix in Epithelial Biology: Shared Molecules and Common Themes in Distant Phyla," *Developmental Biology*, 1996, 180:433-44 (Exhibit 281).

Brun, Regina P. et al., "Differential activation of adipogenesis by multiple PPAR isoforms," *Genes & Development*, 1996, 10:974-84 (Exhibit 282).

Gibbs, W. Wayt, "Gaining on Fat," *Scientific American*, 1996, pp. 88-94 (Exhibit 283).

Guerrerosantos, Jose, "Autologous Fat Grafting for Body Contouring," *Clinics in Plastic Surgery*, 1996, 23:619-31 (Exhibit 284).

Haraida, Sibylle et al., "Distribution of Basement Membrane Components in Normal Adipose Tissue and in Benign and Malignant Tumors of Lipomatous Origin," *Modern Pathology*, 1996, 9:137-44 (Exhibit 285).

Hirschi, Karen K. and Patricia A, D'Amore, "Pericytes in the microvasculature," *Cardiovascular Research*, 1996, 32:687-98 (Exhibit 286).

Werb, Zena et al., "Extracellular matrix remodeling and the regulation of epithelial-stromal interactions during differentiation and involution," *Kidney International*, 1996, 49(Suppl. 54):S68-74 (Exhibit 287).

Adams, Maria et al., "Activators of Peroxisome Proliferator-activated Receptor $\gamma$ Have Depot-specific Effects on Human Preadipocyte Differentiation," *J. Clin. Invest.*, 1997, 100:3149-53 (Exhibit 289).

Crandall, David L. et al., "A Review of the Microcirculation of Adipose Tissue: Anatomic, Metabolic and Angiogenic Perspectives," *Microcirculation*, 1997, 4:211-32 (Exhibit 290).

Dodson, M. V. et al., "The development and utility of a defined muscle and fat co-culture system," *Tissue & Cell*, 1997, 29:517-24 (Exhibit 291).

Aubin, Jane E., "Bone Stem Cells," *Journal of Cellular Biochemistry Supplements*, 1998, 30/31:73-82 (Exhibit 292).

Kawaguchi, Nobuko et al., "*De novo* adipogenesis in mice at the site of injection of basement membrane and basic fibroblast growth factor," *Proceedings of the National Academy of Sciences USA*, 1998, 95:1062-6 (Exhibit 293).

Kim, Jae Burn et al., "ADD1/SREBP1 activates PPAR$\gamma$ through the production of endogenous ligand," *Proceedings of the National Academy of Science USA*, 1998, 95:4333-7 (Exhibit 294).

Novaes, Flavio et al., "Counting Method of Live Fat Cells Used in Lipoinjection Procedures," *Aesthetic Plastic Surgery*, 1998, 22:12-5 (Exhibit 295).

Patrick, Charles W., Jr. et al., "Tissue Engineered Adipose Tissue," *Frontiers in Tissue Engineering*, 1998, Charles W. Patrick et al. (eds.), Pergamon, Houston, TX, pp. 369-82 (Exhibit 296).

Spiegelman, B. M., "PPAR$\gamma$ : Adipogenic Regulator and Thiazolidinedione Receptor," *Diabetes*, 1998, 47:507-14 (Exhibit 297).

Ghilzon, R. et al., "Stromal Mesenchymal Progenitor Cells," *Leukemia and Lymphoma*, 1999, 32:211-21 (Exhibit 298).

Patrick, C. W., Jr. et al., "Preadipocyte Seeded PLGA Scaffolds for Adipose Tissue Engineering," *Tissue Engineering*, 1999, 5:139-51 (Exhibit 299).

Clark, Brian R. and Armand Keating, "Biology of Bone Marrow Stroma," *Annals of New York Academy of Sciences*, pp. 70-78 (Exhibit 300).

Passaniti, Antonino et al., "Methods in Laboratory Investigation: A Simple, Quantitative Method for Assessing Angiogenesis Antiangiogenic Agents Using Reconstituted Basement Membrane, Heparin and Fibroblast Growth Factor," *Laboratory Investigation*, 1992, 67:519-28 (Exhibit 301).

Yoo, Jung U. et al., "The Chondrogenic Potential of Human Bone-Marrow-Derived Mesenchymal Progenitor Cells," *Journal of Bone and Joint Surgery*, 1998, 80:1745-57 (Exhibit 302).

Varzaneh, F. Eslami et al., "Extracellular Matrix Components Secreted by Microvascular Endothelial Cells Stimulate Preadipocyte Differentiation In Vitro," *Metabolism*, 1994, 43:906-12 (Exhibit 303).

Mackay, Alastair M. et al., "Chondrogenic Differentiation of Cultured Human Mesenchymal Stem Cells from Marrow," *Tissue Engineering*, 1998, 4:415-28 (Exhibit 304).

Cryer, Anthony and Robin L. R. Van, "Characterization of the collagen types synthesized by human and rat adipocyte precursors *in vitro*," *European Journal of Clinical Investigation*, 1982, 12:235-8 (Exhibit 305).

Granthos, Stan et al., "Surface Protein Characterization of Human Adipose Tissue-Derived Stromal Cells," *Journal of Cellular Physiology*, 2001, 189:54-63 (Exhibit 306).

Ailhaud, G. et al., "Cellular and Molecular Aspects of Adipose Tissue Development," *Annu. Rev. Nutr.*, 1992, 12:207-33 (Exhibit 308).

Alitalo, Kari et al., "Extracellular Matrix Proteins of Human Epidermal Keratinocytes and Feeder 3T3 Cells," *Journal of Cell Biology*, 1982, 94:497-505 (Exhibit 309).

Aratani, Yasuaki and Yasuo Kitagawa, "Enhanced Synth esis and Secretion of Type IV Collagen and Entactin during Adipose Conversion of 3T3-L1 Cells and Production of Unorthodox Laminin Complex," *Journal of Biological Chemistry*, 1988, 263:16163-9 (Exhibit 310).

Aronow, M. A. et al., "Factors That Promote Progres sive Development of the Osteoblast Phenotype in Cultured Fetal Rat Calvaria Cells," *Journal of Cellular Physiology*, 1990, 143:213-21 (Exhibit 311).

Asahina, Izumi et al., "Huma n Osteogenic Protein-1 Induces Chondroblastic, Osteoblastic, and/or Adipocytic Differentiation of Clonal Murine Target Cells," *Experimental Cell Research*, 1996, 222:38-47 (Exhibit 312).

Asanuma, Masato et al., "Neuroprotective effects of non -steroidal anti-inflammatory drugs by direct scavenging of nitric oxide radicals," *Journal of Neurochemistry*, 2001, 76:1895-904 (Exhibit 313).

Atchley, William R. et al., "Molecular evolution of the MyoD family of transcription factors," *Proceedings of the National Academy of Sciences USA*, 1994, 91:11522-6 (Exhibit 314).

Atkinson, Brent L. et al., "C ombination of Osteoinductive Bone Proteins Differentiates Mesenchymal C3H/10T1/2 Cells Specifically to the Cartilage Lineage," *Journal of Cellular Biochemistry*, 1997, 65:325-39 (Exhibit 315).

Baker, Robert K. and Gary E. Lyons, "Embryonic Stem Ce lls and *in Vitro* Muscle Development," *Current Topics in Developmental Biology*, 1996, 33:263-79 (Exhibit 316).

Ball, Eric H. and B. D. Sanwal, "A Synergistic Effect of Glucocorticoids and Insulin on the Differentiation of Myoblasts," *Journal of Cellular Physiology*, 1980, 102:27-36 (Exhibit 317).

Bang, Y.-J. et al., "Terminal neurendocrine differentiation of human prostate carcinoma cells in response to increased intracellular cyclic AMP," *Proceedings of the National Academy of Sciences USA*, 1994, 91:5330-4 (Exhibit 318).

Barry, Frank P. et al., "The Monoclonal Antibody SH-2, Raised against Human Mesenchymal Stem Cells, Recognizes an Epitope on Endoglin.(CD105)," *Biochemical and Biophysical Research Communications*, 1999, 265:134-9 (Exhibit 319).

Benayahu, D. et al., "Bone Marrow-Derived Stromal Cell Line Expressing Osteoblastic Phenotype In Vitro and Osteogenic Capacity In Vivo," *Journal of Cellular Physiology*, 1989, 140:1-7 (Exhibit 320).

Benson, M. Douglas et al., "Identification of a Homeodomain Binding Element in the Bone Sialoprotein Gene Promoter That is Required for Its Osteoblast-selective Expression," *Journal of Biological Chemistry*, 2000, 275:13907-17 (Exhibit 321).

Beresford, J. N. et al., "Evidence for an inverse relations hip between the differentiation of adipocyte and osteogenic cells in rat marrow stromal cell cultures," *Journal of Cell Science*, 1992, 102:341-51 (Exhibit 322).

Bergman, R. J. et al., "Age-Related Changes in Osteogen ic Stem Cells in Mice," *Journal of Bone and Mineral Research*, 1996, 11:568-77 (Exhibit 323).

Bernlohr, David A. et al., "Expres sion of specific mRNAs during adipose differentiation: Identification of and mRNA encoding a homologue of myelin P2 protein," *Proceedings of the National Academy of Sciences USA*, 1984, 81:5468-72 (Exhibit 324).

Berry, L. et al., "Bone-marro w-derived chondrogenesis in vitro," *Journal of Cell Science*, 1992, 101:333-42 (Exhibit 325).

Bouwmeester, S. J. M. et al., "Long-term results of rib p erichondrial grafts for repair of cartilage defects in the human knee," *International Orthopaedics (SICOT)*, 1997, 21:313-7 (Exhibit 326).

Bradford, Marion M., "A Rapid and Sensitive Method for t he Quantitation of Microgram Quantities of Protein Utilizing the Principle of Protein-Dye Binding," *Analytical Biochemistry*, 1976, 72:248-54 (Exhibit 327).

Brazelton, Timothy R. et al., "From Marrow to Brain: Expr ession of Neuronal Phenotypes in Adult Mice," *Science*, 2000, 290:1775-9 (Exhibit 328).

Brittberg, Mats et al., "Treat ment of Deep Cartilage Defects in the Knee with Autologous Chondrocyte Transplantation," *New England Journal of Medicine*, 1994, 331:889-95 (Exhibit 329).

Bruder, S. P. and A. I. Caplan, "Terminal Differentiation of Osteogenic Cells in the Embryonic Chick Tibia is Revealed by a Monoclonal Antibody Against Osteocytes," *Bone*, 1990, 11:189-98 (Exhibit 330).

Bruder, Scott P. et al., "Mesenchymal Stem Cells in Osteobiology and Applied Bone Regeneration," *Clinical Orthopaedics and Related Research*, 1998, 355(Supp):S247-56 (Exhibit 331).

Brüstle, Oliver and Ronald D. G. McKay, "Neuronal progenitors as tools for cell replacement in the nervous system," *Current Opinion in Neurobiology*, 1996, 6:688-95 (Exhibit 332).

Chase, W. H., "Fine Structure of Rat Adipose Tissue," *J. Ultrastructure Research*, 1959, 2:283-7 (Exhibit 333).

Cheah, Kathryn S. E. et al., "Expression of the mouse α 1 (II) collagen gene is not restricted to cartilage during development," *Development*, 1991, 111:945-53 (Exhibit 334).

Chen, Theresa L. et al., "A Receptor-like Binding Macromolecule for 1α , 25-Dihydroxycholecalciferol in Cultured Mouse Bone Cells," *Journal of Biological Chemistry*, 1979, 254:7491-4 (Exhibit 335).

Chen, Frank S. et al., "Chon drocyte Transplantation and Experimental Treatment Options for Articular Cartilage Defects," *American Journal of Orthopaedics*, 1997, 26:396-406 (Exhibit 336).

Collin, Pascal et al., "Expression of Collagen, Osteocalcin, and Bone Alkaline Phosphatase in a Mineralizing Rat Osteoblastic Cell Culture," *Calcified Tissue International*, 1992, 50:175-83 (Exhibit 337).

Cox, Michael E. et al., "Acq uisition of Neuroendocrine Characteristics by Prostate Tumor Cells Is Reversible: Implications for Prostate Cancer Progression," *Cancer Research*, 1999, 59:3821-30 (Exhibit 338).

Cusella-De Angelis, M. G. et al., "MyoD, Myogenin Indep endent Differentiation of Primordial Myoblasts in Mouse Somites," *Journal of Cell Biology*, 1992, 116:1243-55 (Exhibit 339).

Davis, Robert L. et al., "Expr ession of a Single Transfected cDNA Converts Fibroblasts to Myoblasts," *Cell*, 1987, 51:987-1000 (Exhibit 340).

Deng, Chu-Xia et al., "Murin e FGFR-1 is required for early postimplantation growth and axial organization," *Genes & Development*, 1994, 8:3045-57 (Exhibit 341).

Dennis, James E. et al., "The STRO-1 + Marrow Cell Population Is Multi potential," *Cells Tissues Organs*, 2002, 170:73-82 (Exhibit 342).

Deslex, Sylviane et al., "Differentiation of Human Adipoc yte Precursors in a Chemically Defined Serum-Free Medium," *International Journal of Obesity*, 1986, 10:19-27 (Exhibit 343).

Dessau, W. et al., "Changes in the patterns of collagens and fibronectin during limb-bud chondrogenesis," *J. Embryol. Exp. Morph.*, 1980, 57:51-60 (Exhibit 344).

Dexter, T. M., "Stromal Cell Associated Haemopoiesis," *Journal of Cellular Physiology*, 1982, Supp 1:87-94 (Exhibit 345).

Dias, Peter et al., "Rapid Communication: Myogenic Regulatory Protein (MyoD1) Expr ession in Childhood Solid Tumors: Diagnostic Utility in Rhabdomyosarcoma," *American Journal of Pathology*, 1990, 137:1283-91 (Exhibit 346).

Dinsmore, Jonathan et al., "Embryonic Stem Cells Differentiated In Vi tro as a Novel Source of Cells for Transplantation," *Cell Transportation*, 1996, 5:131-43 (Exhibit 347).

D'Ippolito, Gianluca et al. , "Age-Related Osteogenic Potential of Mesenchymal Stromal Stem Cells from Human Vertebral Bone Marrow," *Journal of Bone and Mineral Research*, 1999, 14:1115-22 (Exhibit 348).

Doherty, Mary Jo et al., "Va scular Pericytes Express Osteogenic Potential In Vitro and In Vivo," *Journal of Bone and Mineral Research*, 1998, 13:828-38 (Exhibit 349).

Elmer, William A. et al., "Im munohistochemical Localization of Cyclic AMP During Normal and Abnormal Chick and Mouse Limb Development," *Tetratology*, 1981, 24:215-23 (Exhibit 350).

Emerson, Charles P., Jr., "S keletal myogenesis: genetics and embryology to the fore," *Current Opinion in Genetics and Development*, 1993, 3:265-74 (Exhibit 351).

Friedenstein, Alexander Jakovlevich et al., "Heterotopic Transplants of Bone Marrow," *Transplantation*, 1968, 6:230-47 (Exhibit 352).

Friedenstein, Alexander J. et al., "Stromal Cells Responsible for Transferring the Microenvironment of the Hemopoietic Tissues," *Transplantation*, 1974, 17:331-40 (Exhibit 353).

Gage, Fred H., "Mammalian Neural Stem Cells," *Science*, 2000, 287:1433-8 (Exhibit 354).

Gazit, Dan et al., "Bone Loss (Osteopenia) in Old Male Mice Results From Diminished Activity and Availability of TGF-β," *Journal of Cellular Biochemistry*, 1998, 70:478-88 (Exhibit 355).

Ghazavi, M. T. et al., "Fresh Osteochondral Allografts for Post-Traumatic Osteochondral Defects of the Knee," *Journal of Bone and Joint Surgery*, 1997, 79-B:1008-13 (Exhibit 356).

Goldberg, Burton, "Kinetics of processing of type I and type III procollagens in fibroblast cultures," *Biochemistry*, 1977, 74:3322-5 (Exhibit 357).

Goshima, Jun et al., "The Origin of Bone Formed in Composite Grafts of Porous Calcium Phosphate Ceramic Loaded with Marrow Cells," *Clinical Orthopaedics and Related Research*, 1991, 269:274-83 (Exhibit 358).

Goshima, Jun et al., "The Osteogenic Potential of Culture-Expanded Rat Marrow Mesenchymal Cells Assayed In Vivo in Calcium Phosphate Ceramic Blocks," *Clinical Orthopaedics and Related Research*, 1991, 262:298-311 (Exhibit 359).

Green, Howard and Mark Meuth, "An Established Pre-Adipose Cell Line and its Differentiation in Culture," *Cell*, 1974, 3:127-33 (Exhibit 360).

Grilli, Mariagrazia et al., "Neuroprotection by Aspirin and Sodium Salicylate Through Blockade of NF-κB Activation," *Science*, 1996, 274:1383-5 (Exhibit 361).

Gronthos, S. et al., "The STRO-1 $^+$Fraction of Adult Human Bone Marrow Contains the Osteogenic Precursors," *Blood*, 1994, 84:4164-73 (Exhibit 362).

Grounds, Miranda D. et al., "Identification of skeletal muscle precursor cells in vivo by use of MyoD1 and myogenin probes," *Cell & Tissue Research*, 1992, 267:99-104 (Exhibit 363).

Hauschka, Stepehen D., "Clonal Analysis of Vertebrate Myogenesis: III. Development Changes in the Muscle-Colony-Forming Cells of the Human Fetal Limb," *Developmental Biology*, 1974, 37:345-68 (Exhibit 364).

Haynesworth, S. E. et al., "Characterization of Cells with Osteogenic Potential from Human Marrow," *Bone*, 1992, 13:81-8 (Exhibit 365).

Henthorn, Paula S. et al., "Sequence and Characterization of the Human Intestinal Alkaline Phosphatase Gene," *Journal of Biological Chemistry*, 1988, 263:12011-9 (Exhibit 366).

Homminga, George N. et al., "Perichondral Grafting for Cartilage Lesions of the Knee," *Journal of Bone and Joint Surgery*, 1990, 72-B:1003-7 (Exhibit 367).

Iwasaki, Motoki et al., "Transforming Growth Factor-β1 Stimulates Chondrogenesis and Inhibits Osteogenesis in High Density Culture of Periosteum-Derived Cells," *Endocrinology*, 1993, 132:1603-8 (Exhibit 368).

Jabs, Ethylin Wang et al., "A Mutation in the Homeodomain of the Human *MSX2* Gene in a Family Affected with Autosomal Dominant Craniosynostosis," *Cell*, 1993, 75:443-50 (Exhibit 369).

Jackson, Kathyjo Ann et al., "Hematopoietic potential of stem cells isolated from murine skeletal muscle," *Proceeding of the National Academy of Sciences USA*, 1999, 96:14482-6 (Exhibit 370).

Jaffe, Eric A. et al., "Synthesis of Antihemophilic Factor Antigen by Cultured Human Endothelial Cells," *Journal of Clinical Investigation*, 1973, 52:2757-64 (Exhibit 371).

Johe, Karl K. et al., "Single factors direct the differentiation of stem cells from the fetal and adult central nervous system," *Genes & Development*, 1996, 10:3129-40 (Exhibit 372).

Johnson, Eric E. et al., "Repair of Segmental Defects of the Tibia with Cancellous Bone Grafts Augmented with Human Bone Morphogenetic Protein," *Clinical Orthopaedics and Related Research*, 1988, 236:249-57 (Exhibit 373).

Johnstone, Brian and Jung U. Yoo, "Autologous Mesenchymal Progenitor Cells in Articular Cartilage Repair," *Clinical Orthopaedics and Related Research*, 1999, 367S:S156-62 (Exhibit 374).

Jonasson, Lena et al., "Immunohistochemical Localization of Lipoprotein Lipase in Human Adipose Tissue," *Atherosclerosis*, 1984, 51:313-26 (Exhibit 375).

Karpati, George et al., "Rapid Communication: Dystrophin is Expressed in mdx Skeletal Muscle Fibers After Normal Myoblast Implantation," *American Journal of Pathology*, 1989, 135:27-32 (Exhibit 376).

Klein-Nulend, J. et al., "Stimulation of Cartilage Differentiation by Osteogenic Protein-1 in Cultures of Human Perichondrium," *Tissue Engineering*, 1998, 4:305-13 (Exhibit 377).

Kopen, Gene C. et al., "Marrow stromal cells migrate throughout forebrain and cerebellum, and they differentiate into astrocytes after injection into neonatal mouse brains," *Proceedings of the National Academy of Sciences USA*, 1999, 96:10711-6 (Exhibit 378).

Krebsbach, Paul H. et al., "Bone Formation In Vivo: Comparison of Osteogenesis by Transplanted Mouse and Human Marrow Stromal Fibroblasts," *Transplantation*, 1997, 63:1059-69 (Exhibit 379).

Krebsbach, Paul H. et al., "Repair of Craniotomy Defects Using Bone Marrow Stromal Cells," *Transplantation*, 1998, 66:1272-8 (Exhibit 380).

Kuri-Harcuch, Walid and Howard Green, "Increasing Activity of Enzymes on Pathway of Triacylglycerol Synthesis during Adipose Conversion of 3T3 Cells," *Journal of Biological Chemistry*, 1977, 252:2158-60 (Exhibit 381).

Lansdorp, Peter M. et al., "Age-Related Decline in Proliferative Potential of Purified Stem Cell Candidates," *Blood Cells*, 1994, 20:376-81 (Exhibit 382).

Lassar, Andrew and Andrea Münsterberg, "Wiring diagrams: regulatory circuits and the control of skeletal myogenesis," *Current Opinion in Cell Biology*, 1994, 6:432-42 (Exhibit 383).

Law, Peter K. et al., "Normal Myoblast Injections Provide Genetic Treatment for Murine Dystrophy," *Muscle & Nerve*, 1988, 11:525-33 (Exhibit 384).

Lazarides, Elias, "Intermediate Filaments: A Chemically Hetergeneous, Developmentally Regulated Class of Proteins," *Ann. Rev. Biochem.*, 1982, 51:219-50 (Exhibit 385).

Lennon, Donald P. et al., "A Chemically Defined Medium Supports *in Vitro* Proliferation and Maintains the Osteochondral Potential of Rat Marrow-Derived Mesenchymal Stem Cells," *Experimental Cell Research*, 1995, 219:211-22 (Exhibit 386).

Lévesque, Jean-Pierre et al., "Vascular cell adhesion molecule-1 (CD106) is cleaved by neutrophil proteases in the bone marrow following hematopoietic progenitor cell mobilization by granulocyte colony-stimulating factor," *Blood*, 2001, 98:1289-97 (Exhibit 387).

Lian, Jane B. and Ceren M. Gundberg, "Osteocalcin: Biochemical Considerations and Clinical Applications," *Clinical Orthopaedics and Related Research*, 1988, 226:267-91 (Exhibit 388).

Liau, Gene et al., "Coordinate Regulation of the Levels of Type III and Type I Collagen mRNA in Most but Not All Mouse Fibroblasts," *Journal of Biological Chemistry*, 1985, 260:531-6 (Exhibit 389).

Lieberman, Jay R. et al., "Regional Gene Therapy with a BMP-2-Producing Murine Stromal Cell Line Induces Heterotopic and Orthotopic Bone Formation in Rodents," *Journal of Orthopaedic Research*, 1998, 16:330-9 (Exhibit 390).

Linsenmayer, Thomas F. et al., "Temporal and Spatial Transitions in Collagen Types during Embryonic Chick Limb Development," *Developmental Biology*, 1973, 35:232-9 (Exhibit 391).

Löffler, G and H. Hauner, "Adipose Tissue Development: The Role of Precursor Cells and Adipogenic Factors," *Klinische Wochenschrift*, 1987, 65:812-7 (Exhibit 392).

Majumdar, Manas K. et al., "Phenotypic and Functional Comparison of Cultures of Marrow-Derived Mesenchymal Stem Cells (MSCs) and Stromal Cells," *Journal of Cellular Physiology*, 1998, 176:57-66 (Exhibit 393).

Maley, Moira A. L. et al., "Intrinsic Differences in MyoD and Myogenin Expression between Primary Cultures of SJL/J and BALB/C Skeletal Muscle," *Experimental Cell Research*, 1994, 211:99-107 (Exhibit 394).

Mizuno, Hiroshi et al., "Myogenic Differentiation by Human Processed Lipoaspirate Cells," *Plast. Reconstr. Surg.*, 2002, 109:199-209 (Exhibit 395).

Nakahara, Haruhiko et al., "*In Vitro* Differentiation of Bone and Hypertrophic Cartilage from Periosteal-Derived Cells," *Experimental Cell Research*, 1991, 195:492-503 (Exhibit 396).

Napolitano, Leonard, "The Differentiation of White Adipose Cells: An Electron Microscope Study," *Journal of Cell Biology*, 1963, 18:663-79 (Exhibit 397).

Narbaitz, R. et al., "Autoradiographic Localization of Target Cells for 1α, 25-Dihydroxyvitamin $D_3$ in Bones from Fetal Rats," *Calcified Tissue International*, 1983, 35:177-82 (Exhibit 398).

Nathanson, Mark A., "Bone Matrix-directed Chondrogenesis of Muscle in Vitro," *Clinical Orthopaedics and Related Research*, 1985, 200:142-58 (Exhibit 399).

Newberry, Elizabeth P. et al., "Reciprocal Regulation of Osteocalcin Transcription by the Homeodomain Proteins Msx2 and Dlx5," *Biochemistry*, 1998, 37:16360-8 (Exhibit 400).

Ohgushi, Hajime and Motoaki Okumura, "Osteogenic capacity of rat and human marrow cells in porous ceramics: Experiments in athymic (nude) mice," *Acta Orthopaedica Scandinavica*, 1990, 61:431-4 (Exhibit 401).

Oreffo, Richard O. C. et al., "Skeletal progenitor cells and ageing human populations," *Clinical Science*, 1998, 94:549-55 (Exhibit 402).

Osdoby, Philip and Arnold I. Caplan, "Osteogenesis in Cultures of Limb Mesenchymal Cells," *Developmental Biology*, 1979, 73:84-102 (Exhibit 403).

Otto, Florian et al., "*Cbfa1*, a Candidate Gene or Cleidocranial Dysplasia Syndrome, Is Essential for Osteoblast Differentiation and Bone Development," *Cell*, 1997, 89:765-71 (Exhibit 404).

Partridge, T. A. et al., "Evidence of fusion between host and donor myoblasts in skeletal muscle grafts," *Nature*, 1978, 273:306-8 (Exhibit 405).

Piper, David R. et al., "Immunocytochemical and Physiological Characterization of a Population of Cultured Human Neural Precursors," *J. Neurophysiol*, 2000, 84:534-48 (Exhibit 406).

Plitzko, Daniela et al., "Short Communication: Insulin promotes functional induction of silent synapses in differentiating rat neocortical neurons," *European Journal of Neuroscience*, 2001, 14:1412-5 (Exhibit 407).

Price, Paul A. et al., "Characterization of a γ-carboxyglutamic acid-containing protein from bone," *Proceedings of the National Academy of Sciences USA*, 1976, 73:1447-51 (Exhibit 408).

Quarto, Rodolfo et al., "Modulation of Commitment, Proliferation, and Differentiation of Chondrogenic Cells in Defined Culture Medium," *Endocrinology*, 1997, 138:4966-76 (Exhibit 409).

Reddi, A. H., "Regulation of Local Differentiation of Cartilage and Bone by Extracellular Matrix: A Cascade Type Mechanism," *Limb Development and Regeneration*, 1983, 110 Pt B:261-8 (Exhibit 410).

Riemann, Dagmar et al., "Induction of Aminopeptidase N/CD13 on Human Lumphocytes After Adhesion to Fibroblast-Like Synoviocytes, Endothelial Cells, Epithelial Cells, and Monocytes/Macrophages," *Journal of Immunology*, 1997, 158:3425-32 (Exhibit 411).

Ribera, Angeles B., "Potassium Currents in Developing Neurons," *Annals New York Academy of Sciences*, 1999, 30:399-405 (Exhibit 412).

Ribera, A. B. and N. C. Spitzer, "Developmental Regulation of Potassium Channels and the Impact on Neuronal Differentiation," *Ion Channels*, 1992, 3:1-38 (Exhibit 413).

Riederer, Beat and Andrew Matus, "Differential expression of distinct microtubule-associated proteins during brain development," *Proceedings of the National Academy of Sciences USA*, 1985, 82:6006-9 (Exhibit 414).

Robinson, John A. et al., "Estrogen Regulation of Human Osteoblastic Cell Proliferation and Differentiation," *Endocrinology*, 1997, 138:2919-27 (Exhibit 415).

Rodgers, Barbara J. et al., "Stimulation of limb cartilage differentiation by cyclic AMP is dependent on cell density," *Cell Differentiation and Development*, 1989, 28:179-87 (Exhibit 416).

Rohwedel, J. et al., "Muscle Cell Differentiation of Embryonic Stem Cells Reflects Myogenesis in Vivo: Developmentally Regulated Expression of Myogenic Determination Genes and Functional Expression of Ionic Currents," *Developmental Biology*, 1994, 164:87-101 (Exhibit 417).

Rokhlin, Oskar W. et al., "Differential Expression of Endoglin on Fetal and Adult Hematopoietic Cells in Human Bone Marrow," *Journal of Immunology*, 1995, 154:4456-65 (Exhibit 418).

Rosai, Juan et al., "MyoD1 Protein Expression in Alveolar Soft Part Sarcoma As Confirmatory Evidence of Its Skeletal Muscle Nature," *American Journal of Surgical Pathology*, 1991, 15:974-81 (Exhibit 419).

Rubin, Charles S. et al., "Development of Hormone Receptors and Hormonal Responsiveness in Vitro: Insulin Receptors and Insulin Sensitivity in the Preadipocyte and Adipocyte Forms of 3T3-L1 Cells," *Journal of Biological Chemistry*, 1978, 253:7570-8 (Exhibit 420).

Russell, Thomas R. and Ren-Jye Ho, "Conversion of 3T3 fibroblasts into adipose cells: Triggering of differentiation by prostoglandin $F_{2α}$1-methyl-3-isobutyl xanthine," *Proceedings of the National Academy of Sciences USA*, 1976, 73:4516-20 (Exhibit 421).

Ryoo, H. M. et al., "Stage-Specific Expression of Dlx-5 during Osteoblast Differentiation: Involvement in Regulation of Osteocalcin Gene Expression," *Molecular Endocrinology*, 1997, 11:1681-94 (Exhibit 422).

Saalbach, Anja et al., "Novel Fibroblast-Specific Monoclonal Antibodies: Properties and Specificities," *Journal of Investigative Dermatology*, 1996, 106:1314-9 (Exhibit 423).

Sampath, T. K. et al., "*In vitro* transformation of mesenchymal cells derived from embryonic muscle into cartilage in response to extracellular matrix components of bone," *Proceedings of the National Academy of Sciences USA*, 1984, 81:3419-23 (Exhibit 424).

Sassoon, David A., "Myogenic Regulatory Factors: Dissecting Their Role and Regulation during Vertebrate Embryogenesis," *Developmental Biology*, 1993, 156:11-23 (Exhibit 425).

Satoh, Akira et al., "Use of Fluorescent Latex Microspheres (FLMs) to Follow the Fate of Transplanted Myoblasts," *Journal of Histochemistry and Cytochemistry*, 1993, 41:1579-82 (Exhibit 426).

Schor, A. M. et al., "Pericytes derived from the retinal microvasculature undergo calcification in vitro," *Journal of Cell Science*, 1990, 97:449-61 (Exhibit 427).

Schultz, Edward and Bruce H. Lipton, "Skeletal Muscle Satellite Cells: Changes in Proliferation Potential as a Function of Age," *Mechanism of Ageing and Development*, 1982, 20:377-83 (Exhibit 428).

Schürch, Walter et al., "Intermediate Filament Proteins and Actin Isoforms as Markers for Soft Tissue Tumor Differentiation and Origin," *American Journal of Pathology*, 1987, 128:91-103 (Exhibit 429).

Scott, Robert E. et al., "Coupling of Proadipocyte Growth Arrest and Differentiation. II. A Cell Cycle Model for the Physiological Control of Cell Proliferation," *Journal of Cell Biology*, 1982, 94:400-5 (Exhibit 430).

Shalhoub, Victoria et al., "Glucocorticoids Promote Development of the Osteoblast Phenotype by Selectively Modulating Expression of Cell Growth and Differentiation Associated Genes," *Journal of Cellular Biochemistry*, 1992, 50:425-40 (Exhibit 431).

Skalli, Omar et al., "A Monoclonal Antibody against α-Smooth Muscle Actin: A New Probe for Smooth Muscle Differentiation," *Journal of Cell Biology*, 1986, 103:2787-96 (Exhibit 432).

Smyth, Miriam J. et al., "Proadipocyte cell lines: models of cellular proliferation and differentiation," *Journal of Cell Science*, 1993, 106:1-9 (Exhibit 433).

Solursh, Michael et al., "Stage- and Position-Related Changes in Chondrogenic Response of Chick Embryonic Wing Mesenchyme to Treatment with Dibutyryl Cyclic AMP," *Developmental Biology*, 1981, 83:9-19 (Exhibit 434).

Spiegelman, Bruce M. and Stephen R. Farmer, "Decreases in Tubulin and Actin Gene Expression prior to Morphological Differentiation of 3T3 Adipocytes," *Cell*, 1982, 29:53-60 (Exhibit 435).

Spiegelman, Bruce M. and Carol A. Ginty, "Fibronectin Modulation of Cell Shape and Lipogenic Gene Expression in 3T3-Adipocytes," *Cell*, 1983, 35:657-66 (Exhibit 436).

Stein, Gary S. et al., "The Onset and Progression of Osteoblast Differentiation is Functionally Related to Cellular Proliferation," *Connective Tissue Research*, 1989, 20:3-13 (Exhibit 437).

Stein, Gary S. et al., "Relationship of cell growth to the regulation of tissue-specific gene expression during osteoblast differentiation," *FASEB Journal*, 1990, 4:3111-23 (Exhibit 438).

Stott, N. Susan et al., "Successive Formative Stages of Precartilaginous Mesenchymal Condensation In Vitro: Modulation of Cell Adhesion by Wnt-7A and BMP-2," *Journal of Cellular Physiology*, 1999, 180:314-24 (Exhibit 439).

Swalla, Billie J. and Michael Solursh, "The Independence of Myogenesis and Chondrogenesis in Micromass Cultures of Chick Wing Buds," *Developmental Biology*, 1986, 116:31-8 (Exhibit 440).

Minas, Tom and Stefan Nehrer, "Current Concepts in the Treatment of Articular Cartilage Defects," *Orthopaedics*, 1997, 20:525-38 (Exhibit 441).

Tanner, J. William et al., "Cellular mechanism of the insulin-like effect of growth hormone in adipocytes," *Biochem. J.*, 1992, 282:99-106 (Exhibit 442).

Tavella, Sara et al., "*N*-CAM and *N*-Cadherin Expression during *in Vitro* Chondrogenesis," *Experimental Cell Research*, 1994, 215:354-62 (Exhibit 443).

Tenenbaum, Howard C. and Johan N. M. Heersche, "Dexamethasone Stimulates Osteogenesis in Chick Periosteum *in Vitro*," *Endocrinology*, 1985, 117:2211-7 (Exhibit 444).

Toma, Jean G. et al., "Isolation of multipotent adult stem cells from the dermis of mammalian skin," *Nature Cell Biology*, 2001, 3:778-84 (Exhibit 445).

Tontonoz, Peter et al., "Stimulation of Adipogenesis in Fibroblasts by PPARγ2, a Lipid-Activated Transcription Factor," *Cell*, 1994, 79:1147-56 (Exhibit 446).

Tropepe, Vincent et al., "Retinal Stem Cells in the Adult Mammalian Eye," *Science*, 2000, 287:2032-6 (Exhibit 447).

Vandenburgh, Herman H., "Cell Shape and Growth Regulation in Skeletal Muscle: Exogenous Versus Endogenous Factors," *Journal of Cellular Physiology*, 1983, 116:363-71 (Exhibit 448).

Vandenburgh, Herman H. and Seymour Kaufman, "Stretch-induced Growth of Skeletal Myotubes Correlates With Activation of the Sodium Pump," *Journal of Cellular Physiology*, 1981, 109:205-14 (Exhibit 449).

Vandenburgh, Herman H. et al., "Maintenance of Highly Contractile Tissue-Cultured Avian Skeletal Myotubes in Collagen Gel," *In Vitro Cellular & Development Biology*, 1988, 24:166-74 (Exhibit 450).

Vescovi, Angelo L. et al., "Isolation and Cloning of Multipotential Stem Cells from the Embryonic Human CNS and Establishment of Transplantable Human Neural Stem Cell Lines by Epigenetic Stimulation," *Experimental Neurology*, 1999, 156:71-83 (Exhibit 451).

Wan, Q. et al., "Recruitment of functional $GABA_A$ receptors to postsynaptic domains by insulin," *Nature*, 1997, 388:686-90 (Exhibit 452).

Wang, Elizabeth A. et al., "Recombinant human bone morphogenetic protein induces bone formation," *Proceedings of the National Academy of Sciences USA*, 1990, 87:2220-4 (Exhibit 453).

Weiss, Mitchell J. et al., "Structure of the Human Liver/Bone/Kidney Alkaline Phosphatase Gene," *Journal of Biological Chemistry*, 1988, 263:12002-10 (Exhibit 454).

Werts, E. D. et al., "Characterization of Marrow Stromal (Fibroblastoid) Cells and Their Association with Erythropoiesis," *Exp. Hemat.*, 1980, 8:423-33 (Exhibit 455).

Westin, Stefan et al., "Interactions controlling the assembly of nuclear-receptor heterodimers and co-activators," *Nature*, 1998, 395:199-202 (Exhibit 456).

Yandava, Booma D. et al., ""Global" cell replacement is feasible via neural stem cell transplantation: Evidence from the dysmyelinated *shiverer* mouse brain," *Proceedings of the National Academy of Sciences USA*, 1999, 96:7029-34 (Exhibit 457).

Yoshida, Mika, "Intermediate Filament Proteins Define Different Glial Subpopulations," *Journal of Neuroscience Research*, 2001, 63:284-9 (Exhibit 458).

Young, Henry E. et al., "Bioactive factors affect proliferation and phenotypic expression in progenitor and pluripotent stem cells," *Wound Repair and Regeneration*, 1998, 6:65-75 (Exhibit 459).

Lanier, Lewis L. et al., "Identity Of Leu-19 (CD56) Leukocyte Differentiation Antigen and Neural Cell Adhesion Molecule," *Journal of Experimental Medicine*, 1989, 169:2233-8 (Exhibit 460).

Hausman, G. J. et al., "Newly Recruited and Pre-Existing Preadipocytes in Cultures of Porcine Stromal-Vascular Cells: Morphology, Expression of Extracellular Matrix Components, and Lipid Accretion," *Journal of Animal Science*, 1998, 76:48-60 (Exhibit 466).

Keating, Armand et al., "Effect of Different Promoters on Expression of Genes Introduced into Hematopoietic and Marrow Stromal Cells by Electroporation," *Experimental Hematology*, 1990, 18:99-102 (Exhibit 467).

Lau, D. C. W. et al., "Paracrine interactions in adipose tissue development and growth," *International Journal of Obesity*, 1996, 20(Supp.3):S16-25 (Exhibit 468).

Petruschke, Th. et al., "Transforming growth factor beta (TGF-β) inhibits the differentiation of human adipocyte precursor cells in primary culture," *International Journal of Obesity*, 1994, 18:532-6 (Exhibit 469).

Su, Hui-Ling et al., "Increased expression of $g_{i\alpha\ 2}$ in mouse embryo stem cells promotes terminal differentiation to adipocytes," *American Journal of Physiology*, 1993, 265:C1729-35 (Exhibit 470).

Winter, Anja et al., "Cartilage-Like Gene Expression in Differentiated Human Stem Cell Spheroids," *Arthritis & Rheumatism*, 2003, 48:418-29 (Exhibit 471).

Gregoire, Francine M. et al. "Understanding Adipocyte Differentiation," *Physiological Reviews*, 1998, 78:783-809 (Exhibit 483).

Feb. 13, 2007 Order Denying in Part and Granting in Part Plaintiff's and Defendants' Motions for Construction of the Claims (Exhibit 484).

Aug. 8, 2007 Order Granting in Part and Denying in Part Plaintiffs' Motion for Summary Judgement that Drs. Katz and Llull are Properly Named Inventors on the '231 Patent and that Drs. Benhaim, Lorenz and Zhu are Not Proper Inventors and Denying Defendants' Motion for Summary Judgement that Drs. Katz and Llull are Not the Sole Inventors of U.S. Patent 6,777,231 (Exhibit 485).

* cited by examiner

A.

B.

C.

A. FS vs. SS

B. Cell-specific markers

C. PLA composition

A.

B.

A.

B.

| Induction Time | | 1 WEEK | 3 WEEK | 6 WEEK |
|---|---|---|---|---|
| | Cell Type/Media | | | |
| Myosin-positive cells (% total PLA cells ±SEM) | PLA/MM | not observed | 3.88 ± 0.46% | 8.42 ± 0.71% |
| | PLA/CM | not observed | not observed | not observed |
| | HFF/CM | not observed | not observed | not observed |

\* $P < 0.0001$, $F = 75.5$
one-way ANOVA comparing experimental (myosin) values from 1, 3 and 6 week differentiation.

B.

A.

B.

A.

SEQUENCE LISTING

<160> NUMBER OF SEQ ID NOS: 58

<210> SEQ ID NO 1
<211> LENGTH: 20
<212> TYPE: DNA
<213> ORGANISM: Artificial Sequence

```
<220> FEATURE:
<223> OTHER INFORMATION: Description of Artificial Sequence: human type
      I collagen alpha1 chain forward primer

<400> SEQUENCE: 1
catctcccct tcgtttttga                                              20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: human type
      I collagen alpha1 chain reverse primer

<400> SEQUENCE: 2
ctgtggagga gggtttcaga                                              20

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: human type
      I collagen alpha1 chain forward primer

<400> SEQUENCE: 3
ctgctcgtcg ccgctgtcct t                                            21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: human type
      I collagen alpha1 chain reverse primer

<400> SEQUENCE: 4
aagggtccca ggttctccat c                                            21

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: human type
      X collagen alpha1 chain forward primer

<400> SEQUENCE: 5
tggagtggga aaaagaggtg                                              20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: human type
      X collagen alpha1 chain reverse primer

<400> SEQUENCE: 6
gtcctccaac tccaggatca                                              20

<210> SEQ ID NO 7
<211> LENGTH: 22
<212> TYPE: DNA
<213> ORGANISM: Artificial Sequence
<220> FEATURE:
```

```
<223> OTHER INFORMATION: Description of Artificial Sequence: human large
      aggregating proteoglycan forward primer

<400> SEQUENCE: 7
gcagagacgc atctagaaat tg                                                    22

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: human large
      aggregating proteoglycan reverse primer

<400> SEQUENCE: 8
ggtaattgca gggaacatca tt                                                    22

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: human
      osteocalcin forward primer

<400> SEQUENCE: 9
gctctagaat ggccctcaca ctc                                                   23

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: human
      osteocalcin reverse primer

<400> SEQUENCE: 10
gcgatatcct agaccgggcc gtag                                                  24

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: MyoD1
      forward primer

<400> SEQUENCE: 11
aagcgccatc tcttgaggta                                                       20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: MyoD1
      reverse primer

<400> SEQUENCE: 12
gcgcctttat tttgatcacc                                                       20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Myosin
```

-continued heavy chain forward primer

<400> SEQUENCE: 13
tgtgaatgcc aaatgtgctt                                               20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Myosin
      heavy chain reverse primer

<400> SEQUENCE: 14
gtggagctgg gtatccttga                                               20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Osteonectin
      forward primer

<400> SEQUENCE: 15
tgtgggagct aatcctgtcc                                               20

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Osteonectin
      reverse primer

<400> SEQUENCE: 16
tcaggacgtt cttgagccag t                                             21

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Osteopontin
      forward primer

<400> SEQUENCE: 17
gctctagaat gagaattgca ctg                                           23

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Osteopontin
      reverse primer

<400> SEQUENCE: 18
gtcaatggag tcctggctgt                                               20

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence: Bone
      sialoprotein forward primer

<400> SEQUENCE: 19
gctctagaat gaagactgct ttaatt                                        26

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Bone
      sialoprotein reverse primer

<400> SEQUENCE: 20
actgccctga actggaaatc                                               20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Core
      binding factor alpha-1 forward primer

<400> SEQUENCE: 21
ctcactacca cacctacctg                                               20

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Core
      binding factor alpha-1 reverse primer

<400> SEQUENCE: 22
tcaatatggt cgccaaacag attc                                          24

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Collagen I
      forward primer

<400> SEQUENCE: 23
gagagagagg cttccctggt                                               20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Collagen I
      reverse primer

<400> SEQUENCE: 24
caccacgatc accactcttg                                               20

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Alkaline
      phosphotase forward primer

```
<400> SEQUENCE: 25
tgaaatatgc cctggagc                                                18

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence: Alkaline
      phosphotase reverse primer

<400> SEQUENCE: 26
tcacgttgtt cctgtttag                                               19

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: aP2 forward
      primer

<400> SEQUENCE: 27
tggttgattt tccatcccat                                              20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: aP2 reverse
      primer

<400> SEQUENCE: 28
tactgggcca ggaatttgat                                              20

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: LPL forward
      primer

<400> SEQUENCE: 29
gagatttctc tgtatggcac c                                            21

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: LPL reverse
      primer

<400> SEQUENCE: 30
ctgcaaatga gacactttct c                                            21

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: PPAR gamma
      1 forward primer

<400> SEQUENCE: 31
```
gctctagaat gaccatggtt gac                                              23

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: PPAR gamma
      1 reverse primer

<400> SEQUENCE: 32
ataaggtgga gatgcaggct c                                                21

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: PPAR gamma
      2 forward primer

<400> SEQUENCE: 33
gctgttatgg gtgaaactct g                                                21

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: PPAR gamma
      2 reverse primer

<400> SEQUENCE: 34
ataaggtgga gatgcaggtt c                                                21

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: PPAR delta
      forward primer

<400> SEQUENCE: 35
gccaacggca gtggctttgt c                                                21

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: PPAR delta
      reverse primer

<400> SEQUENCE: 36
ttagtacatg tccttgtaga tctc                                             24

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Collagen II
      forward primer

<400> SEQUENCE: 37

```
atgattcgcc tcggggctcc                                              20
```

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Collagen II
      reverse primer

<400> SEQUENCE: 38

```
tcccaggttc tccatctctg                                              20
```

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Aggrecan
      forward primer

<400> SEQUENCE: 39

```
gcagagacgc atctagaaat t                                            21
```

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Aggrecan
      reverse primer

<400> SEQUENCE: 40

```
ggtaattgca gggaacatca t                                            21
```

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Decorin
      forward primer

<400> SEQUENCE: 41

```
cctttggtga agttggaacg                                              20
```

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Decorin
      reverse primer

<400> SEQUENCE: 42

```
aagatgtaat tccgtaaggg                                              20
```

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Biglycan
      forward primer

<400> SEQUENCE: 43

```
tgcagaacaa cgacatctcc                                              20
```

```
<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Biglycan
      reverse primer

<400> SEQUENCE: 44
agcttggagt agcgaagcag                                              20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Myf5
      forward primer

<400> SEQUENCE: 45
ccacctccaa ctgctctgat                                              20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Myf5
      reverse primer

<400> SEQUENCE: 46
ggagttcgag gctgtgaatc                                              20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Myogenin
      forward primer

<400> SEQUENCE: 47
tgggcgtgta aggtgtgtaa                                              20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Myogenin
      reverse primer

<400> SEQUENCE: 48
ttgagcaggg tgcttctctt                                              20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: CHaT
      forward primer

<400> SEQUENCE: 49
tacaggctcc accgaagact                                              20
```

```
<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: CHaT
      reverse primer

<400> SEQUENCE: 50
agcagaacat ctccgtggtt                                              20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence:
      Synaptophysin forward primer

<400> SEQUENCE: 51
ttcaggctgc accaagtgta                                              20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence:
      Synaptophysin reverse primer

<400> SEQUENCE: 52
cagggtctct cagctccttg                                              20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Glial
      Fibrillary Acidic Protein forward primer

<400> SEQUENCE: 53
aatgctggct tcaaggagac                                              20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Glial
      Fibrillary Acidic Protein reverse primer

<400> SEQUENCE: 54
ccagcgactc aatcttcctc                                              20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: GAD65
      forward primer

<400> SEQUENCE: 55
tggcgatggg atattttctc                                              20
```

-continued

```
<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: GAD65
      reverse primer

<400> SEQUENCE: 56
gcactcacga ggaaaggaac                                                   20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Nestin
      forward primer

<400> SEQUENCE: 57
ggagtcgttt cagatgtggg                                                   20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Nestin
      reverse primer

<400> SEQUENCE: 58
agctcttcag ccaggttgtc                                                   20
```

ADIPOSE-DERIVED STEM CELLS AND LATTICES

This application is a continuation of U.S. Ser. No. 09/952,522, filed Sep. 10, 2001 now abandoned, which is a continuation-in-part of U.S. Ser. No. 09/936,665, filed Sep. 10, 2001 now U.S. Pat. No. 6,777,231, which corresponds to PCT 371 Application No. PCT/US00/06232, filed Mar. 10, 2000, which claims the priority of U.S. Ser. No. 60/123,711, filed Mar. 10, 1999 and U.S. Ser. No. 60/162,462, filed Oct. 29, 1999, the contents of all of which are incorporated by reference into the present application.

Throughout this application, various publications are referenced. The disclosures of these publications are hereby incorporated by reference herein in their entireties.

BACKGROUND OF THE INVENTION

In recent years, the identification of mesenchymal stem cells, chiefly obtained from bone marrow, has led to advances in tissue regrowth and differentiation. Such cells are pluripotent cells found in bone marrow and periosteum, and they are capable of differentiating into various mesenchymal or connective tissues. For example, such bone-marrow derived stem cells can be induced to develop into myocytes upon exposure to agents such as 5-azacytidine (Wakitani et al., *Muscle Nerve*, 18(12), 1417-26 (1995)). It has been suggested that such cells are useful for repair of tissues such as cartilage, fat, and bone (see, e.g., U.S. Pat. Nos. 5,908,784, 5,906,934, 5,827,740, 5,827,735), and that they also have applications through genetic modification (see, e.g., U.S. Pat. No. 5,591,625). While the identification of such cells has led to advances in tissue regrowth and differentiation, the use of such cells is hampered by several technical hurdles. One drawback to the use of such cells is that they are very rare (representing as few as 1/2,000,000 cells), making any process for obtaining and isolating them difficult and costly. Of course, bone marrow harvest is universally painful to the donor. Moreover, such cells are difficult to culture without inducing differentiation, unless specifically screened sera lots are used, adding further cost and labor to the use of such stem cells. U.S. Pat. No. 6,200,606 by Peterson et al., describes the isolation of CD34+ bone or cartilage precursor cells (of mesodermal origin) from tissues, including adipose.

There remains a need for a more readily available source for large numbers of stem cells, particularly cells that can differentiate into multiple lineages of different germ layers, and that can be cultured without the requirement for costly prescreening of culture materials.

Other advances in tissue engineering have shown that cells can be grown in specially-defined cultures to produce three-dimensional structures. Spacial definition typically is achieved by using various acellular lattices or matrices to support and guide cell growth and differentiation. While this technique is still in its infancy, experiments in animal models have demonstrated that it is possible to employ various acellular lattice materials to regenerate whole tissues (see, e.g., Probst et al. *BJU Int.*, 85(3), 362-7 (2000)). A suitable lattice material is secreted extracellular matrix material isolated from tumor cell lines (e.g., Engelbreth-Holm-Swarm tumor secreted matrix—"matrigel"). This material contains type IV collagen and growth factors, and provides an excellent substrate for cell growth (see, e.g., Vukicevic et al., *Exp. Cell Res*, 202(1), 1-8 (1992)). However, as this material also facilitates the malignant transformation of some cells (see, e.g., Fridman, et al., *Int. J. Cancer*, 51(5), 740-44 (1992)), it is not suitable for clinical application. While other artificial lattices have been developed, these can prove toxic either to cells or to patients when used in vivo. Accordingly, there remains a need for a lattice material suitable for use as a substrate in culturing and growing populations of cells.

SUMMARY OF THE INVENTION

The present invention provides adipose-derived stem cells, adipose-derived stem cell fractions, lattices, and method for obtaining the cells, fractions, and lattices. In one aspect, the present invention provides an adipose-derived stem cell fraction substantially free of adipocytes and red blood cells and populations of connective tissue cells. The present invention also provides stem cells, isolated from the fraction, where the stem cells are pluripotent The pluripotent stem cells have the ability to differentiate into mesoderm, ectoderm, or endoderm. The cells can be employed, alone or within biologically-compatible compositions, to generate differentiated tissues and structures, both in vivo and in vitro. Additionally, the cells can be expanded and cultured to produce growth factors and to provide conditioned culture media for supporting the growth and expansion of other cell populations. In another aspect, the present invention provides a adipose-derived lattice substantially devoid of cells, which includes extacellular matrix material from adipose tissue. The lattice can be used as a substrate to facilitate the growth and differentiation of cells, whether in vivo or in-vitro, into anlagen or even mature tissues or structures.

Adipose tissue is plentiful and represent a ready source of the stem cells, fractions, and lattices. Moreover, the stem cells can be passaged in culture in an undifferentiated state under culture conditions not requiring prescreened lots of serum; the inventive cells can be maintained with considerably less expense than other types of stem cells. These and other advantages of the present invention, as well as additional inventive features, will be apparent from the accompanying drawings and in the following detailed description.

DETAILED DESCRIPTION OF THE INVENTION

Definitions

Figure 1:
FIG. 1. Morphology; growth kinetics and senescence of adipose-derived stem cells over long-term culture. Panel A: The morphology of adipose-derived stem cells (e.g., a processed lipoaspirate or PLA) obtained from liposuctioned adipose tissue. Panel B: adipose-derived stem cells (PLAs) obtained from 3 donors, were cultured for an extended period and cumulative population doubling was measured and expressed as a function of passage number. Panel C: Senescence in adipose-derived stem cells (PLA) cultures as detected by staining for β-galactosidase expression at pH 6.0. Representative senescent cells are shown (arrows).
Figure 1:
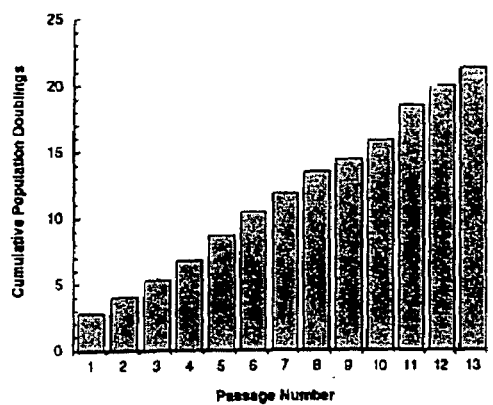
Figure 1:
Figure 1:
Figure 1:
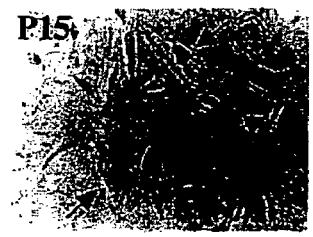

As used herein, "stem cell" defines an adult undifferentiated cell that can produce itself and a further differentiated progeny cell.

As used herein, the "lineage" of a cell defines the heredity of the cell, i.e.; which cells it came from and what cells it can give rise to. The lineage of a cell places the cell within a hereditary scheme of development and differentiation.

As used herein, the term "differentiates or differentiated" defines a cell that takes on a more committed ("differentiated") position within the lineage of a cell. "Dedifferentiated" defines a cell that reverts to a less committed position within the lineage of a cell.

As used herein, "a cell that differentiates into a mesodermal (or ectodermal or endodermal) lineage" defines a cell that becomes committed to a specific mesodermal, ectodermal or endodermal lineage, respectively. Examples of cells that differentiate into a mesodermal lineage or give rise to specific mesodermal cells include, but are not limited to, cells that are adipogenic, chondrogenic, cardiogenic, dermatogenic, hematopoetic, hemangiogenic, myogenic, nephrogenic, urogenitogenic, osteogenic, pericardiogenic, or stromal.

Examples of cells that differentiate into ectodermal lineage include, but are not limited to epidermal cells, neurogenic cells, and neurogliagenic cells.

Examples of cells that differentiate into endodermal lineage include, but are not limited to pleurigenic cells, and hepatogenic cells, cell that give rise to the lining of the intestine, and cells that give rise to pancreogenic and splanchogenic cells.

As used herein, a "pluripotent cell" defines a less differentiated cell that can give rise to at least two distinct (genotypically and/or phenotypically) further differentiated progeny cells.

A "multi-lineage stem cell" or "multipotent stem cell" refers to a stem cell that reproduces itself and at least two further differentiated progeny cells from distinct developmental lineages. The lineages can be from the same germ layer (i.e. mesoderm, ectoderm or endoderm), or from different germ layers. An example of two progeny cells with distinct developmental lineages from differentiation of a multi-lineage stem cell is a myogenic cell and an adipogenic cell (both are of mesodermal origin, yet give rise to different tissues). Another example is a neurogenic cell (of ectodermal origin) and adipogenic cell (of mesodermal origin).

As used here, "adipose tissue" defines a diffuse organ of primary metabolic importance made-up of white fat, yellow fat or brown fat. The adipose tissue has adipocytes and stroma. Adipose tissue is found throughout the body of an animal. For example, in mammals, adipose tissue is present in the omentum, bone marrow, subcutaneous space and surrounding most organs.

As used herein "conditioned media" defines a medium in which a specific cell or population of cells have been cultured in, and then removed. While the cells were cultured in said medium, they secrete cellular factors that include, but are not limited to hormones, cytokines, extracellular matrix (ECM) proteins, vesicles, antibodies, and granules. The medium plus the cellular factors is the conditioned medium.

As used herein "isolated" defines a substance, for example an adipose-derived stem cell, that is separated from contaminants (i.e. substances that differ from the stem cell).

The present invention provides adipose-derived stem cells (ADSCs) and methods for obtaining them from a mesodermal origin (e.g., adipose tissue) and using them. Surprisingly, the inventive ADSCs can differentiate into cells that give rise to more than one type of germ layer, e.g. mesoderm, endoderm or ectoderm, and combinations thereof, and are thus "multi-lineage" or "multipotent" cells.

In another embodiment, the ADSCs can differentiate into two or more distinct lineages from different germ layers (such as endodermal and mesodermal), for example hepatocytes and adipocytes.

The ADSCs of the invention can differentiate into cells of two or more lineages, for example adipogenic, chondrogenic, cardiogenic, dermatogenic, hematopoetic, hemangiogenic, myogenic, nephrogenic, neurogenic, neuralgiagenic, urogenitogenic, osteogenic, pericardiogenic, peritoneogenic, pleurogenic, splanchogenic, and stromal developmental phenotypes. While such cells can retain two or more of these different linages (or developmental phenotypes), preferably, such ADSCs can differentiate into three or more different lineages. The most preferred ADSCs can differentiate into four or more lineages.

The ADSCs of the invention have the capacity to differentiate into mesodermal tissues, such as mature adipose tissue, bone, various tissues of the heart (e.g., pericardium, epicardium, epimyocardium, myocardium, pericardium, valve tissue, etc.), dermal connective tissue, hemangial tissues (e.g., corpuscles, endocardium, vascular epithelium, etc.), hematopeotic tissue, muscle tissues (including skeletal muscles, cardiac muscles, smooth muscles, etc.), urogenital tissues (e.g., kidney, pronephros, meta- and meso-nephric ducts, metanephric diverticulum, ureters, renal pelvis, collecting tubules, epithelium of the female reproductive structures (particularly the oviducts, uterus, and vagina), mesodermal glandular tissues (e.g., adrenal cortex tissues), and stromal tissues (e.g., bone marrow). Of course, inasmuch as the ADSC can retain potential to develop into a mature cell, it also can realize its developmental phenotypic potential by differentiating into an appropriate precursor cell (e.g., a preadipocyte, a premyocyte, a preosteocyte, etc.).

In another embodiment, the ADSCs have the capacity to differentiate into ectodermal tissues, such as neurogenic tissue, and neurogliagenic tissue.

In another embodiment, the ADSCs have the capacity to differentiate into endodermal tissues, such as pleurogenic tissue, and splanchnogenic tissue, and hepatogenic tissue, and pancreogenic tissue.

In yet another embodiment, ADSCs have the capacity to dedifferentiate into developmentally immature cell types. Examples of ADSCs dedifferentiating into an immature cell type, include embryonic cells and fetal cells.

In another embodiment, the inventive ADSCs can give rise to one or more cell lineages from one or more germ layers such as neurogenic cells (of ectodermal origin) and myogenic cells (of mesodermal origin).

The inventive ADSCs are useful for tissue engineering, wound repair, in vivo and ex vivo tissue regeneration, tissue transplantation, and other methods that require cells that can differentiate into a variety of phenotypes and genotypes, or can support other cell types in vivo or in vitro.

One aspect of the invention pertains to an adipose-derived stem cell-enriched fraction (ADSC-EF) that contains adipose-derived stem cells (ADSCs) of the invention. Preferably, the ADSC-EF is substantially free of other cell types (e.g., adipocytes, red blood cells, and other stromal cells, etc.) and extracellular matrix material. More preferably, the ADSC-EF is completely free of such other cell types and matrix material. The ADSC-EF is obtained from adipose tissue of a mammal. The preferred embodiment includes an ADSC-EF obtained from adipose tissue of a higher primate (e.g., a baboon or ape). The most preferred ADSC enriched fraction is obtained from human adipose tissue, using the methods described herein.

Methods of Obtaining ADSC-EF and ADSCs of the Invention

The ADSCs of the invention are isolated from adipose tissue. The adipose tissue can be obtained from an animal by any suitable method. A first step in any such method requires the isolation of the adipose tissue from the source animal. The animal can be alive or dead, so long as adipose stromal cells within the animal are viable. Typically, human adipose tissue is obtained from a living donor, using well-recognized protocols such as surgical or suction lipectomy. The preferred method to obtain human adipose tissue is by excision or liposuction procedures well known in the art Preferably, the inventive ADSCs are isolated from a liposuction aspirate. The ADSCs of the invention are present in the initially excised or extracted adipose tissue, regardless of the method by which the adipose tissue is obtained.

Three deposits of lipoaspirates, each from a different patient, identified as 1', 2', 3', have been deposited on Sep. 7, 2001, with the American Type Culture Collection (ATCC), 10801 University Blvd., Manassas, Va. 20110-2209, under the provisions of the Budapest Treaty, and have been accorded ATCC deposit numbers PTA-3692, PTA-3693, and PTA-3694.

However obtained, the adipose tissue is processed to separate the ADSCs of the invention from the remainder of the adipose tissue. The ADSC-EF that contains the ADSCs is obtained by washing the obtained adipose tissue with a physiologically-compatible solution, such as phosphate buffer saline (PBS). The washing step consists of rinsing the adipose tissue with PBS, agitating the tissue, and allowing the tissue to settle. In addition to washing, the adipose tissue is dissociated. The dissociation can occur by enzyme degradation and neutralization. Alternatively, or in conjunction with such enzymatic treatment, other dissociation methods can be used such as mechanical agitation, sonic energy, or thermal energy. Three layers form after the washing, dissociation, and settling steps. The top layer is a free lipid layer. The middle layer includes the lattice and adipocyte aggregates. The middle layer is referred to as an "adipose-derived lattice enriched fraction." The middle layer or the lattice-enriched fraction is filtered to concentrate the lattice of the invention. A method of filtration involves passing the middle layer through a large pore filter. The material which does not pass through the filter includes the inventive lattice and aggregates of adipocytes. The adipose-derived lattice can be manually separated from the other cells which did not pass through the filter.

The bottom layer contains the ADSC-EF and the inventive ADSCs. The bottom layer is further processed to isolate the ADSCs of the invention. The cellular fraction of the bottom layer is concentrated into a pellet One method to concentrate the cells includes centrifugation.

The bottom layer is centrifuged and the pellet is retained. The pellet is designated the adipose-derived stem cell-enriched fraction (ADSC-EF) which includes the adipose-derived stem cell-enriched fraction (ADSC-EF). The ADSC-EF may contain erythrocytes (RBCs). In a preferred method the RBCs are lysed and removed. Methods for lysis and removed RBCs are well known in the art (e.g., incubation in hypotonic medium). If the RBCs are removed, then the RBC-free fraction contains the ADSC-EF fraction and the ADSCs. However, the RBCs are not required to be removed from the ADSC-EF.

The pellet is resuspended and can be washed (in PBS), centrifuged, and resuspended one or more successive times to achieve greater purity of the ADSCs. The ADSC-EF of the invention maybe a heterogenous population of cells which include the ADSCs of the invention and adipocytes. The cells of the washed and resuspended pellet are ready for plating.

The ADSCs in the resuspended pellet can be separated from other cells of the resuspended pellet by methods that include, but are not limited to, cell sorting, size fractionation, granularity, density, molecularly, morphologically, and immunohistologically.

In one embodiment, the ADSCs are separated from the other cells on the basis of cell size and granularity where ADSCs are small and agranular. Alternatively, a molecular method for separating the ADSCs from the other cells of the pellet is by assaying the length of the telomere. Stem cells tend to have longer telomeres than differentiated cells.

In another embodiment, a biochemical method for separating the ADSCs from the other cells of the pellet is used by assaying telomerase activity. Telomerase activity can serve as a stem cell-specific marker.

In still another embodiment, the ADSCs are separated from the other cells of the pellet immunohistochemically, for example, by panning, using magnetic beads, or affinity chromatography.

Alternatively, the process of isolating the ADSC enriched fraction with the ADSCs is with a suitable device, many of which are known in the art (see, e.g., U.S. Pat. No. 5,786,207). Such devices can mechanically achieve the washing and dissociation steps.

Culturing ADSCs

The ADSCs in the ADSC-EF can be cultured and, if desired, assayed for number and viability, to assess the yield.

In one embodiment, the stem cells are cultured without differentiation using standard cell culture media (e.g., DMEM, typically supplemented with 5-15% (e.g., 10%) serum (e.g., fetal bovine serum, horse serum, etc.). Preferably, the stem cells are passaged at least five times in such medium without differentiating, while still retaining their developmental phenotype, and more preferably, the stem cells are passaged at least 10 times (e.g., at least 15 times or even at least 20 times) while retaining multipotency. Thus, culturing the ADSCs, without inducing differentiation, can be accomplished without specially screened lots of serum. In contrast, mesenchymal stem cells (e.g., derived from bone marrow) would differentiate under the same culturing conditions described above. Methods for measuring viability and yield are known in the art and can be employed (e.g., trypan blue exclusion).

The ADSCs can be separated by phenotypic identification, to identify those cells that have two or more of the aforementioned developmental lineages. To phenotypically separate the ADSCs from the ADSC-EF, the cells are plated at a desired density, such as between about 100 cells/cm² to about 100,000 cells/cm² (such as about 500 cells/cm² to about 50,000 cells/cm², or, more particularly, between about 1,000 cells/cm² to about 20,000 cells/cm²).

In a preferred embodiment the ADSC-EF is plated at a lower density (e.g., about 300 cells/cm²) to facilitate the clonal isolation of the ADSCs. For example, after a few days, ADSCs plated at such densities will proliferate (expand) into a clonal population of ADSCs.

Such ADSCs can be used to clone and expand a multipotent ADSC into clonal populations, using a suitable method for cloning cell populations. The cloning and expanding methods include cultures of cells, or small aggregates of cells, physically picking and seeding into a separate plate (such as the well of a multi-well plate). Alternatively, the stem cells can be subcloned onto a multi-well plate at a statistical ratio for facilitating placing a single cell into each well (e.g., from about 0.1 to about 1 cell/well or even about 0.25 to about 0.5 cells/well, such as 0.5 cells/well). The ADSCs can be cloned by plating them at low density (e.g., in a petri-dish or other suitable substrate) and isolating them from other cells using devices such as a cloning rings. Alternatively, where an irradiation source is available, clones can be obtained by permitting the cells to grow into a monolayer and then shielding one and irradiating the rest of cells within the monolayer. The surviving cell then will grow into a clonal population. While production of a clonal population can be expanded in any suitable culture medium, a preferred culture condition for cloning stem cells (such as the inventive stem cells or other stem cells) is about ⅔ $F_{12}$ medium+20% serum (preferably fetal bovine serum) and about ⅓ standard medium that haw been conditioned with stromal cells (e.g., cells from the stromal vascular fraction of liposuction aspirate), the relative proportions being determined volumetrically).

In any event, whether clonal or not, the isolated ADSCs can be cultured in a specific inducing medium to induce the ADSC to differentiate and express its multipotency. The ADSCs give rise to cells of mesodermal, ectodermal and endodermal lineage, and combinations thereof. Thus, one or more ADSCs derived from a multipotent ADSC can be treated to differentiate into a variety of cell types.

In another embodiment, the ADSCs are cultured in a defined medium for inducing adipogenic differentiation Examples of specific media that induce the ADSCs of the invention to take on a adipogenic phenotype include, but are not limited to media containing a glucocorticoid (e.g., dexamethasone, hydrocortisone, cortisone, etc.), insulin, a compound which elevates intracellular levels of cAMP (e.g., dibutryl-cAMP, 8-CPT-cAMP (8-(4)chlorophenylthio)-adenosine 3', 5' cyclic monophosphate; 8-bromo-cAMP; dioctanoyl-cAMP, forskolin etc.), and/or a compound which inhibits degradation of cAMP (e.g., a phosphodiesterase inhibitor such as isobutyl methyl xanthine (IBMX), methyl isobutylxanthine, theophylline, caffeine, indomethacin, and the like), and serum. Thus, exposure of the ADSCs to between about 1 μM and about 10 μM insulin in combination with about $10^{-9}$ M to about $10^{-6}$ M to (e.g., about 1 μM) dexamethasone can induce adipogenic differentiation. Such a medium also can include other agents, such as indomethacin (e.g., about 100 μM to about 200 μM), if desired, and preferably the medium is serum-free.

In another embodiment, ADSCs cultured in DMEM, 10% FBS, 1 uM dexamthasone, 10 uM insulin, 200 uM indomethacin, 1% antibiotic/antimicotic, (ABAM), 0.5 mM IBMX, take on an adipogenic phenotype.

Culturing media that can induce osteogenic differentiation of the ADSCs include, but are not limited to, about $10^{-7}$ M and about $10^{-9}$ M dexamethasone (e.g., about 1 μM in combination with about 10 μM to about 50 μM ascorbate-2-phosphate and between about 10 nM and about 50 nM β-glycerophosphate. The medium also can include serum (e.g., bovine serum, horse serum, etc.).

In another embodiment, ADSCs cultured in DMEM, 10% FBS, 5% horse serum, 50 µM hydrocortisone, $10^{-7}$M dexamethosone, 50 uM ascorbate-2-phosphate, 1% ABAM, take on an osteogenic phenotype.

Culturing medium that can induce myogenic differentiation of the ADSCs of the invention include, but is not limited to, exposing the cells to between about 10 µM and about 100 µM hydrocortisone, preferably in a serum-rich medium (e.g., containing between about 10% and about 20% serum (either bovine, horse, or a mixture thereof)). Other glucocorticoids that can be used include, but are not limited to, dexamethasone. Alternatively, 5'-azacytidine can be used instead of a glucocorticoid.

In another embodiment, ADSCs cultured in DMEM, 10% FBS, $10^{-7}$M dexamethosone, 50 uM ascorbate-2-phosphate, 10 mM beta-glycerophosphate, 1% ABAM, take on an myogenic phenotype.

Culturing medium that can induce chondrogenic differentiation of the ADSCs of the invention, include but is not limited to, exposing the cells to between about 1 µM to about 10 µM insulin and between about 1 µM to about 10 µM transferrin, between about 1 ng/ml and 10 ng/ml transforming growth factor (TGF) β1, and between about 10 nM and about 50 nM ascorbate-2-phosphate (50 nM). For chondrogenic differentiation, preferably the cells are cultured in high density (e.g., at about several million cells/ml or using micromass culture techniques), and also in the presence of low amounts of serum (e.g., from about 1% to about 5%).

In another embodiment, ADSCs cultured in DMEM, 50 uM ascorbate-2-phosphate, 6.25 ug/ml transferrin, 100 ng/ml insulin growth factor (IGF-1), 5 ng/ml TGF-beta-1, 5 ng/ml basic fibroblast growth factor (bFGF; used only for one week), assume an chondrogenic phenotype.

In yet another embodiment, ADSCs are cultured in a neurogenic medium such as DMEM, no serum and 5-10 mM β-mercaptoethanol and assume an ectodermal lineage.

The ADSCs also can be induced to dedifferentiate into a developmentally more immature phenotype (e.g., a fetal or embryonic phenotype). Such an induction is achieved upon exposure of the ADSC to conditions that mimic those within fetuses and embryos. For example, the inventive ADSCs, or population of ADSCs, can be co-cultured with cells isolated from fetuses or embryos, or in the presence of fetal serum.

The ADSCs of the invention can be induced to differentiate into a mesodermal, ectodermal, or an endodermal lineage by co-culturing the ADSCs with mature cells from the respective germ layer, or precursors thereof.

In an embodiment, induction of the ADSCs into specific cell types by co-culturing with differentiated mature cells includes, but is not limited to, myogenic differentiation induced by co-culturing the ADSCs with myocytes or myocyte precursors. Induction of the ADSCs into a neural lineage by co-culturing with neurons or neuronal precursors, and induction of the ADSCs into an endodermal lineage, may occur by co-culturing with mature or precursor pancreatic cells or mature hepatocytes or their respective precursors.

Alternatively, the ADSCs are cultured in a conditioned medium and induced to differentiate into a specific phenotype. Conditioned medium is medium which was cultured with a mature cell that provides cellular factors to the medium such as cytokines, growth factors, hormones, and extracellular matrix. For example, a medium that has been exposed to mature myoctytes is used to culture and induce ADSCs to differentiate into a myogenic lineage. Other examples of conditioned media inducing specific differentiation include, but are not limited to, culturing in a medium conditioned by exposure to heart valve cells to induce differentiation into heart valve tissue. In addition, ADSCs are cultured in a medium conditioned by neurons to induce a neuronal lineage, or conditioned by hepatoycytes to induce an endodermal lineage.

For co-culture, it may be desirable for the ADSCs and the desired other cells to be co-cultured under conditions in which the two cell types are in contact. This can be achieved, for example, by seeding the cells as a heterogeneous population of cells onto a suitable culture substrate. Alternatively, the ADSCs can first be grown to confluence, which will serve as a substrate for the second desired cells to be cultured within the conditioned medium.

Other methods of inducing differentiation are known in the art and can be employed to induce the ADSCs to give rise to cells having a mesodermal, ectodermal or endodermal lineage.

After culturing the stem cells in the differentiating-inducing medium for a suitable time (e.g., several days to a week or more), the ADSCs can be assayed to determine whether, in fact, they have acquired the desired lineage.

Methods to characterize differentiated cells that develop from the ADSCs of the invention, include, but are not limited to, histological, morphological, biochemical and immunohistochemical methods, or using cell surface markers, or genetically or molecularly, or by identifying factors secreted by the differentiated cell, and by the inductive qualities of the differentiated ADSCs.

Molecular markers that characterize mesodermal cell that differentiate from the ADSCs of the invention, include, but are not limited to, MyoD, myosin, alpha-actin, brachyury, xFOG, Xtbx5 FoxF1, XNkx-2.5. Mammalian homologs of the above mentioned markers are preferred.

Molecular markers that characterize ectodermal cell that differentiate from the ADSCs of the invention, include but are not limited to N-CAM, GABA and epidermis specific keratin. Mammalian homologs of the above mentioned markers are preferred.

Molecular markers that characterize endodermal cell that differentiate from the ADSCs include, but are not limited to, Xhbox8, Endo1, Xhex, Xcad2, Edd, EF1-alpha, HNF3-beta, LFABP, albumin, insulin. Mammalian homologs of the above mentioned markers are preferred.

In an embodiment, molecular characterization of the differentiated ADSCs is by measurement of telomere length. Undifferentiated stem cells have longer telomeres than differentiated cells; thus the cells can be assayed for the level of telomerase activity. Alternatively, RNA or proteins can be extracted from the ADSCs and assayed (via Northern hybridization, RTPCR, Western blot analysis, etc.) for the presence of markers indicative of a specific phenotype.

In an alternative embodiment, differentiation is assessed by assaying the cells immunohistochemically or histologically, using tissue-specific antibodies or stains, respectively. For example, to assess adipogenic differentiation, the differentiated ADSCs are stained with fat-specific stains (e.g., oil red O, safarin red, sudan black, etc.) or with labeled antibodies or molecular markers that identify adipose-related factors (e.g., PPAR-γ, adipsin, lipoprotein lipase, etc.).

In another embodiment, ostogenesis can be assessed by staining the differentiated ADSCs with bone-specific stains (e.g., alkaline phosphatase, von Kossa, etc.) or with labeled antibodies or molecular markers that identify bone-specific markers (e.g., osteocalcin, osteonectin, osteopontin, type I collagen, bone morphogenic proteins, cbfa, etc.).

Myogensis can be assessed by identifying classical morphologic changes (e.g., polynucleated cells, syncitia formation, etc.), or assessed biochemically for the presence of muscle-specific factors (e.g., myo D, myosin heavy chain, etc.).

Chondrogenesis can be determined by staining the cells using cartilage-specific stains (e.g., Alcian blue) or with labeled antibodies or molecular markers that identify cartilage-specific molecules (e.g., sulfated glycosaminoglycans and proteoglycans, keratin, chondroitin, Type II collagen, etc.) in the medium.

Alternative embodiments can employ methods of assessing developmental phenotype, known in the art. For example, the cells can be sorted by size and granularity. The cells can be used as an immunogen to generate monoclonal antibodies (Kohler and Miltein), which can then be used to bind to a given cell type. Correlation of antigenicity can confirm that the ADSC has differentiated along a given developmental pathway.

While an ADSC can be isolated, preferably it is within a population of cells. The invention provides a defined population of ADSCs. In an embodiment, the population is heterogeneous. In another embodiment, the population is homogeneous.

In another embodiment, a population of ADSCs can support cells for culturing other cells. For example, cells that can be supported by ADSC populations include other types of stem cells, such as neural stem cells (NSC), hematopoetic stem cells (HPC, particularly CD34$^+$ stem cells), embryonic stem cells (ESC) and mixtures thereof). In other embodiments, the population is substantially homogeneous, consisting essentially of the inventive adipose-derived stem cells.

Uses of the ADSC-EF, ADSCs and Methods of the Invention

The ADSC-EF can be used as a source of the ADSCs of the invention. The ADSC-EF can be introduced into a subject for tissue regeneration, wound repair or other applications requiring a source of stem cells. In addition, the ADSC-EF can be treated to cause the ADSCs therein to differentiate into a desired cell type for introduction into a subject. The ADSC-EF can also be cultured in vitro to maintain a source of ADSCs, or can be induced to produce further differentiated ADSCs that can develop into a desired tissue.

The ADSCs (and populations of ADSCs) can be employed for a variety of purposes. The ADSCs can support the growth and expansion of other cell types. The invention includes a method of conditioning culture medium using the ADSCs in a suitable medium, and the ADSC-conditioned medium produced by such a method. Typically, the medium is used to support the in vitro growth of the ADSCs, which secrete hormones, cell matrix material, and other factors into the medium. After a suitable period (e.g., one or a few days), the culture medium containing the secreted factors can be separated from the cells and stored for future use. The ADSCs can be re-used successively to condition medium, as desired. In other applications (e.g., for co-culturing the ADSCs with other cell types), the cells can remain within the conditioned medium. Thus, the invention provides an ADSC-conditioned medium obtained using this method, which either can contain the ADSCs, or can be substantially free of the ADSCs, as desired.

The ADSC-conditioned medium can be used to support the growth and expansion of desired cell types, and the invention provides a method of culturing cells (particularly stem cells) using the conditioned medium. The method involves maintaining a desired cell in the conditioned medium under conditions for the cell to remain viable. The cell can be maintained under any suitable condition for culturing them, such as are known in the art. Desirably, the method permits successive rounds of mitotic division of the cell to form an expanded population. The exact conditions (e.g., temperature, $CO_2$ levels, agitation, presence of antibiotics, etc.) will depend on the other constituents of the medium and on the cell type. However, optimizing these parameters is within the ordinary skill in the art.

In another embodiment, the ADSCs can be genetically modified, e.g., to express exogenous genes ("transgenes") or to repress the expression of endogenous genes, and the invention provides a method of genetically modifying such cells and populations. In accordance with this method, the ADSC is exposed to a gene transfer vector comprising a nucleic acid including a transgene, such that the nucleic acid is introduced into the cell under conditions appropriate for the transgene to be expressed within the cell. The transgene generally is an expression cassette, including a polynucleotide operably linked to a suitable promoter. The polynucleotide can encode a protein, or it can encode biologically active RNA (e.g., antisense RNA or a ribozyme). Thus, for example, the polynucleotide can encode a gene conferring resistance to a toxin, a hormone (such as peptide growth hormones, hormone releasing factors, sex hormones, adrenocorticotrophic hormones, cytokines (e.g., interfering, interleukins, lymphokines), etc.), a cell-surface-bound intracellular signaling moiety (e.g., cell adhesion molecules, hormone receptors, etc.), a factor promoting a given lineage of differentiation, (e.g., bone morphogenic protein (BMP)) etc. Of course, where it is desired to employ gene transfer technology to deliver a given transgene, its sequence will be known.

Within the expression cassette, the coding polynucleotide is operably linked to a suitable promoter. Examples of suitable promoters include prokaryotic promoters and viral promoters (e.g., retroviral ITRs, LTRs, immediate early viral promoters (IEp), such as herpesvirus IEp (e.g., ICP4-IEp and ICP0-IEp), cytomegalovirus (CMV) IEp, and other viral promoters, such as Rous Sarcoma Virus (RSV) promoters, and Murine Leukemia Virus (MLV) promoters). Other suitable promoters are eukaryotic promoters, such as enhancers (e.g., the rabbit β-globin regulatory elements), constitutively active promoters (e.g., the β-actin promoter, etc.), signal specific promoters (e.g., inducible promoters such as a promoter responsive to RU486, etc.), and tissue-specific promoters. It is well within the skill of the art to select a promoter suitable for driving gene expression in a predefined cellular context. The expression cassette can include more than one coding polynucleotide, and it can include other elements (e.g., polyadenylation sequences, sequences encoding a membrane-insertion signal or a secretion leader, ribosome entry sequences, transcriptional regulatory elements (e.g., enhancers, silencers, etc.), and the like), as desired.

The expression cassette containing the transgene should be incorporated into a genetic vector suitable for delivering the transgene to the cells. Depending on the desired end application, any such vector can be so employed to genetically modify the cells (e.g., plasmids, naked DNA, viruses such as adenovirus, adeno-associated virus, herpesvirses, lentiviruses, papillomaviruses, retroviruses, etc.). Any method of constructing the desired expression cassette within such vectors can be employed, many of which are well known in the art (e.g., direct cloning, homologous recombination, etc.). Of course, the choice of vector will largely determine the method used to introduce the vector into the cells (e.g., by protoplast fusion, calcium-phosphate precipitation, gene gun, electroporation, infection with vial vectors, etc.), which are generally known in the art.

The genetically altered ADSCs can be employed as bioreactors for producing the product of the transgene. In other embodiments, the genetically modified ADSCs are employed to deliver the transgene and its product to an animal. For example, the ADSCs, once genetically modified, can be introduced into the animal under conditions sufficient for the transgene to be expressed in vivo.

In addition to serving as useful targets for genetic modification, many ADSCs and populations of ADSCs secrete hormones (e.g., cytokines, peptide or other (e.g., monobutyrin) growth factors, etc.). Some of the cells naturally secrete such hormones upon initial isolation, and other cells can be genetically modified to secrete hormones, as discussed herein. The ADSCs that secrete hormones can be used in a variety of contexts in vivo and in vitro. For example, such cells can be employed as bioreactors to provide a ready source of a given hormone, and the invention pertains to a method of obtaining hormones from such cells. In accordance with the method, the ADSCs are cultured, under suitable conditions for them to secrete the hormone into the culture medium. After a suitable period of time, and preferably periodically, the medium is harvested and processed to isolate the hormone from the medium. Any standard method (e.g., gel or affinity chromatography, dialysis, lyophilization, etc.) can be used to purify the hormone from the medium, many of which are known in the art.

In other embodiments, ADSCs (and populations) secreting hormones can be employed as therapeutic agents. Generally, such methods involve transferring the cells to desired tissue, either in vitro (e.g., as a graft prior to implantation or engrafting) or in vivo, to animal tissue directly. The cells can be transferred to the desired tissue by any method appropriate, which generally will vary according to the tissue type. For example, ADSCs can be transferred to a graft by bathing the graft (or infusing it) with culture medium containing the cells. Alternatively, the ADSCs can be seeded onto the desired site within the tissue to establish a population. Cells can be transferred to sites in vivo using devices such as catheters, trocars, cannulae, stents (which can be seeded with the cells), etc. For these applications, preferably the ADSC secretes a cytokine or growth hormone such as human growth factor, fibroblast growth factor, nerve growth factor, insulin-like growth factors, hemopoietic stem cell growth factors, members of the fibroblast growth factor family, members of the platelet-derived growth factor family, vascular and endothelial cell growth factors, members of the TGFb family (including bone morphogenic factor), or enzymes specific for congenital disorders (e.g., dystrophic).

In one application, the invention provides a method of promoting the closure of a wound within a patient using ADSCs. In accordance with the method, ADSCs secreting the hormone are transferred to the vicinity of a wound under conditions sufficient for the cells to produce the hormone. The presence of the hormone in the vicinity of the wound promotes closure of the wound. The method promotes closure of both external (e.g., surface) and internal wounds. Wounds to which the present inventive method is useful in promoting closure include, but are not limited to, abrasions, avulsions, blowing wounds, burn wounds, contusions, gunshot wounds, incised wounds, open wounds, penetrating wounds, perforating wounds, puncture wounds, seton wounds, stab wounds, surgical wounds, subcutaneous wounds, or tangential wounds. The method need not achieve complete healing or closure of the wound; it is sufficient for the method to promote any degree of wound closure. In this respect, the method can be employed alone or as an adjunct to other methods for healing wounded tissue.

Where the ADSCs secrete an angiogenic hormone (e.g., vascular growth factor, vascular and endothelial cell growth factor, etc.), they (as well as populations containing them) can be employed to induce angiogenesis within tissues. Thus, the invention provides a method of promoting or inhibiting neovascularization within tissue using such ADSCs. The presence of the hormone within the tissue promotes or inhibits neovascularization. In accordance with this method, the ADSC is introduced the desired tissue under conditions sufficient for the cell to produce the angiogenic hormone. The presence of the hormone within the tissue promotes neovascularization within the tissue.

Because the ADSCs have a developmental phenotype, they can be employed in tissue engineering. In this regard, the invention provides a method of producing animal matter comprising maintaining the ADSCs under conditions sufficient for them to expand and differentiate to form the desired matter. The matter can include mature tissues, or even whole organs, including tissue types into which the inventive cells can differentiate (as set forth herein). Typically, such matter will comprise adipose, cartilage, heart, dermal connective tissue, blood tissue, muscle, kidney, bone, pleural, splanchnic tissues, vascular tissues, and the like. More typically, the matter will comprise combinations of these tissue types (i.e., more than one tissue type). For example, the matter can comprise all or a portion of an animal organ (e.g., a heart, a kidney) or a limb (e.g., a leg, a wing, an arm, a hand, a foot, etc.). Of course, in as much as the cells can divide and differentiate to produce such structures, they can also form anlagen of such structures. At early stages, such anlagen can be cryopreserved for future generation of the desired mature structure or organ.

To produce such structures, the ADSCs and populations are maintained under conditions suitable for them to expand and divide to form the desired structures. In some applications, this is accomplished by transferring them to an animal (i.e., in vivo) typically at a sight at which the new matter is desired. Thus, for example, the invention can facilitate the regeneration of tissues (e.g., bone, muscle, cartilage, tendons, adipose, etc.) within an animal where the ADSCs are implanted into such tissues. In other embodiments, and particularly to create anlagen, the ADSCs can be induced to differentiate and expand into tissues in vitro. In such applications, the ADSCs are cultured on substrates that facilitate formation into three-dimensional structures conducive for tissue development Thus, for example, the ADSCs can be cultured or seeded onto a bio-compatible lattice, such as one that includes extracellular matrix material, synthetic polymers, cytokines, growth factors, etc. Such a lattice can be molded into desired shapes for facilitating the development of tissue types. Also, at least at an early stage during such culturing, the medium and/or substrate is supplemented with factors (e.g., growth factors, cytokines, extracellular matrix material, etc.) that facilitate the development of appropriate tissue types and structures. Indeed, in some embodiments, it is desired to co-culture the ADSCs with mature cells of the respective tissue type, or precursors thereof, or to expose the cells to the respective conditioned medium, as discussed herein.

To facilitate the use of the ADSCs and populations for producing such animal matter and tissues, the invention provides a composition including the ADSCs (and populations) and biologically compatible lattice. Typically, the lattice is formed from polymeric material, having fibers as a mesh or sponge, typically with spaces on the order of between about 100 µm and about 300 µm. Such a structure provides sufficient area on which the cells can grow and proliferate. Desirably, the lattice is biodegradable over time, so that it will be absorbed into the animal matter as it develops. Suitable polymeric lattices, thus, can be formed from monomers such as glycolic acid, lactic acid, propyl fumarate, caprolactone, hyaluronan, hyaluronic acid, and the like. Other lattices can include proteins, polysaccharides, polyhydroxy acids, polyorthoesters, polyanhydrides, polyphosphazenes, or synthetic polymers (particularly biodegradable polymers). Of course, a suitable polymer for forming such lattice can include more than one monomers (e.g., combinations of the indicated monomers). Also, the lattice can also include hormones, such as growth factors, cytokines, and morphogens (e.g., retinoic acid, aracadonic acid, etc.), desired extracellular matrix molecules (e.g., fibronectin, laminin, collagen, etc.), or other materials (e.g., DNA, viruses, other cell types, etc.) as desired.

To form the composition, the ADSCs are introduced into the lattice such that they permeate into the interstitial spaces therein. For example, the matrix can be soaked in a solution or suspension containing the cells, or they can be infused or injected into the matrix. A particularly preferred composition is a hydrogel formed by crosslinking of a suspension including the polymer and also having the inventive cells dispersed therein. This method of formation permits the cells to be dispersed throughout the lattice, facilitating more even permeation of the lattice with the cells. Of course, the composition also can include mature cells of a desired phenotype or precursors thereof, particularly to potentate the induction of the ADSCs to differentiate appropriately within the lattice (e.g., as an effect of co-culturing such cells within the lattice).

The composition can be employed in any suitable manner to facilitate the growth and generation of the desired tissue types, structures, or anlagen. For example, the composition can be constructed using three-dimensional or sterotactic modeling techniques. Thus, for example, a layer or domain-within the composition can be populated by cells primed for osteogenic differentiation, and another layer or domain within the composition can be populated with cells primed for myogenic and/or chondrogenic development Bringing such domains into juxtaposition with each other facilitates the molding and differentiation of complex structures including multiple tissue types (e.g., bone surrounded by muscle, such as found in a limb). To direct the growth and differentiation of the desired structure, the composition can be cultured ex vivo in a bioreactor or incubator, as appropriate. In other embodiments, the structure is implanted within the host animal directly at the site in which it is desired to grow the tissue or structure. In still another embodiment, the composition can be engrafted on a host (typically an animal such as a pig, baboon, etc.), where it will grow and mature until ready for use. Thereafter, the mature structure (or anlagen) is excised from the host and implanted into the host, as appropriate.

Lattices suitable for inclusion into the composition can be derived from any suitable source (e.g., matrigel), and some commercial sources for suitable lattices exist (e.g., suitable of polyglycolic acid can be obtained from sources such as Ethicon, N.J.). Another suitable lattice can be derived from the acellular portion of adipose tissue—i.e., adipose tissue extracellular matrix matter substantially devoid of cells, and the invention provides such a adipose-derived lattice. Typically, such adipose-derived lattice includes proteins such as proteoglycans, glycoproteins, hyaluronins, fibronectins, collagens (type I, type II, type III, type IV, type V, type VI, etc.), and the like, which serve as excellent substrates for cell growth. Additionally, such adipose-derived lattices can include hormones, preferably cytokines and growth factors, for facilitating the growth of cells seeded into the matrix.

The adipose-derived matrix can be isolated form adipose tissue similarly as described above, except that it will be present in the acellular fraction. For example, adipose tissue or derivatives thereof (e.g; the lattice enriched supernant fraction of the method described above) can be subjected to sonic or thermal energy and/or enzymatic processed to recover the matrix material. Also, desirably the cellular fraction of the adipose tissue is disrupted, for example by treating it with lipases, detergents, proteases, and/or by mechanical or sonic disruption (e.g., using a homogenizer or sonicator). However isolated, the material is initially identified as a viscous material, but it can be subsequently treated, as desired, depending on the desired end use. For example, the raw matrix material can be treated (e.g., dialyzed or treated with proteases or acids, etc.) to produce a desirable lattice material. Thus the lattice can be prepared in a hyrated form or it can be dried or lyophilized into a substantially anhydrous form or a powder. Thereafter, the powder can be rehydrated for use as a cell culture substrate, for example by suspending it in a suitable cell culture medium. In this regard, the adipose-derived lattice can be mixed with other suitable lattice materials, such as described above. Of course, the invention pertains to compositions including the adipose-derived lattice and cells or populations of cells, such as the inventive ADSCs and other cells as well (particularly other types of stem cells).

As discussed above, the ADSCs, populations, lattices, and compositions of the invention can be used in tissue engineering and regeneration. Thus, the invention pertains to an implantable structure (i.e., an implant) incorporating any of these inventive features. The exact nature of the implant will vary according to the use to which it is to be put The implant can be or comprise, as described, mature tissue, or it can include immature tissue or the lattice. Thus, for example, one type of implant can be a bone implant, comprising a population of the inventive cells that are undergoing (or are primed for) osteogenic differentiation, optionally seeded within a lattice of a suitable size and dimension, as described above. Such an implant can be injected or engrafted within a host to encourage the generation or regeneration of mature bone tissue within the patient Similar implants can be used to encourage the growth or regeneration of muscle, fat, cartilage, tendons, etc., within patients. Other types of implants are anlagen (such as described herein), e.g., limb buds, digit buds, developing kidneys, etc, that, once engrafted onto a patient, will mature into the appropriate structures.

The adipose-derived lattice can conveniently be employed as part of a cell culture kit. Accordingly, the invention provides a kit including the inventive adipose-derived lattice and one or more other components, such as hydrating agents (e.g., water, physiologically-compatible saline solutions, prepared cell culture media, serum or derivatives thereof, etc.), cell culture substrates (e.g., culture dishes, plates, vials, etc.), cell culture media (whether in liquid or powdered form), antibiotic compounds, hormones, and the like. While the kit can include any such ingredients, preferably it includes all ingredients necessary to support the culture and growth of desired cell types upon proper combination. Of course, if desired, the kit also can include cells (typically frozen), which can be seeded into the lattice as described herein.

While many aspects of the invention pertain to tissue growth and differentiation, the invention has other applications as well. For example, the adipose-derived lattice can be used as an experimental reagent, such as in developing improved lattices and substrates for tissue growth and differentiation. The adipose-derived lattice also can be employed cosmetically, for example, to hide wrinkles, scars, cutaneous depressions, etc., or for tissue augmentation. For such applications, preferably the lattice is stylized and packaged in unit dosage form. If desired, it can be admixed with carriers (e.g., solvents such as glycerine or alcohols), perfumes, antibiotics, colorants, and other ingredients commonly employed in cosmetic products. The substrate also can be employed autologously or as an allograft, and it can used as, or included within, ointments or dressings for facilitating wound healing. The ADSCs can also be used as experimental reagents. For example, they can be employed to help discover agents responsible for early events in differentiation. For example, the inventive cells can be exposed to a medium for inducing a particular line of differentiation and then assayed for differential expression of genes (e.g., by random-primed PCR or electrophoresis or protein or RNA, etc.).

As any of the steps for isolating the inventive ADSCs or the adipose-derived lattice, the, the invention provides a kit for isolating such reagents from adipose tissues. The kit can include a means for isolating adipose tissue from a patient (e.g., a cannula, a needle, an aspirator, etc.), as well as a means for separating stromal cells (e.g., through methods described herein). The kit can be employed, for example, as an immediate source of ADSCs that can then be re-introduced from the same individual as appropriate. Thus, the kit can facilitate the isolation of adipose-derived stem cells for implantation in a patient needing regrowth of a desired tissue type, even in the same procedure. In this respect, the kit can also include a medium for differentiating the cells, such as those set forth herein. As appropriate, the cells can be exposed to the medium to prime them for differentiation within the patient as needed. In addition, the kit can be used as a convenient source of ADSCs for in vitro manipulation (e.g., cloning or differentiating as described herein). In another embodiment, the kit can be employed for isolating a adipose-derived lattice as described herein.

While one of skill in the art is fully able to practice the instant invention upon reading the foregoing detailed description, the following examples will help elucidate some of its features. In particular, they demonstrate the isolation of a human adipose-derived stem cell substantially free of mature adipocytes, the isolation of a clonal population of such cells, the ability of such cells to differentiate in vivo and in vitro into all cells with a mesodermal phenotype, endodermal phenotype, and extodermal phenotype, and the capacity of such cells to support the growth of other types of stem cells. The examples also demonstrate the isolation of a adipose-derived lattice substantially free of cells that is capable of serving as a suitable substrate for cell culture. Of course, as these examples are presented for purely illustrative purposes, they should not be used to construe the scope of the invention in a limited manner, but rather should be seen as expanding upon the foregoing description of the invention as a whole.

The procedures employed in these examples, such as surgery, cell culture, enzymatic digestion, histology, and molecular analysis of proteins and polynucleotides, are familiar to those of ordinary skill in this art. As such, and in the interest of brevity, experimental details are not recited in detail.

EXAMPLE 1

This example demonstrates the isolation of a human adipose-derived stem cell substantially free of mature adipocytes.

Raw liposuction aspirate was obtained from patients undergoing elective surgery. Prior to the liposuction procedures, the patients were given epinephrine to minimize contamination of the aspirate with blood. The aspirate was strained to separate associated adipose tissue pieces from associated liquid waste. Isolated tissue was rinsed thoroughly with neutral phosphate buffered saline and then enzymatically dissociated with 0.075% w/v collagenase at 37° C. for about 20 minutes under intermittent agitation. Following the digestion, the collagenase was neutralized, and the slurry was centrifuged at about 260 g for about 10 minutes, which produced a multi-layered supernatant and a cellular pellet The supernatant was removed and retained for further use, and the pellet was resuspended in an erythrocyte-lysing solution and incubated without agitation at about 25° C. for about 10 minutes. Following incubation, the medium was neutralized, and the cells were again centrifuged at about 250 g for about 10 minutes. Following the second centrifugation, the cells were suspended, and assessed for viability (using trypan blue exclusion) and cell number. Thereafter, they were plated at a density of about at about $1 \times 10^6$ cells/100 mm dish. They were cultured at 37° C. in DMEM+fetal bovine serum (about 10%) in about 5% $CO_2$.

The majority of the cells were adherent, small, mononucleic, relatively agranular fibroblast-like cells containing no visible lipid droplets and were CD34-negative. The majority of the cells stained negatively with oil-red O and von Kossa. The cells were also assayed for expression of telomerase (using a commercially available TRAP assay kit), using HeLa cells and HN-12 cells as positive controls. Human foreskin fibroblasts and HN-12 heated cell extracts were used as negative controls. Telomeric products were resolved onto a 12.5% polyacrylamide cells and the signals determined by phosphorimaging. Telemeric ladders representing telomerase activity were observed in the adipose-derived stem cells as well as the positive controls. No ladders were observed in the negative controls.

Thus, these cells were not identifiable as myocytes, adipocytes, chondrocytes, osteocytes, or blood cells. These results demonstrate that the adipose-derived cells express telomerase activity similar to that previously reported for human stem cells.

Subpopulations of these cells were then exposed to the following media to assess their developmental phenotype:

| Adipogenesis | Osteogenesis | Myogenesis | Chondrogenesis |
| --- | --- | --- | --- |
| DMEM | DMEM | DMEM | DMEM |
| 10% FETAL BOVINE SERUM | 10% FETAL BOVINE SERUM | 10% FETAL BOVINE SERUM | 1% FETAL BOVINE SERUM |
| 0.5 mM ISOBUTYL-METHYLXANTHINE | 5% horse serum 0.1 μM dexamethasone | 5% horse serum 50 μM hydrocortisone | 6.25 μg/ml insulin 6.25 μg/ml transferrin |
| 1 μM dexamethasone | | | |
| 10 μM insulin | 50 μM ascorbate-2-phosphate | 1% ABAM | 10 ng/ml TGFβ1 |
| 200 μM indomethacin | | | 50 nM ascorbate-2- |

-continued

| Adipogenesis | Osteogenesis | Myogenesis | Chondrogenesis |
|---|---|---|---|
| 1% ABAM | 10 mM β-glycerophosphate 1% ABAM | | phosphate 1% ABAM |

A population was cultured at high density in the chondrogenic medium for several weeks. Histological analysis of the tissue culture and paraffin sections was performed with H&E, alcian blue, toludene blue, and Goldner's trichrome staining at 2, 7, and 14 days. Immunohistochemistry was performed using antibodies against chondroitin-4-sulfate and keratin sulfate and type II collagen. Qualitative estimate of matrix staining was also performed. The results indicated that cartilaginous spheroid nodules with a distinct border of perichondral cells formed as early as 48 hours after initial treatment. Untreated control cells exhibited no evidence of chondrogenic differentiation. These results confirm that the stem cells have chondrogenic developmental phenotype.

A population was cultured until near confluence and then exposed to the adipogenic medium for several weeks. The population was examined at two and four weeks after plating by calorimetric assessment of relative opacity following oil red-O staining. Adipogenesis was determined to be underway at two weeks and quite advanced at four weeks (relative opacity of 1 and 5.3, respectively). Bone marrow-derived stem cells were employed as a positive control, and these cells exhibited slightly less adipogenic potential (relative density of 0.7 and 2.8, respectively).

A population was cultured until near confluence and then exposed to the osteogeneic medium for several weeks. The population was examined at two and four weeks after plating by colorimetric assessment of relative opacity following von Kossa staining. Osteogenesis was determined to be underway at two weeks and quite advanced at four weeks (relative opacity of 1.1 and 7.3, respectively. Bone marrow-derived stem cells were employed as a positive control, and these cells exhibited slightly less osteogenic potential (relative density of 0.2 and 6.6, respectively).

A population was cultured until near confluence and then exposed to the myogenic medium for several weeks. The population was examined at one, three, and six weeks after plating by assessment of multinucleated cells and expression of muscle-specific proteins (MyoD and myosin heavy chain). Human foreskin fibroblasts and skeletal myoblasts were used as controls. Cells expressing MyoD and myosin were found at all time points following exposure to the myogenic medium in the stem cell population, and the proportion of such cells increased at 3 and 6 weeks. Multinucleated cells were observed at 6 weeks. In contrast, the fibroblasts exhibited none of these characteristics at any time points.

These results demonstrate the isolation of a human adipose-derived pluripotent stem cell substantially free of mature adipocytes.

EXAMPLE 2

This example demonstrates that the adipose-derived stem cells do not differentiate in response to 5-azacytidine.

Adipose-derived stem cells obtained in accordance with Example 1 were cultured in the presence of 5-azacytidine. In contrast with bone marrow-derived stem cells, exposure to this agent did not induce myogenic differentiation (see Wakitani et al., supra).

EXAMPLE 3

This example demonstrates the generation of a clonal population of human adipose-derived stem cells from an adipose-derived stem cell enriched fraction.

Cells isolated in accordance with the procedure set forth in Example 1 were plated at about 5,000 cells/100 mm dish and cultured for a few days as indicated in Example 1. After some rounds of cell division, some clones were picked with a cloning ring and transferred to wells in a 48 well plate. These cells were cultured for several weeks, changing the medium twice weekly, until they wore about 80% to about 90% confluent (at 37° C. in about 5% $CO_2$ in ⅔ $F_{12}$ medium+20% fetal bovine serum and ⅓ standard medium that was first conditioned by the cells isolated in Example 1, "cloning medium"). Thereafter, each culture was transferred to a 35 mm dish and grown, and then retransferred to a 100 mm dish and grown until close to confluent. Following this, one cell population was frozen, and the remaining populations were plated on 12 well plates, at 1000 cells/well.

The cells were cultured for more than 15 passages in cloning medium and monitored for differentiation as indicated in Example 1. The undifferentiated state of each clone remained true after successive rounds of culturing.

Populations of the clones then were established and exposed to adipogenic, chondrogenic, myogenic, and osteogenic medium as discussed in Example 1. It was observed that at least one of the clones was able to differentiate into bone, fat, cartilage, and muscle when exposed to the respective media, and most of the clones were able to differentiate into at least three types of tissues. The capacity of the cells to develop into muscle and cartilage further demonstrates the pluripotentiality of these adipose-derived stem cells.

These results demonstrate that the adipose-derived stem cells can be maintained in an undifferentiated state for many passages without the requirement for specially pre-screened lots of serum. The results also demonstrate that the cells retain pluripotentiality following such extensive passaging, proving that the cells are indeed stem cells and not merely committed progenitor cells.

EXAMPLE 4

This example demonstrates the adipose-derived stem cells from an adipose-devired stem cell enriched fraction can support the culture of other types of stem cells.

Human adipose-derived stem cells were passaged onto 96 well plates at a density of about 30,000/well, cultured for one week and then irradiated. Human $CD34^+$ hematopoetic stem cells isolated from umbilical cord blood were then seeded into the wells. Co-cultures were maintained in MyeloCult H5100 media, and cell viability and proliferation were monitored subjectively by microscopic observation. After two weeks of co-culture, the hematopoetic stem cells were evaluated for CD34 expression by flow cytometry.

Over a two-week period of co-culture with stromal cells, the hematopoetic stem cells formed large colonies of rounded cells. Flow analysis revealed that 62% of the cells remained CD34+. Based on microscopic observations, human adipo-derived stromal cells maintained the survival and supported the growth of human hematopoetic stem cells derived from umbilical cord blood.

These results demonstrate that stromal cells from human subcutaneous adipose tissue are able to support the ex vivo maintenance, growth and differentiation of other stem cells.

EXAMPLE 5

This example demonstrates that the adipose-derived stem cells from an adipose-devired stem cell enriched fraction can differentiate in vivo.

Four groups (A-D) of 12 athymic mice each were implanted subcutaneously with hydroxyapatite/tricalcium phosphate cubes containing the following: Group A contained adipose-derived stem cells that had been pretreated with osteogenic medium as set forth in Example 1. Group B contained untreated adipose-derived stem cells. Group C contained osteogenic medium but no cells. Group D contained non-osteogenic medium and no cells. Within each group, six mice were sacrificed at three weeks, and the remaining mice sacrificed at eight weeks following implantation. The cubes were extracted, fixed, decalcified, and sectioned. Each section was analyzed by staining with hematoxylin and eosin (e.g., H&E), Mallory bone stain, and immunostaining for osteocalcin.

Distinct regions of osteoid-like tissue staining for osteocalcin and Mallory bone staining was observed in sections from groups A and B. Substantially more osteoid tissue was observed in groups A and B than in the other groups ($p<0.05$ ANOVA), but no significant difference in osteogenesis was observed between groups A and B. Moreover, a qualitative increase in bone growth was noted in both groups A and B between 3 and 8 weeks. These results demonstrate that the adipose-derived stem cells can differentiate in vivo.

EXAMPLE 6

This example demonstrates the isolation of an adipose-derived lattice substantially devoid of cells.

In one protocol, the lattice-enriched fraction from Example 1 was subjected to enzymatic digestion for three days in 0.05% trypsin EDTA/100 U/ml deoxyribonuclease to destroy the cells. Every day the debris was rinsed in saline and fresh enzyme was added. Thereafter the material was rinsed in saline and resuspended in 0.05% collagease and about 0.1% lipase to partially digest the proteins and fat present. This incubation continued for two days.

In another protocol, the withheld supernatant from Example 1 was incubated in EDTA to eliminate any epithelial cells. The remaining cells were lysed using a buffer containing 1% NP40, 0.5% sodium deoxycholate, 0.1% SDS, 5 mM EDTA, 0.4M NaCl, 50 mM Tris-HCL (pH 8) and protease inhibitors, and 10 µg/ml each of leupeptin, chymostatin, antipain, and pepstatin A. Finally, the tissue was extensively washed in PBS without divalent cations.

After both preparatory protocols, remaining substance was washed and identified as a gelatinous mass. Microscopic analysis of this material revealed that it contained no cells, and it was composed of high amounts of collagen (likely type IV) and a wide variety of growth factors. Preparations of this material have supported the growth of cells, demonstrating it to be an excellent substrate for tissue culture.

EXAMPLE 7

The following description provides adipose-derived stem cells enriched fractions which exhibit mesodermal multi-tissue potential, and methods for isolating said stem cells.

Materials and Methods

All materials were purchased from Sigma (St. Louis, Mo.) unless otherwise stated. All tissue culture reagents were purchased from Life Technologies (New York, N.Y.). Fetal Bovine Serum (FBS) and Horse Serum (HS) were purchased from Hyclone (Logan, Utah) and Life Technologies, respectively.

Cell Lines:

Normal Human Osteoblasts (NHOsts), human Skeletal Muscle (SkM) cells and a population of Mesenchymal Stem Cells derived from bone marrow (MSCs) were purchased from Clonetics (Walkersville, Md.). The murine 3T3-L1 pre-adipocyte cell line (Green H., and Meuth, M., 1974, Cell 3: 127-133) was obtained from ATCC (Rockville, Md.). Human Foreskin Fibroblasts (HFFs) were obtained from Cascade Biologics (Portland, Oreg.).

Isolation and Culture of Stem Cells:

Human adipose tissue was obtained from elective liposuction procedures under local anesthesia according to patient consent protocol, HSPC #98-08 011-02 (Univerisity of California Los Angeles). In this procedure, a hollow blunt-tipped cannula was introduced into the subcutaneous space through small (~1 cm) incisions. The cannula was attached to a gentle suction and moved through the adipose compartment, mechanically disrupting the fat tissue. A solution of saline and the vasoconstrictor, epinephrine, was infused into the adipose compartment to minimize blood loss and contamination of the tissue by peripheral blood cells. The raw lipoaspirate (approximately 300 cc) was processed according to established methodologies in order to obtain a stromal vascular fraction (SVF) (Hauner H., et al., 1987, J. Clin. Endocrinol. Metabol. 64: 832-835; Katz, A. J., et al., 1999 Clin. Plast. Surg. 26: 587-603, viii). To isolate the SVF, lipoaspirates were washed extensively with equal volumes of Phospho-Buffered Saline (PBS) and the extracellular matrix (ECM) was digested at 37° C. for 30 minutes with 0.075% collagenase. Enzyme activity was neutralized with Dulbecco's Modified Eagle's Medium (DMEM), containing 10% Fetal Bovine Serum (FBS) and centrifuged at 1200×g for 10 minutes to obtain a high-density SVF pellet. The pellet was resuspended in 160 mM $NH_4Cl$ and incubated at room temperature for 10 minutes to lyse contaminating red blood cells. The SVF was collected by centrifugation, as detailed above, filtered through a 100 µm nylon mesh to remove cellular debris and incubated overnight at 37° C./5% $CO_2$ in Control Medium (DMEM, 10% FBS, 1% antibiotic/antimycotic solution). Following incubation, the plates were washed extensively with PBS to remove residual non-adherent red blood cells. The resulting cell population was termed an adipose-derived stem cell enriched fraction (ADSC enriched fraction), in order to distinguish it from the SVF obtained from excised adipose tissue. The adipose-derived stem cells were maintained at 37° C./5% $CO_2$ in non-inductive Control Medium. Cells did not require specific FBS sera lots for expansion and differentiation. For immunofluorescent studies, a population of MSCs was obtained from human bone marrow aspirates according to the protocol of Rickard et al. (Rickard D. J., et al., 1996, J. Bone Min. Res. 11: 312-324) and maintained in Control medium. To prevent spontaneous differentiation, cells were maintained at subconfluent levels.

Indirect Immunofluorescence of Stem Cells:

Stem cells and MSCs obtained from human bone marrow aspirates were plated onto glass chamber slides and fixed for 15 minutes in 4% paraformaldehyde in 100 mM sodium phosphate buffer (pH 7.0). The cells were washed for 10 minutes in 100 mM glycine in PBS (PBS/glycine) and blocked for 1 hour in Immunofluorescent Blocking Buffer (IBB; 5% BSA, 10% FBS, 1× PBS, 0.1% Triton X-100). The cells were subsequently incubated for 1 hour in IBB containing the following cell-specific monoclonal antibodies: 1) anti-smooth muscle actin (anti-SMA; Cedarlane Inc, Hornby Ont), to identify smooth muscle cells and pericytes (Skalli, O., et al., 1986, J. Cell Biol. 103:2787-2796; Schurch, W., et al., 1987, Am J. Pathol 128:91-103; Nehls, A. and D. Drenckhahn 1991, J. Cell Biol. 113:147-154; Barghorn, A. et al., 1998, Pediatr. Pathol. Lab. Med. 18:5-22)); 2) anti-Factor VIII (anti-FVIII; Calbiochem, San Diego, Calif.), to identify endothelial cells (Jaffe, E A, et al., 1973, J. Clin. Envest. 52:2757-2764; Nagle, R B, et al., 1987 Lymphology 20:20-24); and 3) ASO2 (dianova, Hamburg, Germany), to identify fibroblasts and cells of mesenchymal origin (Saalbach, A., et al., 1996 J. Invest. Dermatol. 106:1314-1319; Saalbach, A., et al., 1997 Cell and Tiss. Res. 290:595-599). The cells were washed extensively with PBS/glycine and incubated for 1 hour in IBB containing an FITC-conjugated secondary antibody. The cells were washed with PBS/glycine and mounted with a solution containing DAPI to visualize nuclei (VectaShield, Vector Labs, Burlingame, Calif.).

Flow Cytometry:

Adipose-derived stem cells samples from 5 donors were cultured in Control Medium for 72 hours prior to analysis. Flow cytometry was performed on a FACScan argon laser cytometer (Becton Dickson, San Jose, Calif.). Cells were harvested in 0.25% trypsin/EDTA and fixed for 30 minutes in ice-cold 2% formaldehyde. Following fixation, cells were washed in Flow Cytometry Buffer (FCB; 1×PBS, 2% FBS, 0.2% Tween-20). Cell aliquots ($1 \times 10^6$ cells) were incubated in FCB containing monoclonal antibodies to Factor VIII, smooth muscle actin or ASO2. In addition, cells were also incubated with FCB containing a monoclonal antibody to vimentin (anti-VIM; Biogenesis, Brentwood, N.H.), to identify mesenchymal cells (Lazarides, E. 1982 Annu. Rev. Biochem. 51:219-250; Suza, S., et al., 1996 Eur. J. Cell Biol. 70:84-91). To assess viability, duplicate samples were harvested, fixed for 30 minutes with ice-cold 1% paraformaldehyde, permeabilized with 0.05% Nonidet-40 and incubated with propidium iodide (PI) at a concentration of 25 μg/ml. Debris and dead cells were excluded by eliminating PI-positive events. All subsequent adipose-derived stem cell samples were corrected accordingly.

Cumulative Population Doubling:

Adipose-derived stem cells cells were maintained in Control Medium until 80% confluent. Cells were harvested at confluence and population doubling calculated using the formula log $N_1$/log$N_2$, where $N_1$ is the number of cells at confluence prior to passaging and $N_2$ is the number of cells seeded after passaging. Cumulative population doubling was determined in cultures maintained until passage 13 (approximately 165 days). The mean cumulative population doubling obtained from 3 donors was expressed as a function of passage number.

Cell Senescence Assay:

Senescence was assessed using a β-gal staining assay, in which β-galactosidase activity is detected in senescent cells at pH 6.0 but is absent in proliferating cells (Dimri, G P, et al., 1995 Proc. Natl. Acad. Sci. USA 92:9363-9367). Cells from each culture passage (passage 1 to passage 15) were fixed for 5 minutes in 2% formaldehyde/glutaraldehyde and incubated in a β-Gal Reaction Buffer (1 mg/ml X-Gal, 40 mM citric acid/sodium phosphate buffer (pH 6.0), 5 mM each of potassium ferrocyanide and potassium ferricyanide, 150 mM NaCl and 2 mM MgCl$_2$). Senescent cells (blue) were identified by light microscopy.

Confirmation of Multi-lineage Differentiation of Adipose-Derived Stem Cells:

Adipose-derived stem cells at passage 1 were analyzed for their capacity to differentiate toward the adipogenic, osteogenic, chondrogenic and myogenic lineages. To induce differentiation, the stem cells were cultured with specific induction media as detailed in Table 1. Each media has been previously described and shown to induce multi-lineage differentiation of MSCs (Pittenger, M F., et al., 1999 Science 284:143-147; Grigoradis, A., et al., 1988 J. Cell Biol. 106: 2139-2151; Cheng, S-L., et al., 1994 Endo 134:277-286; Loffler, G., et al., 1987 Klin. Wochenschr. 65:812-817; Hauner, H., et al., 1987 J. Clin. Endocrinol. Metabol. 64:832-835). Differentiation was confined using the histological and immunohistological assays outlined in Table 2. A commercial source of bone marrow-derived MSCs and lineage-specific precursors were examined as positive controls. The adipose-derived stem cells were maintained in Control Medium and HFFs were analyzed as negative controls.

1. Adipogenesis: Adipogenic differentiation was induced by culturing the stem cells for 2 weeks in Adipogenic Medium (AM) and assessed using an Oil Red O stain as an indicator of intracellular lipid accumulation (Preece, A. 1972 *A Manual for Histologic Technicians*, Boston, Mass.: Little, Brown, and Co.). Prior to staining, the cells were fixed for 60 minutes at room temperature in 4% formaldehyde/1% calcium and washed with 70% ethanol. The cells were incubated in 2% (w/v) Oil Red O reagent for 5 minutes at room temperature. Excess stain was removed by washing with 70% ethanol, followed by several changes of distilled water. The cells were counter-stained for 2 minutes with hematoxylin.

2. Osteogenesis: Osteogenic differentiation was induced by culturing the stem cells for a minimum of 2 weeks in Osteogenic Medium (OM) and examined for Alkaline Phosphatase (AP) activity and ECM calcification by von Kossa staining. To detect AP activity, cells were incubated in OM for 2 weeks, rinsed with PBS and stained with a 1% AP solution (1% napthol ABSI phosphate, 1 mg/ml Fast Red TR) at 37° C. for 30 minutes. For von Kossa staining, the cells were incubated in OM for 4 weeks and fixed with 4% paraformaldehyde for 60 minutes at room temperature. The cells were rinsed with distilled water and then overlaid with a 1% (w/v) silver nitrate solution in the absence of light for 30 minutes. The cells were washed several times with distilled water and developed under UV light for 60 minutes. Finally, the cells were counter-stained with 0.1% eosin in ethanol.

3. Chondrogenesis: Chondrogenic differentiation was induced using the micromass culture technique (Ahrens, P B, et al., 1977 Develop. Biol. 60:69-82; Reddi, A H 1982 Prog. Clin. Biol. Res. 110 (part B):261-268; Denker, A E., et al., 1995 Differentiation 59:25-34). Briefly, 10 μl of a concentrated adipose-derived stem cell suspension ($8 \times 10^6$ cells/ml) was plated into the center of each well and allowed to attach at 37° C. for two hours. Chondrogenic medium (CM) was gently overlaid so as not to detach the cell nodules and cultures were maintained in CM for 2 weeks prior to analysis. Chondrogenesis was confirmed using the histologic stain Alcian Blue at acidic pH. The stem cell nodules were fixed with 4% paraformaldehyde for 15 minutes at room temperature and washed with several changes of PBS. Studies have shown specific staining of sulfated proteoglycans, present in cartilagenous matrices, at pH levels of 1 and below (Lev, R. and S. Spicer 1964 J. Histochem. Cytochem. 12:309-312). In light of this, the cells were incubated for 30 minutes with 1% (w/v) Alcian Blue (Sigma A-3157) in 0.1N HCl (pH 1.0) and washed with 0.1N HCl for 5 minutes to remove excess stain. In addition to Alcian Blue staining, expression of the cartilage-specific collagen type II isoform was also determined. The stem cells were fixed in 4% paraformaldehyde for 15 minutes at room temperature. Cells were incubated in 0.2 U/ml chondroitinase ABC for 40 min at 37° C. to facilitate antibody access to collagen II. The cells were rinsed in PBS and endogenous peroxidase activity quenched by incubating for 10 minutes in 3% hydrogen peroxide in methanol. Following a wash in PBS, non-specific sites were blocked by incubating cells for 1 hour in Blocking Buffer (PBS, containing 10% Horse Serum). The cells were subsequently incubated for 1 hour in Blocking Buffer containing a monoclonal antibody specific to human collagen type II (ICN Biomedical, Costa Mesa, Calif.). The cells were washed extensively in Blocking Buffer and collagen type II visualized using a commercially available kit for the detection of monoclonal antibodies according to the manufacturer (VectaStain ABC kit, Vector Labs Inc., Burlingame, Calif.).

4. Myogenesis: Myogenic differentiation was induced by culturing the adipose-derived stem cells in Myogenic Medium (MM) for 6 weeks and confirmed by immunohistochemical staining for the muscle-specific transcription factor, MyoD1 and the myosin heavy chain. Cells were rinsed twice with PBS, fixed for 20 minutes with 4% paraformaldehyde and washed several times with PBS. The cells were incubated with 3% hydrogen peroxide in PBS for 10 minutes to quench endogenous peroxidase enzyme activity and non-specific sites were blocked by incubation in Blocking Buffer (PBS, 10% HS, 0.1% Triton X-100) for an additional 60 minutes. The cells were washed 3 times for 5 minutes each in Blocking Buffer and incubated for 1 hour in Blocking Buffer containing a either a monoclonal antibody specific to skeletal muscle myosin heavy chain (Biomeda, Foster City, Calif.) or to MyoD1 (Dako Corp, Carpenteria, Calif.). The cells were washed extensively in Blocking Buffer and the monoclonal antibodies visualized using the VectaStain ABC kit according to manufacturer's specifications. The cells were counter-stained with hematoxylin for 3 minutes.

Results

Human adipose tissue was obtained by suction-assisted lipectomy (i.e. liposuction) and the lipoaspirates were processed based on adapted methodologies (Katz, A J, et al., 1999 Clin. Plast. Surg. 26:587-603, viii), in order to obtain a Processed Lipoaspirate or PLA cell (adipose-derived stem cells) population, containing the putative stem cell fraction. Processing of 300 cc of liposuctioned tissue routinely yielded stem cell samples of $2-6\times10^8$ cells. The cultures were maintained in DMEM supplemented with 10% Fetal Bovine Serum (FBS). Supplementation with FBS has been shown to be important for human and animal MSC attachment and proliferation in vitro (Haynesworth, S E, et al., 1992 Bone 13:81-88; Lennon, D P, et al., 1995 Exp. Cell Res. 219:211-222; Lennon, D P, et al., 1996 In Vitro Cell Dev. Biol. 32:602-611). However, studies suggest that proliferation and differentiation of human MSCs may be dependent upon FBS source and quality, making sera screening critical (Lennon, D P, et al., 1995 Exp. Cell Res. 219:211-222; Lennon, D P, et al., 1996 In Vitro Cell Dev. Biol. 32:602-611). The stem cells expanded easily in vitro and exhibited a fibroblast-like morphology, consistent with that of MSCs obtained from bone marrow and a commercial source (FIG. 1A). The stem cells did not appear to require specific sera lots for expansion and multi-lineage differentiation. Ten FBS lots from three manufacturers were tested and did not appear to alter the stem cell morphology, proliferation rate or their differentiative capacity in vitro.

Growth Kinetics and Composition of the PLA

The adipose-derived stem cells, obtained from 20 donors and cultured under standard conditions (i.e. 10% FBS), exhibited an average population doubling time of 60 hours using several sera sources and lots. Following isolation, an initial lag time of 5 to 7 days was observed in stem cell cultures. Cells then entered a proliferative phase reaching confluence within 48 hours. To examine long-term growth kinetics of the stem cell cultures, we measured cumulative population doublings with respect to passage number in multiple donors. Consistent with the observed lag time upon initial culture, the stem cells underwent an average of three population doublings prior to the first passage (FIG. 1B). An average of 1.5 population doublings was observed upon subsequent passages. A linear relationship between cumulative population doubling and passage number was observed, indicating a relatively constant population doubling rate over the range studied. Furthermore, no appreciable decrease in cumulative population doublings was observed at later passages (P13=165 days in culture), suggesting that the stem cell cultures maintain their proliferative potential during extended culture periods.

In addition to cumulative population doubling, we also examined cell senescence in long-term stem cell cultures using a β-gal staining protocol, in which β-galactosidase expression is absent in proliferating cells but can be detected in senescent cells at a pH of 6.0 (Dimri, G P, et al., 1995 Proc. Natl. Acad. Sci. USA 92:9363-9367). Using this assay, the stem cell cultures were examined for senescence at each passage. The stem cell cultures at passage 1 exhibited no appreciable β-gal staining (FIG. 1C, P1). An increase in β-gal staining was observed at later passages, however the percentage of senescent cells remained below 5% through 10 passages and increased to 15% at passage 15. Taken together, the data indicates that adipose-derived stem cell samples are relatively stable over long-term culture, maintaining a consistent population doubling rate and exhibiting low levels of senescence.

Figure 2:
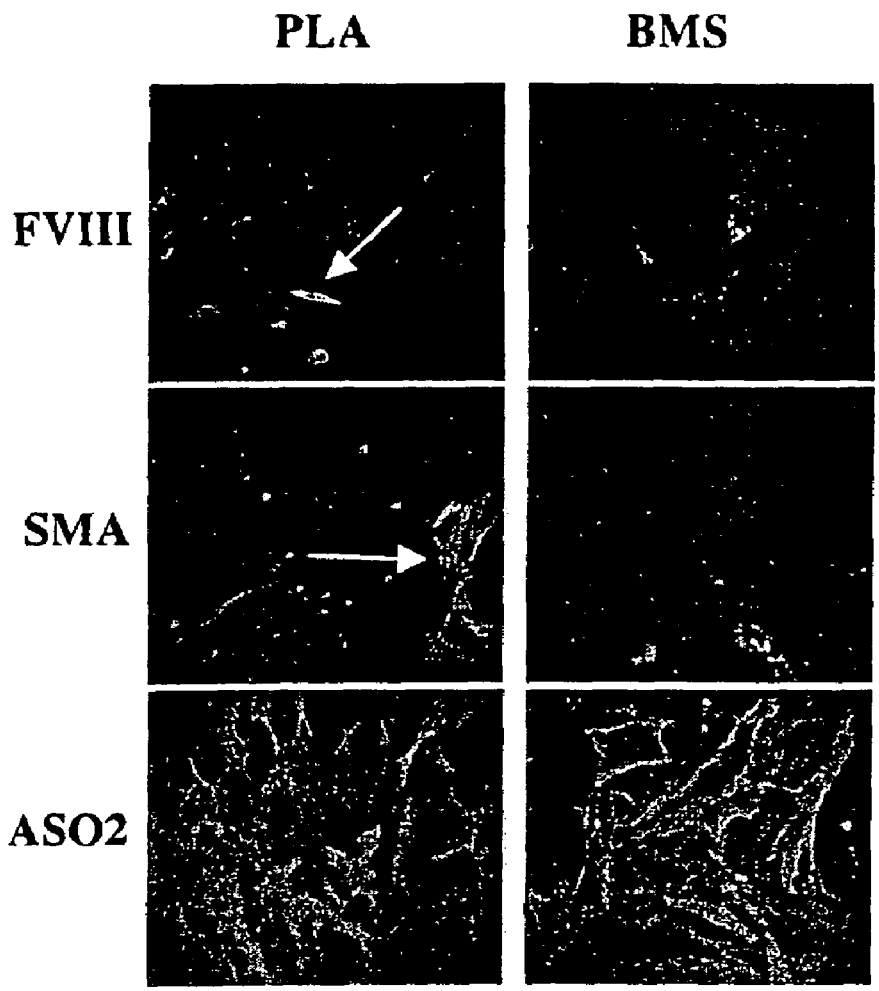
FIG. 2. Composition of the adipose-derived stem cells (PLA) as determined by indirect immunofluorescence (IF). Adipose-derived stem cells (PLA) and bone marrow stromal cells (BMS), were stained with the following antibodies: 1) anti-Factor VIII (FVIII); 2) anti-smooth muscle actin (SMA); and 3) ASO2 (ASO2). Factor VIII and smooth muscle actin expressing cells are shown (arrows).

The SVF processed from excised adipose tissue is a heterogenous population including mast cells, endothelial cells, pericytes, fibroblasts and lineage-committed progenitor cells, or pre-adipocytes (Pettersson, P. et al., 1984 Acta Med. Scand. 215:447-453; Hauner, H., et al., 1987 J. Clin. Endocrinol. Metabol. 64:832-835). These components may also be present, together with the putative stem cell fraction obtained from liposuctioned adipose tissue. However, no literature regarding this has been published. To phenotypically characterize the stem cells, samples from several donors were examined by indirect immunofluorescence using antibodies specific to established cell-surface markers. A bone marrow stromal fraction obtained from human marrow aspirates was also examined as a control. To identify endothelial cells, the stem cells were incubated with a monoclonal antibody to Factor VIII (Jaffe, E A, et al., 1973 J. Clin. Invest. 52:2757-2764; Nagle, R B, et al., 1987 Lymphology 20:20-24). Smooth muscle cells were identified using a monoclonal antibody to smooth muscle actin (Lazarides, E. 1982 Annu. Rev. Biochem. 51:219-250; Suza, S., et al., 1996 Eur. J. Cell Biol. 70:84-91). This antibody has also been shown to react with transitional pericytes (i.e. pericytes of pre- and post-capillaries) and the contractile apparatus of pericytes committed to the smooth muscle lineage (Nehls, A. and D. Drenckhahn 1991 J. Cell Biol. 113:147-154; Herman, I M and P A D'Amore 1985 J. Cell Biol. 101:43-52). Low levels of endothelial cells, smooth muscle cells and pericytes were observed in the stem cell fraction (FIG. 2). In comparison, no staining for these markers was observed in processed bone marrow stromal samples. In addition to Factor VIII and smooth muscle actin, cells were also incubated with a monoclonal antibody (ASO2) specific to fibroblasts and mesenchymal cells (Saalbach, A., et al., 1996 J. Invest. Dermatol. 106:1314-1319; Saalbach, A., et al., 1997 Cell and Tiss. Res. 290:595-599). The majority of the stem cells and bone marrow stromal cells stained positively with ASO2, suggesting a mesenchymal origin (FIG. 2, ASO2 panels).

Figure 3:
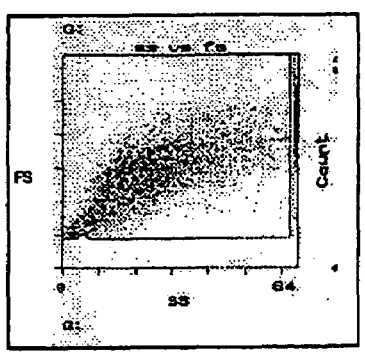
FIG. 3. Composition of the adipose-derived stem cells (PLA) as determined by flow cytometry. Panel A: Flow cytometry of adipose-derived stem cells (PLA) samples using forward and side scatter (FS and SS, respectively). A representative adipose-derived stem cells sample is shown. Panel B: The cell composition of a representative adipose-derived stem cells (PLA) sample from one donor was determined staining with the following monoclonal antibodies: anti-Factor VIII (FVIII), anti-smooth muscle actin (SMA), ASO2 and a monoclonal antibody to vimentin (VIM), an additional marker for cells of mesenchymal origin. Panel C: Flow cytometry data from 5 donors was collected and the mean number of positive events for each cell-specific marker is expressed as a percentage of total adipose-derived stem cells (PLA) cell number.
Figure 3:
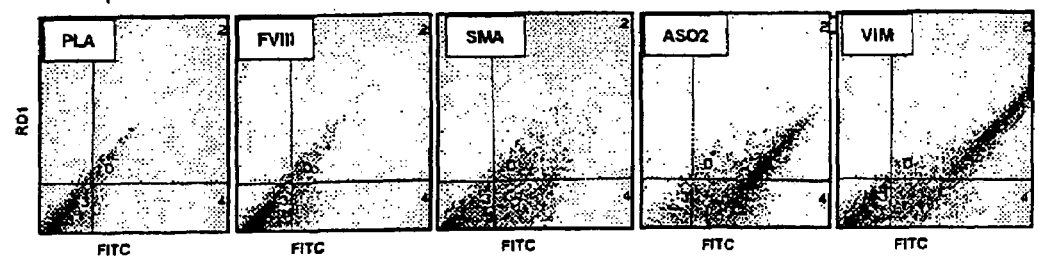
Figure 3:
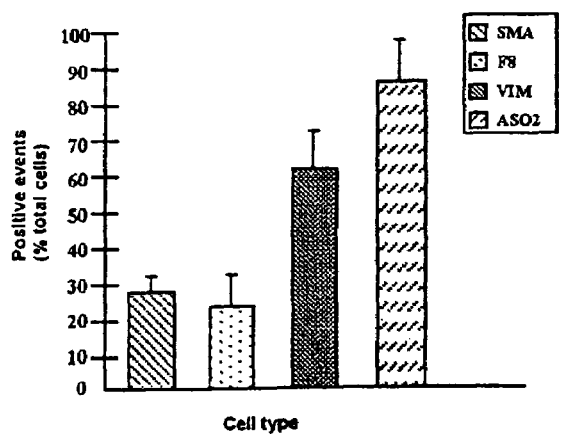

To quantitatively determine the stem cell composition, samples were analyzed by flow cytometry using the cell surface markers described above. The samples were obtained and cultured for 72 hours in Control Medium. Cell size and granularity were measured using forward and side scatter settings (FIG. 3A). The majority of the stem cell sample was comprised of small, agranular cells. In addition, the stem cells were incubated with monoclonal antibodies to Factor VIII, smooth muscle actin and ASO2 and a monoclonal antibody to vimentin, an intermediate filament protein found predominantly in cells of mesenchymal origin (Lazarides, E. 1982 Annu. Rev. Biochem. 51:219-250; Suza, S., et al., 1996 Eur. J. Cell Biol. 70:84-91). Viability was assessed using propidium iodide and samples were corrected for viability, non-specific fluorescence and autofluorescence. Data from a representative patient is shown (FIG. 3B). Cytometry data was collected from 5 donors and the number of positive events for each cell-specific marker was expressed as a percentage of the total stem cell number. Consistent with the immunofluorescent data, a fraction of the stem cells expressed Factor VIII (FVIII-positive cells=24.9%±8.2 of total stem cell number) and smooth muscle actin (SMA-positive cells=29.2%±2.1 of total PLA cell number) (FIG. 3C), indicating that the stem cell fraction contains endothelial cells, smooth muscle cells and, possibly, pericytes. Furthermore, the majority of the stem cells stained positively for ASO2 (ASO2-positive cells=85.0%±12.8 of total PLA cell number) and vimentin (VIM-positive cells=63.2%±5.6 of total cell number), indicative of cells of mesenchymal origin. Taken together, the results suggest that the stem cell fraction is a relatively homogenous population of mesodermal or mesenchymal cells with low contamination by endothelial cells, pericytes and smooth muscle cells.

Adipose-Derived Stem Cells Exhibit Multi-Lineage Potential:

To study the multi-lineage capacity of the adipose-derived stem cells cells, cells were differentiated toward the adipogenic, osteogenic, chondrogenic and myogenic lineages using lineage-specific induction factors (Table 1). Human and animal bone marrow-derived MSCs have been shown to differentiate toward the adipogenic, osteogenic and chondrogenic lineages with appropriate medium supplementation (Pittenger, M F., et al., 1999 Science 284:143-147; Grigoradis, A., et al., 1988 J. Cell Biol. 106:2139-2151; Cheng, S-L., et al., 1994 Endo 134:277-286; Loffler, G., et al., 1987 Klin. Wochenschr. 65:812-817; Hauner, H., et al., 1987 J. Clin. Endocrinol. Metabol. 64:832-835). Following induction, differentiation was assessed using histology and immunohistochemistry (Table 2). Commercially available MSCs and lineage-committed progenitor cells served as positive controls while the stem cells maintained in Control Medium and HFF cells were examined as negative controls.

Figure 4:
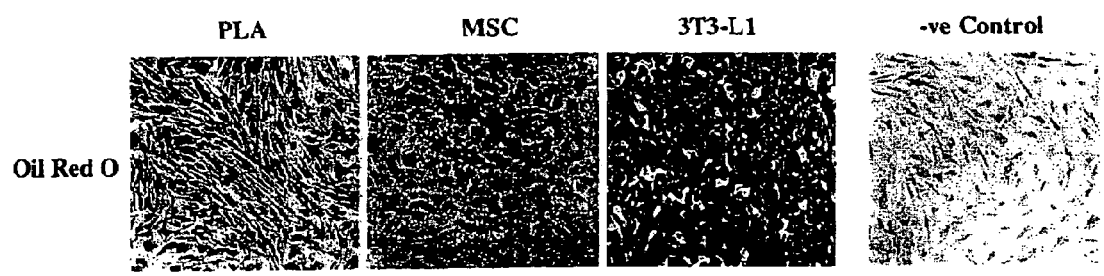
FIG. 4. Adipose-derived stem cells (PLA) accumulate lipid-filled droplets upon treatment with Adipogenic Medium (AM). Adipose-derived stem cells (PLA), bone marrow-derived MSCs (MSC), and 3T3-L1 pre-adipocyte cells (3T3-L1) were cultured for two weeks in AM and stained with Oil Red O to identify lipid-filled intracellular vacuoles. Undifferentiated PLA cells maintained in Control Medium (−ve Control) were stained as a negative control.

Pre-adipocytes and MSCs treated with adipogenic induction medium, containing cAMP agonists and induction agents such as isobutyl-methylxanthine (IBMX), indomethacin, insulin and dexamethasone, develop lipid-containing droplets that accumulate the lipid dye Oil Red-O (Pittenger, M F., et al., 1999 Science 284:143-147; Rubin, C S, et al., 1978 J. Biol. Chem. 253:7570-7578; Deslex, S, et al., 1987 Int. J. Obesity 11:19-27). To determine if PLA cells undergo adipogenesis, cells were cultured in medium containing these agents (Adipogenic Medium, AM) and stained with Oil Red-O. The stem cells cultured in AM were reproducibly induced toward the adipogenic lineage as early as two weeks post-induction (FIG. 4). A significant fraction of the cells contained multiple, intracellular lipid-filled droplets that accumulated Oil Red-O. The Oil Red O-containing stem cells exhibited an expanded morphology with the majority of the intracellular volume (90-98%) occupied by lipid droplets, consistent with the phenotype of mature adipocytes. The mean level of adipogenic differentiation measured in 6 donors under 35 years of age was 42.4%±10.6% (% Oil Red O-positive cells/total PLA cell number). Prolonged culture times (i.e. 4 weeks) resulted in the detachment of differentiating cells from the culture plate and flotation to the surface. The observed morphology and lipid accumulation of differentiated stem cells were similar to that observed upon treatment of bone marrow-derived MSCs and the pre-adipocyte cell line, 3T3-L1, in AM. No lipid droplets were observed in undifferentiated stem cells or in HFF negative controls. In contrast to MSCs, in which adipogenic differentiation dramatically decreases beyond the third culture passage (Conget, P A and J J Minguell 1999 J. Cell. Physiol. 181:67-73), the adipogenic potential of the stem cells was maintained over long-term culture (i.e. passage 15=175 days culture). Taken together, the results indicate that the stem cells undergo adipogenic differentiation.

Figure 5:
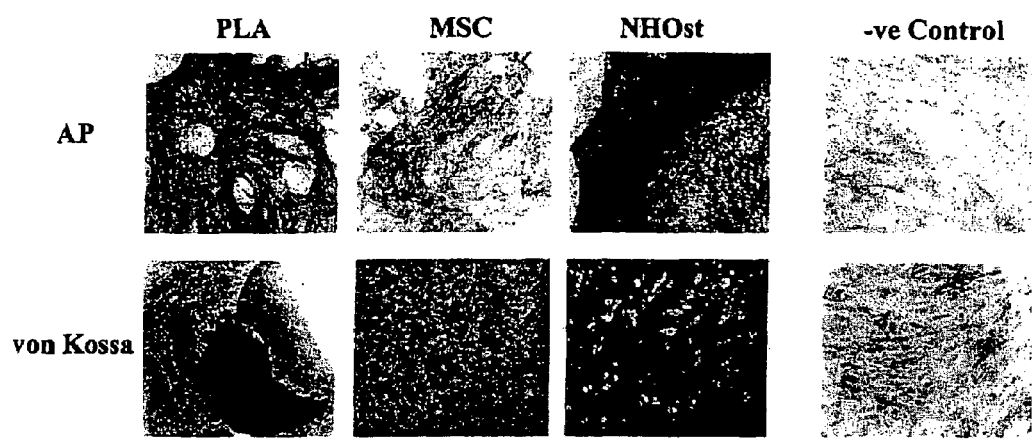
FIG. 5. Adipose-derived stem cells (PLA) induced with Osteogenic Medium (OM) express Alkaline Phosphatase and are associated with a calcified extracellular matrix (ECM). Adipose-derived stem cells (PLA), bone marrow-derived MSCs (MSC) and a human osteoblast cell line (NHOst) were cultured in OM to induce osteogenesis. Cells were stained at 2 weeks for Alkaline Phosphatase activity (AP; red). The presence of a calcified extracellular matrix (black regions) was examined at 4 weeks (von Kossa). Undifferentiated adipose-derived stem cells maintained in Control Medium were examined for AP expression and matrix calcification as a negative control (−ve Control).

Differentiation of osteoprogenitor cells and marrow-derived MSCs into osteoblasts is induced in vitro by treating cells with low concentrations of ascorbic acid, β-glycerophosphate and dexamethasone (Pittenger, M F, et al., 1999 Science 284:143-147; Cheng, S-L, et al., 1994 Endo 134:277-286; Conget, P A and J J Minguell 1999 J. Cell. Physiol. 181:67-73). Early differentiation of these cells into immature osteoblasts is characterized by Alkaline Phosphatase (AP) enzyme activity with human MSCs expressing AP as early as 4 days and maximum levels observed at 12 days post-induction (Jaiswal, N, et al., 1997 J. Cell Biochem. 64:295-312). To confirm their osteogenic capacity, the stem cells were treated with osteogenic medium (OM) for 14 days and the expression of AP was examined. The stem cells cultured in OM formed an extensive network of dense, multi-layered nodules that stained positively for AP (FIG. 5). The mean number of AP-positive staining cells measured in 6 donors was 50.2%±10.8% of total stem cell number. Expression of AP was also observed in both MSCs and NHOst positive controls maintained in OM. In contrast, undifferentiated stem cells and HFF negative controls did not show evidence of AP expression. While AP expression is dramatically upregulated in osteogenic tissues, its expression has been observed in several non-osteogenic cell types and tissues such as cartilage, liver and kidney (Henthorn, P S, et al., 1988 J. Biol. Chem. 263:12011; Weiss, M J, et al., 1988 J. Biol. Chem. 263:12002; Leboy, P S, et al., 1989 J. Biol. Chem. 264: 17281). Therefore, AP expression is frequently used, in conjunction with other osteogenic specific markers, as an indicator of osteogenesis. One such indicator is the formation of a calcified extracellular matrix (ECM). Mature osteoblasts secrete a collagen I-rich ECM that becomes calcified during the later stages of differentiation (Scott, D M 1980 Arch. Biochem. Biophys. 201:384-391). Therefore, in order to confirm osteogenic differentiation, calcification of the ECM matrix was assessed in the stem cells using a von Kossa stain. Calcification appears as black regions within the cell monolayer. Consistent with osteogenesis, several black regions, indicative of a calcified ECM, were observed in the stem cells treated for 4 weeks in OM. Calcification was also identified in MSC and NHOst positive controls, while no calcification was observed in undifferentiated stem cells or HFF cells. The osteogenic potential of the stem cells was maintained over long-term culture, with cells expressing AP as late as 175 days of culture. Taken together, the expression of AP by the adipose-derived stem cells and the production of a calcified ECM strongly suggests that these adipose-derived cells can be induced toward the osteogenic lineage.

Figure 6:
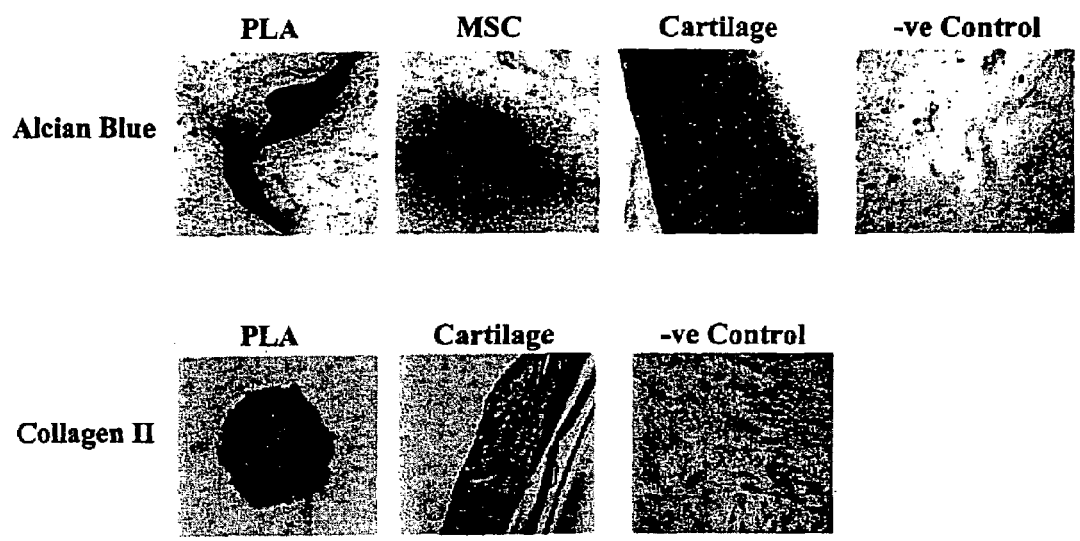
FIG. 6. Adipose-derived stem cells (PLA) treated with Chondrogenic Medium (CM) are associated with a proteoglycan-rich matrix and express collagen type II. Adipose-derived stem cells (PLA) and MSCs (MSC) were cultured for 2 weeks in CM using the micromass technique to induce chondrogenesis. The cells were fixed and processed for the presence of sulfated proteoglycans with Alcian Blue under acidic conditions (Alcian Blue). Paraffin sections of human cartilage were used as a positive control (Cartilage) while undifferentiated PLAs maintained in Control Medium were processed as a negative control (−ve Control). In addition, the expression of cartilage-specific collagen type II (Collagen II) was examined in PLA cells and human cartilage sections. Adipose-derived stem cells cultured in Control Medium (−ve Control) were stained with Alcian Blue and for collagen II expression as a negative control.

Chondrogenic differentiation can be induced in vitro using a micromass culture technique, in which cellular condensation (a critical first event of chondrogenesis) is duplicated (Ahrens P. B., et al., 1977 Develop. Biol. 60: 69-82; Reddi A. H. 1982 Prog. Clin. Biol. Res. 110 Pt B: 261-268; Denker, A. E., et al., 1995 Differentiation 59, 25-34; Tacchetti, C, et al., 1992 Exp Cell Res. 200:26-33). Enhanced differentiation can be obtained by treating cells with dexamethasone and TGFβ1 (Iwasaki, M. et al., 1993 Endocrinology 132:1603-1608). Marrow-derived MSCs, cultured with these agents under micromass conditions, form cell nodules associated with a well-organized ECM rich in collagen II and sulfated proteoglycans (Pittenger, M F, et al., 1999 Science 284:143-147; Mackay, A M, et al., 1998 Tissue Eng. 4:415-428). These sulfated proteoglycans can be specifically detected using the stain Alcian Blue under acidic conditions (Lev, R and S. Spicer 1964 J. Histochem. Cytochem. 12:309-312). To assess the chondrogenic capacity of the stem cells, the cells were cultured via micromass in Chondrogenic Medium (CM), containing dexamethasone and TGFβ1. Micromass culture of the stem cells resulted in the formation of dense nodules consistent with chondrogenic differentiation. The stem cell nodules were associated with an Alcian Blue-positive ECM, indicative of the presence of sulfated proteoglycans within the matrix (FIG. 6). Cartilaginous nodules were also observed upon micromass culture of MSC controls. To confirm the specificity of Alcian Blue for cartilaginous matrices, human cartilage and bone sections were stained with Alcian Blue under acidic conditions. As expected, human cartilage sections stained positively with Alcian Blue, while no staining was observed in bone sections. In addition to the presence of sulfated proteoglycans within the ECM, both stem cells and human cartilage sections expressed the cartilage-specific collagen type II isoform, while no staining was observed in undifferentiated stem cells. Consistent with adipogenic and osteogenic differentiation, the stem cells retained their chondrogenic differentiation potential after extended culture periods (i.e. up to 175 days). The above results suggest that the adipose-derived stem cells possess the capacity to differentiate toward the chondrogenic lineage.

Figure 7:
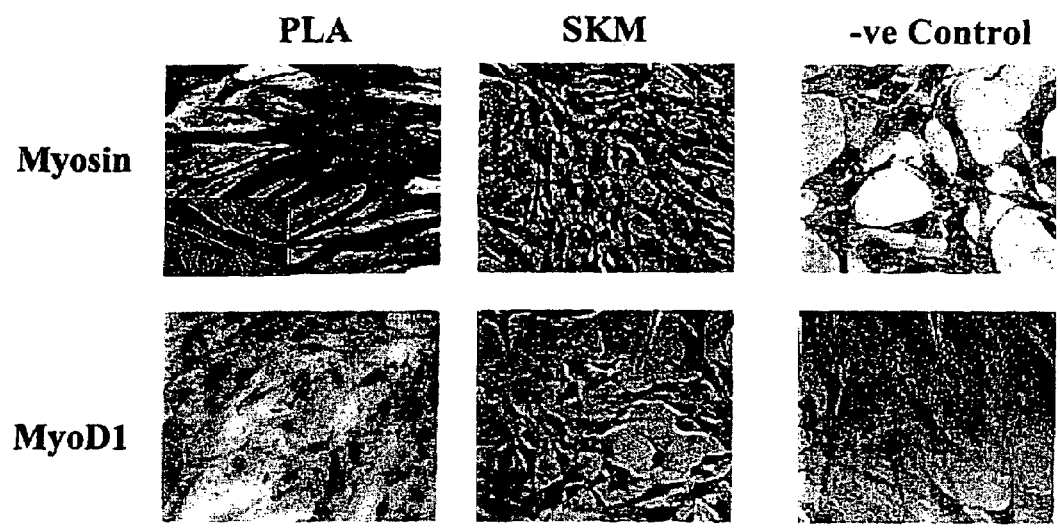
FIG. 7. Adipose-derived stem cells (PLA) cultured in Myogenic Medium (MM) express the myosin heavy chain and MyoD1. Adipose-derived stem cells (PLA) were treated with MM and stained with antibodies specific to skeletal muscle myosin heavy chain (Myosin) or MyoD1 (MyoD1). A human skeletal muscle cell line (SKM) was examined as a positive control. In addition, the presence of multinucleated cells in adipose-derived stem cells cultures is shown (PLA, inset box). Myosin and MyoD1 expression was also assessed in undifferentiated adipose-derived stem cells (−ve Control) as a negative control.

Myogenesis is characterized by a period of myoblast proliferation, followed by the expression of muscle-specific proteins and fusion to form multinucleated myotubules. Early myogenic differentiation is characterized by the expression of several myogenic regulatory factors including Myogenic Determination factor1 (MyoD1; (Davis, R. L., et al., 1987 Cell 51:987-1000; Weintraub, H., et al., 1991 Science 251: 761-763; Dias, P., et al., 1994 Semin. Diagn. Pathol. 11:3-14). Terminally differentiated myoblasts can be characterized by the expression of myosin and the presence of multiple nuclei (Silberstein, L., et al., 1986 Cell 46:1075-1081). Proliferation and myogenic differentiation of muscle precursors and bone marrow-derived stem cells can be induced by dexamethasone and results in the expression of muscle-specific proteins (Grigoradis, A, et al., 1988 J. Cell Biol. 106:2139-2151; Ball, E H and B D Sanwal 1980 J. Cell. Physiol 102:27-36; Guerriero, V and J R Florini 1980 Endocrinology 106:1198-1202). Furthermore, addition of hydrocortisone is known to stimulate human myoblast proliferation, prior to their transition into differentiated myotubules (Zalin, R J 1987 Exp. Cell Res. 172:265-281). To examine if the stem cells undergo myogenesis, the cells were cultured for 6 weeks in the presence of dexamethasone and hydrocortisone, and incubated with antibodies specific to MyoD1 and myosin (heavy chain). Consistent with early myogenic differentiation, treatment of the stem cells with MM for 1 week induced the expression of MyoD1 (FIG. 7). The stem cells treated for longer time periods (6 weeks) stained positively for myosin. In addition to myosin expression, the presence of discrete 'patches' of large, elongated cells with multiple nuclei were also observed, suggesting that the stem cells underwent myoblast fusion (PLA panel, inset). MyoD1 and myosin heavy chain expression were also detected in human skeletal muscle positive control cells. Using Myogenic Medium, myogenic differentiation was not observed in MSC controls even at 6 weeks of induction. These cells may be adversely affected by hydrocortisone and may require alternate conditions to induce differentiation. Myogenic differentiation levels in the stem cells averaged 12%. Multi-nucleation, myosin heavy chain and MyoD1 expression were not observed in undifferentiated stem cells nor in HFF negative controls. The presence of multi-nucleated cells and the expression of both MyoD1 and myosin heavy chain suggests that the adipose-derived stem cells have the capacity to undergo myogenic differentiation.

TABLE 1

Lineage-specific differentiation induced by media supplementation

| Medium | Media | Serum | Supplementation |
|---|---|---|---|
| Control | DMEM | 10% FBS | none |
| Adipogenic (AM) | DMEM | 10% FBS | 0.5 mM isobutyl-methylxanthine (IBMX), 1 µM dexamethasone, 10 µM insulin, 200 µM indomethacin, 1% antibiotic/antimycotic |
| Osteogenic (OM) | DMEM | 10% FBS | 0.1 µM dexamethasone, 50 µM ascorbate-2-phosphate, 10 mM β-glycerophosphate, 1% antibiotic/antimycotic |
| Chondrogenic (CM) | DMEM | 1% FBS | 6.25 µg/ml insulin, 10 ng/ml TGFβ1, 50 nM ascorbate-2-phosphate, 1% antibiotic/antimycotic |
| Myogenic (MM) | DMEM | 10% FBS, 5% HS | 0.1 µM dexamethasone, 50 µM hydrocortisone, 1% antibiotic/antimycotic |

TABLE 2

Differentiation markers and assays of lineage-specific differentiation

| Lineage | Lineage-specific determinant | Histologic/immuno-histochemical assay |
|---|---|---|
| Adipogenic | Lipid accumulation | Oil Red O stain |
| Osteogenic | 1. Alkaline phosphatase activity<br>2. Calcified matrix production | 1. Alkaline Phosphatase stain<br>2. Von Kossa stain |
| Chondrogenic | 1. Sulfated proteoglycan-rich matrix<br>2. Collagen II synthesis | 1. Alcian Blue (pH 1.0) stain<br>2. Collagen II-specific monoclonal antibody |
| Myogenic | 1. Multi-nucleation<br>2. Skeletal muscle myosin heavy chain & MyoD1 expression | 1. Phase contrast microscopy<br>2. Myosin & MyoD1 specific monoclonal antibodies |

Discussion

Conceptually, there are two general types of stem cells: Embryonic Stem Cells (ESCs) and autologous stem cells. Although theoretically appealing because of their pluripotentiality, the practical use of ESCs is limited due to potential problems of cell regulation and ethical considerations. In contrast, autologous stem cells, by their nature, are immunocompatible and have no ethical issues related to their use. For the engineering of mesodermally derived tissues, autologous stem cells obtained from bone marrow have proven experimentally promising. Human bone marrow is derived from the embryonic mesoderm and is comprised of a population of Hematopoeitic Stem Cells (HSCs), supported by a mesenchymal stroma (Friedenstein A. J., et al., 1968 Transplantation 6: 230-47; Friedenstein A. J., et al., 1974 Transplantation 17: 331-40; Werts E. D., et al., 1980 Exp. Hematol. 8: 423; Dexter T. M. 1982 J. Cell Physiol. 1: 87-94; Paul S. R., et al., 1991 Blood 77: 1723-33). While the proliferation and differentiation of HSCs has been well documented, less is known about the stromal component. The bone marrow stroma, in both animals and humans, is heterogenous in composition, containing several cell populations, including a stem cell population termed Mesenchymal Stem Cells or MSCs (Caplan A I 1991 J. Orthop. Res. 9:641-650). Studies on MSCs have demonstrated their differentiation into adipocytes (Beresford J. N., et al., 1992 J. Cell Sci. 102; 341-351; Pittenger M. F., et al., 1999 Science 284: 143-147), chondrocytes (Caplan A. I. 1991 J. Orthop. Res. 9: 641-50; Pittenger M. F., et al., 1999 Science 284: 143-147; Berry L., et al., 1992 J. Cell Sci. 101: 333-342; Johnstone B., et al., 1998 Exp. Cell Res. 238: 265-272; Yoo J. U., et al., 1998 J. Bone Joint Surg. Am. 80: 1745-1757), myoblasts (Wakitani S., et al., 1995 Muscle Nerve 18: 1417-1426; Ferrari G., et al., 1998 Science 279: 1528-1530) and osteoblasts (Caplan A. I. 1991 J. Orthop. Res. 9: 641-50; Pittenger M. F., et al., 1999 Science 284: 143-147; Grigoradis A., et al., 1988 J. Cell Biol. 106:2139-2151; Cheng S-L., et al., 1994 Endo 134: 277-286, 1994; Haynesworth S. E., et al., 1992 Bone 13: 81-8; Rickard D. J., et al., 1996 J. Bone Min. Res. 11: 312-324; Prockop D. J. 1997 Science 276: 71-74; Dennis J. E., et al., 1999 J. Bone Miner. Res. 14: 700-709). These cells represent a promising option for future tissue engineering strategies. However, traditional bone marrow procurement procedures may be painful, frequently requiring general or spinal anesthesia and may yield low numbers of MSCs upon processing (approximately 1 MSC per $10^5$ adherent stromal cells (Pittenger, M F et al., 1999 Science 284:143-147; Rickard, D J, et al., J. Bone Min. Res. 11:312-324: Bruder, S P, et al., 1997 J. Cell. Biochem. 64:278-294)). From a practical standpoint, low stem cell numbers necessitate an ex vivo expansion step in order to obtain clinically significant cell numbers. Such a step is time consuming, expensive and risks cell contamination and loss. An ideal source of autologous stem cells would, therefore, be both easy to obtain, result in minimal patient discomfort yet be capable of yielding cell numbers substantial enough to obviate extensive expansion in culture.

We report that a cellular fraction with multiple mesodermal lineage capabilities can be processed from human lipoaspirates. This cellular fraction is the adipose-derived stem cells which is designated a Processed Lipoaspirate (PLA), comprising fibroblast-like cells that can be expanded easily in vitro without the need for specific sera lots or media supplementation. The stem cell samples maintained a linear growth rate with no appreciable senescence over extended culture periods. The stem cell population was heterogenous in nature, with the majority of the cells being mesenchymal in origin. However, contaminating endothelial, smooth muscle and pericyte cell populations were identified. The stem cells also exhibited multi-lineage potential in vitro, differentiating toward the adipogenic, osteogenic, chondrogenic and myogenic lineages when cultured in the presence of established lineage-specific differentiation factors. The differentiation results were consistent with those observed upon lineage-specific differentiation of bone marrow-derived MSCs and lineage-committed precursors.

While the apparent multi-differentiative capacity of the stem cells suggests the presence of a stem cell population within human liposuctioned adipose tissue, it is not conclusive. Multi-lineage differentiation may also be due to the presence of: (1) multiple lineage-committed progenitor cells; (2) multi-potent cells from other sources (e.g. pericytes, marrow-derived MSCs from peripheral blood); or (3) a combination of the above.

The observed differentiation may be due to the presence of lineage-committed progenitor cells, such as pre-osteoblasts, pre-myoblasts or pre-adipocytes within the stem cell fraction. Cellular fractions (i.e. SVFs) obtained from excised adipose tissue are known to contain pre-adipocytes that differentiate into mature adipocytes (Pettersson, P, et al., 1984 Acta Med. Scand. 215:447-453; Pettersson, P, et al., 1985 Metabolism 34:808-812). It is possible that the observed adipogenic differentiation by the stem cells is simply the commitment of existing pre-adipocytes and not the differentiation of a multipotent cell. However, we do not believe this to be the case. As little as 0.02% of the SVF obtained from excised adipose tissue have been identified as pre-adipocytes capable of adipogenic differentiation (Pettersson, P, et al., 1984 Acta Med. Scand. 215:447-453). If pre-adipocyte numbers within the stem cell fraction are comparable to those levels measured in the SVF from excised tissue, one would expect a relatively low level of adipogenesis. However, the degree of adipogenesis observed in the stem cells is significant (approximately 40% of the total PLA cell number) and may result from the differentiation of additional cell types.

Damage to the underlying muscle during liposuction may introduce myogenic precursor cells or satellite cells into the stem cell fraction, resulting in the observed myogenic differentiation by these cells. Located between the sarcolemma and the external lamina of the muscle fiber, myogenic precursor cells in their undifferentiated state are quiescent and exhibit no distinguishing features, making their identification difficult. Several groups have attempted to identify unique markers for these precursors with limited success. Currently, the expression of the myogenic regulatory factors, MyoD1 and myogenin have been used to identify satellite cells during embryogenesis and in regenerating adult muscle in rodents (Cusella-DeAngelis, M. C., et al., 1992 Cell Biol. 116:1243-

1255; Grounds, M. D., et al., 1992 Cell Tiss. Res. 267:99-104; Sassoon, D. A. 1993 Develop. Biol. 156:11; Maley, M. A. L., et al., 1994 Exp. Cell Res. 211:99-107; Lawson-Smith, M. J. and McGeachie, J. K. 1998 J. Anat. 192:161-171). In addition, MyoD1 expression has been identified in proliferating myoblasts prior to the onset of differentiation (Weintraub, H, et al., Science 251:761-763). While these markers have not been used to identify myogenic precursors in human subjects, MyoD1 is expressed during early myogenic differentiation in normal skeletal muscle and has been used to identify the skeletal muscle origin of rhabdosarcomas in humans 77-79 (Dias, P., et al., 1990 Am. J. Pathol. 137:1283-1291; Rosai, J., et al., 1991 Am. J. Surg. Pathol. 15:974; Nakano, H., et al., 2000 Oncology 58:319-323). The absence of MyoD1 expression in the stem cells maintained in non-inductive Control Medium (see FIG. 28), suggests that our observed myogenic differentiation is not due to the presence of myogenic precursors or proliferating myoblasts within the stem cell fraction. Consistent with this, the blunt contour of the liposuction cannula would make it extremely difficult to penetrate the fibrous fascial cavity surrounding the muscle and introduce these precursors into the adipose compartment.

Human adipose tissue is vascularized and, as such, contains potential systemic vascular 'conduits' for contamination by multi-potent cells, such as pericytes and marrow-derived MSCs. Disruption of the blood supply during liposuction may result in the release of pericytes, known to possess multi-lineage potential both in vivo and in vitro (Schor, A M, et al., 1990 J. Cell Sci. 97:449-461; Doherty, M J 1998 J. Bone Miner. Res. 13:828-838; Diefenderfer, D L and C T Brighton 2000 Biochem. Biophys. Res. Commun. 269:172-178). Consistent with this, our immunofluorescent and flow cytometry data show that a small fraction of the stem cells is comprised of cells that express smooth muscle actin, a component of transitional pericytes and pericytes committed to the smooth muscle lineage (Nehls, A. and D Drenckhahn 1991 J. Cell Biol. 113:147-154). The multi-lineage differentiation observed in the stem cells may be, in part, due to the presence of pericytes. Disruption of the blood supply may also introduce MSCs into the stem cell fraction. However, the literature is conflicted as to the presence of these stem cells in the peripheral blood Huss, R 2000 Stem Cells 18:1-9; Lazarus, H M, et al., 1997 J. Hematother. 6:447-455). If the peripheral blood does indeed represent a source of MSCs, our observed multi-lineage differentiation may be due to the contamination of adipose tissue by these stem cells (MSCs). However, MSCs are a small constituent of the bone marrow stroma in humans (approximately 1 MSC per $10^5$ adherent stromal cells (Pittenger, M F, et al., 1999 Science 284:143-147; Rickard, D J 1996 J. Bone Min. Res. 11:312-324; Bruder, S P, et al., 1997 J. Cell. Biochem. 64:278-294). If these cells do exist in peripheral blood, they are likely to be in even smaller quantities than in the bone marrow and contamination levels of the adipose-derived stem cells fraction by these cells may be negligible.

While these arguments may provide support for the presence of a multi-potent stem cell population within liposuctioned adipose tissue, definitive confirmation requires the isolation and characterization of multiple clones derived from a single cell. Preliminary data confirms that clonal stem cell populations possess multi-lineage potential, capable of adipogenic, osteogenic, and chondrogenic differentiation.

Current research has demonstrated positive results using bone marrow-derived MSCs. MSCs can differentiate into osteogenic and chondrogenic tissues in vivo (Benayahu, D. et al., 1989 J. Cell Physiol 140:1-7; Ohgushi, H M 1990 Acta Orthop. Scand. 61:431-434; Krebsbach, P H, et al., 1997 Transplantation 63:1059-1069; Bruder, S P, et al., 1998 J. Orthop. Res. 16:155-162) and preliminary data suggests that these cells can be used to repair bony and cartilagenous defects (Wakitani, S., et al., 1995 Muscle Nerve 18:1417-1426; Krebsbach, P H, et al., 1997 Transplantation 63:1059-1069; Bruder, S P, et al., 1998 J. Orthop. Res. 16:155-162; Bruder, et al., 1998 Clin. Orthop. S247-56; Krebsbach, P H 1998 Transplantation 66:1272-1278; Johnstone and Yoo 1999 Clin. Orthop. S156-162). The stem cells obtained from liposuctioned adipose tissue may represent another source of multi-lineage mesodermal stem cells. Like the bone marrow stroma, these data suggests that adipose tissue may contain a significant fraction of cells with multi-lineage capacity. These adipose-derived stem cells may be readily available in large quantities with minimal morbidity and discomfort associated with their harvest.

EXAMPLE 8

The following description provides adipose-derived stem cells which differentiate into osteogenic tissue, and methods for isolating said stem cells. The osteogenic potential of the stem cells decreases with the age of the donor. However, adipogenesis is not affected by age of the donor.

Materials and Methods

Lipoaspirate Collection and Processing:

Human adipose tissue was obtained from elective liposuction procedures under local anesthesia according to patient consent protocol HSPC #98-08 011-02 (University of California Los Angeles). The raw lipoaspirate was processed to obtain the adipose-derived stem cells population (Zuk, P, et al., 2001 Tissue Engineering 7:209-226). Briefly, raw lipoaspirates were washed extensively with equal volumes of Phospho-Buffered Saline (PBS) and the extracellular matrix (ECM) was digested at 37° C. for 30 minutes with 0.075% collagenase. Enzyme activity was neutralized with Dulbecco's Modified Eagle's Medium (DMEM; Life Technologies), containing 10% Fetal Bovine Serum (FBS; HyClone) and centrifuged at 1200×g for 10 minutes. The stem cell pellet was resuspended in DMEM/10% FBS and filtered through a cell strainer to remove any remaining tissue. The cells were incubated overnight at 37° C., 5% $CO_2$ in non-inductive control medium (DMEM, 10% FBS, 1% antibiotic/antimycotic solution). Following incubation, the plates were washed extensively with PBS to remove residual non-adherent red blood cells. The stem cells were maintained at 37° C., 5% $CO_2$ in control medium (Table 3). To prevent spontaneous differentiation, cultures were maintained at sub-confluent levels.

TABLE 3

Lineage-Specific Differentiation Induced By Media Supplementation

| Medium | Media | Serum | Supplementation |
|---|---|---|---|
| Control | DMEM | 10% FBS | none |
| Adipogenic | DMEM | 10% FBS | 0.5 mM isobutyl-methylxanthine (IBMX), 1 µM dexamethasone, 10 µM insulin, 200 µM indomethacin, 1% antibiotic/antimycotic |
| Osteogenic | DMEM | 10% FBS | 0.1 µM dexamethasone, 50 µM ascorbate-2-phosphate, 10 mM β-glycerophosphate, 1% antibiotic/antimycotic |

Induction and Analysis of Differentiation:

1. Adipogenic Differentiation: PLA cells (passage 1) were seeded into six well plates (Costar, Cambridge, Mass.) at a density of $4 \times 10^4$ cells per well and cultured in control medium for 72 hours. To induce adipogenic differentiation, PLA cells were cultured for 2 weeks in Adipogenic Medium (Table 3). PLA cells, at the same density, were maintained in control medium as a negative control.

Oil Red O Staining: Adipogenesis was confirmed at two weeks post-induction by staining with Oil Red O to identify intracellular lipid vacuoles. Cells were fixed for 60 minutes at room temperature in 4% formaldehyde/1% calcium and washed with 70% ethanol. The cells were incubated in 2% (w/v) Oil Red O reagent (Sigma, St Louis, Mo.) for 5 minutes at room temperature. Excess stain was removed by washing with 70% ethanol, followed by several changes of distilled water. The cells were counter-stained for 1 minute with hematoxylin.

2. Osteogenic Differentiation: PLA cells (passage 1) were seeded into six well plates at a density of $1 \times 10^4$ cells per well and cultured for 72 hours in control medium. Based on previous studies on bone marrow-derived Mesenchymal stem cells (Pittenger, M F 1999 Science 284:143-147), PLA cells were maintained for a minimum of two weeks in Osteogenic Medium (Table 3) to induce osteogenesis. PLA cells were maintained in control medium as a negative control.

Alkaline Phosphatase Staining: Alkaline phosphatase (AP) activity was examined at 14 days post-induction. PLA cells were rinsed with PBS and incubated for 30 minutes at 37° C. in 0.05M Tris-HCl (pH 9) containing 1% (v/v) of a 50 mg/ml solution of naphthol AS-Biphosphate (Sigma) dissolved in dimethyl sulfoxide (DMSO) and 1 mg/ml Fast Red TR salt (Sigma). Following incubation, cells were fixed for 10 minutes with an equal volume of 8% paraformaldehyde, followed by a rinse with distilled water.

Von Kossa Staining: Extracellular matrix calcification was detected at four weeks post-induction by von Kossa staining. PLA cells were fixed with 4% paraformaldehyde at room temperature for 1 hour, followed by a 30 minute incubation with a 5% (w/v) silver nitrate solution (Sigma) in the absence of light. The cells were washed several times with distilled water, developed under UV light for 60 minutes and counter-stained with 0.1% eosin in ethanol. Matrix calcification was identified by the presence of black extracellular deposits.

Quantitation of Differentiation:

Adipogenic and osteogenic differentiation levels in each donor were quantified using a Zeiss Axioscope 2 microscope fitted with a Spot 2 digital camera and a 20× objective (magnification 200×). The total number of Oil Red O- and AP-positive cells (adipogenesis and osteogenesis, respectively) in duplicate samples from each donor were counted within three consistent regions from each well (e.g., at positions 3, 6 and 9 o'clock). The total number of positive-staining cells was expressed as a percentage of total PLA cell number counted within each region. Values from the three regions were averaged to give the mean differentiation level for each donor. The mean level of differentiation was expressed with respect to patient age. Von Kossa identifies regions of matrix production rather than individual differentiated cells, therefore this staining procedure was used to confirm osteogenic differentiation.

Quantitation of Osteogenic Precursors within PLA Samples:

In order to estimate the number of osteogenic precursors within the PLA population, cells with osteogenic activity were counted and related to patient age. Specifically, two age groups were examined: Group A=20 to 39 years and Group B=40 to 60 years. First-passage PLA cells (P1) were seeded onto 100 mm dishes, induced toward the osteogenic lineage as described above and stained for AP activity to confirm differentiation. Precursor number within each PLA sample was determined by counting the number of AP-positive colony forming units (CFU/AP$^+$). Based on a previous study, a minimum of ten AP-positive cells was used to identify a CFU/AP$^+$ (Long, M, et al., 1999 J. Gerontol. A. Biol. Sci. Med. Soc. 54:B54-62). The average number of CFU/AP$^+$ was determined and expressed with respect to age group. The optimal number of PLA cells required for osteogenic differentiation was determined empirically ($1 \times 10^4$, $5 \times 10^4$, $1 \times 10^5$ and $5 \times 10^5$ cells plated per dish). While osteogenic differentiation levels were greatest at $5 \times 10^5$ cells per dish, confluency levels prevented accurate colony counting. Data was therefore obtained using a density of $1 \times 10^5$ cells per dish.

Growth Kinetics:

To measure PLA cell growth kinetics (population doubling) with respect to donor age, PLA cells from each donor (P1) were seeded at a density of $1 \times 10^4$ cells into multiple dishes. Cell number was determined from triplicate samples 24 hours after plating and every 48 hours until day 11. A growth curve (cell number vs. culture time) was derived and population doubling was calculated from the log phase.

Statistical Analysis:

Significant differences in PLA cell osteogenesis and adipogenesis according to donor age were determined by linear regression analysis (r value). In addition, the mean levels of differentiation across donor age were compared using an unpaired student t-test (assuming unequal variances) and a one way analysis of variance (ANOVA).

Results

PLA Cell Growth Kinetics Vary with Respect to Donor Age

Initial PLA cultures were relatively homogenous in appearance, with the majority of cells (85 to 90%) exhibiting a fibroblast-like morphology. A small fraction of endothelial cells, macrophages and pre-adipocytes could be identified (less than 10% of the total population). PLA cells reached 80-90% confluency within 14 days of culture in control medium. Growth curves derived from first-passage PLA cell cultures (P1) were characterized in each donor by an initial lag phase (typically 48 hrs), followed by a log phase (average=7 days) and a plateau phase. Representative growth kinetic curves are shown in FIG. 8A. No significant difference in the duration of the lag and log phases was observed in any donor. Similarly, no significant differences in PLA growth kinetics were observed in younger patients (20 years vs. 39 years). However, a decrease in the log phase of PLA cells was observed in older patients (eg. day 13; 58 years—$12.6 \times 10^4$ cells, 20 years—$26.9 \times 10^4$ cells). Based on the growth kinetics data, the average PLA cell population doubling time calculated from 15 donors was 52.67±8.67 hours. PLA cell population doubling time ranged from 38 to 77 hours (FIG. 8B; 20 years vs. 53 years). Regression analysis of population doubling and donor age yielded a positive correlation of r=0.62 (n=15), indicating a trend toward increasing population doubling (i.e. decreasing proliferative potential) with age. However, statistical analysis of donors grouped according to decade (i.e. 20-30 years, 30-40 years, 40-50 years, 50-60 years), using an unpaired t-test, did not show a significant difference in population doubling (p>0.05), suggesting that PLA proliferation does not significantly decrease with increasing donor age.

Adipogenic Differentiation Potential does not Change with PLA Age

Figure 9:
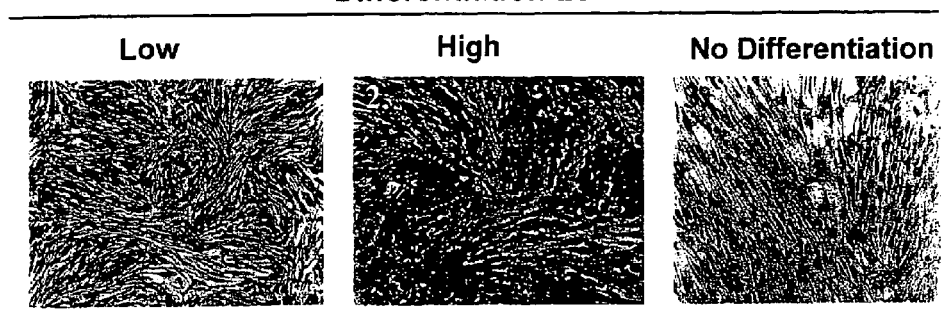
FIG. 9. Histological confirmation of adipogenic and osteogenic differentiation by adipose-derived stem cells (PLA). A: To confirm adipogenesis, cells were stained at 2 weeks post-induction with Oil Red O. Low and extensive adipogenic levels are shown (Panel 1—low; Panel 2—high). Adipose-derived stem cells cultured in non-inductive control medium were analyzed as negative controls (Panel 3). B: To quantify adipogenic differentiation, the number of Oil Red O-positive stained cells were counted within three defined regions. Two samples were analyzed from each donor. The mean number of Oil Red O-positive cells was determined and expressed as a percentage of total adipose-derived stem cells number as an indication of adipogenic differentiation. Differentiation was expressed with respect to age and the line of regression calculated (n=20; r=0.016).
Figure 9:
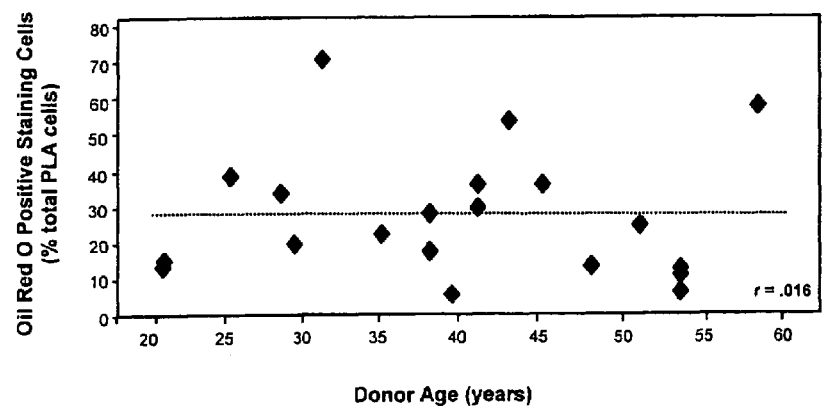

Adipogenesis and lipid vacuole formation in PLA cells were confirmed by staining cells with the lipid dye Oil Red O. In all donors, low levels of adipogenic differentiation in PLA cells were apparent as early as 5 days induction in Adipogenic Medium. Differentiating cells assumed an expanded morphology consistent with adipocytes and accumulated lipid-rich intracellular vacuoles that stained with Oil Red O (FIG. 9A, Panels 1 and 2). By 14 days post-induction, differentiating cells contained large, Oil Red O-positive lipid droplets within the cytoplasm. Differentiation levels varied from donor to donor with several donors exhibiting low levels of adipogenesis, in which individual Oil Red O-positive cells containing a moderate amount of stain were easily identified (FIG. 9A, Panel 1). In addition, several donors exhibited enhanced levels of adipogenesis, in which both the number of Oil Red O-positive cells and the accumulation of the stain increased dramatically (FIG. 9A, Panel 2). Cells cultured in non-inductive control media exhibited no change in morphology and did not accumulate Oil Red O, confirming the specificity of the inductive medium conditions (FIG. 9A, Panel 3). To measure changes in adipogenic differentiation potential with respect to donor age, the number of Oil Red O-positive cells was directly counted within a defined region and expressed as a percentage of the total number of PLA cells counted. Values from each region were averaged to give the mean level of adipogenic differentiation and expressed with respect to donor age (FIG. 9B). Adipogenic differentiation levels ranged from 4.51% to 57.78% of the total PLA cells (n=20). An average differentiation potential of 26.55%±18.14% was calculated. However, a negligible regression value was obtained upon analysis (r=0.016), suggesting that no significant changes in adipogenic differentiation occur with increasing donor age.

Osteogenic Differentiation Decreases with Donor Age

Figure 10:
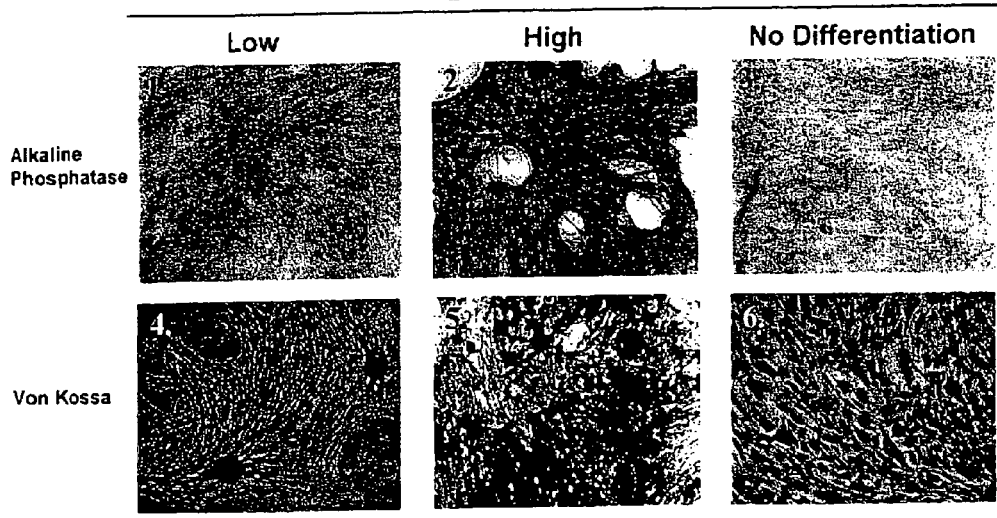
FIG. 10. Osteogenic differentiation decreases with increasing donor age. Panel A: To confirm osteogenesis, adipose-derived stem cells (PLA) were stained at 2 weeks post-induction for alkaline phosphotase (AP) activity (Panels 1 to 3) and at 4 weeks post-induction for matrix calcification using von Kossa staining (Panels 4 to 6). Osteogenic differentiation levels are shown (Panels 1/2—low; Panels 4/5—high). Adipose-derived stem cells cultured in non-inductive control medium were analyzed as negative controls (Panels 3 and 6). Panel B: To quantity osteogenic differentiation, the number of AP-positive stained cells were counted within three defined regions. Two samples were analyzed from each donor. The mean number of AP-positive cells was determined and expressed as a percentage of total adipose-derived stem cells number as an indication of the osteogenic differentiation. Differentiation was expressed with respect to age and the line of regression calculated (n=18; r=−0.70). Panel C: Based on the results of Panel B, the donor pool was divided into two age groups [(20 to 36 years (n=7) and 37 to 58 years (n=11)]. The average level of osteogenic differentiation was calculated for each group and expressed as a percentage of total adipose-derived stem cells number. Statistical significance was determined using an unpaired student t test assuming unequal variances (p<0.001). Differentiation is expressed as mean±SEM.
Figure 10:
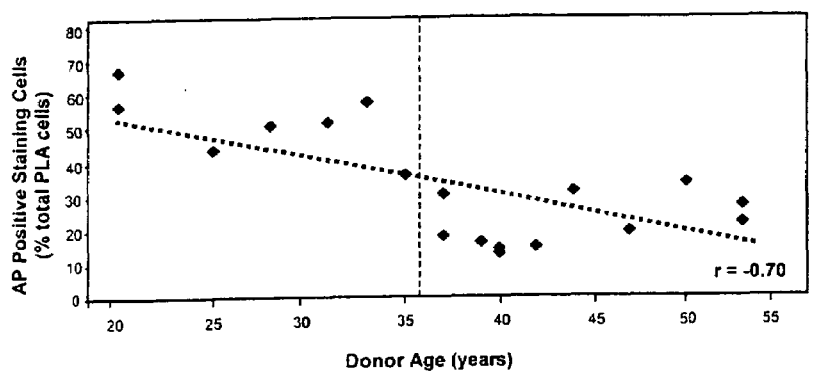
Figure 10:
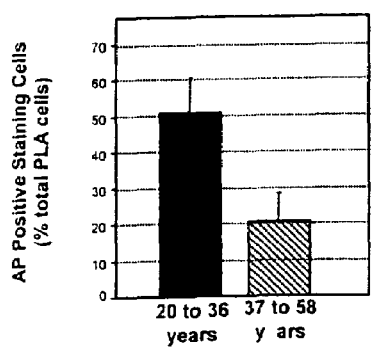

To confirm osteogenesis, cells were stained for Alkaline Phosphatase (AP) activity and extracellular matrix calcification using a silver nitrate/Von Kossa stain. PLA cells, cultured in Osteogenic Medium, underwent a dramatic change in cellular morphology as early as 4 days post-induction, changing from spindle-shaped to cuboidal, characteristic of osteoblasts. Low levels of osteogenesis were characterized in some donors by the formation of a monolayer of AP-positive cells (FIG. 10A, Panel 1). Higher levels of osteogenesis were characterized in some patients by the presence of multi-layered AP-positive nodular structures with well-defined inter-nodular regions containing no cells (FIG. 10A, Panel 2). In addition to AP activity, regions of mineralization, as detected by von Kossa staining, were evident after 3 weeks of culture, further substantiating osteogenic differentiation (FIG. 10A, Panels 4 and 5). Control PLA cells did not exhibit AP activity or matrix mineralization (FIG. 10A, Panels 3 and 6). To measure potential changes in osteogenic differentiation with donor age, the mean level of osteogenesis (i.e. AP-positive cells) was determined using the same method to calculate adipogenic levels.

In contrast to adipogenesis, a significant decrease in osteogenesis was observed in older donors. Osteogenic differentiation ranged from 11.64% to 64.69% of the total PLA cells (FIG. 10B). Regression analysis of donor age and osteogenesis yielded a significant negative correlation (r=−0.70, n=19), suggesting that osteogenic differentiation decreases with respect to age. A similar trend was observed using von Kossa staining. Interestingly, a distinct decrease in osteogenic differentiation was observed in donors older than 36 years of age (FIG. 10B, dashed line). Consistent with this, a significant difference in osteogenesis (p<0.001) was observed when the subjects were divided into two age groups. Donors from the younger age group (20 to 36 years; n=7) exhibited a mean osteogenic potential of 50.7±10% (total PLA cells) while a significantly lower level of osteogenesis (20.7±7.9% total PLA cells) was measured in the older age group (37 to 58 years; n=11) (FIG. 10C). Based on this data, cells from the younger group exhibited a 2.4-fold increase in osteogenic potential, forming 59% more AP-positive cells.

Figure 11:
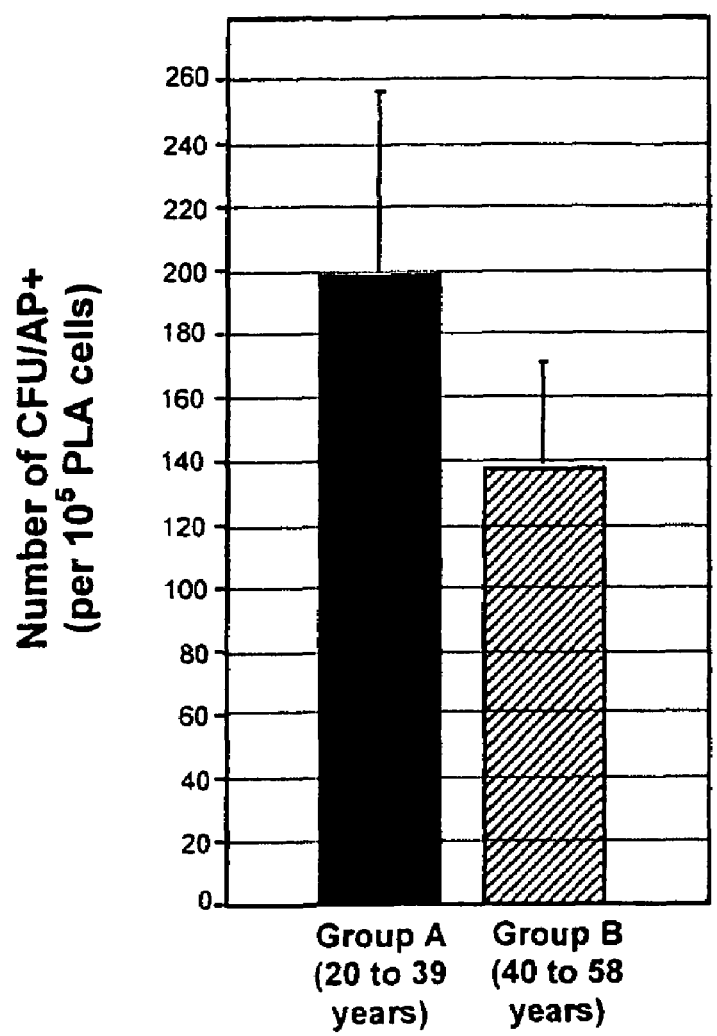
FIG. 11. Osteoprogenitor cell number within an adipose-derived stem cell fraction (PLA fraction) does not significantly change with age. Osteoprogenitor cell number within the fraction was determined by identifying cells with osteogenic potential. Two groups of donors were examined [Group A=20 to 39 years (n=5), Group B=40-58 years (n=6)]. Osteogenesis was confirmed by staining for AP activity. Colonies containing more than 10 AP-positive cells (CFU/AP$^+$) were counted and averaged as an indicator of the number of osteogenic precursors within each age group. Statistical significance was determined using an unpaired student t test assuming unequal variances (p=0.11). Values are expressed as mean CFU/AP$^+$±SEM.

Relative Proportion of Osteogenic Precursors within PLA:

In order to determine if the decrease in PLA osteogenesis is due to a decrease in the number of PLA cells with osteogenic potential, the relative proportion of osteogenic precursor cells within the PLA was calculated with respect to donor age. PLA cells were induced for 2 weeks in Osteogenic Medium and the number of precursors within the PLA determined by calculating the number of AP-positive Colony Forming Units (CFU/AP$^+$) (Grigoradis, A, et al., 1988 J. Cell Biol. 106: 2139-2151; Pittenger, M F, et al., 1999 Science 284:143-147; Jaiswal, N., et al., 1997 J. Cell Biochem. 64:295-312). The number of precursors was calculated in two age groups (Group A=20-39 years, n=5 and Group B=40-58 years, n=6). Consistent with the diminished osteogenic potential observed in older PLA samples, a slight decrease in CFU/AP$^+$ number was observed with increasing age. The average number of CFU/AP$^+$ in Group A was 194±61 per $10^5$ PLA cells, while the number of CFU/AP$^+$ in Group B decreased to 136±32 per $10^5$ PLA cells (FIG. 11). While a decreasing trend in osteoprogenitor cells was observed, this decrease was not statistically significant (p=0.11), suggesting that the decrease in osteogenic potential by PLA cells may not be directly due to a decrease in the number of osteogenic precursors.

Discussion

Mesenchymal stem cells can be isolated from bone marrow. Mesenchymal stem cells are a component of the bone marrow stroma and possess the capacity to differentiate into various mesodermal tissues including fat, bone and cartilage (Grigoradis, A., et al., 1988 J. Cell Biol. 106:2139-2151; Caplan, A. I. 1991 J. Orthop. Res. 9:641-650; Beresford, J. N., et al., 1992 J. Cell Sci. 102:341-351; Berry, L., et al., 1992 J. Cell Sci. 101:333-342; Ferrari, G., et al., 1998 Science 279: 1528-1530; Johnstone, B., et al., 1998 Exp. Cell Res. 238: 265-272; Pittenger, M. F., et al., 1999 Science 284:143-147). This multi-lineage potential may be clinically useful for the repair of complex post-traumatic and congenital defects. Indeed, several in vitro and in vivo studies have suggested the clinical potential for these stem cells (Benayahu, D., et al., 1989 J. Cell Physiol. 140:1-7; Wakitani, S., et al., 1995 Muscle Nerve 18:1417-1426; Krebsbach, P. H., et al., 1997 Transplantation 63:1059-1069; Bruder, S. P., et al., 1998 Clin. Orthop. (355 Suppl):S247-56; Johnstone, B., and Yoo, J. U. 1999 Clin. Orthop. (367 Suppl):S156-62). However, bone marrow procurement is painful, requires general anesthesia and yields low numbers of mesenchymal stem cells upon processing (Pittenger, M. F., et al., 1999 Science 284:143-147; Rickard, D J, et al., 1996 J. Bone Miner. Res. 11:312-324; Bruder, S P, et al., 1997 J. Cell. Biochem. 64:278-294), thus requiring an ex vivo expansion step prior to clinical use. In light of these factors, an additional source of multi-lineage stem cells may be desirable. We have identified a population of stem cells in the stromal-vascular fraction of liposuctioned human adipose tissue (Example 7, supra). This cell population is designated a Processed Lipoaspirate (PLA), and appears to be similar to bone marrow-derived mesenchymal stem cells in many aspects. Like mesenchymal stem cells, PLA cells are stable over long-term culture, expand easily in vitro and possess multi-lineage potential, differentiating into adipogenic, osteogenic, myogenic and chondrogenic cells.

PLA cells possess a fibroblast-like morphology, expand stably in vitro, and proliferate with an average population doubling time of 53 hours. Previous studies have shown that the size and number of adipocytes within adipose tissue increases with age (Hauner, H. et al., 1987 J. Clin. Endocrinol. Metabol. 64:832-835) suggesting an overall increase in adipogenesis in the adipose stores with advancing age. In contrast to these studies, we do not observe a significant age-related change in adipogenesis by PLA cells, suggesting that the adipogenic potential of older PLA cells is unaffected by advancing age. The development of adipose tissue requires the activity of several growth factors and steroid hormones (Hauner, H. et al., 1987 J. Clin. Endocrinol. Metabol. 64:832-835). Therefore, the adipogenic potential of PLA cells may be influenced by the genetic background and/or hormonal levels within each donor. Proenza et al. has reported that adipogenesis can be affected by alterations in the expression of several genes, including lipoprotein lipase, adrenoreceptor and uncoupling protein (Rickard, D J, et al., 1996 J. Bone Miner. Res. 11:312-324; Glowacki J. 1995 Calcif. Tiss. Int. 56 (Suppl 1):S50-51). In addition, Chen et al. has shown that the expression of specific obesity-related genes in pre-adipocytes is related to the differentiation of these cells into mature adipocytes (Chen, X., et al., 1997 Biochim. Biophys. 1359: 136-142). Therefore, gene expression levels, together with hormonal activity, may differ from donor to donor, influencing the adipogenic potential of PLA cells and resulting in varying levels of adipogenesis, irrespective of donor age.

In contrast to adipogenesis, a decrease in PLA osteogenic potential (as measured by AP activity) is observed with increasing donor age. A significant negative correlation between osteogenesis and donor age is found by regression analysis (r=−0.70). Furthermore, a significant difference in osteogenesis is observed when donors are segregated into two age groups (20 to 36 years and 37 to 58 years), with cells from the younger age group possessing over a two-fold greater osteogenic potential.

Figure 8:
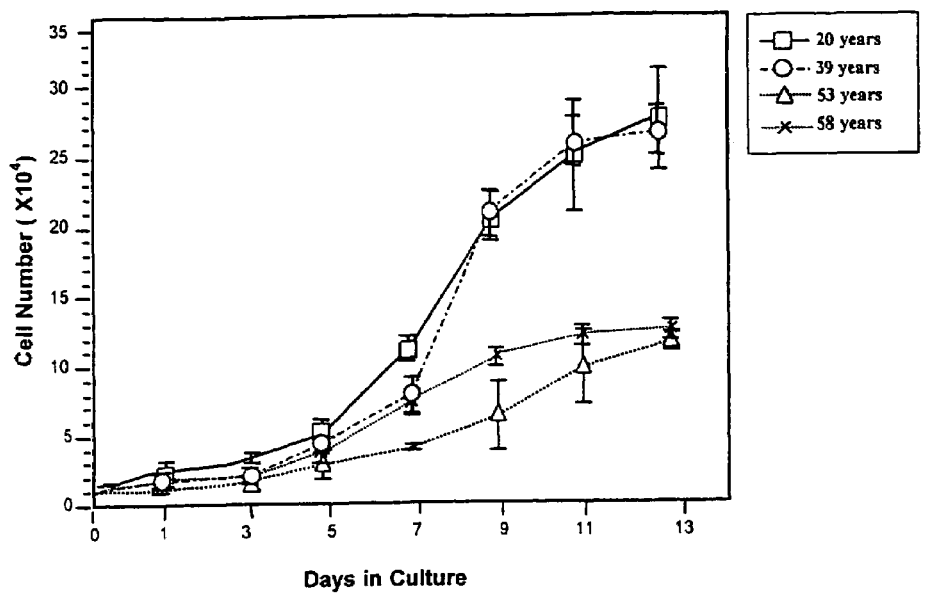
FIG. 8. Growth kinetics of adipose-derived stem cells (PLA). Panel A: adipose-derived stem cells, isolated from each donor, were seeded in triplicate at a density of $1 \times 10^4$ cells per well. Cell number was calculated after 24 hours (day 1) and every 48 hours subsequent to day 1 (days 3 through 11). Mean cell number for each donor was expressed with respect to culture time. The growth curves from 4 representative donors are shown (20 years—open squares, 39 years—open circles, 50 years—open triangles and 58 years—crosses). Results are expressed as mean±SEM. Panel B: Population doubling was calculated in all donors from the log phase of each growth curve (i.e. from day 3 to day 9) and expressed according to age. The line of regression was calculated (n=20; r=0.62)
Figure 8:
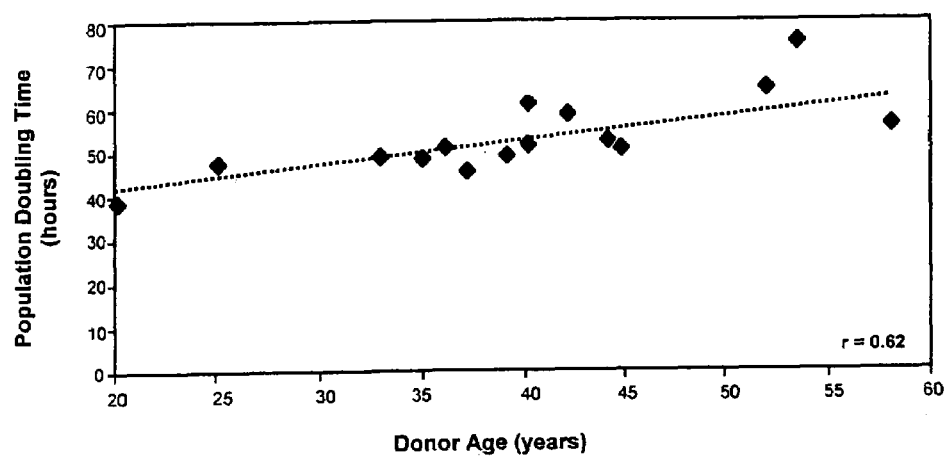

Osteogenesis is defined by three phases: the proliferation of osteogenic precursors, maturation of these precursors into osteoblasts (accompanied by matrix deposition) and a mineralization phase. Each phase is essential and can dramatically affect the development of mature bone. The decrease in osteogenesis observed in older donors may be due to three possibilities: 1) a decrease in PLA cell proliferation, 2) a decrease in the number of PLA-derived osteogenic precursors themselves or 3) a decrease in osteogenic differentiation capacity. As shown in FIG. 8, PLA population doubling time increases slightly in older donors suggesting that the proliferative capacity of older PLA cells diminishes with age. However, this increase in population doubling time is not statistically significant and is not likely to contribute to the age-dependent decrease in osteogenic potential.

In order to determine if a decrease in the number of osteogenic precursors within the PLA contributed to our results, the average number of CFU/AP$^+$ colonies was determined. Colonies with AP activity are considered to be osteoprogenitors and have been previously used to determine the number of osteogenic precursors and/or stem cells in bone marrow (Owen, T A, et al., 1990 J. Cell Physiol. 143:420-430). While animal studies indicate a decrease in the number of osteoprogenitors in bone marrow with advancing age (Bergman R J, et al., 1996 J. Bone Miner. Res. 11:568-577; Huibregtse, B A, et al., 2000 J. Orthop. Res. 18:18-24)), conflicting results have been reported for human samples. Work by Glowacki and Rickard et al. indicate no age-related changes in bone marrow osteoprogenitor cells (Rickard, D J, et al., 1996 J. Bone Miner. Res. 11:312-324; Glowacki, J. 1995 Calcif. Tiss. Int. 56(Suppl 1):S50-51)). In support of these studies, we find a small, but statistically insignificant, change in the number of CFU/AP$^+$ colonies with age. This suggests that the observed age-dependent decrease in osteogenic potential may not be due to a drop in the number of osteogenic precursors and/or stem cells within the PLA.

The decrease in PLA osteogenesis may be due to the loss of osteogenic capacity. Several factors may influence the osteogenic capacity of stem cells, including: 1.) cell-cell and cell-matrix interactions; and 2.) growth factors and hormones. A recent study by Becerra et al. demonstrates a significant decrease in the osteogenic response of older Mesenchymal stem cells to demineralized bone matrix in rats (Becerra, J., et al., 1996 J. Bone Miner. Res. 11:1703-1714), suggesting age-related alterations in MSC-matrix interactions. Similarly, decreases in osteogenic potential in older donors have been correlated to the degradation of the extracellular matrix (Bailey, A J, et al., 1999 Calcif. Tiss. Int. 65:203-210). The microenvironment surrounding PLA cells may change with increasing age, altering cell-cell and cell-extracellular matrix interactions that could inhibit osteogenic differentiation of PLA cells or favor their differentiation to another lineage (e.g adipogenic). Furthermore, the diminishment of osteogenic potential in PLA cells may be due to gender. All donors in this study were female. It is well documented that aging in the female is accompanied by the loss of estrogen, coupled to a decrease in skeletal bone mass (Parfitt, A M 1990 in *Bone* ed B K Hall, Vol. 1, 351-431, New Jersey: Caldwell; Hahn, T J 1993 in *Textbook of Rheumatology* ed W N Kelly, 1593-1627, New York: Saunders). Since osteocytes do not replicate, bone remodeling and repair requires a continuous supply of osteoblasts, the principal source of which is the bone marrow stroma. Estrogen is known to regulate the differentiation of bone marrow-derived stem cells and decreases in circulating estrogen levels can be linked to a loss of stem cell osteogenic potential (Robinson, J A, et al., 1997 Endocrinology 138: 2919-2927; Ankrom, M A, et al., 1998 Biochem. J. 333:787-794). Like bone marrow stem cells, the loss of osteogenic capacity by PLA cells in older female donors may simply reflect the changes that are associated with estrogen loss. A possibility is that the decrease in PLA osteogenic potential may be due to relatively small changes in all three factors discussed above, reflecting a general phenomenon observed in aging women.

A reduction in osteoblast number and bone-forming activity, coupled to an increase in marrow cavity adipogenesis, contributes to type II or age-related, osteoporosis (Parfitt, A M 1990 in *Bone*, ed B K Hall, Vol. 1, 351-431, New Jersey: Caldwell; Hahn, T J 1993 in *Textbook of Rheumatology*, ed W N Kelly, 1593-1627, New York: Saunders). While current research is focusing on the role of bone marrow-derived Mesenchymal stem cells in osteoporosis, the age-related loss of osteogenic capacity by adipose-derived PLA cells may provide researchers with an alternate model system for the study of this disease. Furthermore, PLA cells may represent another viable cell-based therapeutic paradigm for the treatment of osteoporosis and other metabolic bone disorders.

The use of stem cells for tissue engineering applications may be dramatically influenced by stem cell number, growth kinetics and differentiation potential. Each of these factors, in turn, may be affected by the age of the donor. Several studies on bone marrow-derived mesenchymal stem cells have reported alterations in MSC number, population doubling and differentiation potential with respect to donor age in both animal and human models (Lansdorp, P. M., et al., 1994 Blood Cells 20:376-380; Becerra, J., et al., 1996 J. Bone Miner. Res. 11:1703-1714; Bergman, R. J., et al., 1996 J. Bone Miner. Res. 11:568-77; Gazit, D., et al., 1998 J. Cell Biochem. 70:478-88; Oreffo, R. O., et al., 1998 Clin. Sci (Colch.) 94:549-555; D-Ippoliot, G., et al., 1999 J. Bone Miner. Res. 14:1115-1122; Long, M. W., et al., 1999 J. Gerontol. A. Biol. Sci. Med. Soc. 54:B54-62; Huibregtse, B. A., et al., 2000 J. Orthop. Res. 18:18-24). We have characterized several PLA populations by determining population doubling, differentiation potential and average colony forming unit number with respect to donor age.

EXAMPLE 9

The following description provides adipose-derived stem cells which differentiated into chondrogenic tissue, and method for isolating said stem cells.

Materials and Methods:

Reagents and Antibodies:

Sodium acetate, bovine serum albumin (BSA), N-ethylmaleimide (NEM), 6-aminocaproic acid, phenylmethyl-sulfonyl fluoride (PMSF), and benzamidine hydrochloride were all purchased from Sigma (St. Louis, Mo.). Monoclonal antibodies to type II collagen (clone II-4C11), chondroitin-4-sulfate, and keratan sulfate (clone 5-D-4) were purchased from ICN Biomedical (Aurora, Ohio).

Lipoaspirate Processing:

Human liposuction aspirates were obtained from ten healthy elective cosmetic surgery patients ranging in age from 20-55 years, and processed to obtain the processed lipoaspirate (PLA) cell populations. All procedures were approved by the Human Subject Protection Committee (HSPC) under protocol number HSPC #98-08-011-02. Raw lipoaspirates were processed based on the method described in Example 7, supra. Briefly, the lipoaspirates were washed extensively in phosphate-buffered saline (PBS) and then incubated with 0.075% collagenase (Sigma, St. Louis, Mo.) at 37° C. for thirty minutes with gentle agitation. The collagenase was neutralized by adding an equal volume of Dulbecco's Modified Eagle Medium (DMEM, Cellgro, Herndon, Va.), and FBS, and the cellular suspension was centrifuged at 260 g for five minutes. The resultant cell pellet was resuspended in 1% erythrocyte lysis buffer (0.16 M $NH_4Cl$) to lyse the contaminating reb blood cells. The cell suspension was centrifuged at 260 g for five minutes to isolate the PLA fraction. The PLA pellet was resuspended in control medium (DMEM, 10% FBS, and 1% antibiotics-antimycotics) and maintained at subconfluent concentrations at 37° C. with 5% $CO_2$. Human foreskin fibroblasts (HFFs) were similarly harvested through enzymatic digestion with collagenase and maintained at subconfluent levels in control medium.

Chondrogenic Differentiation

After culture expansion to three passages (P3), the PLA cells were trypsinized and resuspended in control medium at a concentration of $10^7$ cells/ml. Chondrogenic differentiation was induced using a micromass culture protocol as previously described with some modifications (Ahrens, P B, et al., 1977 Dev. Biol. 60:69-82; Denker, A E 1995 Differentiation 59:25-34). Ten microliter drops of the PLA cellular suspension were placed in the center of each well of a 24-well tissue culture plate and on chamber slides. The cells were placed in an incubator at 37° C. at 5% $CO_2$ for two hours to allow cell adherence. The pellets were gently overlaid with control medium and incubated overnight. The medium was replaced by chondrogenic medium [DMEM with 1% FBS supplemented with 10 ng/ml TGF-β1 (R&D Systems, Minneapolis, Minn.), 6.25 µg/ml insulin (Sigma), and 6.25 µg/ml transferrin (Sigma)]. The pellets were induced for six days in chondrogenic medium. At day six and thereafter, 50 µg/ml ascorbic acid-2-phosphate (Sigma) was added to the chondrogenic medium mixture. PLA pellets were harvested at days two, seven, and fourteen after initial induction for analysis. In order to identify optimal culture conditions for the induction of chondrogenic differentiation, PLA cells were also induced with dexamethasone (Sigma) alone at a concentration of 0.1 µM and in combination with TGF-β1. HFF cells were cultured as above under micromass and monolayer conditions as a negative control. PLA cells, incubated as monolayer cultures, did not form three-dimensional nodules and were unavailable for paraffin embedding and histologic and immunohistologic analysis.

Differential Cell Density Plating:

In order to assess the relationship of chondrogenic induction to PLA cell, micromass cultures were plated in chondrogenic medium at cell concentrations of $1\times10^5$, $1\times10^6$, $2.5\times10^6$, $5\times10^6$, $1\times10^7$, $2\times10^7$, and $5\times10^7$ cells per milliliter (cells/ml). The micromass cultures were then subjected to chondrogenic culture conditions and the onset of nodule formation noted.

Alcian Blue Staining:

In order to detect the presence of highly sulfated proteoglycans, characteristic of cartilaginous matrices, induced PLA pellets were stained using Alcian blue at acidic pH (Lev, R and S Spicer 1964 J. Histochem Cytochem. 12:309). Micromass cultures were fixed with 4% paraformaldehyde in PBS for fifteen minutes, followed by a five minute incubation in 0.1 N HCl to decrease the pH to 1. The cultures were stained overnight with 1% Alcian blue 8GX (Sigma) in 0.1 N HCl (pH 1). The cells were washed twice with 0.1 N HCl to remove nonspecific staining and then air-dried. For paraffin sections, cellular nodules were harvested, washed twice in PBS and fixed in 4% paraformaldehyde for one hour. The nodules were embedded in paraffin and cut into five-micrometer sections. Paraffin sections of PLA nodules were prepared as described and stained with standard Alcian blue staining at pH 1 in order to determine the spatial distribution of sulfated proteoglycans within the three-dimensional structure of the nodules. Digital images were acquired with a Zeiss Axioskop II microscope (Carl Zeiss, Munich, Germany) and Spot software.

Histology and Immunohistochemistry:

Histologic evaluation of PLA paraffin sections was performed using standard hematoxylin & eosin (H&E) to determine cellular morphology and Goldner's trichrome stain to detect the presence of collagen in the extracellular matrix. For immunohistochemistry, paraffin sections were first deparaffinized in xylene and then hydrated in decreasing ethanol solutions (100% to 70%). To facilitate antibody access to epitopes, sections were predigested for one hour at 37° C. in 0.5 ml chondroitinase ABC (Sigma) in 50 mM Tris (Gibco BRL), pH 8.0, 30 mM sodium acetate containing 0.5 mg/ml BSA, 10 mM NEM. The sections were incubated in 3% $H_2O_2$ for fifteen minutes to quench endogenous peroxidase activity, followed by incubation in 10% horse serum to block nonspecific binding. The sections were subsequently incubated for one hour at 37° C. with primary antibodies to the following: human type II collagen, chondroitin-4-sulfate, and keratan sulfate at dilutions of 1:10, 1:50, and 1:250, respectively. Incubation in normal horse serum in lieu of monoclonal antibodies was performed to serve as a negative control. Reactivity was detected with the Vectastain ABC kit (Vector Laboratories, Burlingame, Calif.) according to the manufacturer.

cDNA Synthesis and RT-PCR:

Total RNA was isolated from untreated PLA cells, PLA nodules, and HFFs. Briefly, RNA was isolated using the following method (RNA-Easy, Qiagen). The RNA was used for oligo dT-primed cDNA synthesis using MMLV-RT enzyme (Promega). Equivalent amounts of cDNA were subjected to PCR amplification using primer pairs designed to: human type I collagen α1 chain (CN I), human type II collagen α1 chain (CN II), human type X collagen α1 chain (CN X), human large aggregating proteoglycan or aggrecan (AG) and human osteocalcin (OC). The primer pairs used were obtained from published GeneBank sequences (Table 4) and are as follows:

24-well plates and expanded. PLA clones were induced toward the chondrogenic lineage as described above and chondrogenic differentiation was confirmed by Alcian blue staining and type II collagen immunohistochemistry.

Results:

Human lipoaspirates were processed to obtain the PLA cell population. The PLA was placed into high-density micromass cultures supplemented with TGF-β1, insulin, transferrin, and ascorbic acid to induce chondrogenic differentiation. Chondrogenesis was assessed histologically at two, seven, and fourteen days using standard histologic assays. In addition, immunohistochemistry was performed with antibodies to type II collagen, chondroitin-4-sulfate, and keratan sulfate. Finally, RT-PCR analysis was performed to confirm the expression of type I, type II, and type X collagen as well as cartilage-specific proteoglycan and aggrecan.

All TGF-β1-treated micromass cultures formed three-dimensional spheroids within 48 hours of induction that stained

TABLE 4

| Gene | accession # | Primer #1 | Primer #2 | Expected Product Size |
|---|---|---|---|---|
| CN I | NM_000088 | 5'-CAT CTC CCC TTC GTT TTT GA-3' (SEQ ID NO:1) | 5'-CTG TGG AGG AGG GTT TCA GA-3' (SEQ ID NO:2) | 598 bp |
| CN II | Published (148) | 5'-CTG CTC GTC GCC GCT GTC CTT-3' (SEQ ID NO:3) | 5'-AAG GGT CCC AGG TTC TCC ATC-3' (SEQ ID NO:4) | IIA*: 432 bp IIB*: 225 bp |
| N X | NM_000493 | 5'-TGG AGT GGG AAA AAG AGG TG-3' (SEQ ID NO:5) | 5'-GTC CTC CAA CTC CAG GAT CA-3' (SEQ ID NO:6) | 601 bp |
| AG | X17406 | 5'-GCA GAG ACG CAT CTA GAA ATT G-3' (SEQ ID NO:7) | 5'-GGT AAT TGC AGG GAA CAT CAT T-3' (SEQ ID NO:8) | 504 bp |
| OC | X04143 | 5'-GCT CTA GAA TGG CCC TCA CAC TC-3' (SEQ ID NO:9) | 5'-GCG ATA TCC TAG ACC GGG CCG TAG-3' (SEQ ID NO:10) | 310 bp |

*Collagen type IIA splice - prechondrocytes and mesenchymal chondrocytic precursors; type IIB - mature chondrocytes (148).

Primer pairs for type II collagen, type X collagen and aggrecan were confirmed against articular cartilage samples as a positive control. Calculated optimal annealing temperatures (OLIGO Primer Analysis Software, National Biosciences Inc., Plymouth, Minn.) were used for each primer pair. Templates were amplified for 35 cycles and the PCR products were analyzed using conventional agarose gel electrophoresis.

Effect of Passage on the Chondrogenic Potential of PLA Cells

To examine the effect of multiple cell passaging on the chondrogenic potential of human PLA cells, monolayer cultures were passaged fifteen times, with cell fractions taken at the first, third and fifteenth passages. The cell fractions were placed in micromass cultures, grown in chondrogenic medium and chondrogenic differentiation was assessed by Alcian blue staining.

PLA Clonal Isolation

Freshly isolated PLA cells were plated out at a density of 100 cells per 100 mm² tissue culture dish, to promote the formation of colonies from single cells. Cultures were expanded in control medium until the appearance of distinct colonies. Colonies derived from single PLA cells were isolated using sterile cloning rings, then harvested with 0.25% trypsin digestion. The dissociated cells were seeded into positively with Alcian blue, suggestive of cartilaginous nodule formation. Immunohistochemistry confirmed the presence of type II collagen, chondroitin-4-sulfate, and keratan sulfate throughout the extracellular matrix of the nodules. Finally, RT-PCR analysis confirmed the expression of cartilage-specific type II collagen, aggrecan, and cartilage-specific proteoglycan.

PLA Cells Form Chondrogenic Nodules

Pre-cartilage mesenchymal cells and multi-lineage stem cells can be induced toward the chondrogenic lineage using a high-density micromass culture technique, followed by induction with pro-chondrogenic factors (Ahrens, P B, et al., 1977 Dev. Biol. 60:69-82; Denker, A E, et al., 1995 Differentiation 59:25-34; Johnstone, B, et al., 1998 Exp. Cell Res. 238:265-272). Consistent with these studies, human Processed Lipoaspirate (PLA) cells, cultured under high-density micromass conditions and induced with chondrogenic medium, containing transforming growth factor-beta 1 (TGF-β1), insulin, and transferrin, condensed into three-dimensional spheroids as early as twenty-four hours post-induction. At this time period, the PLA nodules were visible to the naked eye as white, round structures measuring approximately 1-2 mm in diameter. Nodules formed in 100% of over 500 treated micromass cultures. Small spheroids formed in untreated micromass cultures occasionally (10%) and may be an effect of the culture conditions themselves. No PLA nodules were observed in TGF-β1-treated or untreated PLA monolayer cultures. PLA nodules became larger in size with culture time and smaller adjacent nodules could be visualized under a microscope after seven days in culture. In some cases, adjacent PLA nodules coalesced into a larger, cellular aggregates with increased culture time and is consistent with the proposed cellular interactions and recruitment that are essential to chondrogenesis (Ahrens, P B, et al., 1977 Dev. Biol. 60:69-82).

In order to assess the effect of cell number on PLA nodule formation, differential plating studies were performed. No evidence of spheroid formation was seen in cultures plated at a density of less than $5\times10^6$ cells/ml. PLA cells plated at increasing densities (i.e. above $1\times10^7$ cells/ml) underwent nodule formation more rapidly and, in some cases, were more likely to undergo spheroid formation in the absence of TGF-β1. The addition of dexamethasone to chondrogenic medium, containing TGF-β1, has been shown to lead to the formation of larger cartilaginous aggregates (Johnstone, B., et al., 1998 Exp. Cell Res. 238:265-272). Consistent with this, the addition of dexamethasone resulted in larger spheroids when compared to nodules formed with TGF-β1 stimulation. Cultures treated with dexamethasone alone did not form nodules, suggesting that TGF-β1 is crucial to nodule formation by PLA cells. Finally, no evidence of nodule formation was observed in micromass and monolayer HFF cultures treated with chondrogenic medium, confirming the specificity of our chondrogenic conditions.

PLA Nodules Contain an Extracellular Matrix Rich in Sulfated Proteoglycans

Figure 12:
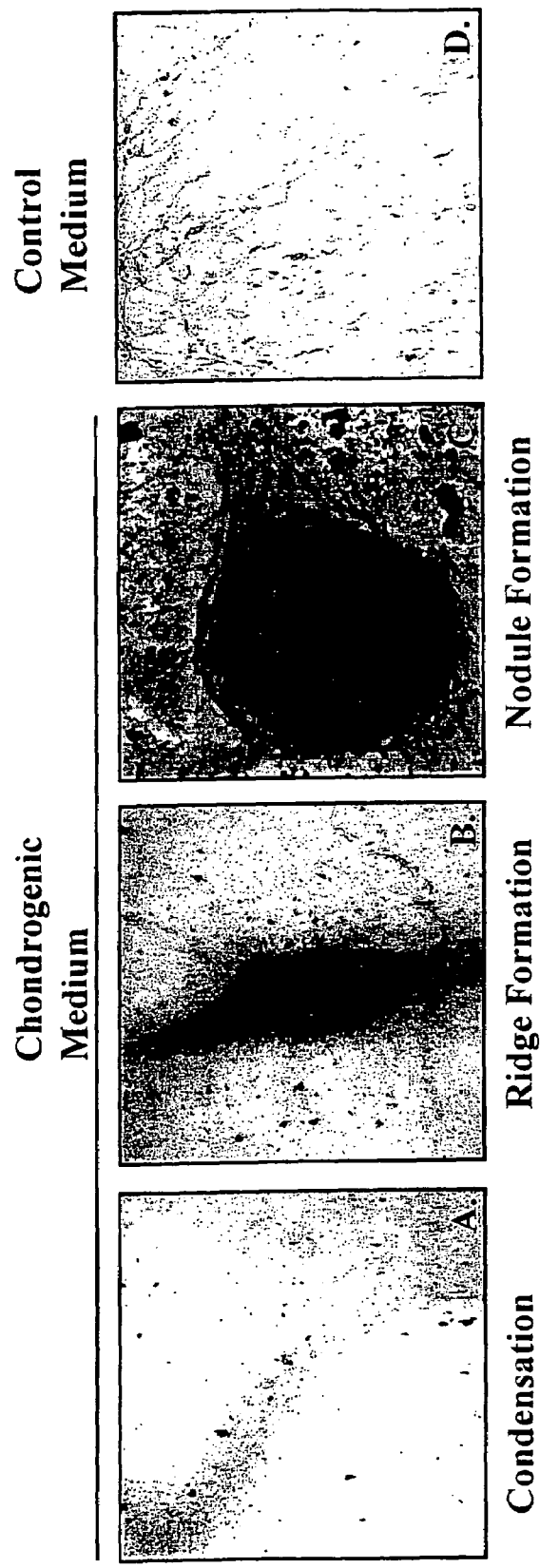
FIG. 12. Human adipose-derived stem cells (PLA) placed in micromass cultures and induced with chondrogenic media undergo cellular condensation and nodule formation. Adipose-derived stem cells induced under micromass conditions were stained with Alcian blue staining at pH 1 to detect the presence of sulfated proteoglycans. Panel A: cellular condensation; (Panel B) ridge formation; (Panel C) formation of three-dimensional spheroids are shown (magnification 100×); (Panel D) negative control (control medium).

Cartilaginous matrices contain very high quantities of polyanionic sulfated glycoasminoglycans (GAGs), such as chondroitin 4- and 6-sulfate, and are characterized by the ability to stain positively with Alcian blue at low pH (R Lev and S Spicer 1964 J. Histochem. Cytochem. 12:309). In order to confirm the cartilaginous nature of the PLA nodules, histologic analysis was performed on whole-mount PLA nodules, plated on chamber slides, and paraffin sections. Initial treatment of PLA cultures with chondrogenic medium resulted in cellular condensation within 24 hours (FIG. 12, Panel A). Condensing PLA cells exhibited a low level of Alcian Blue staining, suggesting the initial formation of a sulfated extracellular matrix. PLA condensation was followed by ridge formation and increased staining by Alcian Blue, indicating an increase in matrix secretion (Panel B). Intense Alcian Blue staining and spheroid formation was observed after 48 hours post-induction (Panel C). In contrast, untreated PLA cells in micromass cultures did not show any regions of positive Alcian blue staining (Panel D).

Figure 13:
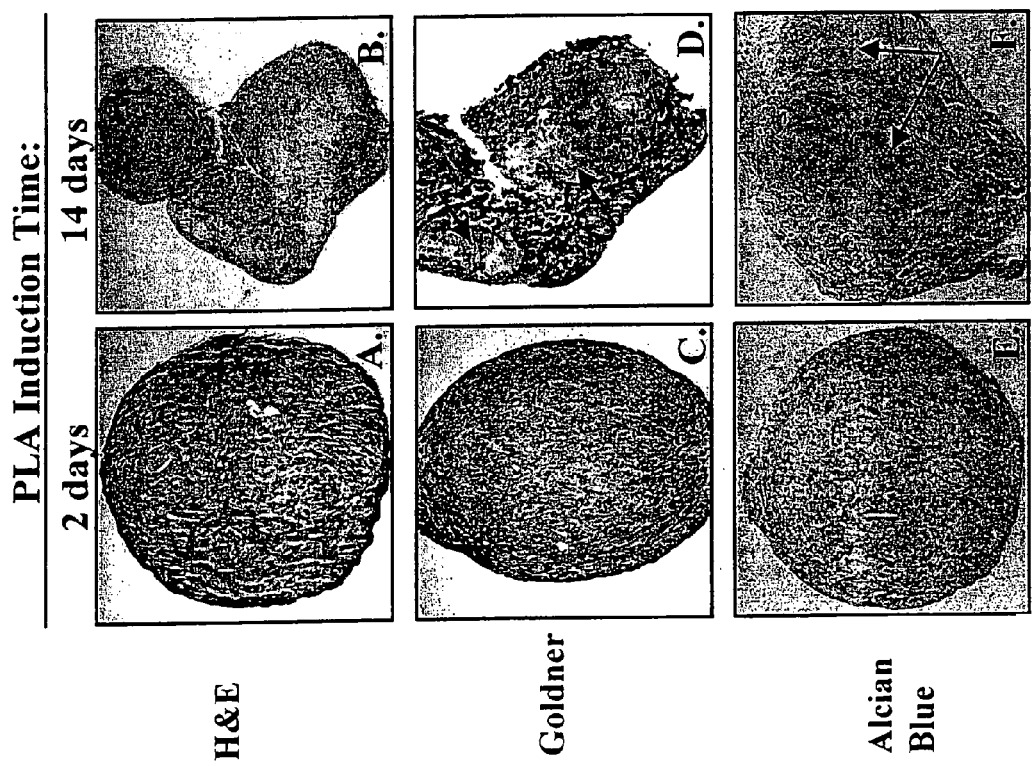
FIG. 13. Hematoxylin & Eosin, Goldner's trichrome, and Alcian blue staining of nodule paraffin sections from adipose-derived stem cells (PLA). Micromass cultures adipose-derived stem cells were treated with chondrogenic medium to form nodules, the nodules were embedded in paraffin and sectioned. Nodule sections were stained using conventional hematoxylin and eosin (Panels A and B) and a Goldner's trichrome stain to detect collagens (green) (Panels C and D). Adipose-derived stem cells induced for 2 days are shown at a magnification of 200× (Panels A and C) and 14 days are shown at 100× (Panels B and D). In addition, sections were stained with Alcian blue staining at pH 1, to detect highly sulfated proteoglycans. Day two nodules (Panel E) are shown at a magnification of 200× and day fourteen nodules (Panel F) are shown at 100×.

In addition to whole-mount PLA samples, paraffin sections of PLA nodules were prepared in order to assess the three-dimensional architecture of the nodule. The morphology of the paraffin-embedded sections, as analyzed by hematoxylin and eosin staining, showed a flat, peripheral layer of fibroblast-like cells that resembled perichondral cells, surrounding an inner core of rounder cells at two days post-induction (FIG. 13, Panel A). After fourteen days of treatment, nodules became more hypocellular with increasing deposits of extracellular matrix into the core (Panel B). Goldner's trichrome staining, which indicates the presence of collagenous matrix (green color), confirmed the H&E pattern (Panels C and D). Faint background levels of collagenous matrix were observed in the nodule sections at two days (Panel C), compared with higher levels of collagen seen in the nodule core at fourteen days post-induction (Panel D). Alcian blue staining of the paraffin sections was similar to the whole-mount preparations, confirming the formation of cartilaginous matrix rich in sulfated proteoglycans after two days induction (Panel E). Increased staining intensity in the central core region was observed at fourteen days post-induction (Panel F), suggesting an increased secretion of sulfated proteoglycans as the cells mature down the chondrocytic pathway. In summary, our histological staining results confirm the formation of cartilage-like PLA nodules, associated with an extracellular matrix rich in collagens and sulfated proteoglycans.

Figure 14:
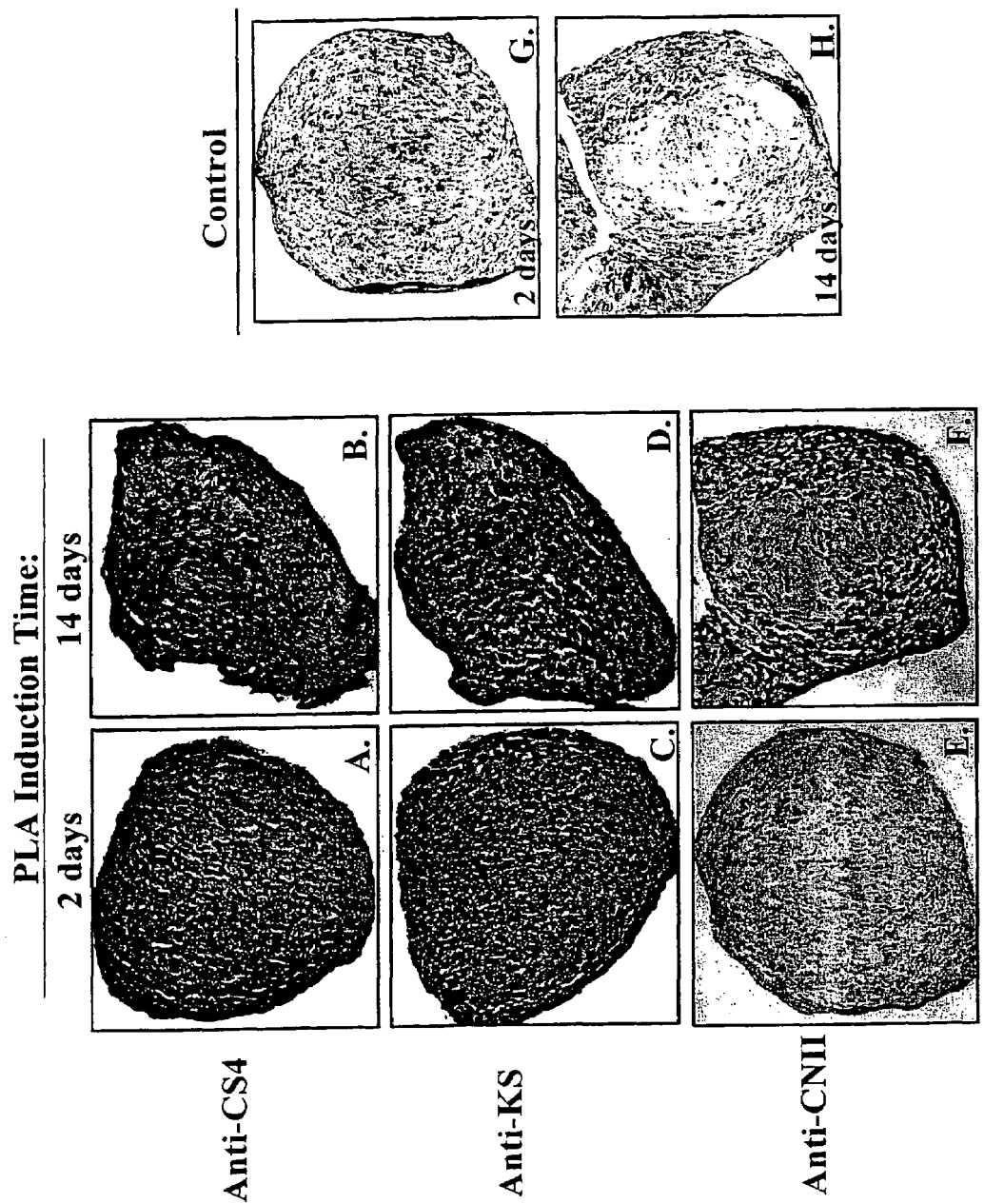
FIG. 14. Nodule differentiated from adipose-derived stem cells (PLA) express chondroitin-4-sulfate and keratin sulfate as well as cartilage-specific collagen type II. Nodules induced from adipose-derived stem cells for 2 days (Panels A and C) and 14 days (Panels B and D) were embedded in paraffin and sectioned. Sections were stained with monoclonal antibodies to the sulfated proteoglycans chondroitin-4-sulfate and keratin sulfate. Sections were also stained with monoclonal antibodies to collagen type II (Panels E and F) (magnification 200×).

PLA Nodules Express Cartilage-Specific Proteins:

Immunohistochemical analysis was used to detect the presence of type II collagen, an extracellular matrix component highly specific for cartilaginous tissue, and chondroitin-4-sulfate and keratan sulfate, two of the main monomeric components of cartilage proteoglycans. After two days induction, areas of strong immunoreactivity to chondroitin-4-sulfate and keratan sulfate were seen along the outer periphery of the spheroids and throughout the core and is supportive of our Alcian Blue staining results (FIG. 14, Panels A and C). A significant increase in chondroitin-4-sulfate and keratan sulfate expression within the nodule core was noted over the course of two weeks (Panels B and D). In contrast, positive type II collagen immunoreactivity was not evident in the PLA nodules at day two (Panel E). Rather, collagen type II expression appeared at day seven post-induction, with strong expression appearing at day fourteen (Panel F). Whole-mount cultures of TGF-β1-treated PLA micromass cultures also showed intense type II collagen reactivity while untreated micromass PLA cultures showed no staining. In addition, no staining was observed in paraffin sections incubated in normal horse serum instead of primary monoclonal antibodies, supporting the specificity of the type II collagen, chondroitin-4-sulfate, and keratan sulfate antibodies. Taken together, the immunohistochemical results support the histological staining data and suggest the presence of a cartilaginous matrix in PLA nodules.

Chondrogenic Differentiation of Single-Cell Derived Clonal Populations:

The apparent chondrogenic differentiation by PLA cells may result from contamination of the lipoaspirate by pre-chondrogenic cells rather from the presence of a multipotential cell. Therefore to determine if our results are due to differentiation of multipotential PLA cells, we isolated and confirmed the multilineage potential of single-cell derived PLA clones. PLA clonal populations (i.e. adipo-derived mesodermal stem cells or ADSCs) demonstrated the ability to undergo chondrogenic differentiation in addition to osteogenic and adipogenic differentiation. PLA clonal populations induced toward the osteogenic and adipogenic lineages exhibited classic lineage-specific histological markers (alkaline phosphatase activity-osteogenesis; Oil-Red-O accumulation-adipogenesis) (unpublished data). Like the heterogeneous PLA cultures, PLA clonal populations also underwent spheroid formation within forty-eight hours of induction in chondrogenic medium. In addition, the PLA nodules secreted an extracellular matrix rich in type II collagen and highly sulfated proteoglycans.

Figure 22:
FIG. 22. Long-term chrondrogenic potetial of adipose-derived stem cells. Adipose-derived stem cells, at passage 1 (panel A), 3 (panel B), and 15 (panel C), were induced under micromass conditions and stained with Alcian blue staining at pH 1 to detect the presence of sulfated proteoglycans.
Figure 22:
Figure 22:

PLA Cells Retain Chondrogenic Potential After Extended Culture:

Culture time and passage number can affect the differentiative capacity of many cell types. To assess the effect of passaging on the chondrogenic potential of PLA cells, PLA cells were passaged in monolayer cultures as many as fifteen times (175 culture days) and cultured under high-density conditions to induced chondrogenesis. PLA cells retained their chondrogenic differentiation potential throughout this extended culture period, as evidenced by their ability to form three-dimensional spheroids after induction with chondrogenic medium. Finally, both early and late passage PLA nodules secreted an extracellular matrix rich in highly-sulfated proteoglycans as evidenced by the positive staining with Alcian blue (FIG. 22). Cellular nodules from all culture passages (i.e. P1 to P15) had a very similar appearance: a flat, peripheral layer of fibroblast-like cells resembling the perichondrium surrounding an inner core of rounder cells.

Figure 15:
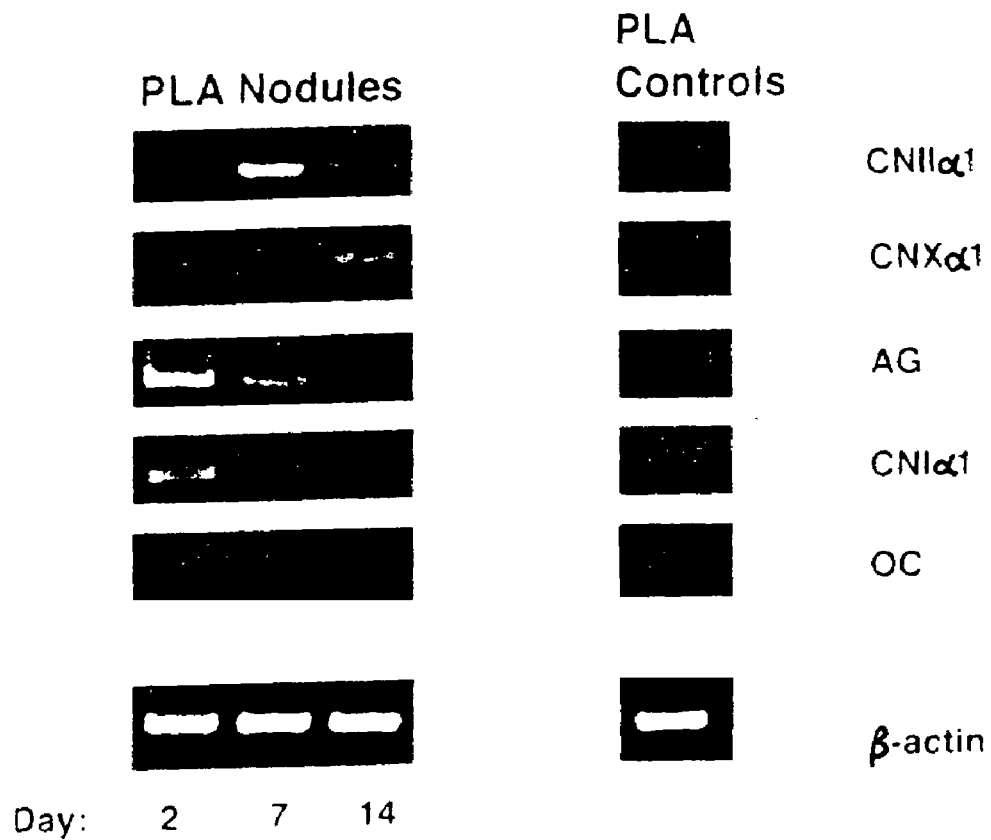
FIG. 15. RT-PCR analysis of nodules induced from adipose-derived stem cells confirms the expression of collagens type II and type X as well as expression of cartilage-specific proteoglycan and aggrecan. Adipose-derived stem cells induced for 2, 7, and 14 days in chondrogenic medium and non-inductive control medium were analyzed by RT-PCR for the expression of collagen type I (CN I), type II (CN II), and type X (CN X) as well as cartilage-specific proteoglycan (PG), aggrecan (AG), and osteocalcin (OC).

RT-PCR Analysis Confirms the Expression of Cartilage-Specific Collagens:

RT-PCR analysis of PLA nodules was performed using primers specific to the genes for human type I collagen, type II collagen, and type X collagen, as well as aggrecan and osteocalcin. Untreated HFF and human PLA cells cultured under micromass conditions were analyzed as negative controls. RT-PCR analysis of PLA nodules confirmed the expression of type II collagen$\alpha$1 (CN II) at day 7 and day 14 only (FIG. 15). Moreover, decrease in CN II expression was observed between 7 and 14 days induction. Both splice variants of CN II (IIA and IIB—type IIB variant shown) were observed at both time points.

In contrast to day seven and fourteen nodules, CN II expression was not observed in 2-day nodules, confirming our immunohistochemical data. As expected, CN II was not observed in HFF micromass cultures. However, small amounts of CN II mRNA were present in the untreated PLA cells. Chondrogenic differentiation was further confirmed by examining nodules for the expression of the large aggregating proteoglycan, or aggrecan. Aggrecan has been shown to be specific to cartilage and accumulates at the onset of over chondrogenesis (Kosher, R A, et al., 1986 J. Cell Biol. 102: 1151-1156). Aggrecan expression was observed at both 2 and 7 days induction and was absent in 14 day PLA nodules. Aggrecan expression was specific to treated PLA nodules, as no expression was noted in control PLA cells or in HFF cultures.

Further characterization of PLA nodules was performed by assessing the expression of the $\alpha$1 chains of type I and type X collagen. Collagen type I expression is known to be up-regulated in osseous tissues and is down-regulated during chondrogenic differentiation (Kosher, R A, et al., 1986 J. Cell Biol. 102:1151-1156; Shukunami, C., et al., 1998 Exp. Cell Res. 241:1-11). Consistent with this, CN I expression was observed in 2-day treated PLA nodules only. Similar to CN II, low levels of CN I were observed in untreated PLA cells, suggesting that undifferentiated PLA cells are associated with a collagenous matrix that is dramatically remodeled as differentiation proceeds. CN X expression was not observed in PLA nodules at two and seven days post-induction but appeared at the 14-day time point. No CN X was observed in untreated PLA cells or in HFF controls. Collagen type X is specific to hypertrophic chondrocytes and may signal the progression to endochondral ossification and bone formation (Linsenmayer, T F, et al., 1988 Pathol. Immunopathol. Res. 7:14).

To confirm the absence of ossification and bone formation within the PLA nodules, RT-PCR analysis was performed using primers to osteocalcin, a bone-specific gene (Price P A 1989 Connect. Tissue Res. 21:51-57). As expected, osteocalcin expression was absent in all treated and untreated PLA samples. Taken together, the expression of cartilage-specific aggrecan, both type II and X collagen, together with the decreased expression of type I collagen supports the chondrogenic differentiation by PLA cells.

Discussion

The repair of cartilaginous defects remains a significant clinical challenge. Damaged articular cartilage has a limited potential for repair and large defects do not heal spontaneously. When the damage extends into the subchondral bone, the repair process is sporadic and the original articular cartilage is replaced by fibrocartilage and scar tissue, which are structurally inferior to the hyaline architecture of normal articular cartilage.

Conventional treatment modalities for cartilage defects include marrow stimulation techniques (e.g. subchondral drilling) and joint arthroplasty (I H Beiser and O I Knat 1990 J. Foot Surg. 29:595-601; Gilbert, J E 1998 Am. J. Knee Surg. 11:42-46; T Minas and S Nehrer 1997 Orthopedics 20:525-538; O'Driscoll, SW 1998 J. Bone Joint Surg. Am. 80:1795-1812). More recently, newer strategies have been developed, such as the use of osteochondral, perichondral, and periosteal allografts (Bouwmeester, S J, et al., 1997 Int. Orthop. 21:313-317; Carranza-Bencano, A, et al., 1999 Calcif. Tissue Int. 65:402-407; Ghazavi, M T, et al., 1997 J. Bone Joint Surg. Br. 79:1008-1013; Homminga, G N, et al., 1990 J. Bone Joint Surg. Br. 72:1003-1007). Unfortunately, these options do not result in complete regeneration of the original hyaline architecture. More importantly, the joint is not capable of normal weight-bearing and physical activity over prolonged periods of time.

Cell-based tissue engineering strategies represent a promising alternative to conventional techniques. First-generation tissue engineering strategies are currently employed clinically using autologous chondrocyte implantation (Brittberg, M., et al., 1994 New Engl. J. Med. 331:889-95; Chen, F S, et al., 1997 Am. J. Orthop. 26:396-406; Gilbert J E 1998 Am. J. Knee Surg. 11:42-46; Richardson J B, et al., 1999 J. Bone Joint Surg. Br. 81:1064-1068). However, limited availability of donor sites for chondrocyte harvest, the requirement for lengthy in vitro culture expansion, and donor site morbidity limit the practicality of this technique. It is important to identify other sources of chondrocytic precursors.

Several cell types have been shown to undergo in vitro and in vivo chondrogenesis, including rat calvarial clonal cell lines and primary cells, the murine embryonic C3H10T1/2 cells, and periosteum-derived and bone marrow-derived precursors from several animals including rabbits, rats, horses, and goats (Denker, A E, et al., 1995 Differentiation 59:25-34; Fortier, L A, et al., 1998 Am J. Vet. Res. 59:1182-1187; Grigoriadis, et al., 1996 Differentiation 60:299-307; Grigoriadis, et al., 1988 J. Cell. Biol. 106:2139-2151; Iwasaki, et al., 1995 J. Bone Joint Surg. Am. 77:543-554; Johnstone, et al., 1998 Exp. Cell Res. 238:265-272; Nakahara, et al., 1990 Bone 11:181-188; Shukunami, et al., 1996 J. Cell. Biol. 133: 457-468). However, there remains a large potential reservoir of osteochondrogenic precursors from other tissue types that have yet to be studied. The interconversion ability of various mesodermal cell types has been reported in many studies. Specifically, both mature human adipocytes and adipocytes isolated from bone marrow exhibit the potential to differentiate into bone (Bennett, J H, et al., 1991 J. Cell Sci. 99(Pt1): 131-139; Park, et al., 1999 Bone 24:549-554). In addition, osteoblasts transdifferentiate into chondrocytes and muscle cells are capable of commitment to the cartilage lineage (Manduca, et al., 1992 Eur. J. Cell Biol. 57:193-201; Nathanson, M A 1985 Clin. Orthop. 200:142-158; Sampath, et al., 1984 Proc. Natl. Acad. Sci. USA 81:3419-3423).

The presence of mesenchymal stem cells capable of osteochondrogenic differentiation in human bone marrow has been well-documented (Mackay, et al., 1998 Tissue Eng. 4:414-428; Pittinger, et al., 1999 Science 284:143-147; Yoo, et al., 1998 J. Bone Joint Surg. Am. 80:1745-1757). Some of the advantages of using mesenchymal stem cells include their ability to proliferate rapidly in culture, their ability to differentiate into chondrogenic cells even after multiple passages, their regenerative capacity, and a broad range of resultant chondrogenic cell types (i.e. prechondroctyes, mature chondrocytes, and hypertrophic chondrocytes). Researchers have anticipated that the differentiated chondrogenic tissue derived from stem cells will more closely resemble that seen in developing embryonic limb buds. Moreover, chondrocytes proliferate poorly in culture, are difficult to maintain, and dedifferentiate when expanded in monolayer cultures (von der Mark, et al., 1977 Nature 267:531-532). The use of autologous stem cells in place of harvested chondrocytes in tissue engineering may be a more efficacious alternative in the future for treatment of cartilage defects. Unfortunately, the limited availability of donor sites and the discomfort and pain associated with bone marrow procurement remain a concern.

The presence of a multipotential cell population within adipose tissue, capable of differentiation into several mesenchymal tissues may be an important finding. Adipose tissue is available in large quantities and relatively easy to obtain. Moreover, liposuction procedures have minimal donor site morbidity and patient discomfort. Because of these practical advantages as a cell source, we sought to determine if PLA cells, like bone marrow- and periosteum-derived mesenchymal stem cells, represent a cell population with the ability to undergo chondrogenic differentiation.

We have confirmed the chondrogenic potential of multilineage human processed lipoaspirate (PLA) cells. Human PLA cells in high-density micromass cultures treated with TGF-$\beta$1 resulted in the formation of three-dimensional cellular nodules with cartilaginous characteristics. The chondrogenic nature of the differentiated cells was supported by several findings: 1) whole-mount PLA nodules and histologic sections stained positively with Alcian blue, 2) H&E morphology revealing a perichondral border of cells surrounding a hypocellular chondrogenic core, 3) a collagen-rich extracellular matrix as shown by Goldner's trichrome staining, 4) expression of type II collagen, chondroitin-4-sulfate, and keratan sulfate as confirmed by immunohistochemistry, and 5) expression of collagen type II as well as cartilage-specific aggrecan as shown by RT-PCR.

One of the earliest features of cartilage development in vivo is the formation of cellular condensations that represent skeletal primordia. Cartilage initially differentiates in the center of these condensations and is followed by a period in which the cells secrete and are surrounded by a characteristic extracellular matrix. Similar to this situation, chondrogenic differentiation in vitro is characterized by the formation of multi-layered cellular aggregates, called spheroids or nodules. Primary nodule formation is followed by ridge formation, the accumulation of matrix and the recruitment of adjacent cells, resulting in the expansion of the original nodule (Ahrens, et al., 1977 Dev. Biol. 60:69-82; Denker, et al., 1995 Differentiation 59:25-34; Stott, et al., 1999 J. Cell Physiol. 180:314-324; Tacchetti, et al., 1992 Exp. Cell Res. 200:26-33; Tavella, et al., 1994 Exp. Cell Res. 215:354-362). Consistent with these studies, PLA cells began condensing within twenty-four hours induction with TGF-$\beta$1-containing chondrogenic medium and formed well-defined three-dimensional spheroids by forty-eight hours post-induction. The appearance of smaller adjacent nodules in addition to the original cartilage nodule was noted after cultures were treated for extended periods in chondrogenic medium, suggesting the presence of further chondrogenic induction through possible paracrine growth factor signaling by the maturing cartilaginous nodule. PLA nodule formation was evident only in micromass cultures plated at a cell density higher than $5 \times 10^6$ cells/ml, consistent with previous studies describing the high cell density requirement for chondrogenesis (Rodgers, et al., 1989 Cell Differ. Dev. 28:179-187; Tsonis and Goetinck 1990 Exp. Cell Res. 190:247-253).

Cartilage is comprised of a mixture of collagen fibrils and proteoglycans that give the tissue high tensile strength and internal swelling pressure. The predominant collagen of cartilage is collagen type II. Although this collagen is not specific to cartilage it is highly characteristic of this tissue, as collagen type II is produced by a limited number of non-chondrogenic cell types. Positive staining using a Goldner Trichrome stain, specific for collagens in general, confirmed these proteins within the PLA nodule after both 2 and 14 days induction with chondrogenic medium. Specifically, PLA nodules treated with TGF-$\beta$1 for 48 hours were associated with an extracellular matrix containing low levels of collagen type II, suggesting that PLA cells have undergone preliminary chondrogenic differentiation. Collagen type II levels appeared to increase with induction time. In addition to collagen type II, cartilagenous matrices also contain high levels of sulfated GAGs, such as chondroitin-4- and -6-sulfate that are typically associated with proteoglycans such as aggrecan. Consistent with this, histological staining with Alcian Blue confirmed the presence of sulfated proteoglycans as early as 24 hours induction, increasing as the PLA nodule became more defined (i.e. 2 days). Increased Alcian Blue staining was also observed as far as 14 days induction, localizing to the nodule core and surrounding individual cells. Similar results were also observed when nodules were stained with antibodies specific to keratan- and chondroitin-sulfate confirmed and immunohistochemical studies confirmed the presence of these components and further supports the presence of chondrogenic cells within the PLA nodule.

In support of our immunohistochemical results, RT-PCR analysis confirmed the expression of CN II in PLA nodules induced for 7 and 14 days, with a lower level of this gene being observed at day 14. No CN II expression was observed after 48 hours induction with chondrogenic medium. The expression of CN II in PLA nodules is supportive of the chondrogenic phenotype. Our immunohistochemical results showed a significant level of both chondroitin- and keratan-sulfate specifically in induced PLA nodules. It is known that chondroitin-4- and 6-sulfate are the main monomeric components of the cartilage-specific protein, aggrecan (Hall, BK 1981 Histochem. J. 13:599-614). Aggrecan has been shown to be cartilage-specific and accumulates at the onset of overt chondrogenesis, coincident with cellular condensation (Kosher, et al., 1986 J. Cell Biol. 102:1151-1156).

We confirmed the chondrogenic nature of the PLA nodule by assessing the expression of aggrecan. As shown in FIG. 22, the expression pattern of aggrecan overlapped with that of CN II at day 7. In addition, the expression of aggrecan preceded that of CN II. However, in contrast to CN II, aggrecan was not observed in PLA nodules induced for 14 days. Aggrecan is a cartilage-specific protein that consists of a multidomain protein core containing binding sites for sulfated proteoglycans (Hardinghamn, et la., 1984 Prog. Clin. Biol. Res. 151:17-29). The primers used to detect aggrecan in this study were designed to the C-terminus, which contains the G3 globular domain, a site that undergoes alternative splicing and is proteolytically cleaved in mature cartilage (Fulop, et al., 1993 J.

Biol. Chem. 268:17377-17383). The absence of aggrecan in day 14 PLA nodules may therefore represent an alternatively spliced form of aggrecan that lacks the C-terminus. However, no aggrecan at day 14 was observed when RT-PCR was performed using primers designed to the N-terminus, suggesting that aggrecan is no longer expressed after two weeks induction with chondrogenic medium.

In addition to aggrecan and CN II, PLA nodules expressed both type I and type X collagen at distinct time points. Day 2 PLA nodules were characterized by the expression of both CN I and CN II. However, in contrast to aggrecan and CN II, the expression pattern of CN I was highly restricted and did not appear beyond the two day time point. Interestingly, low levels of both CN I and CN II were observed in untreated PLA control cells. Consistent with this, both type I and type II collagen mRNA have been found in many developing embryonic tissues and basal levels of these collagen subtypes can be detected in pre-cartilage mesenchymal precursors prior to chondrogenic differentiation (Lisenmeyer, et al., 1973 Dev. Biol. 35:232-239; Dessau, et al., 1980 J. Embryol. Exp. Morphol. 57:51-60; Cheah, et al., 1991 Development 111:945-953; Kosher and Solursh 1989 Dev. Biol 131:558-566; Poliard, et al., 1995 J. Cell Biol. 130:1461-1472). Finally, the decrease in CN II expression in day fourteen nodules coincided with the appearance of CN X, a collagen indicative of hypertrophic chondrocytes (Kirsch, et al., 1992 Bone Miner. 18:107-117; Linsenmayer, et al., 1988 Pathol. Immunopathol. Res. 7:14-19).

The appearance of collagen type X and the hypertrophic phenotype may precede possible nodule ossification and bone formation. However, PLA nodules did not express osteocalcin, a bone-specific gene expressed in cells differentiating toward the osteogenic lineage (Price, et al., 1983 Biochem. Biophys. Res. Commun. 117:765-771). Despite the expression of collagen type X, mature hypertrophic chondrocytes with their characteristic lacunae were not seen in PLA nodules. However, a similar result has been described by Denker et al. when C3H10T1/2 murine pluripotent cells were placed in micromass cultures and treated with TGF-β1 (Denker, et al., 1995 Differentiation 59:25-34). Hypertrophic chondrocytes were only observed in place of nodules when cultures were treated with BMP-2 (139). It therefore may be necessary to induce PLA micromass cultures with BMP-2 to fully induce hypertrophy and induce the formation of mature chondrocytes.

Taken together, our histologic, immunohistochemical, and RT-PCR data support the differentiation of PLA cells toward the chondrogenic lineage. However, the processed lipoaspirate is a heterogeneous population of cells and may contain several cell types of various mesodermal lineages. Specifically, there may exist chondrogenic precursors in the lipoaspirate that are capable of spontaneous differentiation, as well as a subpopulation of multipotential cells (i.e. PLA stem cells). The isolation of PLA clones derived from single PLA cells and their multilineage differentiation (chondrogenesis, osteogeneis, and adipogenesis) supports the presence of multipotential stem cells (adipo-derived mesodermal stem cells) within this heterogeneous cell population.

In order to apply cell-based tissue engineering techniques to the clinical setting, a number of criteria must be met. The cell population used as the cellular vehicle should be abundant and easy to obtain, expandable in tissue culture, able to maintain its differentiative ability through multiple passages, and exhibit properties equivalent to the native target tissue. The healing of articular cartilage defects using stem cells harvested from bone marrow has been successfully reported in various animal models (Angele, et al., 1999 Tissue Eng. 5:545-554; Butnariu-Ephrat, M., et al., 1996 Clin. Orthop. 330:234-43; Wakitani, et al., 1994 J. Bone Joint Surg. Am. 76:579-592). However, the bone marrow harvest is painful and yields low number of stem cells for clinical use, usually requiring in vitro expansion. Adipose tissue is plentiful and easy to obtain with relatively minimal discomfort. PLA cells can be harvested from a relatively small amount of adipose tissue in large numbers (Zuk, P., et al., 2001 Tissue Engineering 7:209-226), thereby, obviating the need for lengthy culture expansions. While elective cosmetic surgery is the most common source of lipoaspirates, sufficient adipose tissue could also be obtained through a small-bore cannula for non-cosmetic surgery patients requiring reconstruction, making this technique available to a wide variety of patients. In this example, the chondrogenic capacity of multipotential adipose-derived stem cells is demonstrated and shows that the stem cells retain their ability to differentiate even after long-term culture. Finally, adipose-derived stem cell nodules exhibit many properties consistent with native cartilage tissue.

The fulfillment of these properties, together with the potential abundance of PLA cells, make these multipotential cells an ideal system for tissue engineering strategies. In addition, these cells may be appropriate for the study of chondrogenesis in both in vitro culture studies and in vivo animal models. The identification of chondrogenic precursors has important implications for the repair of articular cartilage defects. The abundance and easy accessibility of adipose tissue makes it a feasible alternative for cartilage reconstruction (Asahina, et al., 1996 Exp. Cell Res. 222:38-47; Atkinson, et al., 1997 J. Cell Biochem. 65:325-339; Chimal-Monroy and Diaz de Leon 1999 Int. J. Dev. Biol. 43:59-67; Denker, et al., 1999 Differentiation 64:67-76; Klein-Nulend, et al., 1998 Tissue Eng. 4:305-313; Martin, et al., 1999 Exp. Cell Res. 253:681-688; Quarto, et al., 1997 Endocrinology 138:4966-4976; Shukunami, et al., 1998 Exp. Cell Res. 241:1-11).

EXAMPLE 10

The following description provides methods for isolating stem cells from adipose tissues, where the stem cells differentiate into myogenic tissue.

Methods

Differentiation and Tissue Culture Reagents

Hydrocortisone, collagenase and paraformaldehyde were purchased from Sigma (St. Louis, Mo.). Horse Serum (HS) was purchased from Life Technologies (Grand Island, N.Y.). Phospho-Buffered Saline (PBS), 0.25% trypsin/1 mM EDTA (trypsin/EDTA), Dulbecco's Modified Eagle's Medium (DMEM) and antibiotic/antimycotic solution were purchased from CellGro (Herndon, Va.). Fetal Bovine Serum (FBS) was purchased from Hyclone (Logan, Utah).

PLA Preparation and Culture

Human adipose tissue, obtained from eight patients (mean age=39.3 years, range 25-58 years) undergoing elective Suction-Assisted Lipectomy (SAL), according to patient consent protocol HSPC #98-08 011-02 (University of California Los Angeles) was processed as described, according to the method described in Example 7, supra, to obtain the Processed Lipoaspirate (PLA) cell population. Briefly, the raw liposuctioned aspirates were washed extensively with sterile PBS in order to remove blood cells, saline and local anesthetics. The extracellular matrix was digested with 0.075% collagenase 37° C. for 30 minutes to release the cellular fraction.

Collagenase was inactivated with an equal volume of DMEM containing 10% FBS. The infranatant was centrifuged at 250×g for 10 minutes to obtain a high-density PLA cell pellet. The pellet was resuspended in DMEM/10% FBS and an Erythrocyte Lysis Buffer (0.16M $NH_4Cl$) was added for 10 minutes to lyse contaminating erythrocytes. Following an additional centrifugation step, the PLA cell pellet was resuspended in DMEM/10% FBS and plated in 100 mm tissue culture dishes at a density of $1\times10^6$ cells per plate. PLA cells were maintained in Control Medium (CM-DMEM, 10% FBS, 1% antibiotic/antimycotic) at 37° C. and 5% $CO_2$. The culture medium was changed twice weekly. Confluent PLA cultures (approximately 80% confluence) were passaged at a ratio of 1:3 in trypsin/EDTA. For control studies, a human foreskin fibroblast cell line, HFF (American Type Culture Collection, Manassas, Va.) and a human skeletal muscle cell line, SKM (Clonetics, Walkersville, Md.) were maintained at 37° C./5% $CO_2$ in CM and a myogenic maintenance medium (SKM-Clonetics), respectively.

Myozenic Differentiation:

To induce optimal myogenesis, PLA cells were plated at a density of $1\times10^4$ cells onto 35 mm tissue culture dishes and incubated overnight in CM to allow adherence. Optimal myogenesis was obtained by incubating PLA cells in Myogenic Medium (MM=CM supplemented with 5% Horse Serum and 50 μm hydrocortisone to promote proliferation, a key event in myogenic differentiation) (196). PLA cells were induced in MM for 1, 3 and 6 weeks. Medium was changed twice weekly until the experiment was terminated. SKM and HFF cells were induced for 1, 3 and 6 weeks in MM as positive and negative controls, respectively.

Immunohistochemistry:

To assess myogenic differentiation, PLA cells were seeded onto 8-well chamber slides at a density of $5\times10^3$ cells per well and allowed to adhere in CM overnight. Cells were induced in MM for 1, 3 and 6 weeks. Following induction, the cells were rinsed twice with PBS and fixed with 4% paraformaldehyde for 20 minutes at 4° C. The cells were incubated with 3% hydrogen peroxide for 5 minutes to quench endogenous peroxidase activity. Non-specific epitopes were blocked by a 30 minute incubation in Blocking Buffer (BB; PBS, 1% HS, 0.1% Triton X-100). The cells were incubated at 4° C. overnight with either a monoclonal antibody to human MyoD1 (Dako; Carpenteria, Calif.) or monoclonal antibody to human fast twitch skeletal muscle myosin heavy chain (Biomeda Corp.; Foster City, Calif.). Following incubation, the cells were washed with BB and incubated at room temperature for 2 hours in BB containing a horse anti-mouse IgG secondary antibody conjugated to biotin. The secondary antibody was visualized using the VectaStain ABC kit (Vector Labs; Burlingame, Calif.) according to manufacturer's specifications. The cells were counterstained with hematoxylin for 3 minutes. SKM cells induced in MM were processed as above as a positive control. PLA cells cultured in CM and HFF cells induced in MM were analyzed as negative controls.

RT-PCR Analysis:

Total RNA was isolated from PLA cells treated with MM for 1, 3 and 6 weeks. RNA was isolated according to the method described in Example 9 above. Five micrograms (5 ug) of total RNA was used for oligo dT-primed cDNA synthesis using Murine Maloney Leukemia Virus Reverse Transcriptase (MMLV-RT; Promega; Madison, Wis.). The resulting cDNA was used as a template for PCR analysis using primer pairs designed to human MyoD1 (Accession; NM_002478) and human skeletal muscle myosin heavy chain (Accession; X03740). The primer pairs used and the expected PCR product sizes were as follows: MyoD1: 5'-AAGCGCCATCTCTTGAGGTA-3' (forward primer) (SEQ ID NO:11) and 5'-GCGCCTTTATTTTGATCACC-3' (reverse primer) (SEQ ID NO:12); 500 bp; myosin heavy chain: 5'-TGTGAATGCCAAATGTGCTT-3' (forward primer) (SEQ ID NO:13) and 5'-GTGGAGCTGGGTATC-CTTGA-3' (reverse primer) (SEQ ID NO:14); 750 bp. MyoD1 and myosin were amplified using Taq polymerase (Promega) for 35 cycles in a total reaction volume of 100 ul. Duplicate reactions were performed using primers designed to the housekeeping gene, β-actin, as an internal control. PCR products were resolved by agarose gel electrophoresis. PCR amplification of cDNA obtained from PLA cells cultured in CM and HFF cells induced in MM was performed as negative controls.

Immunohistochemical Quantification and Data Analysis:

To quantitate myogenesis, a total of five hundred PLA cells from each induction time point were manually counted at 200× magnification using an "Axioskop 2" inverted microscope (Carl Zeiss Inc; Thornwood, N.Y.) and the number of MyoD1 and myosin positive cells determined. The number of MyoD1 and myosin-positive cells was expressed as a percentage of the total 500 cells (% total PLA cells) and was used as an indication of the degree of myogenic differentiation. All studies were performed on eight patients and the mean number of MyoD1 and myosin-positive cells calculated, together with the standard error of the mean (± SEM). Myogenic differentiation in both the experimental and control groups described above was analyzed for statistical significance using a one-way analysis of variance (ANOVA). A p value of less than 0.05 was considered significant.

Results

Induced Stem Cells Express Myod1 and Myosin Heavy Chain:

Consistent with the previous examples, no qualitative changes in PLA growth kinetics and morphology between the 8 patients used in this study, suggesting that the isolated PLA populations are relatively consistent between all patients. PLA cells were isolated from raw lipoaspirates and induced using MM, containing hydrocortisone. Myogenesis by PLA cells was specific to the myogenic conditions used in this study, as no differentiation was observed in non-inductive control medium, or in media inductive for alternate mesodermal lineages (i.e. osteogenic and adipogenic). Furthermore, no osteogenic or adipogenic differentiation was noted in PLA cells induced for up to 6 weeks in MM.

Figure 16:
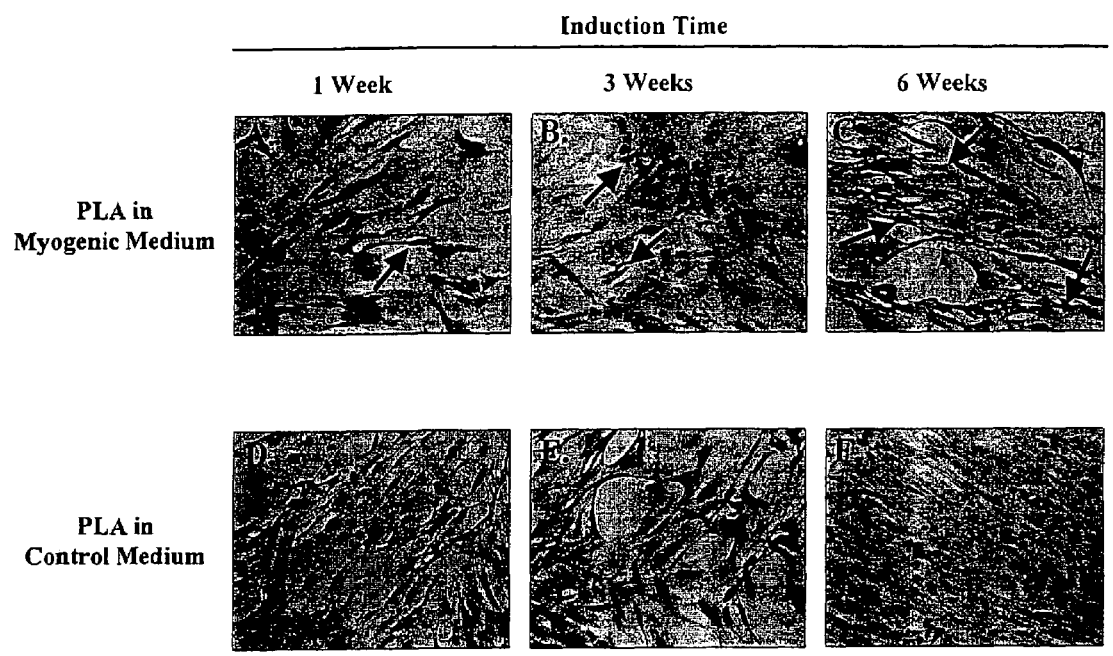
FIG. 16. Adipose-derived stem cells induced in Myogenic Medium express MyoD1. Panels A to C: adipose-derived stem cells (PLA) were stained with an antibody to MyoD1 following 1 week (Panel A), 3 weeks (Panel B) and 6 weeks (Panel C) induction in MM. Expression of MyoD1 in the nucleus of positive staining PLA cells is shown (arrows, magnification 200×). Panels D to F: PLA cells induced for 1 week (Panel D), 3 weeks (Panel E) and 6 weeks (Panel F) in non-inductive control medium (CM) were processed as above as a negative control (magnification 200×).

To confirm PLA myogenic potential, the expression of established muscle-specific markers was determined by immunohistochemistry. Differentiation of myogenic precursors and stem cells into myogenic precursor cells can be confirmed by the expression of several transcription factors, that include MyoD1, Myf-5, myogenin and structural proteins such as myosin heavy chain (Butler-Browne, et al., 1990 Anat. Embryol. (Berl) 181:513-522; Thornell, et al., 1984 J. Neurol. Sci. 66:107-115; Megeney, et al., 1996 Genes Dev. 10:1173-1183; Seale and Rudnicki 2000 Dev. Biol. 218:115-124; Tapscott, et al., 1988 Science 242:405-411; Weintraub, et al., 1991 Science 251:761-766; Molkentin and Olson 1996 Curr. Opin. Genet. Dev. 6:445-453). Commitment to the myogenic lineage was identified by staining cells with a monoclonal antibody specific to MyoD1. Nuclear expression of MyoD1 in PLA cells was observed at 1, 3 and 6 weeks induction with MM, suggesting initiation of the myogenic differentiation pathway in these cells (FIG. 16, Panels A to C). Similar to the PLA results, nuclear expression of MyoD1 was observed in positive control SKM cells as early as 1 week post-induction with MM and increased MyoD1 expression was observed in SKM cells by 6 weeks induction. In contrast to induced PLA cells, MyoD1 expression was not observed in PLA cells treated for 1, 3 and 6 weeks with CM (FIG. 16, Panels D to F). Similarly, no MyoD1 expression was observed in HFF cells treated with MM. The expression of MyoD1 in induced PLA cells suggests that these cells have initiated a program of myogenic differentiation.

Figure 17:
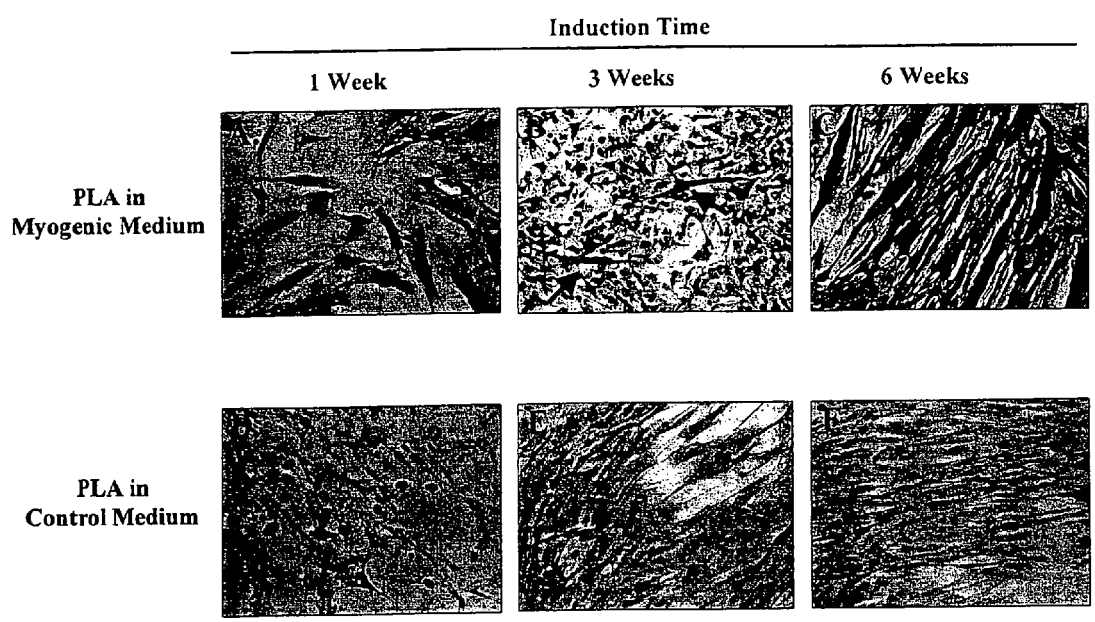
FIG. 17. Adipose-derived stem cells induced in Myogenic Medium express skeletal muscle myosin heavy chain. Panels A to C: adipose-derived stem cells (PLA) cells were stained with an antibody to the myosin heavy chain (myosin) following 1 week (Panel A), 3 weeks (Panel B) and 6 weeks (Panel C) induction in MM. Myosin-positive staining PLA cells are shown (arrows, magnification 200×). Panels D to F: adipose-derived stem cells (PLA) cells induced for 1 week (Panel D), 3 weeks (Panel E) and 6 weeks (Panel F) in non-inductive CM were processed as above as a negative control (magnification 200×).

To further confirm myogenesis, cells were stained with a monoclonal antibody specific to skeletal muscle myosin heavy chain (myosin), in order to identify terminally differentiated myoblasts (Butler-Browne, et al., 1990 Anat. Embryol. (Berl) 181:513-522; Thornell, et al., 1984 J. Neurol. Sci. 66:107-115). Consistent with the nuclear expression of MyoD1, PLA cells induced with MM also expressed myosin (FIG. 17, Panels A to C). However, in contrast to MyoD1, myosin expression was restricted to later induction time points (3 and 6 weeks only), consistent with the expression of this marker in mature, fully differentiated myoblasts (Butler-Browne, et al., 1990 Anat. Embryol. (Berl) 181:513-522; Thornell, et al., 1984 J. Neurol. Sci. 66:107-115). Similar to our MyoD1 results, no myosin expression was observed in PLA cells cultured in CM (FIG. 17, Panels D to F) or in HFF cells induced with MM. Extensive myosin expression was also observed in SKM positive controls induced for 3 and 6 weeks with MM. Taken together, the expression of both MyoD1 and myosin in induced PLA cells suggests that these cells possess myogenic potential.

Figure 18:
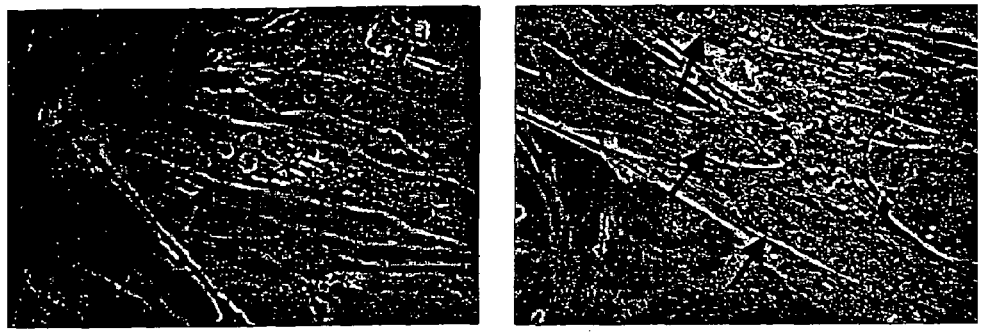
FIG. 18. Adipose-derived stem cells cultured in Myogenic Medium form multi-nucleated cells. Panel A: Phase contrast of adipose-derived stem cells (PLA) at 3 weeks (1) and 6 weeks (2) post-induction with MM (magnification 400×). Multi-nucleated cells are shown (arrows). Panel B: Immunostaining of adipose-derived stem cells (PLA) cells at 6 weeks post-induction with an antibody to the myosin heavy chain. Myosin-expressing multi-nucleated cells are shown (arrows).
Figure 18:

Terminal differentiation of myogenic precursors is accompanied by the fusion of the differentiated myoblast into long, multi-nucleated myotubes. Therefore, we examined induced PLA cultures for the formation of putative myotubes. Treatment of PLA cells with MM for a minimum of three weeks resulted in the formation of long multi-nucleated cells (FIG. 18A). The number and size of these multi-nucleated cells gradually increased with induction time with multi-nucleated cells observed in all PLA cultures at 6 weeks induction. No fusion was observed at 1-week post-induction with MM Furthermore, multi-nucleation was not observed in PLA cells cultured for similar time periods in CM or in HFF cells treated with MM. To confirm the myogenic origin of these putative myotubes, the expression of myosin was examined in PLA cultures at 6 weeks post-induction. As shown in FIG. 18B, multi-nucleated PLA cells at 6 weeks also expressed the myosin heavy chain. The formation of multi-nucleated cells expressing myosin upon induction with MM suggests that PLA cells underwent fusion to form myotubes and further confirms their myogenic potential in vitro.

Figure 19:
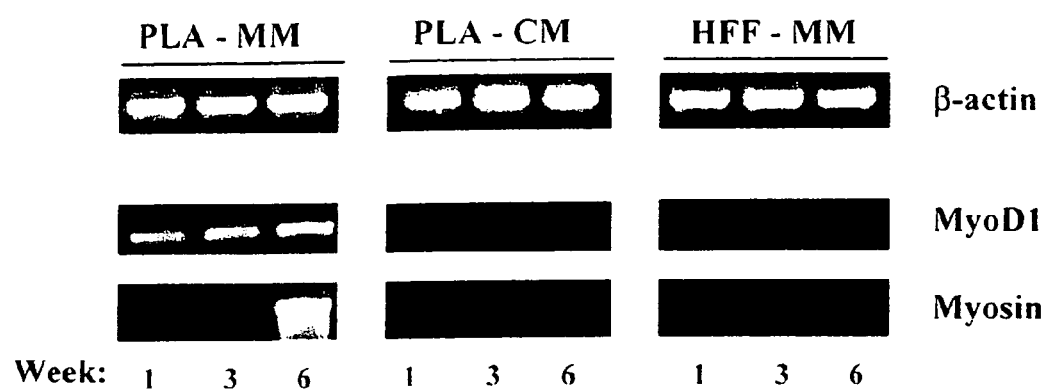
FIG. 19: RT-PCR analysis of adipose-derived stem cells induced in MM. RT-PCR was performed on adipose-derived stem cells induced for 1, 3 and 6 weeks in MM (PLA-MM) or in CM (PLA-CM), using primers to human MyoD1 and myosin. RT-PCR analysis of human foreskin fibroblast (HFF) cells induced in MM (HFF-MM) was also performed as a negative control. Duplicate reactions were performed using a primer set to β-actin as an internal control. PCR products were resolved by agarose gel electrophoresis and equalized using β-actin levels.

RT-PCR Analysis:

Finally, myogenic differentiation was confirmed using RT-PCR (FIG. 19). Consistent with our immunohistochemistry data, RT-PCR analysis confirmed the expression of MyoD1 in PLA cells induced for 1, 3 and 6 weeks in MM. In contrast, MyoD1 expression was not observed in PLA cells cultured in CM nor in HFF cells induced with MM. Low levels of myosin expression were observed in induced PLA cells at 3 weeks, while increased expression of this marker was seen at 6 weeks post-induction with MM. Myosin was not detected in these cells after 1 week of induction and was supportive of the immunohistochemistry results. The expression of myosin was specific to induced PLA cells as no expression was detected in control PLA cells or in myo-induced HFF cells. The RT-PCR results confirm our immunohistochemistry data and further support the myogenic potential of PLA cells.

Figure 20:
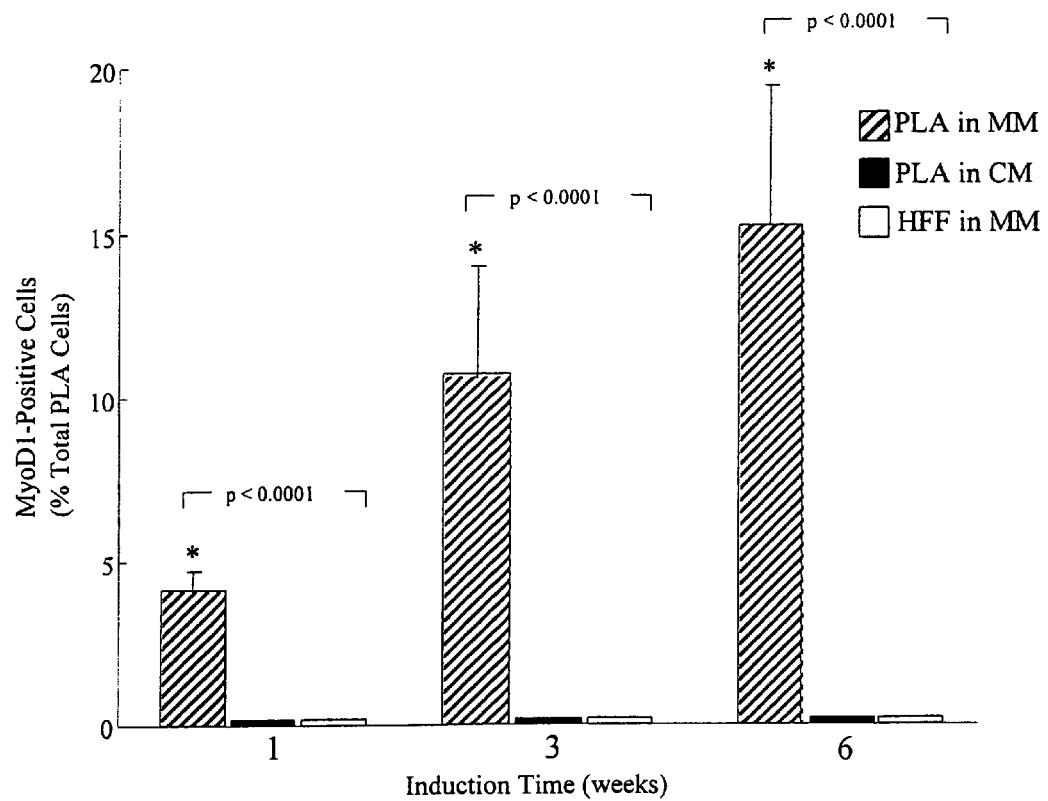
FIG. 20. The proportion of MyoD1-positive adipose-derived stem cells increases with induction time. Histogram showing the mean number of MyoD1-positive, adipose-derived stem cells (PLA) after a 1, 3 and 6 week induction in MM (% of total PLA cells±SEM–hatched bars). The mean number of MyoD1-positive cells observed after induction of adipose-derived stem cells with CM (black bars) and HFF cells in MM (open bars) was also measured. The values for each experiment are shown in table format below. A statistical comparison of MyoD1 values from 1 to 6 weeks using a one-way ANOVA was performed (asterisks; $P<0.001$, $F=18.9$). Furthermore, an ANOVA was performed comparing the experimental and control values for each time point. The p-values are shown ($p<0.0001$).

Quantitation of Myogenic Differentiation by PLA Cells:

In order to determine the degree of myogenic differentiation by induced PLA cells, the immunohistochemistry data was quantitated. To do so, the number of MyoD1- or myosin-positive cells was counted as an indicator of myogenic marker expression level and expressed as a percentage of total PLA cells counted±the standard error of the mean (% total PLA±SEM). The number of MyoD1-positive PLA cells upon MM induction is shown in FIG. 20. Low levels of MyoD1-positive PLA cells were observed after 1 week induction in MM (4.11±0.51% total PLA cells). By 3 weeks post-induction, 10.11±3.85% of the total PLA cells were MyoD1 positive while 15.37±4.33% of the total PLA cells were MyoD1 positive at 6 week post-induction. Based on the cell count, a 2.4-fold increase in the number of MyoD1-positive cells was observed within the first 3 weeks of induction. In contrast to the first 3 weeks, MyoD1 expression levels only increased 1.5-fold in the last 3 weeks of myogenic induction. The greater number of MyoD1-positive cells in the first 3 weeks of induction relative to the last 3 weeks may reflect the early role this regulatory factor plays in myogenic differentiation (Megeney, et al., 1996 Genes Dev. 10:1173-1183; Seale and Rudnicki 2000 Dev. Biol. 218:115-124; Tapscott, et al., 1988 Science 242:405-411; Weintraub, et al., 1991 Science 251: 761-766).

In contrast to myo-induced PLA cells, no appreciable myogenic differentiation was observed at any time point upon treatment of PLA cells with CM or in HFF cells with MM, confirming the specificity of the induction conditions. To confirm if the increase in MyoD1 expression in PLA cells over time was significant, statistical analysis was performed using a one-way ANOVA. Comparison of the MyoD1 experimental values only, from 1 to 6 weeks, yielded statistical significance ($P<0.001$; $F=18.9$). In addition, analysis of 1 and 3 week MyoD1 levels using an unpaired t-test confirmed a significant difference ($p=0.0021$). A reduced level of significance was determined between 3 and 6 weeks ($p=0.0335$) and is likely a reflection of the reduced role MyoD1 plays in maturing myoblasts. Finally, the increased expression of MyoD1 in the experimental group versus controls within each differentiation time period was found to be statistically significant using a one-way ANOVA ($p<0.0001$).

Figure 21:
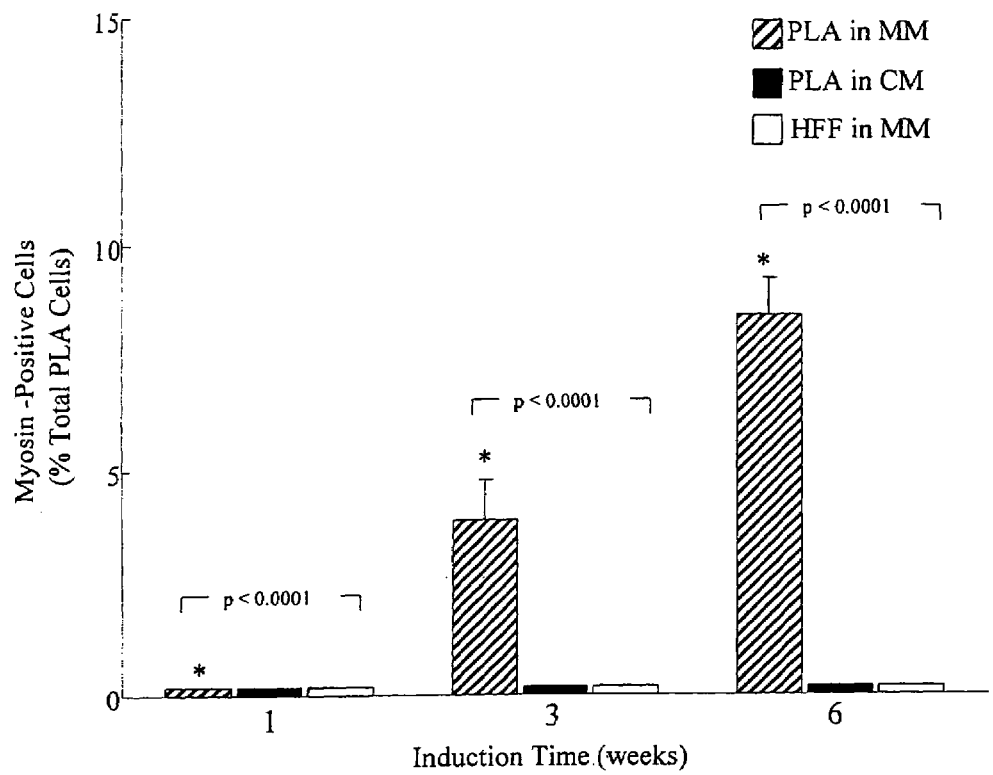
FIG. 21. A time-dependent increase in myosin expression is observed in induced adipose-derived stem cells. Histogram showing the mean number of myosin-positive adipose-derived stem cells (PLA) after a 1, 3 and 6 week induction in myosin medium (MM) (% of total PLA cells±SEM–hatched bars). The mean number of myosin-positive cells observed after induction of adipose-derived stem cells with control medium (CM) (black bars), and human foreskin fibroblast cells (HFF) in myosin medium (MM) (open bars) was also measured. The values for each experiment are shown in table format below. A statistical comparison of myosin values from 1 to 6 weeks using a one-way ANOVA was performed (asterisks; $P<0.0001$, $F=75.5$). Furthermore, an ANOVA was performed comparing the experimental and control values for each time point. The p-values are shown ($p<0.0001$).

A time-dependent increase in the number of myosin-positive PLA cells was also observed upon induction with MM (FIG. 21). Negligible levels of myosin expression were observed at 1 week post-induction, consistent with expression of this protein in maturing myoblasts. Following 3 weeks induction, 3.88±0.46% of the total PLA cells counted were positive for myosin expression, while 8.42±0.71% were myosin positive at 6 weeks, a 2.2-fold increase in the number of myosin-positive cells in the last 3 weeks of induction. The increased number of myosin expressing cells from 3 to 6 weeks post-induction was greater than that measured for MyoD1 and is consistent with a shift from differentiating to maturing myogenic cells (Butler-Browne, et al., 1990 Anat. Embryol. (Berl) 181:513-522; Thornell, et al., 1984 J. Neurol. Sci. 66:107-115). No myosin expression was observed in PLA cells cultured with CM or in HFF cells induced with MM, confirming the specificity of the induction conditions. Analysis of the increase in myosin expression levels from 1 to 6 weeks confirmed statistical significance (one-way ANOVA—$P<0.0001$; $F=75.5$). Statistical significance was also observed using an unpaired t-test to compare 3 and 6 week myosin expression levels only ($p<0.0001$). As in the MyoD1 studies, statistical analysis of both PLA and control cultures confirmed statistical significance (one-way ANOVA—P<0.0001). Finally, myogenic differentiation levels, as measured using both MyoD1 and myosin expression levels, were found to be consistent from patient to patient. Furthermore, regression analysis did not demonstrate a significant correlation of myogenic differentiation with patient age (MyoD1, correlation=0.27; myosin, correlation=0.30).

Discussion

Muscle loss due to trauma, vascular insult, tumor resection or degenerative muscle disease such as muscular dystrophy represents a significant clinical problem with few solutions. For focal muscle loss, vascularized muscle transplantation has been performed, but incumbent donor site morbidity is both cosmetically and functionally limiting. System muscle disorders, such as degenerative muscle loss, are generally considered to be fatal disorders resulting in progressive muscle loss, diaphragmatic paralysis or dysfunction and eventual suffocation. Current therapeutic approaches, such as gene therapy, have proven unsuccessful thus far. However, recent developments in the field of tissue engineering may allow eventual replacement or repair of both focal and generalized muscle tissue loss.

Two cell types are generally considered candidate cells for muscle tissue engineering: embryonic stem cells and post-natally derived progenitor cells or stem cells. Unfortunately, ethical issues and potential problems with cell regulation have limited the use of embryonic stem cells (Baker, et al., 1996 Curr. Top. Dev. Biol. 33:263-279; Dinsmore, et al., 1996 Cell Transplant 5:131-143; Lenoir, N. 2000 Science 287: 1425-1427; Rohwedel, et al., 1994 Dev. Biol. 164:87-101; Young, F E 2000 Science 287:1424). Post-natal skeletal muscle progenitors or satellite cells have been introduced for the treatment of Duchenne's muscular dystrophy by Myoblast Transfer Therapy (MITI) (Karpati, et al., 1989 Am J. Pathol. 135:27-32; Law, et al., 1988 Muscle Nerve 11:525-533; Rando, et al., 1995 Exp. Cell Res. 220:383-389; Partridge, et al., Nature 273:306-308). Although potentially beneficial, the practical use of satellite cells is limited primarily due to cell availability (such cells must be harvested from viable donor muscle tissue), as well as decreased self-renewal potential with increasing age (Rando, et al., 1994 J. Cell Biol. 125:1275-1287; Satoh, et al., 1993 J. Histochem. Cytochem. 41:1579-1582; Schultz and Lipton 1982 Mech. Ageing Dev. 20:377-383). In addition to satellite cells, mesenchymal stem cells derived from bone marrow (MSCs) have also been reported to have myogenic capability under special culture conditions (Ferrari, et al., 1998 Science 279:1528-1530; Wakitani, et al., 1995 Muscle Nerve 18:1417-1426).

In this study, we show that human Processed Lipoaspirate (PLA) cells obtained from Suctioned-Assisted Lipectomy (SAL) have myogenic potential in vitro. Immunohistochemical and RT-PCR analyses reveal that PLA cells induced with MM express both MyoD1 and myosin heavy chain, markers that are expressed in skeletal muscle precursors undergoing differentiation and maturation. MyoD1 expression in PLA cells is highest during the first 3 weeks of induction, consistent with its early role in myogenic differentiation. A time-dependent increase in myosin is also observed, with the highest number of myosin-positive cells observed during the latter stages of differentiation (i.e. 3 to 6 weeks post-induction). Such an increase may reflect the maturation of PLA cells into myoblasts. Consistent with terminal differentiation and myoblast fusion, long, multi-nucleated myotubes, expressing myosin, are first observed at three weeks post-induction, with the number and the size of these multi-nucleated cells increasing over time. Finally, immunohistochemical quantification showed that approximately 15% of PLA cells undergo myogenesis.

In post-natal life, mature skeletal muscle fibers cannot regenerate if damaged. In response to muscle injury or in individuals with chronic degenerative myopathies, satellite cells, located between the sarcolemma and the basal lamina of the muscle fiber, activate to become myogenic precursor cells. These precursors divide and fuse to repair the damaged muscle (Campion, D R 1984 Int. Rev. Cytol. 87:225-251). However, the number of satellite cells within mature muscle is only 1-5% of the total cell number and their self-renewal potential decreases with age (Schultz and Lipton 1982 Mech. Ageing Dev. 20:377-383; Alameddine, et al., 1989 Muscle Nerve 12:544-555). For focal muscle loss, vascularized muscle transplantation has been performed, but incumbent donor site morbidity is both cosmetically and functionally limiting. Furthermore, for systemic muscle diseases, autologous skeletal tissue transplantation cannot be used because of the generalized nature of the disease process. Therefore, other cell-based therapeutic approaches are required.

One such emerging treatment strategy is Myoblast Transfer Therapy or MTT. Myoblast Transfer Therapy involves implanting large numbers of healthy myoblasts. This method was first performed in 1978 and has been shown to be a promising treatment for Duchenne's muscular dystrophy patients (Karpati, et al., 1989 Am J. Pathol. 135:27-32; Law, et al., 1988 Muscle Nerve 11:525-533; Rando, et al., 1995 Exp. Cell Res. 220:383-389; Partridge, et al., Nature 273: 306-308). Although theoretically beneficial for muscle tissue replacement or augmentation, its success has been limited (Rando, et al., 1994 J. Cell Biol. 125:1275-1287; Satoh, et al., 1993 J. Histochem. Cytochem. 41:1579-1582). As an alternative, multipotential stem cells have become promising candidates for future cell-based therapeutic strategies since they can rapidly proliferate in culture and retain the ability to differentiate into several mesodermal cell types (Caplan 1991 J. Orthop. Res. 9:641-650; Pittenger, et al., 1999 Science 284:143-147).

Previous reports have demonstrated that mesodermal stem cells can be isolated from both prenatal and post-natal organisms (Ferrari, et al., 1998 Science 279:1528-1530; Caplan 1991 J. Orthop. Res. 9:641-650; Elmer, et al., 1981 Teratology 24:215-223; Swalla, et al., 1986 Dev. Biol. 116:31-38; Hauschka, et al., 1974 Dev. Biol. 37:345-68; Solursh, et al., 1981 Dev. Biol. 83:9-19; Nakahara, et al., 1991 Exp. Cell Res. 195:492-503; Goshima, et al., 1991 Clin. Orthop. 274-283; Goshima, et al., 1991 Clin. Orthop. 298-311; Benayahu, et al., 1989 J. Cell Physiol. 140:1-7; Bennett, et al., 1991 J. Cell Sci. 99: 131-139; Calcutt, et al., 1993 Clin. Res. 41:536A; Lucas, et al., 1992 In Vitro Cell Dev. Biol. 28:154A; Lucas, et al., 1993 J. Cell Biochem. 17E:122). Williams et al. has shown that post-natal cells isolated from skeletal muscle tissue possess adipogenic, osteogenic, chondrogenic and myogenic potential (Williams, et al., 1999 Am Surg. 65:22-26). Moreover, several groups have demonstrated the differentiation of Mesenchymal Stem Cells (MSCs) obtained from both human and animal bone marrow into adipogenic, osteogenic and chondrogenic lineage cells (Pittenger, et al., 1999 Science 284:143-147; Grigoriadis, et al., 1988 J. Cell Biol. 106: 2139-2151; Beresford, et al., 1992 J. Cell Sci. 102:341-351; Cheng, et al., 1994 Endocrinology 134:277-286; Johnstone, et al., 1998 Exp. Cell Res. 238:265-272; Yoo, et al., 1998 J. Bone Joint Surg. Am. 80:1745-1757). These findings suggest that bone marrow and skeletal muscle may be a promising source of stem cells. However, there are drawbacks to the use of bone marrow and skeletal muscle as sources of myogenic cells. Bone marrow procurement is painful and yields a low number of MSCs, often requiring ex vivo expansion prior to clinical use. Moreover, only a few stem cells can be obtained from skeletal muscle without a functional loss to patients.

In this example we demonstrate the expression of established myogenic markers by adipose-derived stem cells (MyoD1, myosin, multi-nucleation), confirming and quantitating their myogenic potential. Since adipose tissue is plentiful and liposuction procedures are relatively safe with minimal patient discomfort, human adipose-derived stem cells can provide an an additional source of multi-lineage cells, together with those obtained from bone marrow and skeletal muscle, for treating muscular disorders.

While the expression of myogenic markers in stem cells was shown, the exact origin of these cells cannot be confirmed. It is possible, though unlikely, that our results are due to the contamination of the adipose compartment with satellite cells or myogenic precursors from a non-adipose tissue source. One possibility is the contamination of the adipose compartment with myogenic precursor cells from skeletal muscle. However, it is very unlikely from a technical standpoint that the investing fascia of the skeletal muscle could be entered with the blunt-tip liposuction cannula. Another possibility is the contamination of the adipose compartment by MSCs from the peripheral blood. Conflicting reports have been presented as to the presence of MSCs in peripheral blood (Lazarus, et al., 1997 J. Hematother. 6:447-455; Huss 2000 Stem Cell 18:1-9), although we believe that the level of myogenesis observed in our study is inconsistent with the low percentage of MSCs that might be contributed by peripheral blood. Finally, while no clear marker exists for the identification of satellite cells and myogenic precursors, MyoD1 is one of the earliest markers expressed during differentiation and has been used to identify myogenic precursors (Weintraub, et al., 1991 Science 251:761-766; Grounds, et al., 1992 Cell Tiss. Res. 267:99-104; Sassoon, DA 1993 Develop. Biol. 156:11). As shown in FIG. 16, MyoD1 expression was not observed in non-induced PLA cultures, suggesting that our results are not due to the presence of myogenic precursor cells in the PLA, but are due to the myogenic differentiation of a multi-lineage stem cell.

The goal of skeletal muscle tissue engineering is the treatment of intrinsic skeletal muscle diseases and the loss of skeletal muscle following trauma or ischemia. Present medical and surgical therapies for these disorders are either ineffective or impractical. The use of human PLA cells in these areas is promising. Human PLA cells are plentiful, easily obtainable with minimal morbidity and discomfort and exhibit myogenic potential. As such, these cells may have important applications for myogenic tissue engineering and repair.

While the degree of myogenic differentiation of PLA cells is relatively low compared to observed levels of adipogenic and osteogenic differentiation (Zuk, P., et al., 2001 Tissue Engineering 7:209-226), application of exogenous factors such as passive and active mechanical forces (Periasamy, et al., 1989 Biochem. J. 257:691-698; Vandenburgh and Kaufnan 1981 J. Cell Physiol. 109:205-214; Vandenburgh 1983 J. Cell Physiol. 116:363-371; Vandenburgh, et al., 1988 In Vitro Cell Dev. Biol. 24:166-174; Vandenburgh 1989 In Vitro Cell Dev. Biol. 25:607-616) and refinement of culture conditions may augment myogenic differentiation, making these cells clinically useful.

EXAMPLE 11

The following description provides adipose-derived stem cells which differentiate into osteogenic, chondrogenic, adipogenic, myogenic, and neurogenic tissues. The description also provides methods for isolating and inducing differentiation of said stem cells.

Materials and Methods

All materials were purchased from Sigma (St. Louis, Mo.), VWR (San Dimas, Calif.) and Fisher Scientific (Pittsburgh, Pa.) unless otherwise stated. All tissue culture reagents were purchased from Life Technologies (New York, N.Y.). Fetal Bovine Serum (FBS) and Horse Serum (HS) were purchased from Hyclone (Logan, Utah) and Life Technologies, respectively. 1,25-dihydroxyvitamin $D_3$ was purchased from BioMol (Plymouth Meeting, Pa.).

Cell Lines:

Normal human osteoblasts (NHOsts), normal human chondrocytes from the knee (NHCK) and a population of MSCs from human bone marrow were purchased from Clonetics (Walkersville, Md.). The murine 3T3-L1 preadipocyte cell line (Green and Meuth 1974 Cell 3:127-133) was obtained from ATCC (Rockville, Md.). The human neuroendocrine cell line, PC12, was the generous gift of Dr. Harvey Herschman (UCLA, Los Angeles, Calif.).

Antibodies:

A monoclonal antibody to human osteocalcin was purchased from TaKaRa Shizo Co. (Japan). The polyclonal antibodies to human osteopontin ($\alpha$OP-LF123), osteonectin ($\alpha$ON-LF37), biglycan, ($\alpha$BG-LF51), decorin ($\alpha$DEC-LF136) and alkaline phosphatase ($\alpha$AP) were obtained from Dr. Larry Fisher (NIH). Monoclonal antibodies to MAP2 ($\alpha$MAP), neurofilament 70 ($\alpha$NF70) and $\tau$-tau ($\alpha$tau) were purchased from Leinco Technologies (St. Louis, Mo.). Monoclonal antibodies to trk-a ($\alpha$TRK) and NeuN ($\alpha$Neu) were purchased from Santa Cruz Biotech (Santa Cruz, Calif.) and Chemicon (Temecula, Calif.), respectively. Polyclonal antibodies to glial fibrillary acidic protein ($\alpha$GFAP) and were purchased from Dako and Stressgen (Victoria, BC), respectively. Secondary antibodies conjugated to alkaline phosphatase were obtained from Zymed, while secondary antibodies conjugated to FITC were purchased from BioSource (Camarillo Calif.).

Cell Harvest, Culture and Differentiation Conditions:

Adipose-derived stem cells (PLA) cells were obtained from raw lipoaspirates and cultured as described in a previous study (Zuk, 2001 Tissue Engineering 7(2):209-226). Adipose-derived stem cells and 3T3-L1 cells were maintained in non-inductive Control medium (Table 5). NHOst, MSC and NHCK cells were maintained in specialized commercial Control media (Clonetics). Adipose-derived stem cells cells were induced toward the desired mesenchymal lineages as outlined in Table 5. MSCs were induced using commercial control medium supplemented with the growth factors outlined in Table 5. 3T3-L1 cells were induced toward using. Adipogenic Medium (AM). NHOst and NHCK cells were induced using commercially available induction media (Clonetics).

Histology, Immunohistochemistry and Indirect Immunofluorescence:

Indirect Immunofluorescence (IF): PLA cells and MSCs were processed for IF as described in Zuk, P. et al., 2001 Tissue Engineering 7:209-226 using monoclonal antibodies to specific CD markers (Table 6).

Histology and Immunohistochemistry (IH): To confirm lineage-specific differentiation, differentiated cells were processed as described in Zuk, P. et al., 2001 Tissue Engineering 7:209-226, using the following histological assays: Alkaline Phosphatase (osteogenesis), Oil Red O (adipogenic) and Alcian Blue (chondrogenic). In addition, PLA nodules induced toward the chondrogenic lineage were processed by IH for the expression of collagen type 2, keratan sulfate (KS) and chondroitin-4-sulfate (CS), as previously described in Zuk, P. et al., 2001 Tissue Engineering 7:209-226.

Spectrophotometric Assays:

Alkaine Phosphatase (AP): Triplicate samples of PLA cells were differentiated in Osteogenic Medium (OM) for up to 6 weeks. Cells were washed with PBS and harvested into PBS/0.1% Triton X-100 (PBS/TX100). AP enzyme activity was assayed using a commercial AP enzyme kit (Sigma) and measured at an absorbance of 405 nm. Total protein in each sample was measured based on the Bradford method (Bradford 1976 Anal. Biochem. 72:248-254) using a BCA Protein Assay Kit (Pierce, Rockford, Ill.). AP activity was expressed a nmol p-nitrophenol produced/minute/ug protein. The assay was calibrated using standard p-nitrophenol solutions. Differentiated MSC and NHOst cells were assayed as positive controls while non-induced PLA cells were assayed as a negative control. Values are expressed as the mean±SD.

Total Calcium ($Ca^{2+}$): Triplicate samples of PLA cells were differentiated in OM as described above. Cells were washed with PBS (no $Ca^{2+}$, no $Mg^{2+}$) and harvested in 0.1N HCl. Cells were extracted for a minimum of 4 hours at 4° C. and centrifuged at 1000×g for 5 minutes. Total calcium in the supernatant was determined using Sigma kit #587 and measured at A575 nm. The assay was calibrated using calcium standard solutions. Total protein was determined and the samples were expressed as mM Ca/ug protein. Differentiated MSC and NHOst cells were assayed as positive controls, while non-induced PLA cells were assayed as a negative control. Values are expressed as the mean±SD.

Glycerol-3-Phosphate Dehydrogenase (GPDH): Triplicate samples of PLA cells were differentiated in AM for up to 5 weeks. The cells were harvested in 25 mM Tris-Cl, 1 mM EDTA (pH 7.5), 0.1 mM β-mercaptoethanol and sonicated for 5 sec and 40 W to lyze. The suspension was centrifuged at 10000×g and GPDH in the supernatant assayed by measuring the oxidation of NADH at A340 nm, according to the method of Wise and Green (Wise, 1979). One unit of GPDH was defined as the oxidation of 1 mmol of NADH per minute. Samples were normalized with respect to protein and expressed as units GPDH/ug. Differentiated MSC and 3T3-L1 cells were assayed as positive controls while non-induced PLA cells were assayed as a negative control. Values are expressed as the mean±SD.

Dimethyldimethylene Blue (DMMB): Triplicate samples of PLA cells were differentiated in Chondrogenic Medium (CM) for up to 3 weeks using established micromass protocols (Ahrens, et al., 1977 Develop. Biol. 60:69-82; Denker, et al., 1995 Differentiation 59:25-34; Reddi, et al., 1982 Prog. Clin. Biol. Res. 110(Part B):261-268). PLA nodules were harvested and assayed for the sulfated glycosaminoglycans keratan sulfate (KS) and chondroitin sulfate (CS) according to the method of Farndale et al. (Farndate, et al., 1986 Biochimica et Biophysica Acta 883:173-177). The assay was calibrated by the use of standard KS and CS solutions. Samples were normalized with respect to protein and expressed as μg KS or CS per μg protein. Non-induced PLA cells were assayed as a negative control. Values are expressed as the mean±SD.

RT-PCR Analysis:

PLA cells were induced toward the five lineages outlined in Table 5 for defined time periods. Total cellular RNA was isolated from the differentiated cells using a commercially available kit (QiaEasy, Qiagen). RNA was reverse transcribed using an oligo-dT primer and MMLV-Reverse Transcriptase (Promega, Madison, Wis.) for 60 minutes at 42° C. PCR amplification was performed by the addition of Taq buffer (Promega), 2.5 mM $MgCl_2$, 1 mM dNTPs and 50 pmol of the appropriate primer set (Table 7). The mix was incubated for 1 minute at 94° C. and 2.5 units of Taq polymerase (Promega) was added. PCR was performed for 40 cycles (1 minute—94° C., 1 minute—57° C., 1 minute—72° C.: final extension—5 minutes at 72° C.). All primer sequences were determined using established GenBank sequences and the Primer3 program. PCR reactions with primers designed to the housekeeping gene β-actin were amplified for 35 cycles as an internal control. The sequence of each PCR product was confirmed using automated sequencing. Non-induced PLA cells were examined as a negative control. Lineage-specific cell lines were analyzed as a positive controls for the osteogenic, adipogenic and chondrogenic lineages. Total human skeletal muscle and brain RNA were reverse-transcribed and amplified by PCR as a positive control for the myogenic and neurogenic lineages, respectively.

Western Blotting:

PLA cells were differentiated and harvested in 1% SDS. Lysates were homogenized and total protein assayed. Equivalent amounts of protein from each lineage were denatured for 5 minutes at 100° C. in SDS Load Buffer (0.5M Tris-Cl (pH 6.8), 1% SDS, 1 mM DTT, 50% Glycerol, 1% Bromophenol Blue). Lysates were resolved by polyacrylamide gel electrophoresis (10% separating gel, 5% stacking gel), according to standard protocols. Proteins were transferred overnight to nitrocellulose membranes and the membranes blocked for a minimum of 60 minutes in Western Blocking Buffer (WBB: 5% non-fat milk, 1×PBS, 0.1% Tween-20). Membranes were incubated for a minimum of 60 minutes in WBB, supplemented with the following antibodies: osteogenesis: αOP, αON, αCNI, αDEC and αBG and adipogenesis: αG4 and αLEP. Membranes were also incubated with antibodies to the transferrin receptor and the soluble heat shock protein HSC70 as internal controls. Membranes were washed a minimum of 3 times with PBS/0.1% Tween-20 and then incubated for 60 minutes with WBB supplemented with the appropriate secondary antibody conjugated to alkaline phosphatase. The membranes were washed, as described above, and the secondary antibodies visualized using a commercial kit (CSPD Ready-To-Use, Tropix, Bedford, Mass.) according to the manufacturer. Non-induced PLA cells were also analyzed as a negative control.

Neurogenic Differentiation:

Immunohistochemistry: Subconfluent PLA cells were cultured in Preinduction Medium (DMEM, 20% FBS, 1 mM β-mercaptoethanol) for 24 hours. Following preinduction, cells were induced for up to 8 hours in Neurogenic Medium (NM) and assessed by IH in order to determine specific neurogenic lineages (Table 8).

RT-PCR: PLA cells were pre-induced for 24 hours in Preinduction Medium, followed by induction in NM for up to 9 hours. PLA samples were harvested, RNA isolated (QiaEasy, Qiagen) and analyzed by RT-PCR for the expression of specific neurogenic genes (Table 7) as detailed above.

Isolation and Analysis of PLA Clones:

Clone Isolation: PLA cells were plated at extremely low confluency in order to result in isolated single cells. Cultures were maintained in Control medium until proliferation of single PLA cells resulted in the formation of well-defined colonies. The single PLA-cell derived colonies were harvested using sterile cloning rings and 0.25% trypsin/EDTA. The harvested clones were amplified in Cloning Medium (15% FBS, 1% antibiotic/antimycotic in F12/DMEM (1:1)).

Confirmation of Multi-lineage capacity: Expanded clones were analyzed for multi-lineage potential as described earlier (see Histology and Immunofluorescence).

Molecular Characterization: Clones were analyzed by RT-PCR for the expression of several lineage-specific genes as described above.

Results

Figure 23:
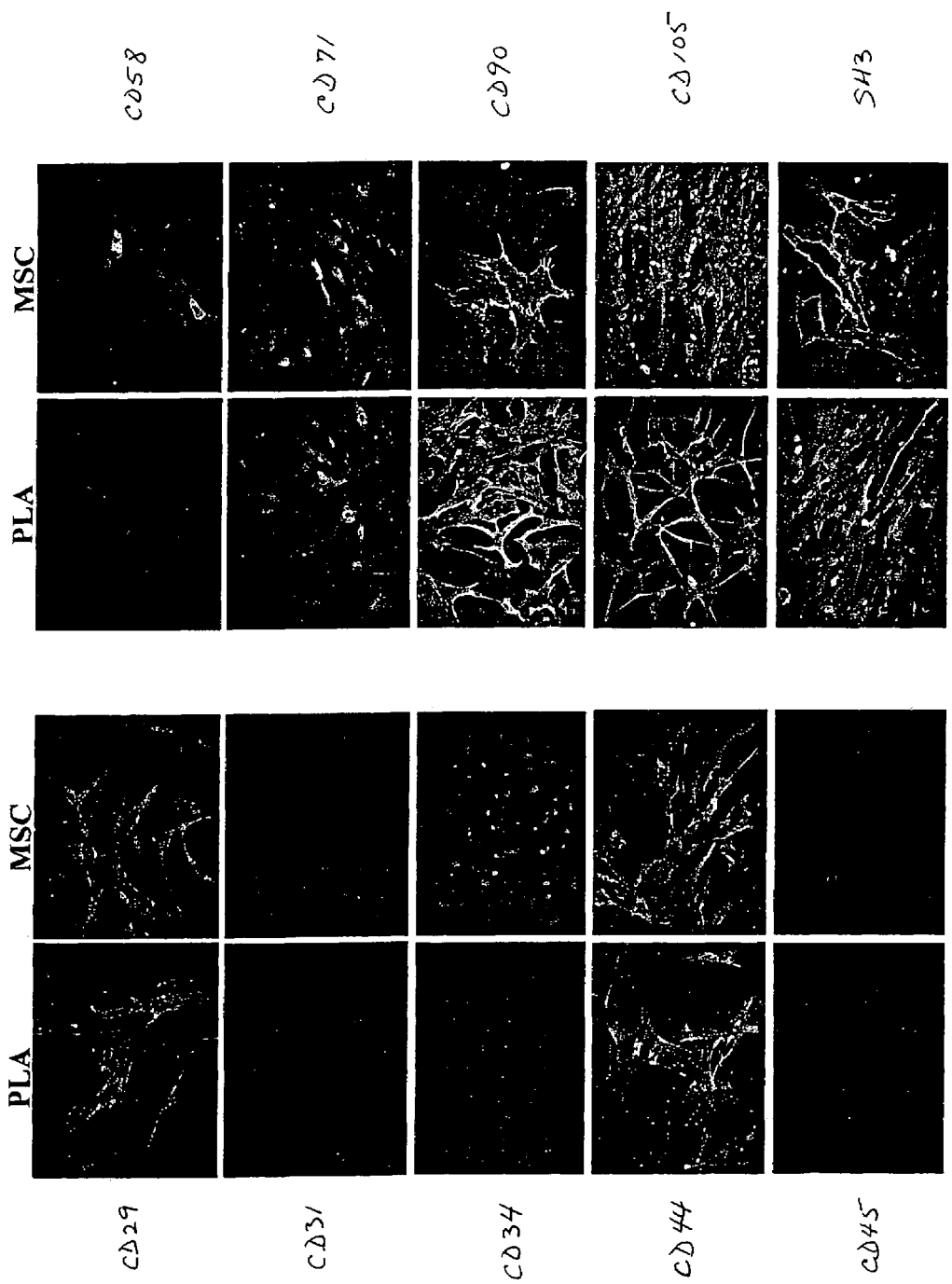
FIG. 23. The adipose-derived stem cells (PLA) express a unique set of CD markers. PLA cell and MSCs from human bone marrow were processed for IF for the indicated CD antigens. Cells were co-stained with DAPI to visualize nuclei (blue) and the fluorescent images combined.
Figure 24:
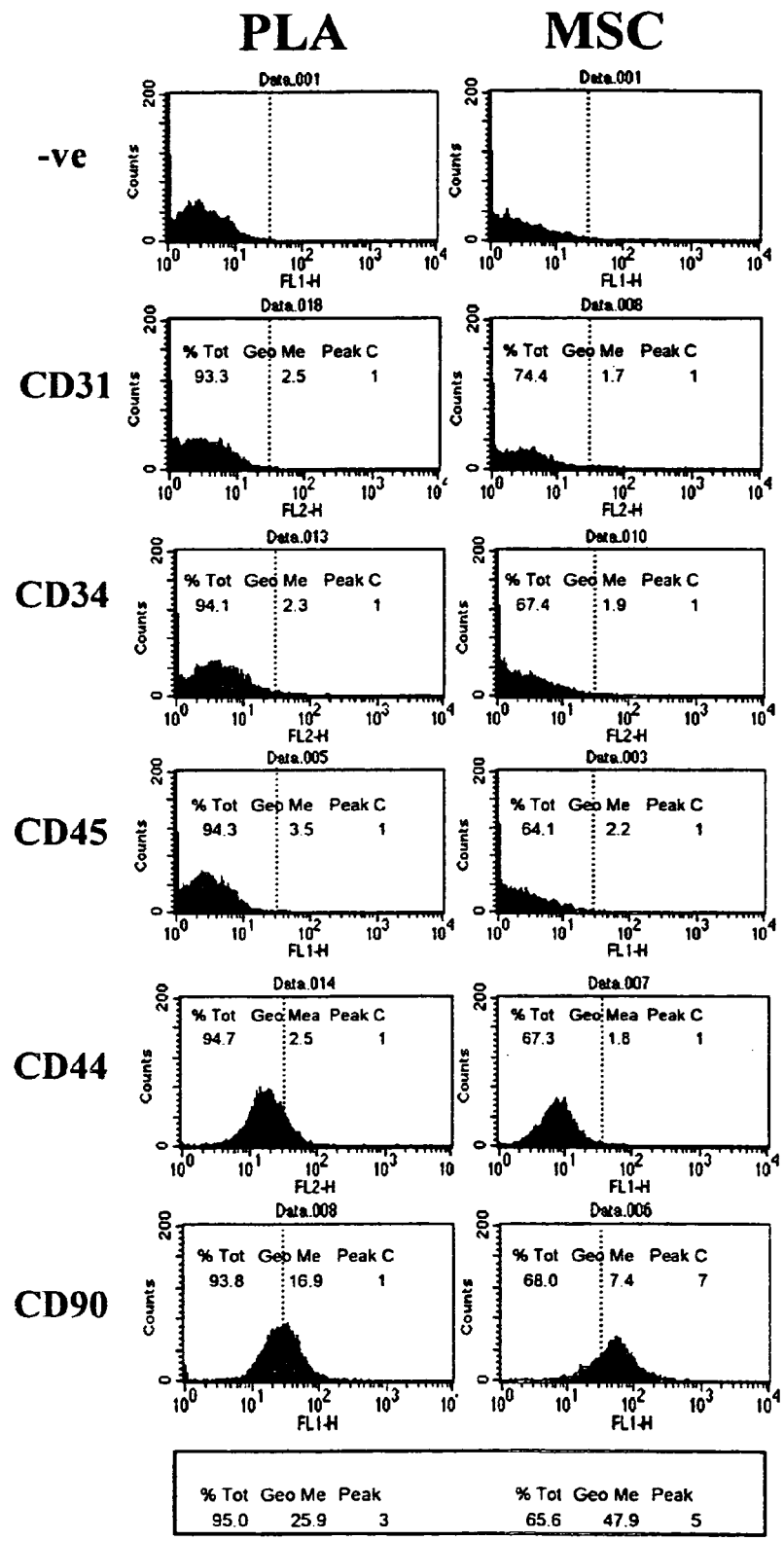
FIG. 24. CD marker profile of adipose-derived stem cells (PLA) and bone marrow MSCs using flow cytometry. Panel A: Adipose-derived stem cells were analyzed by FC using forward and side scatter to assess cell size and granularity (FSC-H and SSC-H, respectively). MSCs were analyzed as a control. Panel B: PLA cells were fixed and incubated for the indicated CD markers using fluorochrome-conjugated primary antibodies. Stained PLA cells were subsequently analyzed by FC. MSCs and PLA cells stained with fluorochrome-conjugated non-specific IgG were examined as a positive and negative control, respectively. All results were corrected for senescence and represent a total of $10^5$ events.

Stem Cells Share Many Similarities With MSCs:

In order to characterize the PLA population further, cells were examined using indirect IF and compared to a commercial population of human MSCs. MSCs have been shown to express a unique set of cell surface markers that can be used to help identify this stem cell population (Table 6) (Bruder, et al., 1998 J. Orthop. Res. 16:155-162; Cheng, et al., 1994 Endo 134:277-286; Jaiswal, et al., 1997 J. Cell Biochem. 64:295-312; Pittenger, et al., 1999 Science 284:143-147). Like MSCs, PLA cells expressed several of these proteins (FIG. 23), supporting the characterization of these cells as stem cells. Approximately 100% of the PLA and MSC cultures were positive for the expression of CD29, CD44, CD90 and CD105/SH2 with high expression levels for each of these markers being observed in both cell populations. Both cell populations also expressed the SH3 antigen, which, together with SH2, is considered a specific marker for MSCs (Haynesworth, et al., 1992 Bone 13:69-80). In addition, the majority of PLA cells and MSCs were also positive for the transferrin receptor, CD71, indicating that a fraction of these cell populations were replicating. PLA and MSCs did not express the haematopoietic lineage markers, CD31 and CD34. A small number of PLA samples did show negligible staining for CD45, although the number of CD45-positive cells did not exceed 5% of the total PLA cell number. Unlike MSCs, no staining for the adhesion molecule CD58 was observed in PLA cells. Flow cytometric analysis for CD marker expression confirmed the IF results (FIG. 24). Taken together, the immunofluorescent and flow results demonstrate several similarities in CD expression profiles between PLA populations and bone marrow-derived MSCs.

Figure 25:
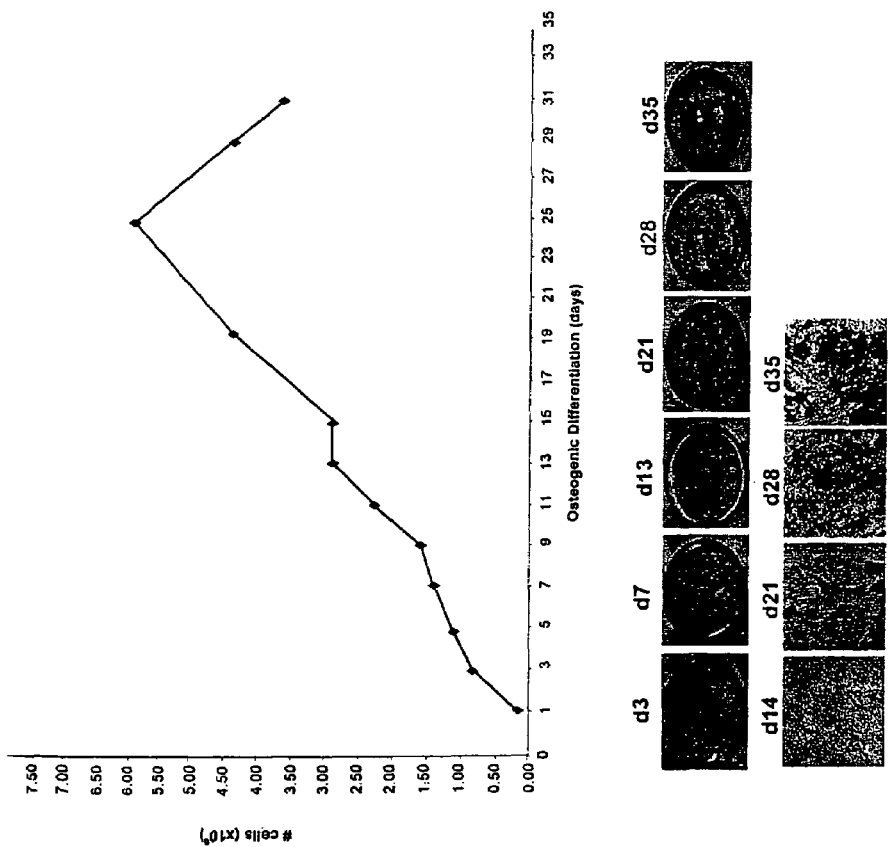
FIG. 25. Osteogenic adipose-derived stem cells (PLA) can be characterized by distinct proliferative, synthetic and mineralization phases. Adipose-derived stem cells were harvested and plated into 35 mm tissue culture dishes in two sets of four plates per differentiation period. All dishes were maintained in Control medium until approximately 50% confluence was reached. The cells were induced with Osteogenic medium (OM) and cell number was counted at the indicated days. Cell number was expressed as the number of adipose-derived stem cells (# cells ($10^5$)) and plotted versus differentiation time (Panel A). For each time period, one dish was stained for alkaline phosphatase (AP) activity and one dish was stained using a Von Kossa stain (VK) to detect calcium phosphate (Panel B).

PLA Cells Undergo Distinct Changes upon Osteogenic Induction:

In this Example, we demonstrate that PLA cells undergo distinct proliferative, synthetic and mineralization phases upon osteogenic induction. In order to characterize the osteogenic capacity of PLA cells further, the proliferation of osteo-induced PLA cells was measured and correlated to AP activity and calcium phosphate formation (FIG. 25, Panel A). PLA cell number increased upon initiation of osteogenic differentiation (day 1 to day 3), however, negligible AP and Von Kossa staining was observed (FIG. 25, Panel B). A linear increase in PLA cell number was observed from day 3 to day 9 and minimal AP staining was observed up until day 13. PLA proliferation rates leveled off briefly between day 13 and day 15, a phenomenon that was observed in several PLA populations. A dramatic increase in AP activity was seen between day 15 and day 19 and the first appearance of calcium phosphate deposits were observed by 3 weeks induction. An enhanced rate of PLA proliferation was measured from day 15 to day 25 and coincided with a time-dependent increase in both AP and VK staining. In addition, the formation of multilayered nodular structures and increased matrix synthesis were also observed during this time period. PLA cell number decreased from day 25 onward and was accompanied by the development of internodular regions lacking adherent cells, together with increased matrix mineralization. Together, these results suggest that PLA cells may undergo distinct proliferative and metabolic phases as osteogenic differentiation proceeds.

Alkaline Phosphatase Activity and Time-Dependent Increase in Matrix Mineralization:

Bone formation in vivo is a complex process involving morphogens, hormones and growth factors. Recent work has questioned the efficacy of synthetic glucocorticoids, like dexamethasone (Dex), in mediating osteogenesis. Glucocorticoids appear to inhibit the action of several osteogenic genes including osteocalcin, CBFA-1 and CNI (as reviewed in Cooper, et al., 1999 J. Endocrinol. 163:159-164). It is well established that bone tissue and osteoprogenitor cells are targets of vitamin D action (Chen, et al., 1983 J. Biol. Chem. 258:4350; Chen, et al., 1979 J. Biol. Chem. 254:7491; Narbaitz, et al., 1983 Calcif. Tiss. Int. 35:177) and this metabolite stimulates both AP activity and CNI synthesis by human bone cell populations (Beresford, et al., 1986 Endo 119:1776-1785). Therefore, PLA cells were induced using two osteogenic media compositions: containing either dexamethasone (Dex at $10^{-7}$ M) or 1,25-dihydroxyvitamin $D_3$ (VD at $10^{-8}$ M). AP activity and $Ca^{2+}$ accumulation were measured over time using commercial kits and normalized with respect to protein and/or time.

Figure 26:
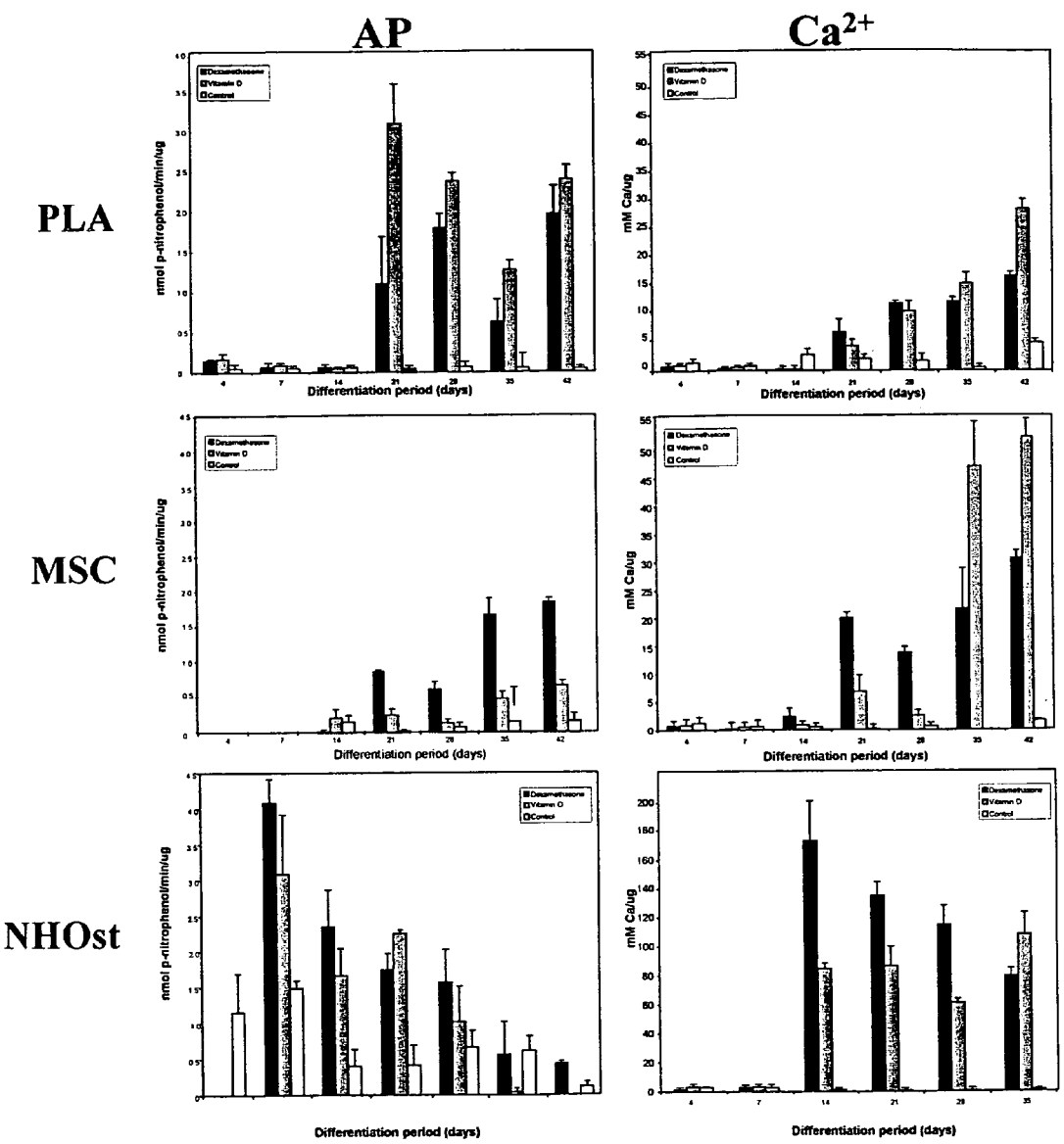
FIG. 26. Dexamethasone and 1,25-dihydroxyvitamin $D_3$ differentially affect PLA osteogenesis: AP enzyme and calcium phosphate quantitation. Triplicate samples of PLA cells, MSCs and NHOsts were induced for up to 6 weeks in OM, containing either $10^{-7}$ M Dexamethasone (OM/Dex) or $10^{-8}$ M 1,25-dihydroxyvitamin $D_3$ (OM/VD). Cells were assayed for AP activity, total calcium content and total protein. AP levels were expressed as nmol p-nitrophenol formed per minute per microgram protein (nmol p-nitrophenol/min/ug). Calcium levels were expressed as mM calcium per microgram protein (mM $Ca^{2+}$/ug). Non-induced PLA cells (Control) were analyzed as a negative control. Values were expressed as the mean±SD.

Induced PLA, MSC and NHOst cells were measured for AP activity and stage-specific induction levels presented in Table 9. AP activity in PLA cells, resulting from either Dex or VD-induction, first appeared at 3 weeks and undifferentiated PLA cells exhibited negligible AP levels at all time points (FIG. 26, Panel A). AP activity from 3 to 6 weeks was biphasic upon both Dex and VD stimulation of PLA cells, with peak activities at days 21 and 42 and decreasing levels at day 35. VD induction of PLA cells resulted in higher enzyme activities at 3, 4 and 5 weeks, while no significant difference could be measured between the two induction conditions at 6 weeks. Maximum AP levels were detected at 3 weeks in VD-induced PLA cells, whereas no significant maximum was detected upon Dex treatment. Moreover, PLA cells appeared to be more responsive to VD stimulation at 3 weeks with an enhanced level of enzyme induction being measured in these cells compared to Dex treatment (17.2-fold induction/Dex vs. 71.3-fold induction/VD). Like PLA cells, negligible AP activity was measured in Dex-treated MSCs until day 21. In contrast to PLA cells, Dex stimulation of MSCs resulted in higher enzyme activities at 3, 4 and 5 weeks. The overall pattern of MSC AP activity observed under Dex and VD induction was similar to VD-induced PLA cells (i.e. bi-phasic). However, decreasing levels were measured at day 28 in MSCs rather than day 35. Moreover, maximum enzyme activities in MSCs were detected at a later differentiation stage (i.e. 5/6 weeks). Finally, as observed in PLA cells, induction of MSCs from 2 to 3 weeks resulted in the greatest induction of AP activity. However, dexamethasone, rather then VD treatment, affected enzyme levels more in these cells (54.2-fold induction/Dex vs. 1.1-fold induction/VD). The pattern of AP enzyme activity was dramatically different in NHOst osteoblasts. Maximum AP levels were observed at 7 days in these cells and enzyme levels decreased after this time point to reach minimum levels at 6 weeks. Negligible enzyme activity could be detected in VD-treated osteoblasts at day 35 and 42. Furthermore, no significant difference in AP activity could be measured from day 7 to day 28 under either induction condition.

Induction of PLA cells and MSCs with either Dex or VD resulted in a time-dependent increase in matrix mineralization (FIG. 26 and Table 10). Consistent with AP activity, PLA cells were more responsive to VD-induction, producing a greater overall increase in matrix mineralization (122-fold/VD vs. 56-fold/Dex), with maximum levels detected at 6 weeks. A similar effect was also observed in VD-treated MSCs, although maximum levels were reached one week earlier. As with AP activity, negligible mineralization in both PLA cells and MSCs was observed until 3 weeks. A true effect of induction condition was only observed in PLA cells at 6 weeks, with VD-treated cells associated with significantly more calcium phosphate. In contrast to PLA cells, induction condition significantly affected mineralization in MSC samples with Dex treatment resulting in greater calcium levels early in differentiation (3 and 4 weeks), consistent with the AP levels under this induction condition. This trend was reversed at 5 and 6 weeks, with VD resulting in enhanced mineral levels. Interestingly, a decrease in $Ca^{2+}$ was observed in both Dex- and VD-treated MSCs at 28 days and appeared to correlate with the decrease in AP activity at this time point. In contrast to PLA cells and MSCs, maximum $Ca^{2+}$ accumulation occurred at 2 weeks in induced NHOst cells and decreased beyond this time point, consistent with observed NHOst AP activity. Like MSCs, Dex induction resulted in greater $Ca^{2+}$ levels at all induction points with the exception of 5 weeks. Control osteoblasts were associated with minimal levels of $Ca^{2+}$, indicating that these cells do not spontaneously mineralize without appropriate induction. Taken together, the AP and $Ca^{2+}$ spectrophotometric data further supports the osteogenic phenotype of PLA cells.

Figure 27:
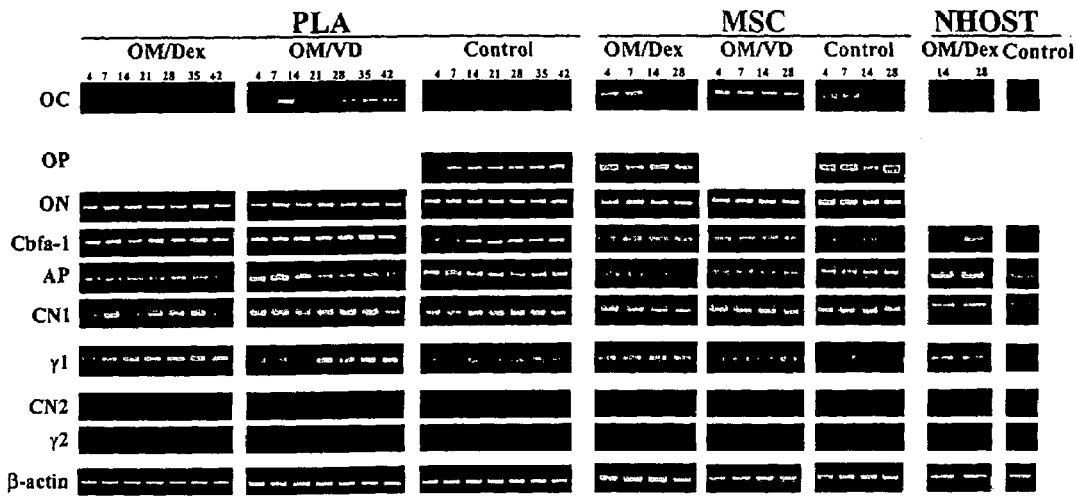
FIG. 27. Osteo-induced PLA cells express several genes consistent with osteogenic differentiation: RT-PCR and Microarray analyses. Panel A: PLA cells were cultured in either OM/Dex, OM/VD or non-inductive Control medium (Control) for the indicated days. Total RNA was isolated, cDNA synthesized and PCR amplification performed for the indicated genes. MSCs were induced in OM/Dex or OM/VD and NHOsts were induced for 2 and 3 weeks in OM/Dex as controls. Duplicate reactions were amplified using primers to β-actin as an internal control. Panel B: PLA cells were induced for 3 weeks in OM/Dex or maintained in non-inductive control medium. Total RNA was isolated and subject to microarray analysis using a customized array containing the genes, OC, OP, ON, CBFA1, CNI and BSP.

Osteo-induced PLA Cells Express Osteocalcin and CBFA-1:

To confirm the osteogenic phenotype of PLA cells at the molecular level, osteo-induced PLA cells were analyzed using RT-PCR and Western blotting. For RT-PCR analysis, PLA cells were induced for increasing time periods in OM containing either Dex or VD. Dex and VD-induced MSCs were also analyzed, in addition to NHOst cells. Osteogenic differentiation did not appear to affect PLA cells, as β-actin levels did not differ significantly from control cells (FIG. 27). Induction with Dex or VD did not significantly affect the expression of the majority of the genes examined. However, a dramatic effect was observed in the expression of the bone-specific gene, OC. OC expression was not detected in Dex-treated and control PLA cells, nor in control and Dex-induced NHOst osteoblasts. Treatment of PLA cells with VD produced a bi-phasic OC expression pattern. Negligible levels of OC were detected at 4 and 14 days of induction, whereas a significant increase was observed at day 7. Finally, a relatively consistent level of OC expression was detected from day 21 to day 42. Elimination of Dex and replacement with VD for the last 48 hours of PLA induction was sufficient to overcome the effects of Dex and induce significant levels of OC expression. In contrast to the RT-PCR results, analysis using a gene microarray detected a slight increase in OC expression in Dex-treated PLA cells versus non-induced controls (FIG. 27, Panel B). OC was not specific to osteo-induced MSCs, as detectable levels were observed in control MSCs. Dex treatment of MSCs appeared to increase OC levels at 4 and 7 days and, like control cells, was followed by a decrease at 2 and 4 weeks. Unlike PLA cells, VD induction of MSCs did not result in a bi-phasic OC expression pattern. Rather, expression levels of this gene appeared to remain consist across the 4 week induction period and were elevated when compared to Dex treatment.

In addition to OC, expression of the bone-specific transcription factor CBFA1 was observed in osteo-induced PLA cells using RT-PCR. CBFA1 was expressed at all induction points and no discernible effect on expression was observed upon Dex or VD induction. In addition, CBFA1 expression was not specific to osteo-induced PLA cells as a lower level of this gene was seen in controls. However, an increased level of CBFA1 expression (approx. two-fold) was measured in osteo-induced PLA cells using gene arrays (FIG. 27, Panel B). Like PLA cells, CBFA1 was expressed in Dex- and VD-induced MSCs at each induction point, in addition to being expressed in undifferentiated MSC controls at a decreased level. CBFA1 expression was more restricted in osteoblasts, detected in 4 week osteo-induced NHOst cells only. AP expression was observed at all time points in differentiated and control PLA cells, MSCs and NHOst cells. In addition to CBFA1 and AP, high levels of CNI were observed in these cells. While, no appreciable difference in CNI expression level was seen upon Dex or VD induction of PLA cells by RT-PCR, gene array analysis confirmed a decrease in CNI level upon osteogenic induction (FIG. 27, Panel B). In addition to OC, CBFA1, AP and CNI, differentiated PLA cells, MSCs and NHOsts expressed other markers consistent with bone differentiation, including OP and ON. As seen with CNI, decreased levels of ON and OP were also measured in Dex-treated PLA cells using arrays (FIG. 27, Panel B). An increased expression of the transcription factor, PPARγ1 was also observed in Dex-treated PLA and MSCs when compared to non-induced controls. In addition, a lower level of PPARγ1 was seen in the early stages of VD induction of PLA cells (day 4 to day 14) and was followed by increased expression beyond four weeks induction. Osteogenic induction did not result in the expression of genes consistent with fat and cartilage differentiation (PPARγ2 and CNII, respectively). Together, the expression of bone-specific OC and other genes characteristic of osteogenic differentiation in osteo-induced PLA cells further supports the osteogenic capacity of these cells.

Figure 28:
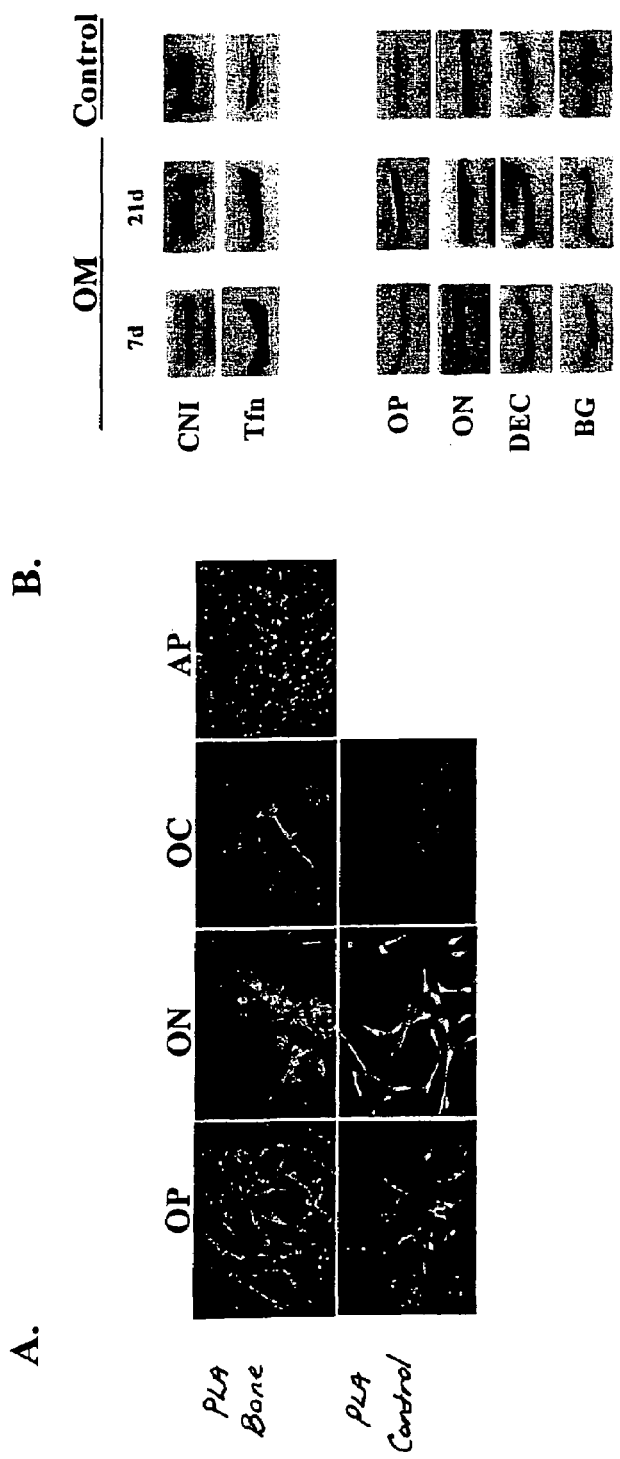
FIG. 28. Osteo-induced PLA cells express several proteins consistent with osteogenic differentiation: Immunofluorescent and Western analyses. Panel A: PLA cells and MSCs were induced in OM/Dex or maintained in non-inductive Control medium (Control) for 21 days. Cells were processed for IF for the expression of OC, OP and ON. Cells were co-stained with DAPI to visualize nuclei (blue) and the fluorescent images combined. Panel B: PLA cells were cultured in OM/Dex or non-inductive Control medium (Control) for 7 and 21 days. Cell lysates were separated by electrophoresis and analyzed by Western blotting using antibodies to OP (αOP), ON (αON), Decorin (αDEC), Biglycan (αBG) and CNI (αCNI). The expression of the transferrin receptor (αTfR) was used as an internal control.

Finally, osteogenic differentiation by PLA cells was confirmed at the protein level by immunofluorescent analysis and Western blotting. Osteo-induced PLA cells (OM/Dex) were analyzed by IF for the expression of OP, ON and OC. MSCs, induced under identical conditions were also examined as a control. As shown in FIG. 28, non-induced and osteo-induced PLA cells specifically expressed both OP and ON (FIG. 28, Panel A). OP was distributed evenly throughout control and induced cells, in addition to a distinct perinuclear concentration. No extracellular OP staining could be observed. A punctate intracellular pattern was also observed for ON in both cell types. In addition, increased nuclear staining for this protein was also observed in controls. Upon osteo-induction, ON staining appeared to increase in areas of concentrated cells and was expressed both intracellularly and extracellularly. No expression of OC could be observed in non-induced cells and was consistent with the RT-PCR results. A small percentage of the osteogenic PLA cells appeared to express low levels of OC intracellularly. Similar expression patterns for these proteins were observed in MSCs. Control and induced MSCs expressed high levels of both OP and ON. Like PLA cells, a punctate intracellular and nuclear staining pattern were observed for ON with the nuclear staining decreasing upon induction (FIG. 28, Panel B). Control and induced MSCs expressed OP intracellularly. However, unlike PLA cells, no perinuclear concentration for this protein could be seen. Finally, consistent with the RT-PCR data, both control and induced MSCs expressed OC.

To confirm the expression of osteogenic proteins by Western analysis, PLA cells were maintained in OM for 7, 14 and 21 days and lyzed. Cell lysates were analyzed for CNI, OP, ON, Decorin and Biglycan expression. In addition, lysates were also analyzed for the transferrin receptor (TfR) as internal controls. OC was not assessed due to the small size of the protein (6 kDa). Osteogenic differentiation did not appear to alter the expression of the TfR as equivalent levels were seen in osteo-induced cells and controls maintained for 3 weeks in Control medium. Comparable levels of CNI, Decorin and Biglycan were seen in osteo-induced PLA cells at all three induction periods. In addition, these proteins were also seen in controls, suggesting that both differentiated and undifferentiated PLA cells are associated with a proteinaceous ECM. Like these matrix proteins, both ON and OP were seen in differentiated cells and undifferentiated controls. However, ON levels appeared to decrease upon initial induction of PLA cells and returned to control levels by 3 weeks. In addition, osteogenic induction was accompanied by a slight increase in OP at day 21. Taken together, the immunofluorescent and Western data confirms the expression of proteins consistent with osteogenic differentiation by PLA cells.

Figure 29:
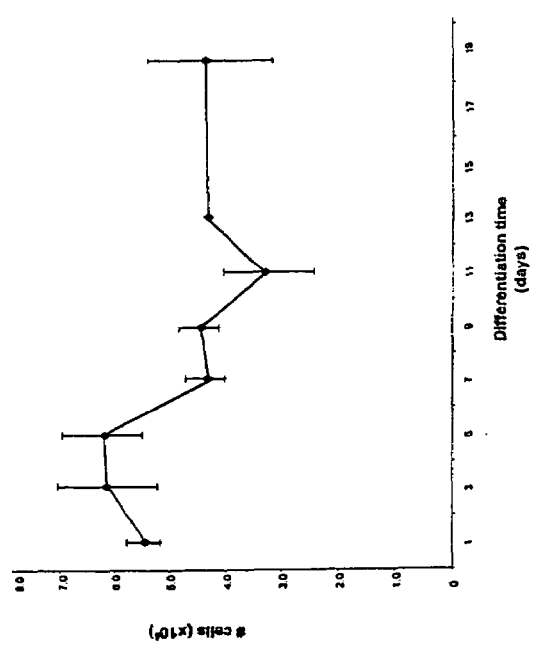
FIG. 29. Adipogenic differentiation by adipose-derived stem cells (PLA) is accompanied by growth arrest. Adipose-derived stem cells were harvested and plated into 35 mm tissue culture dishes in one set of four plates per differentiation period. All dishes were maintained in Control medium until approximately 80% confluence was reached. The cells were induced with Adipogenic medium (AM) and cell number was counted at the indicated days. Cell number was expressed as the number of PLA cells (# cells ($10^5$)) and plotted versus differentiation time Panel A). For each time period, one dish was stained with Oil Red O to detect lipid accumulation (panel B).
Figure 29:

PLA Cells Undergo Adipogenic Differentiation:

Adipogenic differentiation is associated with the growth arrest of preadipocytes before commitment to the differentiation program (reviewed in Ailhaud, et al., 1992 Annu. Rev. Nutr. 12:207-233; MacDougald and Lane 1995 Annu. Rev. Biochem. 64:345-373; Smyth, et al., 1993 J. Cell Sci. 106:1-9). To determine the correlation between PLA proliferation and adipogenic differentiation, PLA cells were induced toward the adipogenic lineage in AM for up to 3 weeks and cell numbers determined, together with the degree of differentiation using Oil Red O staining. The differentiation (i.e. appearance of intracellular lipid vacuoles) first appeared as early as 4 days induction. Consistent with the commitment of preadipocytes, no appreciable increase in PLA cell number was detected over the course of adipogenic induction (FIG. 29, Panel A) despite a time-dependent increase in Oil Red O staining/lipid accumulation levels (FIG. 29, Panel B). Differentiation levels were greatest in culture regions in which the PLA cells were confluent and in contact with one another. These results suggest that the commitment of PLA cells to the adipogenic lineage is influenced by cell-cell contact and coincides with growth arrest.

Figure 30:
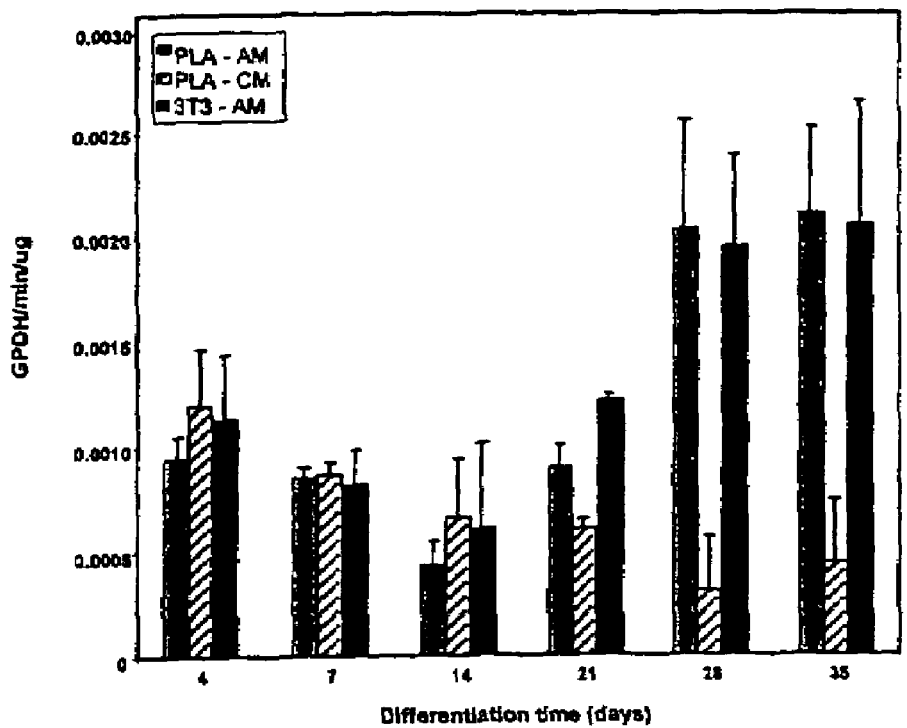
FIG. 30. Adipogenic PLA cells express GPDH activity. Triplicate samples of PLA cells and 3T3-L1 cells were induced for up to 5 weeks in AM (PLA-AM, 3T3-AM, respectively). The cells were assayed for GPDH activity and total protein. GPDH levels were expressed as units GPDH per microgram protein (GPDH/ug). Non-induced PLA cells were analyzed as a negative control (PLA-Control). Values were expressed as mean±SD.

Adipose conversion of preadipocyte cells lines, such as 3T3-L1, is also characterized by an increase in the activity of lipogenic enzymes, including glycerol-3-phosphate dehydrogenase (GPDH) (Wise, et al., 1979 J. Biol. Chem. 254:273-275). PLA cells were therefore induced with AM and the level of GPDH activity determined. 3T3-L1 cells were similarly induced as a positive control. Initial induction of PLA and 3T3-L1 cells (day 4 to day 7) resulted in comparable GPDH activities and were similar to control PLA levels (FIG. 30). Induction of PLA cells for two weeks resulted in a decrease in enzyme activity and no significant difference between control, induced PLA and 3T3-L1 cells was observed. This decrease was also observed in adipo-induced MSCs. Adipogenic differentiation beyond 2 weeks resulted in an increase in GPDH activity specifically in induced PLA and 3T3-L1 cells. Enzyme activity leveled off between 4 and 5 weeks and was significantly higher than control PLA cells. The time-dependent increase in GPDH activity correlated with the increased percentage of lipid-filled PLA cells within adipo-induced cultures (FIG. 29) and was consistent with adipogenic differentiation by these cells.

Figure 31:
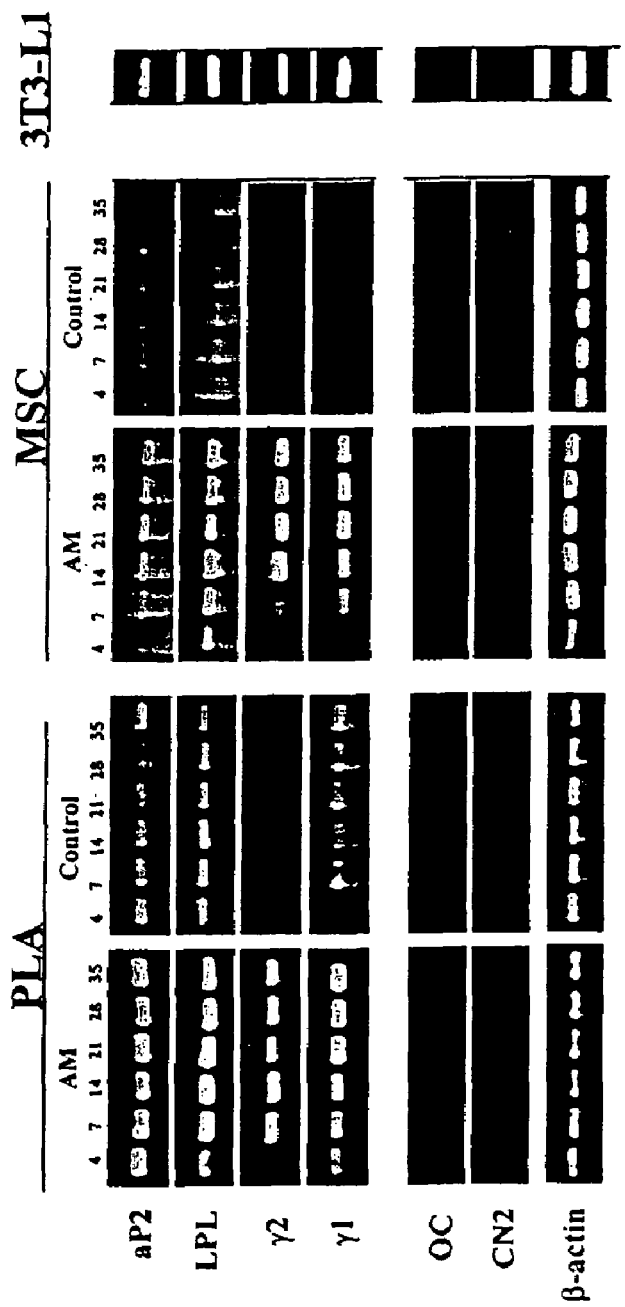
FIG. 31. Adipose-derived stem cells express several genes consistent with adipogenic differentiation: RT-PCR: Adipose-derived stem cells were induced in AM (AM) or maintained in non-inductive Control medium (Control) for the indicated days. Cells were analyzed by RT-PCR for the indicated genes. MSCs and 3T3-L1 cells were induced in AM as controls. Duplicate reactions were amplified using primers to β-actin as an internal control.

To confirm PLA adipogenesis, adipo-induced cells were analyzed by RT-PCR. As shown in (FIG. 31), PLA induction resulted in the expression of the adipose-specific transcription factor PPARγ2. Expression of PPARγ2 was observed at day 7 and the levels appeared to remain consistent throughout the remainder of the 5 week induction period. No expression of this gene was detected in non-induced PLA cells. In addition to PPARγ2, low levels of the adipogenic genes LPL and aP2 were expressed in induced PLA cells. Low levels of these genes were observed upon early adipose induction (4 days) and were followed by significant increase at 1 week. Increased levels were maintained in these cells as far as 5 weeks induction. Basal expression of LPL and aP2 was also observed in control PLA cells, although at a significantly lower level than induced samples. Like osteo-induced PLA cells, PPARγ1 was expressed in adipo-induced cells. However, the expression pattern of this gene appeared to be distinct from osteo-induced cells, with low expression levels observed at early time periods (day 4 to 14) followed by increased expression from 3 to 6 weeks. Adipogenic induction of MSCs resulted in similar gene expression patterns. Like PLA cells, PPARγ2 expression was specific to adipo-induced MSCs and did not appear at the earliest stages of induction. Extremely low levels of aP2 and LPL were also observed in control MSCs and adipogenic induction resulted in a significant increase in these genes beyond 7 days. However, in contrast to PLA cells, PPARγ1 was not observed in control MSCs. Rather, expression of this transcription factor was restricted to adipo-MSCs. Furthermore, the expression pattern of this gene paralleled that of PPARγ2, with no expression being observed until 1 week of induction. Finally, expression of these genes was examined in 3T3-L1 cells induced toward the adipogenic lineage or induced via growth to confluence. Expression of aP2 and LPL were observed in adipo-induced 3T3-L1 cells, while an apparent inhibition of PPARγ2 expression was seen. Adipogenic differentiation of PLA cells, MSCs and 3T3-L1 cells did not result in the expression of the bone-specific gene, OC and the cartilagenous marker, CNII, confirming the specificity of the adipogenic induction conditions. In summary, the restricted expression of PPARγ2 by adipo-induced PLA cells, together with the increased expression of aP2 and LPL upon induction supports the in vitro adipogenic capacity of these cells.

Chondrogenic Differentiation:

Induction of PLA cells cultured under micro-mass conditions with CM resulted in the formation of well-defined, compact nodules consistent with those seen upon chondrogenic induction of MSCs (Johnstone, et al., 1998 Exp. Cell Res. 238:265-272; Yoo, et al., 1998 J. Bone Joint Surg. Am. 80:1745-1757) Chondrogenic differentiation of PLA cells was dependent upon cell density and induction conditions. Specifically, PLA nodules formed in induction medium containing TGFβ1 alone, while the addition of dexamethasone increased the size of TGFβ1-induced PLA nodules. Nodule formation was not observed in the presence of dexamethasone alone. Attempts to initiate PLA chondrogenesis in monolayer culture was unsuccessful. To assess the ECM produced by chondrogenic PLA cells, nodules were examined by IH for the expression of CNII and sulfated proteoglycans.

Figure 32:
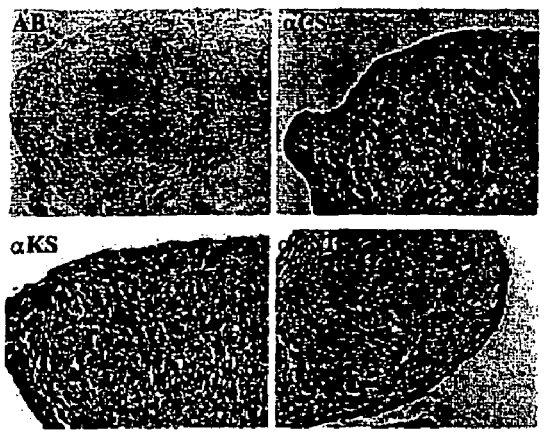
FIG. 32. Adipose-derived stem cell induced toward the chondrogenic lineage are associated with the proteoglycans keratan and chondroitin sulfate: Immunohistochemistry and Dimethyldimethylene blue assay. Panel A: Adipose-derived stem cells (PLA), under micromass conditions, were induced in chondrogenic medium (CM) or maintained in non-inductive Control medium (Control) for 7 days. Nodules were fixed, embedded in paraffin, sectioned and stained with Alcian Blue to identify sulfated proteoglycans. Sections were also stained for the expression of CNII, keratan sulfate (KS) and chondroitin-4-sulfate (CS), followed by counter-staining using H&E. Panel B: Triplicate samples of PLA cells and NHCK cells were induced for up to 3 weeks in CM (PLA-CM, NHCK-CM, respectively). Proteoglycan levels (keratan sulfate and chondroitin sulfate) were determined and expressed as microgram proteoglycan per microgram total protein (ug PG/ug). Non-induced, Adipose-derived stem cells (PLA-Control) were analyzed as a negative control. Values were expressed as the mean±SD.
Figure 32:
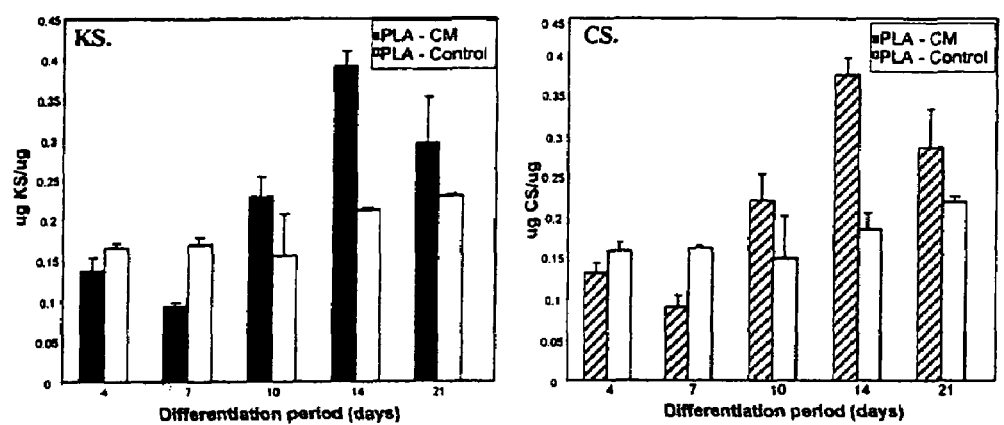

PLA nodules, induced for 14 days in CM, stained positively using Alcian Blue, which specifically identifies sulfated proteoglycans (FIG. 32, Panel A, AB). In support of this, 14 day PLA nodules also stained positively using monoclonal antibodies specific for keratan and chondroitin-4-sulfate (Panel A, KS and CS, respectively). Expression of CNII was also observed in these nodules. Alcian Blue and CNII staining were also detected in sections of human cartilage and were not seen in high density PLA cultures maintained in Control medium, confirming the specificity of our histologic and IH protocols.

In addition to IH staining for KS and CS, the level of these sulfated proteoglycans was measured using a quantitative dimethyldimethylene blue assay (FIG. 32, Panel B). PLA nodules and NHCK controls were predigested with papain to eliminate possible interference by proteins and glycoproteins prior to assay. A time-dependent increase in KS and CS was observed in PLA nodules up to 2 weeks of chondrogenic induction. A slight decrease was observed at 3 weeks for both PGs. Non-induced PLA cells, maintained under high-density conditions, were also associated with an ECM containing these proteoglycans. Furthermore, control PLA cells at 4 and 7 days induction contained more KS and CS in comparison to induced samples. However, significantly more proteoglycan accumulation was observed in induced PLA cells at days 14 and 21.

Figure 33:
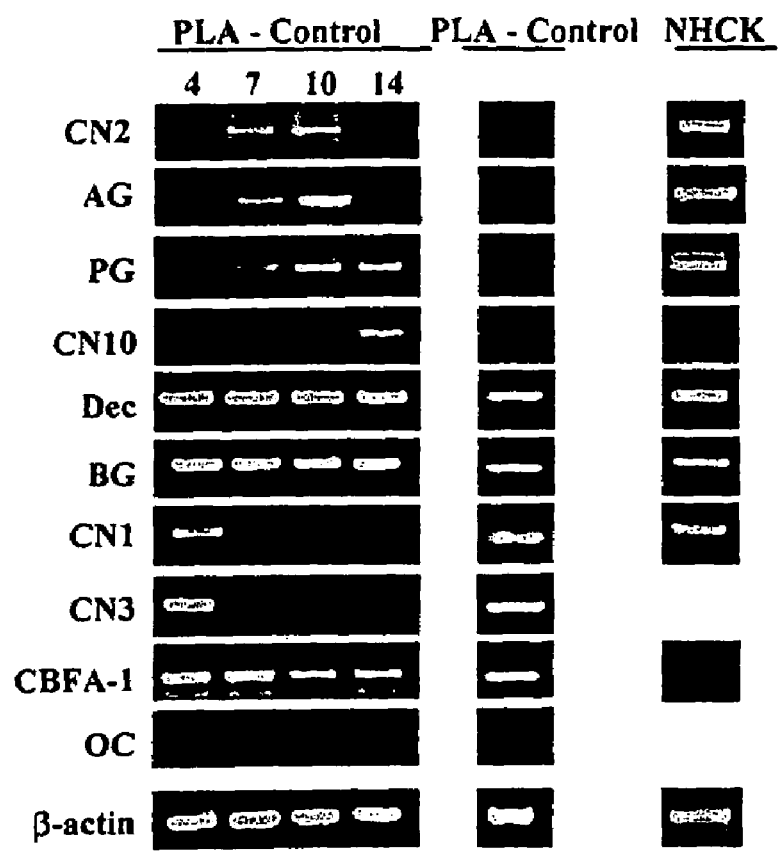
FIG. 33. Chondrogenic PLA cells express several genes consistent with cartilage differentiation: RT-PCR. PLA cells, under micromass culture conditions, were induced in CM for 4, 7, 10 and 14 days or maintained in non-inductive Control medium for 10 days (Control). Cells were analyzed by RT-PCR for the indicated genes. NHCK cells were induced in a commercial pro-chondrogenic medium as a positive control. Duplicate reactions were performed using primers to β-actin as an internal control.

Treatment of PLA cells for 2 weeks in CM resulted in the expression of several genes consistent with chondrogenesis as shown by RT-PCR (FIG. 33). CNII expression was observed specifically in induced PLA cells and was restricted to day 7 and 10. RT-PCR analysis confirmed the presence of both the IIA and IIB splice variants of CNII, although the IIB variant only is shown in FIG. 33. A low level of CNII expression was also observed upon chondrogenic induction of NHCK controls. A similar expression pattern to CNII was observed in induced PLA nodules using primers designed to the amino terminus of the large proteoglycan, aggrecan (AG). Expression of this proteoglycan was also observed using primers to the carboxy terminus (PG). However, aggrecan expression by the PLA nodule using the carboxy primers was observed from day 7 to day 14. In support of the PLA results, chondrogenic induction of NHCK controls also resulted in the expression of aggrecan using both primer sets. Finally, like CNII, aggrecan expression was specific to induced PLA nodules and NHCK cells. In addition to CNII, chondrogenic induction of PLA nodules resulted in the specific expression of CNX, a marker of hypertrophic chondrocytes, at day 14 only. In contrast to this, no expression of CNX could be observed in NHCK controls and may be due to their derivation from articular cartilage. PLA cells were also associated with additional collagen types. Both induced and control PLA cells expressed CNI and CNIII. While the majority of PLA samples examined exhibited a restricted collagen expression pattern (day 4 only), a few PLA samples showed expression of CNI and CNIII up to day 14. Induced PLA cells also expressed the proteoglycans, decorin and biglycan and the gene Cbfa-1. Expression of these genes was observed throughout the entire induction period and was also seen in control PLA cells. While decorin and biglycan levels remained consistent, a slight decrease in CBFA-1 levels appeared at later stages of induction (i.e. days 10 and 14). No expression of OC was seen at any time point, confirming the absence of osteogenic differentiation. Taken together, the specific expression of CNII, aggrecan and CNX in induced PLA nodules, in addition to the presence of keratan- and chondroitin-sulfate within the ECM supports the chondrogenic phenotype of these cells.

Figure 34:
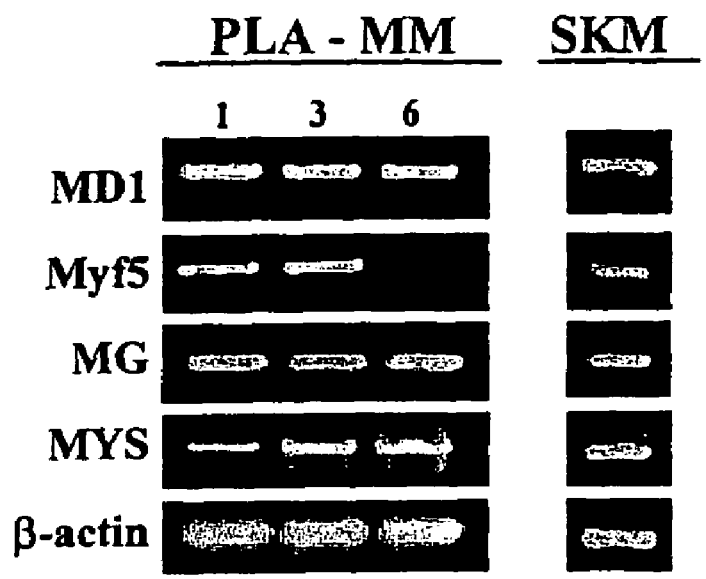
FIG. 34. PLA cells induced toward the myogenic lineage express several genes consistent with myogenic differentiation: RT-PCR analysis. PLA cells were induced in MM (PLA-MM) for 1, 3 and 6 weeks. Cells were analyzed by RT-PCR for the expression of MyoD1 (MD1), myosin (MYS), myogenin (MG) and myf5 (MYF5). Total RNA prepared from human skeletal muscle (SKM) was analyzed as a positive control. Duplicate reactions were amplified using primers to β-actin as an internal control.

PLA Cells Express Myod1, Myf5, Myogenin And Myosin Transcipts:

MSCs from rat have been shown to possess myogenic potential (Saito, 1995; Wakitani, 1995). To examine if PLA cells possess this capacity, cells were examined for the expression of the early myogenic regulatory factors, myoD1 and myf5, in addition to myogenin and the myosin heavy chain, a later marker of myogenic differentiation. Expression of myod1, myogenin and myosin was observed at all induction points, while expression of myf5 appeared to be restricted to 1 and 3 weeks only (FIG. 34). Consistent with the role of myod1 myogenic determination, increased levels of this gene were observed at 1 week. Furthermore, while myogenin levels appeared to remain consistent, a time dependent increase in expression was detected for myosin, consistent with the expression of this protein in mature myoblasts. In support of the PLA results, expression of these four myogenic genes was also observed in samples of total RNA prepared from human skeletal muscle. Therefore the expression of these myogeic regulatory proteins indicates possible myogenic differentiation by PLA cells.

Clones Derived from Single PLA Cells Possess Multi-lineae Capacity: Adipose Derived Stem Cells (ADSCs)

Figure 35:
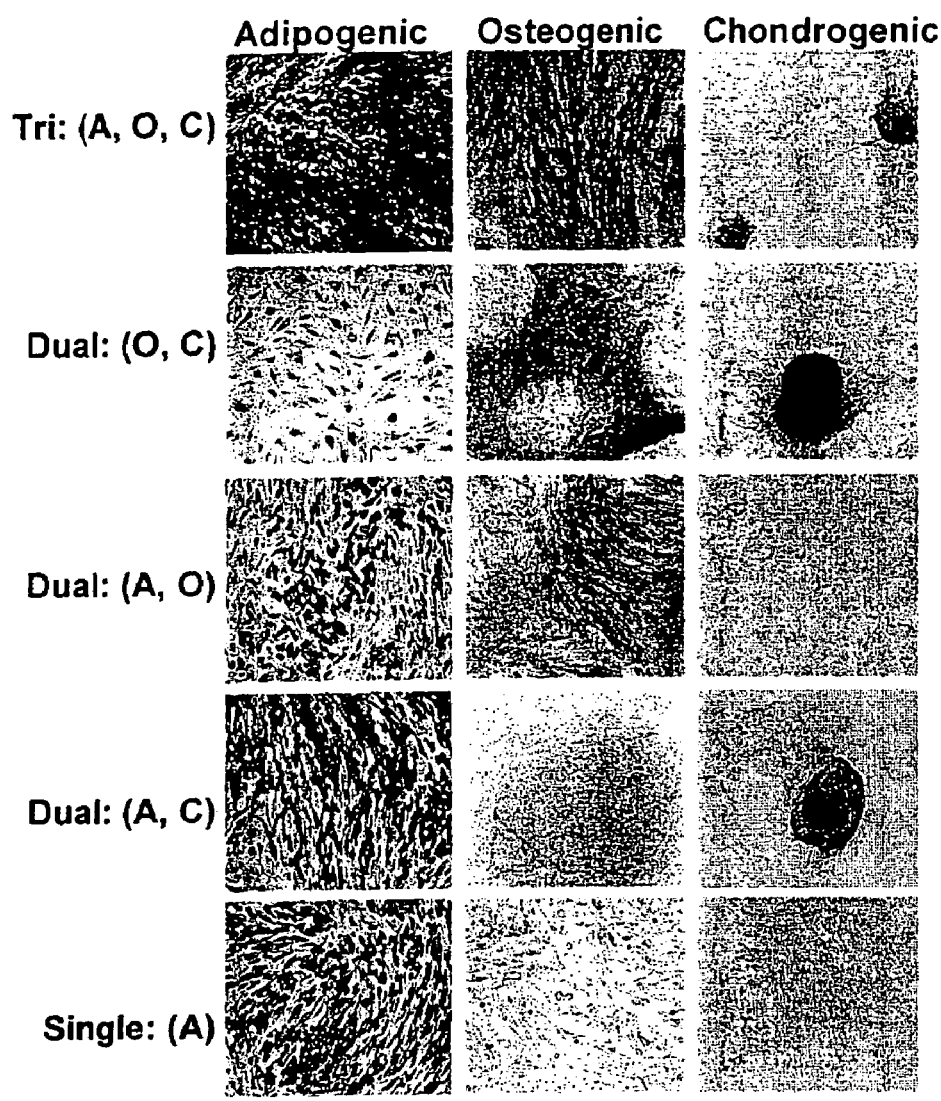
FIG. 35. ADSCs express multiple markers consistent with multi-lineage capacity. ADSC Isolation: PLA cells were plated at extremely low confluency in order to result in isolated single cells. Cultures were maintained in Control medium until proliferation of single PLA cells resulted in the formation of well-defined colonies. The single PLA-cell derived colonies were termed Adipose Derived Stem Cells (ADSCs). ADSCs were harvested using sterile cloning rings and 0.25% trypsin/EDTA. The harvested ADSCs were amplified in Cloning Medium (15% FBS, 1% antibiotic/antimycotic in F12/DMEM (1:1)). Tri-lineage ADSC clones were differentiated in OM, AM and CM and multi-lineage capacity by IH using the following histological and IH assays: Alkaline Phosphatase (osteogenesis), Oil Red O (adipogenic) and Alcian Blue (chondrogenic).
Figure 36:
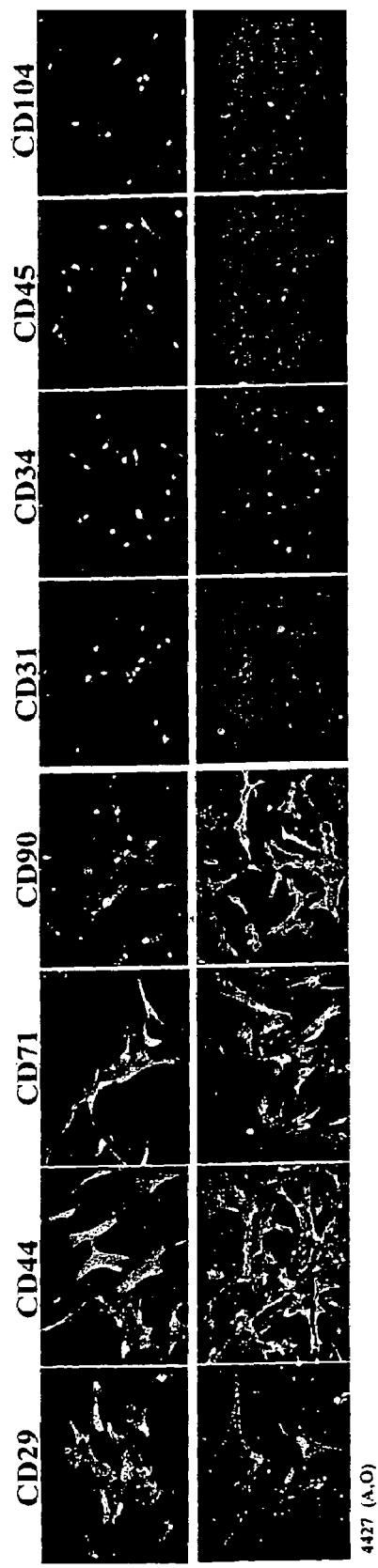
FIG. 36. Isolation of multi-lineage clones from PLA populations does not alter the expression profile of CD markers. Dual- and tri-lineage clones were isolated and expanded from single PLA cells. The clone populations were processed for the expression of the indicated CD markers using IF. The ADSCs were co-stained with DAPI to visualize nuclei (blue) and the fluorescent images combined.
Figure 37:
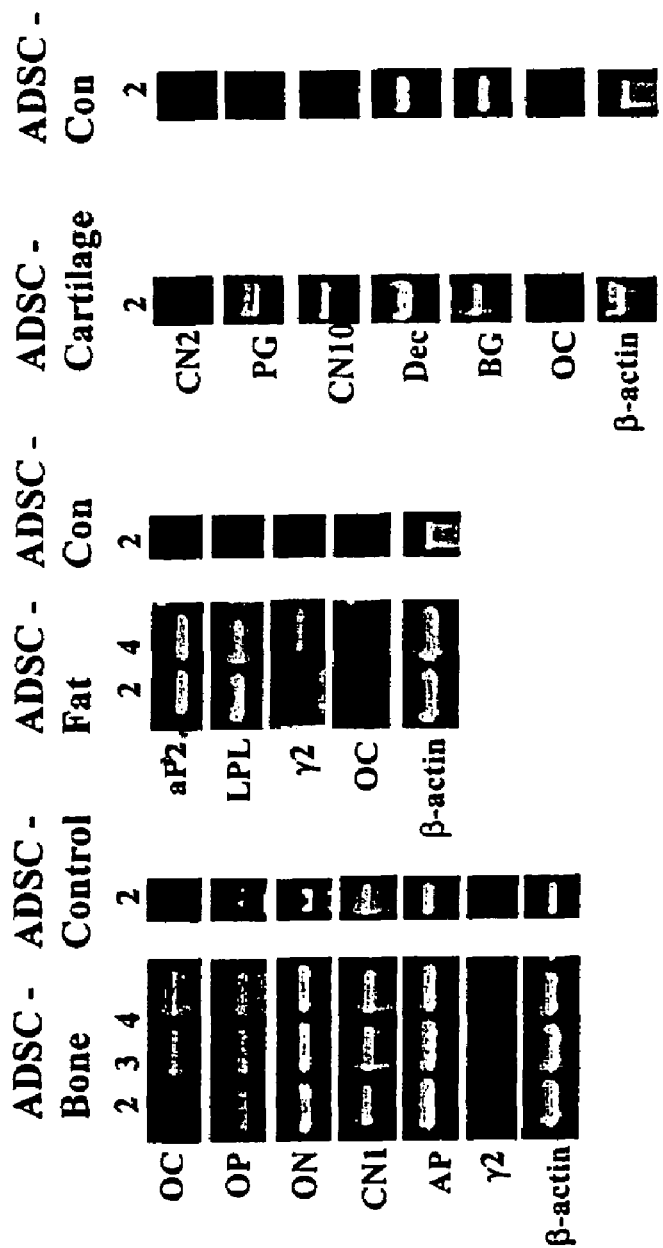
FIG. 37. ADSCs express multiple genes consistent with multi-lineage capacity. Tri-lineage ADSC clones were cultured in OM/VD (ADSC-Bone), AM (ADSC-Fat) and CM (ADSC-Cartilage), in addition to control medium (ADSC-Control), followed by RT-PCR analysis for the indicated lineage-specific genes. β-actin levels were analyzed as an internal control.

The presence of multiple mesodermal potential in PLA cells is strong support for the characterization of these cells as stem cells. However, this phenomenon may simply be due to the contamination by lineage-specific precursors. To determine if this is the case, PLA cells were cultured at a low enough confluence to promote the formation of colonies derived from single PLA cells. Several multi-lineage clones were isolated and those possessing tri-lineage potential were termed termed Adipose Derived Stem Cells or ADSCs. Like PLA cells, ADSCs were fibroblastic in morphology. Following expansion, no evidence of other cell morphologies could be observed, confirming the homogeneity of ADSC cultures. Analysis of 500 PLA clonal isolates confirmed differentiation potential in approximately 6% of the total number of clones examined. Seven ADSC isolates exhibited tri-lineages potential, differentiating into cells of the osteogenic, adipogenic and chondrogenic lineages (Table 11). In addition to tri-lineage ADSCs, several dual-lineage clones (O/A, O/C and A/O) and single adipogenic lineage clones were also isolated (FIG. 35). A qualitative increase in differentiation level, as measured by histologic staining, was observed in all PLA clonal populations. Finally, isolation and expansion of tri-lineage ADSCs did not alter the CD expression profile as shown by IF, nor could differences be detected in the dual lineage clones (FIG. 36). RT-PCR analysis of tri-lineage ADSCs confirmed their multi-lineage potential (FIG. 36).

Induction of ADSCs in OM/VD for 2 to 4 weeks resulted in the expression of OC and 3 and 4 weeks only, consistent with osteo-induced PLA cells, in which no OC expression could be detected at 2 weeks. In addition to OC, expression of ON, OP, CNI and AP were seen at all induction points. Like PLA cells, expression of OC was specific to induced ADSCs, nor could the fat marker PPARγ2 be detected in both induced and control clones. Fat induction of ADSCs for 2 and 4 weeks resulted in the specific expression of aP2 and LPL. Interestingly, a dramatic decrease in PPARγ2 was observed in fat ADSCs, expressed weakly at 4 weeks only. As seen in the heterogenous PLA population, no osteogenic differentiation was detected in adipogenic ADSCs. Finally, expression of aggrecan, CNX, decorin and biglycan was detected upon 2 weeks of chondrogenic induction. No expression of CNII could be observed in these cells at this induction point. Like PLA cells, expression of aggrecan and CNX was restricted to chondrogenic ADSCs, nor could OC expression be detected. Together with the IH data, the RT-PCR results confirms the multi-lineage capacity of ADSC isolates and suggests that the multi-lineage capacity of the PLA population may be due to the presence of a putative stem cell population.

Figure 38:
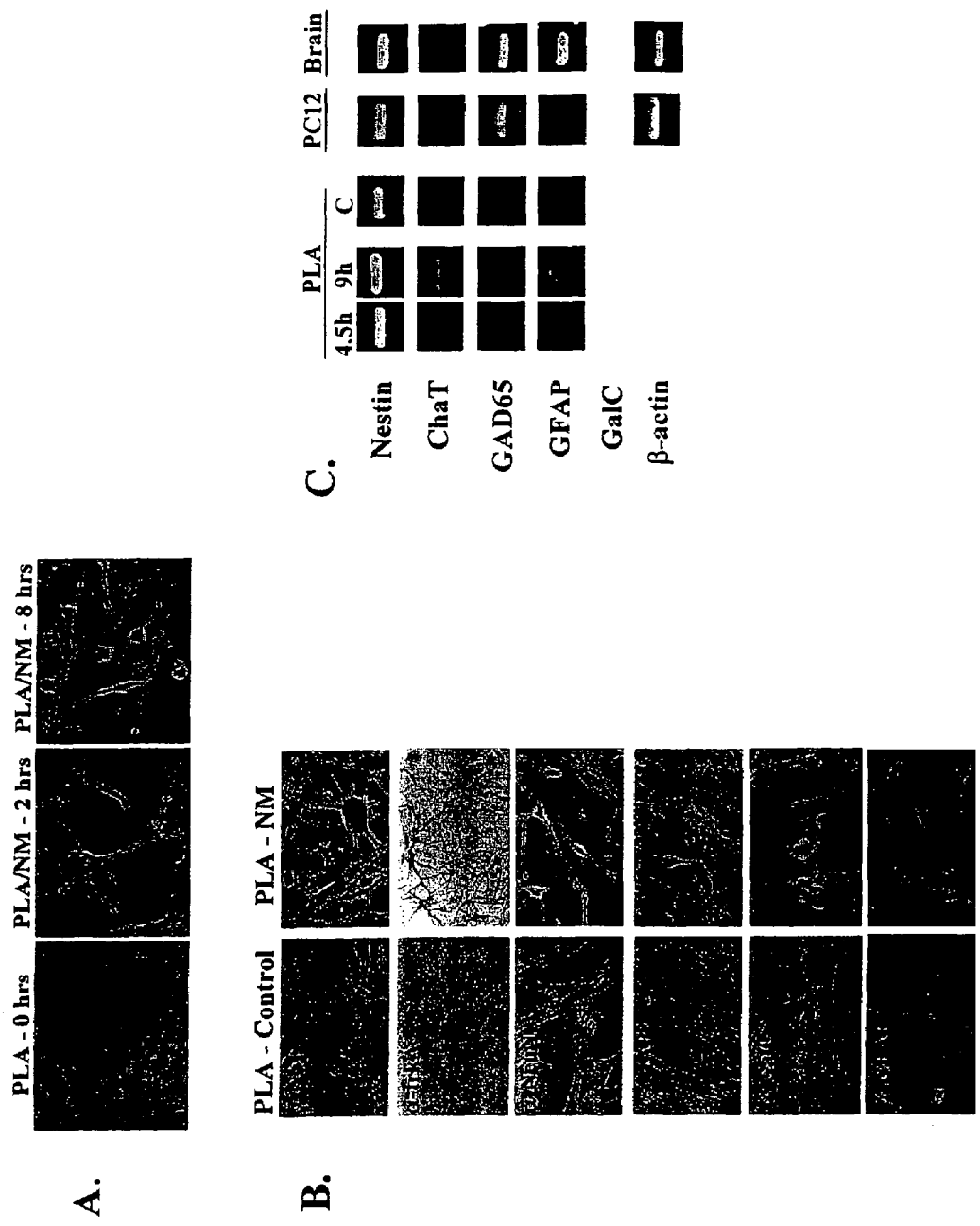
FIG. 38. PLA cells appear to exhibit neurogenic capacity in vitro. Panel A: Light micrographs of non-induced PLA cells (PLA-0 hrs) and PLA cells induced with NM for 2 and 8 hrs (PLA-2 hrs, PLA-8 hrs, respectively). Panel B: PLA cells were maintained in NM or Control medium for 5 hours (PLA-NM, PLA-Control, respectively) and analyzed by IH for expression of the following lineage-specific markers: NSE, trk-A, NeuN and MAP-2 (neural), GFAP (astrocytic). PC12 cells treated with NGF were also assessed as a positive control. Panel C: PLA cells were induced in NM for 4.5 and 9 hrs and analyzed by RT-PCR for the indicated genes. In addition, PLA cells were induced in NM for 9 hrs and maintained in NPMM for 1 week (NPMM). Non-induced PLA cells (Control) were analyzed as a negative control. PC12 cells were examined as a positive control, together with total RNA prepared from human brain (Brain).

PLA Cells May Possess Neurogenic Potential:

The mesodermal embryonic layer gives rise to several connective tissues while the overlying ectoderm is the progenitor of multiple neural tissues and cell types. Recent evidence suggests that MSCs can be induced toward non-mesodermal lineages, differentiating to cells with putative neurogenic potential (Deng, et al., 2001 Biochem. Biophys. Res. Commun. 282:148-152; Sanches-Ramos, et al., 2000 Exp. Neurol. 164:247-256; Woodbury, et al., 2000 J. Neurosci. Res. 61:364-370). It is possible that the similarities between PLA and MSCs may extend beyond mesodermal potential. Therefore, PLA cells were induced toward the neuroectodermal lineage based on the protocol of Woodbury et al. (Woodbury, et al., 2000 J. Neurosci. Res. 61:364-370) and examined for the expression of neural markers, including NSE, trk-a and MAP-2, or the expression of GFAP and GalC, markers of astrocytes and oligodendrocytes, respectively. To induce the PLA cells, subconfluent cultures were pre-treated with 1 mM β-mercaptoethanol (βME) and 20% FBS for a maximum of 24 hours (pre-induction), followed by induction in serum-free medium with 5-10 mM βME (Neurogenic Medium/NM) for up to 8 hours. Pre-induction did not change the fibroblastic morphology of the PLA cells (FIG. 38, Panel A-PLA/0 hrs). A morphologic change was noted as early as 30 minutes induction in NM, with 10% of the cultures assuming a neuronal-like phenotype. No morphological changes were observed if FBS was added to the NM. Sixty minutes of induction increased the proportion of neuronal-like cells to 20% of the culture. Induction for three hours increased this phenotype to a maximum of 70% and no significant increase was observed beyond this induction time. NM-induced PLA cells underwent retraction, forming compact cells bodies with multiple extensions. Cell bodies became more spherical and cell processes exhibited secondary branches with increasing induction time (Panel A-PLA/2 hrs vs. PLA/8 hrs). Induction in NM resulted in significant expression of NSE, trk-a and NeuN, consistent with the neuronal lineage (Panel B). Virtually 100% of the PLA culture stained positively for both NSE and trk-a. In contrast to the NSE results, not all PLA cells appeared to be NeuN positive, and may represent a more defined subset of neuronal-like cells within the PLA culture. No expression of the mature neuronal markers MAP-2 and NF-70 were observed, suggesting that induced PLA cells represent an early developmental stage. In addition, induced PLA cells did not express GalC and GFAP, indicating that PLA cells did not differentiate into oligodendrocytes and astrocytes, respectively. Finally, control PLA cells did not express any neuronal, oligodendrictyic or astrocytic markers, confirming the specificity of our induction conditions and staining protocol.

To further assess the resulting lineage upon NM induction, PLA cells were analyzed by RT-PCR (FIG. 38, Panel C). PLA cells induced for 4.5 hours in NM expressed significant amounts of nestin, an intermediate filament protein expressed in significant quantities in neural stem cells and precursors (Lendahl, 1990). Nestin expression was also detected in non-induced PLA cells and in total RNA prepared from human brain. No expression of ChaT, a marker of peripheral nerves, was observed in NM-induced cells or in brain. In addition, NM-induced PLA cells did not express GAD65, a marker of mature neurons and was consistent with the lack of IH staining using antibodies to this neuronal stage (eg. MAP-2, NF-70). As seen in the IH results, PLA cells also did not express GFAP. Similar expression patterns were observed in PLA cells induced for 9 hours. The expression of nestin, NSE, NeuN and trk-a, together with the lack of ChaT, or GFAP expression suggests that PLA cells may be capable of differentiating into an early neuronal phenotype, characteristic of the CNS. Thus the PLA cultured in NM can differentiate into an ectodermal lineage. Furthermore, recent data by Lumelsky et al. (Lumelsky, N., et al. 2001 Science 292:1389) show that an embryonic stem cell can be induced to differentiate into a cell that expresses nestin. The nestin-postive cell was further characterized to be a pancreatic precursor cell. Therefore, Lumelsky's data suggests that nestin-positive cells can differentiate into both an endodermal lineage and an ectodermal lineage. An endodermal phenotype can be further confirmed by the additional expression of one or more of the following: insulin, glucose transporter 2, islet amyloid polypeptide, GATA4, GATA6, albumin, tyrosin aminotransferase.

TABLE 5

Lineage-specific differentiation induced by media supplementation

| Medium | Media | Serum | Supplementation |
|---|---|---|---|
| Control | DMEM | 10% FBS | none |
| Adipogenic (AM) | DMEM | 10% FBS | 0.5 mM isobulyl-methylxanthine (IBMX), 1 μM dexamethasone, 10 μM insulin, 200 μM indomethacin, 1% antibiotic/antimycotic |
| Osteogenic (OM) | DMEM | 10% FBS | 0.1 μM dexamethasone, 50 μM ascorbate-2-phosphate, 10 mM β-glycerophosphate, 1% antibiotic/antimycotic |
| Chondrogenic (CM) | DMEM | 1% FBS | 6.25 μg/ml insulin, 10 ng/ml TGFβ1, 50 nM ascorbate-2-phosphate, 1% antibiotic/antimycotic |
| Myogenic (MM) | DMEM | 10% FBS, 5% HS | 0.1 μM dexamethasone, 50 μM hydrocortisone, 1% antibiotic/antimycotic |
| Neurogenic (NM) | DMEM | none | 5-10 mM β-mercaptoethanol |

TABLE 6

Monoclonal antibodies to CD antigens: Reported cell specificity and distribution

| CD Antigen | | Clone | Cell Specificity |
|---|---|---|---|
| 29 | Integrin β1 | MAR4 | broad distribution - lymphocytes, monocytes, granulocytes NOT on erythrocytes |
| 31 | PECAM-1 | 9G11 | endothelial cells, platelets, monocytes, granulocytes, haematopoietic precursors |
| 34 | — | 581 | endothelial cells, some tissue fibroblasts, haematopoietic precursors |
| 44 | Pgp-1 | G44-26 | leucocytes, erythrocytes, epithelial cells, platelets |
| 45 | LCA | HI30 | leucocytes, haematopoietic cells |
| 58 | LFA-3 | L306.4 | wide distribution - haematopoietic cells, endothelial cells, fibroblasts |
| 71 | TfR | H68.4 | most dividing cells |
| 90 | Thy-1 | 5E10 | immature CD34+ cells, cells capable of long term culture, primitive progenitor cells |
| 105 | Endoglin | — | endothelial cells, B cell precursors, MSCs |
| SH3 | — | — | mesenchymal stem cells |

TABLE 7

Oligonucleotide primer sequences and expected PCR product sizes

| Lineag | Gene | Oligonucleotide primers | Product size |
|---|---|---|---|
| BONE | Osteonectin (ON) | 5' TGTGGGAGCTAATCCTGTCC (SEQ ID NO:15)<br>3' T CAGGACGTTCTTGAGCCAGT (SEQ ID NO:16) | 400 bp |
| | Osteopontin (OP) | 5' GCTCTAGAATGAGAATTGCACTG (SEQ ID NO:17)<br>3' GTCAATGGAGTCCTGGCTGT (SEQ ID NO:18) | 270 bp |
| | Osteocalcin (OC) | 5' GCTCTAGAATGGCCCTCACACTC (SEQ ID NO:9)<br>3' GCGATATCCTAGACCGGGCCGTAG (SEQ ID NO:10) | 300 bp |
| | Bone sialoprotein (BSP) | 5' GCTCTAGAATGAAGACTGCTTTAATT (SEQ ID NO:19)<br>3' ACTGCCCTGAACTGGAAATC (SEQ ID NO:20) | 185 bp |
| | Core binding factor α-1 (CBFA-1) | 5' CTCACTACCACACCTACCTG (SEQ ID NO:21)<br>3' TCAATATGGTCGCCAAACAGATTC (SEQ ID NO:22) | 320 bp |
| | Collagen I (CNI) (α1 chain) | 5' GAGAGAGAGGCTTCCCTGGT (SEQ ID NO:23)<br>3' CACCACGATCACCACTCTTG (SEQ ID NO:24) | 300 bp |
| | Alkaline phosphatase (AP) | 5' TGAAATATGCCCTGGAGC (SEQ ID NO:25)<br>3' TCACGTTGTTCCTGTTTAG (SEQ ID NO:26) | 475 bp |
| FAT | aP2 | 5' TGGTTGATTTTCCATCCCAT (SEQ ID NO:27)<br>3' TACTGGGCCAGGAATTTGAT (SEQ ID NO:28) | 150 bp |
| | LPL | 5' GAGATTTCTCTGTATGGCACC (SEQ ID NO:29)<br>3' CTGCAAATGAGACACTTTCTC (SEQ ID NO:30) | 275 bp |
| | PPAR gamma1 | 5' GCTCTAGAATGACCATGGTTGAC (SEQ ID NO:31)<br>3' ATAAGGTGGAGATGCAGGCTC (SEQ ID NO:32) | |
| | PPAR gamma2 | 5' GCTGTTATGGGTGAAACTCTG (SEQ ID NO:33)<br>3' ATAAGGTGGAGATGCAGGTTC (SEQ ID NO:34) | |
| | PPAR delta | 5' GCCAACGGCAGTGGCTTTGTC (SEQ ID NO:35)<br>3' TTAGTACATGTCCTTGTAGATCTC (SEQ ID NO:36) | |
| CARTILAGE | Collagen II (α1 chain) | 5' ATGATTCGCCTCGGGGCTCC (SEQ ID NO:37)<br>3' TCCCAGGTTCTCCATCTCTG (SEQ ID NO:38) | 260 bp |
| | Aggrecan | 5' GCAGAGACGCATCTAGAAATT (SEQ ID NO:39)<br>3' GGTAATTGCAGGGAACATCAT (SEQ ID NO:40) | 505 bp |
| | Decorin | 5' CCTTTGGTGAAGTTGGAACG (SEQ ID NO:41)<br>3' AAGATGTAATTCCGTAAGGG (SEQ ID NO:42) | 300 bp |
| | Biglycan | 5' TGCAGAACAACGACATCTCC (SEQ ID NO:43)<br>3' AGCTTGGAGTAGCGAAGCAG (SEQ ID NO:44) | 475 bp |
| | Collagen X | 5' TGGAGTGGGAAAAAGAGGTG (SEQ ID NO:5)<br>3' GTCCTCCAACTCCAGGATCA (SEQ ID NO:6) | 600 bp |
| MUSCLE | MyoD1 | 5' AAGCGCCATCTCTTGAGGTA (SEQ ID NO:11) | 500 bp |

TABLE 7-continued

Oligonucleotide primer sequences and expected PCR product sizes

| Lineag | Gene | Oligonucleotide primers | Product size |
|---|---|---|---|
| | | 3' GCGCCTTTATTTTGATCACC (SEQ ID NO:12) | |
| | Myf5 | 5' CCACCTCCAACTGCTCTGAT (SEQ ID NO:45) | 250 bp |
| | | 3' GGAGTTCGAGGCTGTGAATC (SEQ ID NO:46) | |
| | Myogenin | 5' TGGGCGTGTAAGGTGTGTAA (SEQ ID NO:47) | 130 bp |
| | | 3' TTGAGCAGGGTGCTTCTCTT (SEQ ID NO:48) | |
| | Myosin | 5' TGTGAATGCCAAATGTGCTT (SEQ ID NO:13) | 750 bp |
| | | 3' GTGGAGCTGGGTATCCTTGA (SEQ ID NO:14) | |
| NERVE | CHaT | 5' TACAGGCTCCACCGAAGACT (SEQ ID NO:49) | 375 bp |
| | | 3' AGCAGAACATCTCCGTGGTT (SEQ ID NO:50) | |
| | Synaptophysin (SYN) | 5' TTCAGGCTGCACCAAGTGTA (SEQ ID NO:51) | 350 bp |
| | | 3' CAGGGTCTCTCAGCTCCTTG (SEQ ID NO:52) | |
| | Glial Fibrillary Acidic Protein | 5' AATGCTGGCTTCAAGGAGAC (SEQ ID NO:53) | 405 bp |
| | (GFAP) | 3' CCAGCGACTCAATCTTCCTC (SEQ ID NO:54) | |
| | GAD65 | 5' TGGCGATGGGATATTTTCTC (SEQ ID NO:55) | 300 bp |
| | | 3' GCACTCACGAGGAAAGGAAC (SEQ ID NO:56) | |
| | Nestin | 5' GGAGTCGTTTCAGATGTGGG (SEQ ID NO:57) | 240 bp |
| | | 3' AGCTCTTCAGCCAGGTTGTC (SEQ ID NO:58) | |

TABLE 8

Assessment of neurogenic differentiation by PLA cells: antibodies and established neurogenic lineages

| Antibody Name | Protein | Lineage |
|---|---|---|
| NeuN | Neuron-specific nuclear protein | Neurons & Neural progenitors |
| NF-70 | Neurofilament 70 kDa | Neurons |
| trk-A | trk-A (NGF receptor) | Neurons |
| MAP2 | microtubule associated protein-2 | Neuron (mature) |
| GalC | galactocerebroside | Oligodendrocytes |
| GFAP | glial acidic fibrillary protein | Astrocytes |
| τ-tau | tau | Neurons, Oligodendrocytes Astrocytes |

TABLE 9

Alkaline phosphatase induction levels

| | AP Induction ("x"-fold) | | | |
|---|---|---|---|---|
| Cell line | day 14-21 | day 21-28 | day 28-35 | day 35-42 |
| PLA-Dex | +17.2 | +1.6 | −2.9 | +3.2 |
| PLA-VD | +71.3 | −1.3 | −1.9 | +1.9 |
| MSC-Dex | +54.2 | −1.2 | +2.7 | NS |
| MSC-VD | NS | −1.5 | +3.5 | +1.5 |

TABLE 9-continued

Alkaline phosphatase induction levels

| | AP Induction ("x"-fold) | | | |
|---|---|---|---|---|
| Cell line | day 14-21 | day 21-28 | day 28-35 | day 35-42 |
| NHOst-Dex | −1.4 | NS | −2.8 | −1.2 |
| NHOst-VD | +1.4 | −2.2 | −25.5 | ND |

+upregulated enzyme induction
−downregulated enzyme induction
NS no significant difference detected
ND Not Determined

TABLE 10

Quantitation of calcium phosphate levels

| Cell line | Change in Overall Calcium Content ("x"-fold increase/decrease) |
|---|---|
| PLA-Dex | 56 |
| PLA-VD | 122 |
| MSC-Dex | 12 |
| MSC-VD | 67 |
| NHOst-Dex | ND |
| NHOst-VD | ND |

ND: Not Determined

TABLE 11

Summary of Lineage-Specific ADSC Differentiation
Lineage Specific Differentiation

|  | O, A, C | O, C | A, O | A, C | O only | A only | C only |
|---|---|---|---|---|---|---|---|
| # ADSC Clones | 7 | 10 | 3 | 3 | 0 | 6 | 0 |

TABLE 12

Flow cytometric analysis of CD marker expression on control PLA cells

| CD Antigen | Geometric Mean |
|---|---|
| CD4 | 2.44 |
| CD8 | 2.31 |
| CD11c | 2.49 |
| CD13 | 148.88 |
| CD14 | 2.43 |
| CD16 | 2.38 |
| CD19 | 2.92 |
| CD31 | 2.22 |
| CD33 | 2.61 |
| CD34 | 3.55 |
| CD44 | 16.92 |
| CD45 | 2.52 |
| CD49d | 5.33 |
| CD56 | 2.66 |
| CD61 | 3.68 |
| CD62E | 2.30 |
| CD71 | 3.76 |
| CD90 | 25.96 |
| CD104 | 2.31 |
| CD105 | 8.39 |
| CD106 | 2.45 |
| SH3 | 8.95 |
| STRO-1 | 31.26 |
| −ve | 2.59 |

Discussion

To further confirm if PLA cells represent a mesenchymal stem cell population, we conducted an extensive molecular and biochemical characterization of this cell population and several PLA clones termed Adipose-Derived Stem Cells, or ADSCs. PLA populations were induced toward multiple mesodermal lineages, including bone and fat, and the expression of lineage-specific genes and proteins confirmed by RT-PCR, indirect immunofluorescence (IF) and Western blotting. In addition, established biochemical assays were used to measure the activities of alkaline phosphatase, a marker for bone metabolism, the lipogenic enzyme glycerol-3-phosphate dehydrogenase (GPDH), together with the accumulation of sulfated proteoglycans upon chondrogenic induction. Histological analysis and RT-PCR were also used to confirm the multi-lineage differentiation of ADSCs. Finally, the potential of PLA cells to differentiate into cells of the neurogenic lineage was also examined.

We have demonstrated the multi-lineage capacity of the heterogenous PLA cell population and its clonal derivatives, ADSCs, obtained from human lipoaspirates. In agreement with this work, we confirm that PLA cells and ADSC clones are capable of osteogenic, adipogenic, chondrogenic and myogenic differentiation as shown by the expression of several lineage-specific genes and proteins. In addition to mesodermal lineages, PLA cells also appeared to undergo differentiation to a lineage consistent with the neurogenic phenotype. Taken together, the molecular and biochemical data suggest that PLA cells may represent a putative stem cell population that can be isolated from human adipose tissue.

PLA Cells Express A Similar Complement of CD Markers as Observed in MSCs:

Characterization of a cell population can be accomplished through identification of unique proteins expressed on the cell surface. Several groups have subsequently characterized MSCs based on their expression of cell-specific proteins (e.g. STRO-1, SH2, SH3, SH4) and "cluster designation" (CD) markers (Bruder, et al., 1998 J. Orthop. Res. 16:155-162; Conget, et al., 1999 J. Cell Physiol. 181:67-73; Pittenger, et al., 1999 Science 284:143-147). This study confirms that a unique combination of cell surface proteins is expressed on PLA cells. Moreover, both PLA and MSC populations show similar expression profiles. Like MSCs, PLA cells expressed CD29, CD44, CD71, CD90, CD105/SH2, SH3 and STRO-1 as shown by IF, in addition to CD13 as confirmed by FC (FIG. 24). Like MSCs, PLA cells did not express CDs 4, 8, 11, 14, 16, 19, 31, 33, 34, 45, 56, and 62E on the cell surface (FIG. 24). The similar CD profiles suggest that PLA cells may be a stem cell population like MSCs. However, the degree of similarity may indicate that PLA cells are simply an MSC population located within or contaminating the adipose compartment. Lipoplasty results in the rupture of multiple blood vessels and while vasoconstrictors are used to minimize blood loss, the processed PLA pellet may be MSCs obtained from the peripheral blood supply (Zvaifler, et al., 2000 Arthritis Res. 2:477-488). However, there appear to be a few subtle distinctions between PLA and MSC populations. In contrast to MSCs, no expression of CD58 could be detected on PLA cells using IF, while expression was seen on MSCs (FIG. 23). Furthermore, MSCs have also been reported to express CD104, CD106 and CD140a (Bruder, et al., 1998 J. Orthop. Res. 16:155-162; Conget, et al., 1999 J. Cell Physiol. 181:67-73; Pittenger, et al., 1999 Science 284:143-147). No expression of these CD antigens were detected on PLA cells using IF or FC (Table 12). These differences may indicate that the PLA population is a distinct population of stem cells. However, the possibility that PLA cells are a clonal variant of MSCs cannot be ruled out.

PLA Cells Undergo Osteogenesis:

The mesengenic process involves: 1) proliferation of progenitor cells, 2) commitment of these cells via the action of specific growth factors and cytokines, 3) lineage progression into transitory cell types expressing specific genes and 4) terminal differentiation characterized by the cessation of proliferation and biosynthesis of tissue-specific products (Bruder, et al., 1997 J. Cell Biochem. 64:278-294; Caplan 1994 Clin. Plas. Surg. 21:429-435; Jaiswal, et al., 1997 J. Cell Biochem. 64:295-312). Osteogenesis follows this pattern closely with osteogenic precursors developing into mitotic pre-osteoblasts and secretory osteoblasts, which lose their mitotic potential and form the mature osteocyte (Owen, et al., 1990 J. Cell Physiol. 143:420-430; Stein, et al., 1989 Conncet. Tissue. Res. 20:3-13). Therefore, osteogenic differentiation is characterized by distinct phases of proliferation, matrix synthesis/maturation and mineralization (Owen, et al., 1990 J. Cell Physiol. 143:420-430). Consistent with this, distinct phases were observed upon osteogenic differentiation of PLA cells. A relatively linear growth rate was measured within the first week of induction, a period characterized by negligible AP activity and $Ca^{2+}$ deposition. Proliferation rates increased between day 9 and day 13 and were accompanied by the appearance of AP by day 13. Proliferation ceased temporarily between day 13 and day 15 and no significant increase in AP staining was observed during this time point. An increase in cell number and enhanced AP staining was observed beyond 2 weeks induction. These findings are similar to the sequence of events in reported calvarial cultures in which cells first proliferate and then show elevated levels of AP (Aronow, et al., J. Cell. Physiol. 143:213-221; Owen, et al., 1990 J. Cell Physiol. 143:420-430). Moreover, glucocorticoids have been postulated to stimulate the proliferation of osteogenic progenitors (Shalhoub, et al., 1989 Biochem. 28:5318-5322; Tenenbaum, et al., 1985 Endo 117: 2211-2217. In addition to AP activity, significant levels of calcium were seen by 3 weeks and marked the onset of the mineralization phase in PLA cells. Increased matrix mineralization was accompanied by a dramatic increase in AP staining and was consistent with results found in rat calvarial cultures (Collin et al., 1992 Calcif. Tiss. Int. 50:175-183; Shalhoub, et al., 1989 Biochem. 28:5318-5322). Increased mineralization was also accompanied by the cessation of proliferation (day 25), followed by a reduction in PLA cell number. This reduction was likely due to the increase in mineral deposition and coincided with the increased appearance of ECM and the formation of cell-free intermodular zones. In support of this, ECM formation has been suggested to contribute to the shutdown of proliferation by rat osteoblasts (Owen, et al., 1990 J. Cell Physiol. 143:420-430) and rat marrow stromal cells (Malaval, et al., 1994 J. Cell. Physiol. 158:555-572). Taken together, the results suggest that PLA cells possess distinct proliferative, synthetic and mineralization phases during osteogenic differentiation.

Glucocorticoid excess and/or prolonged treatment in vivo is associated with decreased bone formation (Baylink 1983 N. Engl. J. Med. 309:306-308), possibly through a reduction of progenitor conversion to osteoblasts (Chyun, et al., 1984 Endo. 114:477-480). In contrast to dexamethasone, treatment with vitamin D metabolites restores bone mineralization and bone formation by bone-derived cells in vitro (Beresford, et al., 1986 Endo. 119:1776-1785; Kanis, et al., 1982 in *Endocrinology of Calcium Metabolism*, ed. J A Parsons, New York: Raven Press, pp 321). Therefore, the effects of dexamethasone and 1,25-dihydroxyvitamin D3 (VD) on PLA osteogenesis were examined. The bone/kidney/liver isoform of AP catalyzes the cleavage of inorganic and organic phosphates at alkaline pH. While its precise function during in vivo osteogenesis is unclear, AP expression levels in pre-osteoblasts and MSCs are upregulated upon the onset of osteogenic differentiation and this enzyme thought to play a key role in matrix mineralization through its pyrophosphatase activity (Mc-Comb, et al., 1979 *Alkaline Phosphatase*, New York: Plenum Press; Robison 1923 Biochem. J. 17:286-293; Siffert 1951 J. Exp. Med. 93:415-426). Therefore, analysis of AP levels and matrix mineralization are important indicators of osteogenesis. Based on this, these parameters were measured in induced PLA samples and compared to similarly treated MSCs and human osteoblasts as controls.

While, the overall effect of osteogenic differentiation on AP activity and matrix mineralization appeared to be similar in PLA cells and MSCs, the kinetics of enzyme activity and the response to induction conditions differed depending on differentiation stage, suggesting that these two populations may possess distinct phenotypes. AP activity appeared in both PLA and MSC populations between 2 and 3 weeks induction. VD treatment of PLA cells resulted in a significantly higher level of AP activity at 3 weeks versus Dex induction and a greater level of enzyme induction from 2 and 3 weeks (17.2 fold/Dex vs. 71.3 fold/VD). This VD effect was seen at each differentiation stage. In contrast, the effect of induction condition was reversed in MSCs, with Dex producing greater AP activities at each differentiation stage. In addition to differences in measured enzyme activity and induction level, the kinetics of AP activity differed between PLA cells and MSCs. AP activity in both Dex and VD-induced PLA cells was bi-phasic. Specifically, peak AP levels were measured under both induction conditions at 3 and 6 weeks and a decreased level detected at 5 weeks. Like PLA cells, a bi-phasic response was also observed in Dex-treated MSCs. However, the kinetics of AP activity appeared to be accelerated in Dex-treated MSCs with peaks detected at 3 and 5 weeks and a decrease in enzyme at 4 weeks. Moreover, a distinct bi-phasic pattern was not observed upon VD stimulation of MSCs, lending further support to a putative distinction between these two cell populations.

The reason for the biphasic response in PLA and MSC populations is unclear. Time course studies using rat calvarial models have shown that AP activity peaks early, during the deposition of the bony ECM, and is subsequently downregulated (Owen, et al., 1990 J. Cell Physiol. 143:420-430; Rodan and Rodan 1984 in *Bone and Mineral Research*, ed. W. A., Amsterdam: Elsevier Science Publishers, pp. 244-285; Stein, et al., 1990 FASEB J. 4:3111-3123). A similar pattern is observed in marrow stromal cell cultures and correlates with advanced matrix mineralization and terminal osteogenic differentiation into osteocytes (Bruder and Caplan 1990 Bone 11:189-198; Jaiswal, et al., 1997 J. Cell Biochem. 64:295-312; Malaval, et al., 1994 J. Cell. Physiol. 158:555-572). The drop in PLA AP activity observed from 4 to 5 weeks correlates to increasing calcium phosphate levels within the matrix. However, we know of no studies in which AP levels are quantitated beyond this matrix synthesis phase. Therefore, this study may be the first to examine AP activity in stem cells over an extended time period. It is possible that the pattern of PLA and MSC AP activity represents a stage-specific response to osteogenic induction. In support of this, increases in AP have been observed in VD-treated immature osteosarcoma cultures (Majeska, et al., 1982 J. Biol. Chem. 257:3362) whereas a dose-dependent inhibition was detected in more mature cells, an effect thought to represent the return of a cell fraction to the osteoprogenitor pool or their differentiation to osteocytes, a cell population with low AP activity. Therefore, the decrease in AP levels in PLA and MSC samples may be due to the terminal differentiation of a cell fraction whereas the second AP peak could be due to the delayed development of a fraction of osteogenic progenitor cells.

Consistent with the AP results, induction of PLA cells with VD produced a greater overall increase in calcium levels compared to dexamethasone. Like AP activity subtle distinctions in calcium accumulation could be observed between PLA cells and MSCs. In support of the AP data, matrix mineralization by PLA cells was not observed until 3 weeks induction. Beyond this time point, Dex stimulation did not appear to significantly affect the rate of matrix mineralization. However, a dramatic increase was detected in VD-treated PLA samples, with 6 week samples containing significantly more calcium phosphate. This increased mineralization rate occurred despite the fact that AP did not differ dramatically between 3 and 6 week VD samples. Moreover, the decrease in AP activity observed between 4 and 5 weeks in PLA cells did not translate into decreases in calcium level. Rather, mineral accumulation continued to increase in these cells. This pattern has previously been observed in human MSCs (Jaiswal, et al., 1997 J. Cell Biochem. 64:295-312). Like PLA cells, a time dependent increase in mineralization was observed in MSCs with a greater overall increase observed in VD-treated samples. The pattern of matrix mineralization in these cells correlated well with AP activity within the first 4 weeks of induction. Specifically, higher AP levels in Dex-treated MSCs resulted in greater calcium accumulation. However, between 4 and 5 weeks induction a dramatic shift takes place, with small increases in AP activity in VD-treated MSCs producing dramatic increases in calcium level. Moreover, AP activity in VD-induced MSCs were significantly lower than Dex-treated cells, yet VD treatment resulted in dramatically more calcium, suggesting that MSCs became more sensitive to VD induction over time. Taken together, the appearance of AP upon osteogenic induction and the accumulation of a mineralized ECM support the osteogenic phenotype of PLA cells. In addition, differences observed in the kinetics and pattern of these two markers indicates that the PLA population may be distinct from MSCs.

During osteogenesis, osteoblasts synthesize a wide repertoire of no proteins that are incorporated into a surrounding ECM scaffold. The composition of the matrix, together with the kinetics of secretion, help define the unique properties of bone tissue and can be used to confirm osteogenic differentiation. However, with few exceptions, the actual matrix proteins are not unique to bone. One of these exceptions is the protein osteocalcin (OC). A highly conserved protein containing three γ-carboxyglutamic acid residues, OC is an inhibitor of hydroxyapatite formation in vitro, suggesting that this protein participates in mineralization (Boskey, et al., 1985 Calc. Tiss. Int. 37:75; Price, et al., 1976 Proc. Natl. Acad. Sci. USA 73:1447-1451). In support of this, OC is expressed by mature osteoblasts and its expression level rises dramatically during the mineralization phase (Collin, et al., 1992 Calcif. Tiss. Int. 50:175-183; Malaval, et al., 1994 J. Cell. Physiol. 158:555-572; Owen, et al., 1990 J. Cell Physiol. 143:420-430; Shalhoub, et al., 1992 J. Cell. Biochem. 50:425-440; Stein, et al., 1990 FASEB J. 4:3111-3123). While OC is considered a relatively late marker of osteoblast differentiation, it is expressed early in bone formation in marrow stromal cell cultures before large amounts of matrix are synthesized (Malaval, et al., 1994 J. Cell. Physiol. 158:555-572). Consistent with osteogenic differentiation, osteo-induced PLA cells expressed OC. However, its expression was dependent upon the composition of the osteoinductive medium. Specifically, osteocalcin expression was not observed in non-induced PLA cells nor in PLA cells induced with OM containing dexamethasone. The lack of OC expression in Dex-treated PLA cells may be due to an inhibitory effect associated with glucocorticoids (Cooper, et al., 1999 J. Endocrinol. 163:159-164). In support of this, negligible levels of OC have been observed in rat MSCs and human bone cell cultures induced with dexamethasone (Beresford, et al., 1986 Endo. 119:1776-1785; Leboy, et al., 1991 J. Cell Physiol. 146:370-378). Furthermore, OC was not observed upon induction of a human osteoblast cell line, NHOst, in this study (FIG. 27). In contrast to dexamethasone induction, OC expression was seen only upon VD stimulation and is consistent with studies confirming VD-dependent increases in OC expression by osteosarcoma cells (Price, et al., 1980 J. Biol. Chem. 225:11660-11663) and its stimulation of the OC promoter (Lian, et al., 1988 Clin. Orthop. Rel. Res. 226:276-291; Yoon, et al., 1988 Biochem. 27:8521-8526). In addition to its appearance upon VD induction, a distinct bi-phasic expression pattern of OC was observed. Consistent with bone marrow MSCs, the appearance of OC was associated with an initial stage of differentiation, appearing as early as 4 days induction. A dramatic increase in OC level was detected after one week induction. Induction for 2 weeks resulted in an apparent inhibition of OC expression and was followed by increased expression beyond three weeks. The reappearance of OC at three weeks was coincident with the synthesis and mineralization of the surrounding ECM and may be supportive of the proposed role for OC in matrix calcification. With regards to OC's biphasic, pattern, a similar effect to that observed in AP expression may be occuring: i.e. a developmental stage-specific response to VD. In addition to VD, several other induction agents also exert stage-specific effects on osteogenesis, including TGFβ (Breen, et al., 1994 J. Cell. Biochem. 160:323-335). Similar to VD-induced PLA cells, OC was also detected in MSCs with several differences observed in OC expression pattern observed in these cells. First, in contrast to PLA cultures, a low level of OC expression was observed in non-induced MSCs. The basal level of OC expression in control MSCs was extremely low and is consistent with reports of constitutive OC expression in cultures of rat MSCs (Malaval, et al., 1994 J. Cell. Physiol. 158:555-572). Second, OC expression was observed in Dex-treated MSCs. Finally, while VD-induction increased the expression of OC in MSCs, no apparent biphasic pattern was observed. Taken together, the expression of bone-specific OC by osteo-induced PLA cells supports their osteogenic capacity. In addition, the distinct pattern of OC expression and the differential response to induction factors observed between MSCs and PLA cells further suggests that these two populations may possess unique phenotypes.

In addition to OC, osteo-induced PLA cells also expressed several other genes characteristic of the osteogenic lineage, including OP, ON, CBFA1, AP and CNI. Cbfa-1 (core binding factor-1 or Osf-2) is a transcriptional regulatory factor encoded by the gene, CBFA1, a member of the runt domain gene family (Kania, et al., 1990 Genes Dev. 4:1701-1713). Isolated from the nuclear extracts of primary osteoblasts, the Cbfa1 factor has been shown to bind to the promoters of several osteogenic genes, including OC, OP BSP and CN type I, thus acting as a master regulator of osteoblast differentiation (Ducy, et al., 1997 Cell 89:747-754). Moreover, mutations to the C-terminal region of human CBFA1 is associated with Cleidocranial dysplasia (CCD), an autosomal-dominant condition characterized by deformities in skeletal patterning (Jones, et al., 1997 *Smith's Recongizable Patterns of Human Malformation*, 5$^{th}$ edition, Philadelphia: W B Saunders Company; Mondlos, et al., 1997 Cell 89:773-779; Otto, et al., 1997 Cell 89:765-771. Consistent with its proposed role, both Dex and VD-induced PLA cells expressed CBFA1 at all induction points and no significant difference in expression level was observed between the two induction conditions. In support of the PLA results, CBFA1 was also expressed in osteo-induced MSCs and was restricted to a late differentiation stage in NHOst cells. Finally, both undifferentiated PLA cells and MSCs expressed low levels of this growth factor. However, osteogenic induction of PLA cells resulted in an approximate 2-fold increase in CBFA1 expression as confirmed using gene arrays. Moreover, recent studies in developing mice have suggested that Cbfa1 is expressed in progenitors of both the osteogenic and chondrogenic lineages (Ducy, et al., 1997 Cell 89:747-754). Therefore, the expression of CBFA1 in control PLA cells may represent basal gene expression in cells with a progenitor phenotype.

Like CBFA1, the expression of OP, ON, AP and CNI was observed in control and osteo-induced PLA cells, MSCs and NHOsts throughout differentiation. Expression of CNI in these cell types appeared to be equivalent under each induction condition using RT-PCR. However, decreased expression of this gene was detected in osteo-induced PLA cells using gene arrays and is consistent with the proposed inhibitory effect of glucocorticoids on collagen expression (as reviewed in Cooper, et al., 1999 J. Endocrinol. 163:159-164).

As with other genes, ON and OP expression did not appear to be affected by induction condition. Moreover, osteogenic induction resulted in significant decreases in OP level, as measured by microarrays, and was consistent with decreases observed upon induction of rat bone marrow stromal cells (Malaval, et al., 1994 J. Cell. Physiol. 158:555-572). While not restricted to osteogenic cells, both OP and ON are found in high amounts in bone tissue. Therefore, their expression, together with osteoblast-specific genes like OC, supports the osteogenic capacity of PLA cells. In addition to these osteogenic genes, osteo-induced PLA cells expressed several other genes, including the proteoglycans decorin and biglycan and the transcription factors PPARγ1 and PPARδ.

In addition to the RT-PCR results, expression of several proteins characteristic of osteogenic differentiation was also observed using both IF and Western blotting. In support of the RT-PCR data, control and osteo-induced PLA cells expressed several proteins consistent with an osteogenic phenotype, including CNI, decorin, biglycan, OP and ON. Significant differences in CNI, decorin, biglycan and ON expression were not observed upon osteogenic induction and an increase in OP expression was seen after 3 weeks induction. Expression of ON and OP was also observed in control and osteo-induced PLA cells using IF with differences in intracellular expression pattern detected between the two cell populations. Specifically, OP expression in both control and induced PLA cells concentrated to a perinuclear location, while its distribution appeared to be more uniform in MSC samples. This perinuclear concentration has been observed in MSCs during osteogenesis and is a characteristic of secreted proteins (Zohar, et al., 1998 Eur. J. Oral Sci. 106:401-407). However, contrary to this study, a defined perinuclear concentration of OP was not observed in our MSC populations and may represent a clonal variant or specific culture conditions. Rather, OP in the MSCs concentrated to the cell surface and at cell processes. This focal distribution has also been observed in MSCs and may indicate cell migration by these cells during differentiation (Zohar, et al., 1998 Eur. J. Oral Sci. 106:401-407). Similar intracellular patterns were observed for ON in control PLA and MSC samples. In these cells, ON was distributed throughout the cell in a fine punctate pattern and a low level was also found in the nucleus. Osteogenic induction did not alter this pattern in MSCs. However, the nuclear expression was lost upon differentiation of PLA cells. Furthermore, while ON was found in virtually all control PLA cells, not all osteo-induced PLA cells were ON-positive. Rather, expression of this protein was found in regions of high cell density. Finally, no expression of OC was observed in control PLA cells, whereas a very low level was detected in undifferentiated MSCs, consistent with the RT-PCR findings. Osteogenic induction resulted in OC expression by a small percentage of the osteogenic PLA cells, while a larger percentage of osteogenic MSCs expressed this protein. The expression pattern of OC was similar in both osteogenic PLA and MSCs: distributed throughout the cell and concentrated at defined regions along the cell surface. Together, with CNI, OP and ON, the expression of OC is supportive of the RT-PCR data and further confirms the osteogenic capacity of PLA cells in vitro.

PLA Cells Undergo Adipogenic Differentiation:

The differentiation of adipocytes in culture is dependent upon many factors, including serum, hormonal supplementation (insulin) and pharmacologic agents (indomethacin, IBMX) (Green, et al., 1974 Cell 3:127-133; Russell, TR 1976 Proc. Natl. Acad. Sci. USA 73:4516-4520; Williams and Polakis 1977 Biochem. Biophys. Res. Commun. 77:175-186). However, initiation of the adipogenic program, in contrast to terminal differentiation, does not require such adipogenic agents but may be dependent upon increased culture confluence. Moreover, it is known that reversible growth arrest at confluence must occur before most pre-adipocytes can commit to the adipogenic lineage (Scott, et al., 1982, J. Cell Biol. 94:400-405; Speigelman and Farmer 1982 Cell 29:53-60; Trayhum and Ashwell 1987 Proc. Nutr. Soc. 46:135-142). As adipogenic differentiation proceeds, a loss of proliferative potential is observed and the irreversible loss of replication potential is a characteristic of terminal adipocyte differentiation. To investigate if PLA cells exhibit the same characteristics, PLA proliferation was correlated to adipogenesis, as measured by Oil Red 0 accumulation. Consistent with studies on pre-adipocyte cell lines, high levels of differentiation occurred in confluent PLA cultures. Differentiating PLA cells assumed a more expanded morphology and began to accumulate intracellular lipid droplets as early as 2 weeks induction. Differentiation proceeded with no significant increase in PLA cell number, suggesting that cell number and growth kinetics are linked to PLA adipogenesis (FIG. 29).

PLA-Cd Markers and ECM-Supplements

Adipogenic differentiation is accompanied by several molecular and biochemical events, including the increase in lipogenic enzymes that catalyze the conversion of glucose into fatty acids and triglycerides. Glycerol-3-phosphate (G3P) is the primary substrate for triglyceride synthesis in adipose tissue and the adipose conversion of 3T3 cells is characterized by a dramatic increase in the enzymatic source of G3P, glycerophosphate dehydrogenase (GPDH) (Kuri-Harcuch, et al., 1978 J. Biol. Chem. 252:2158-2160; Pairault Greem 1979 J. Biol. Chem. 76). Based on this, GPDH activity was measured in adipo-induced PLA and 3T3-L1 cells. No significant difference in GPDH levels was detected between differentiated cells and non-induced controls until 3 weeks differentiation. Moreover, the initial period of differentiation was associated with higher basal GPDH levels. The increased level of GPDH in adipo-induced PLA cells was associated with the appearance of Oil Red O staining (FIG. 29). Induction from 3 to 4 weeks resulted in a significant increase in GPDH in both differentiated PLA cells and 3T3-L1 controls and coincided with increased lipid accumulation. Continued differentiation for an additional week did not significantly change enzyme levels in these cell populations. A similar pattern of GPDH activity was also observed in adipo-induced MSCs. Therefore, the increase in GPDH enzyme activity in PLA cells induced toward the adipogenic lineage indicates that these cells may be undergoing adipogenic differentiation.

Like osteogenesis, adipogenesis is characterized by the expression of a distinct set of genes that are involved in lipid synthesis and storage. One of these genes, PPARγ2, is a member of the PPAR nuclear hormone receptor superfamily, together with PPARγ1 and PPARδ (reviewed in (Fajas, et al., 1998 Curr. Biol. 10:165-173). PPARγ2 has been identified as part of a heterodimeric complex (with ARF6 and the retinoid X receptor) that acts as a key transcriptional regulator of the tissue-specific aP2 gene (Totonoz, et al., 1995 Nucl. Acid Res.). Moreover, PPARγ2 is expressed at high levels specifically in fat and is induced early in the differentiation of cultured adipocyte cell lines (Totonoz, et al., 1994 Genes Dev. 8:1224-1234; Totonoz, et al., 1994 Cell 79:1147-1156). Consistent with this, PPARγ2 was specifically detected in adipo-induced PLA and MSC samples. Initial differentiation (i.e. 4 days) of these cell populations was characterized by the absence of this transcription factor and is agreement with previous results from differentiating 3T3 adipocytes (Totonoz, et al., 1994 Genes Dev. 8:1224-1234; Totonoz, et al., 1994 Cell 79:1147-1156). Detectable levels of PPARγ2 were observed after one week induction. However, expression levels were significantly higher at this time point in adipo-induced PLA cells, suggesting that the kinetics of PPARγ2 expression may differ slightly between MSC and PLA populations. Distinctions in PPARγ1 expression were also observed between PLA cells and MSCs. A similar time-dependent increase in PPARγ1 expression was observed in PLA cells and MSCs. However, early differentiation (i.e. 4 days) of MSCs was associated with an absence of this transcription factor while low levels were observed in induced PLA cells. Moreover, no PPARγ1 was detected in control MSCs. Finally, while detectable levels of PPARγ1 were seen in non-induced PLA cells, adipogenic induction was associated with a significant increase in expression, consistent with adipogenic differentiation.

PPARγ2 is associated with growth arrest and early commitment of pre-adipose cells to the adipogenic lineage. This period of differentiation also marks the point at which the gene LPL is expressed (Ailhaud, et al., 1992 Annu. Rev. Nutr. 12:207-233; Fajas, et al., 1998 Curr. Biol. 10:165-173). LPL (Lipoprotein Lipase) is ubiquitously expressed but is significantly upregulated in adipose tissue. Through its hydrolysis of triglycerides, LPL promotes the exchange of lipids and affects the metabolism of several triglyceride-rich lipoproteins, including HDL and LDL (Eisenberg, et al., 1984 J. Lipid Res. 25:1017-1058). Consistent with its ubiquitous expression, non-induced PLA and MSC controls expressed a low level of LPL. However, adipogenic induction of both PLA cells and MSCs was associated with a significant increase in the expression of this gene. This increase was observed after one week induction and levels remained equivalent throughout the remaining differentiation period. Finally, extended differentiation of preadipocytes results in the expression of the late adipogenic markers and is associated with the accumulation of lipid within the maturing adipocyte (Ailhaud, et al., 1992 Annu. Rev. Nutr. 12:207-233; Fajas, et al., 1998 Curr. Biol. 10:165-173). One such late marker is the fatty acid binding protein, aP2 (Bernlohr, et al., 1984 Proc. Natl. Acad. Sci. USA 81:468-472; Bernlohr, et al., 1985 Biochem. Biophys. Res. Comun. 132:850-855). Consistent with previous results (Bernlohr, et al., 1985 Biochem. Biophys. Res. Comun. 132:850-855), aP2 was detected in 3T3-L1 controls, along with LPL and PPARγ2. However, despite its classification as a late marker in adipocytes, aP2 expression was observed throughout adipogenic induction in both PLA cells and MSCs and levels appeared to be equivalent at each induction point. Moreover, aP2 expression preceded that of PPARγ2, in direct contrast to the pattern of expression observed in pre-adipocyte differentiation ((Totonoz, et al., 1994 Genes Dev. 8:1224-1234; Totonoz, et al., 1994 Cell 79:1147-1156). Consistent with its function in adipogenesis, extremely low levels of aP2 were found in non-induced controls. This constitutive expression was in agreement with the expression of aP2 in tissues other than fat (Zezulak and Green 1985 1985 Mol. Cell Biol. 5:419-421) and is similar to the LPL results. Taken together, the adipogenic-specific expression of PPARγ2 in adipo-induced PLA cells, together with the upregulated expression of LPL and aP2 is supportive of the adipogenic capacity of these cells. Furthermore, the adipogenic capacity in combination with the osteogenic potential of these cells suggests that PLA cells may possess multi-lineage potential.

PLA Cells Undergo Chondrogenesis

Chondrogenic differentiation of cell lines requires high density culture (Johnstone, et al., 1998 Exp. Cell Res. 238: 265-272), duplicating the process of cellular condensation (Fell 1925 J. Morphol. Physiol. 40), in addition, to supplementation with specific growth factors, such as TGFβ1, TGFβ3 or BMP2 (Johnstone, et al., 1998 Exp. Cell Res. 238:265-272; Mackay, et al., 1998 Tissue Eng. 4:415-428). Consistent with this, aggregate culture of PLA cells in CM, containing TGFβ1, resulted in the formation of small, compact micromass nodules as early as 24 hours induction. Induced PLA nodules stained positively using the stain Alcian Blue, consistent with the presence of sulfated proteoglycans within the nodule ECM and in agreement with the results described in Example 7 above. Alcian blue staining appeared to concentrate more in the interior of the nodule and was apparent as early as 3 days induction. Consistent with Alcian Blue staining, PLA nodules also contained keratan- and chondroitin-4-sulfate, two proteoglycans expressed in high amounts in cartilage. In support of these results, the expression of KS and CS has also been observed in human bone marrow MSCs induced toward the chondrogenic lineage (Yoo, et al., 1998 J. Bone Joint Surg. Am 80:1745-1757: Yoo, et al., 1998 Clin. Orthop. S73-81). In addition to sulfated proteoglycans, PLA nodules also expressed collagen type II, a collagen isoform characteristic of cartilage tissue. Finally, PLA nodules cultured under high-density conditions and maintained in non-inductive control medium did not form nodules and failed to stain for any cartilage-specific histologic marker, thus confirming the specificity of our induction conditions.

Quantitation of sulfated proteoglycans can be accomplished using a metachromatic dimethyldimethylene blue assay (Farndale, et al., 1986 Biochimica et Biophysica Acta 883:173-177). Consistent with our immunohistochemical results, the DMMB assay confirmed the presence of sulfated proteoglycans in the differentiated PLA samples. Moreover, a time-dependent increase in KS and CS within chondrogenic PLA nodules was observed up to 2 weeks of induction. A similar increase has also been observed in induced MSC cultures (Yoo, et al., 1998 J. Bone Joint Surg. Am 80:1745-1757: Yoo, et al., 1998 Clin. Orthop. S73-81) and suggests that PLA cells have accumulated an ECM characteristic of cartilage tissues. PG levels decreased slightly beyond 2 weeks induction and may represent remodeling of the cartilagenous ECM. Non-induced PLA cells, maintained under high-density conditions, were also associated with an ECM containing these proteoglycans. Moreover, basal PG levels were greater than induced PLA sample at 4 and 7 days. However, significantly more proteoglycan accumulation was observed in induced PLA nodules at days 14 and 21. The significant accumulation of KS and CS within the ECM of induced PLA nodules, together with the histological results suggests that PLA cells also possess in vitro chondrogenic capacity when cultured under high-density conditions.

Induction of PLA cells in CM resulted in the expression of several genes consistent with chondrogenesis. CNII expression was observed specifically in induced PLA cells and was restricted to day 7 and 10 and supported our immunohistochemical results. A restricted expression pattern similar to CNII was observed in PLA nodules using primers designed to the amino terminus of aggrecan (AG), a large proteoglycan expressed in high amounts in cartilage. Expression of aggrecan was also observed in PLA samples using primers to the carboxy terminus (PG). However, in addition to expression at days 7 and 10, PG was also detected at day 14 in these nodules. In support of the PLA results, expression of aggrecan in induced NHCK nodules was detected using both amino and carboxy primer sets. Like CNII, the expression of aggrecan was specific to induced PLA and NHCK nodules. In addition to CNII, chondrogenic induction of PLA cells resulted in the restricted expression of CNX, a marker of hypertrophic chondrocytes. Expression of CNX was detected at day 14 and suggests that PLA nodules undergo hypertrophy over time. Induced NHCK samples also expressed CNX, although at a lower level. PLA nodules were also associated with additional collagen types, including CNI and CNIII. While the majority of PLA samples examined exhibited a restricted collagen pattern (day 4 only), CNI and was detected in a few PLA samples up to day 14. The expression of CNI has also been observed in human MSC nodules by fibroblastic cells located in the outer nodule, leading researchers to suggest that this region is comprised of perichondrium-like cells involved in the differentiation process (Yoo, et al., 1998 J. Bone Joint Surg. Am 80:1745-1757: Yoo, et al., 1998 Clin. Orthop. S73-81). In support of this, perichondrium-like cells have also been observed in high-density embryonic chick limb-bud cell cultures and cell aggregates (Osdoby and Caplan 1979 Devel. Biol. 73:84-102; Tachetti, et al., 1987 J. Cell Biol. 106:999-1006). Therefore, the continued expression of CNI in select PLA samples may be due to the presence of a similar cell population.

Induced and control PLA cells also expressed the proteoglycans, decorin and biglycan and the gene CBFA1. Decorin and biglycan make up the majority of the small leucine-rich proteoglycans within the cartilagenous ECM and their expression within PLA nodules further supports the chondrogenic phenotype. In addition to its expression during osteogenesis, a role for CBFA-1 in the hypertrophy and terminal differentiation of chondrocytes has recently been confirmed (Enomoto, et al., 2000 J. Biol. Chem. 275:8695-8702. Therefore, the expression of CBFA-1, together with CNX, may indicate terminal differentiation of PLA cells within the nodule. Chondrocyte hypertrophy may also precede the ossification of cartilagenous tissue. However, expression of bone-specific OC by chondrogenic PLA or NHCK cells was not seen at any time point, confirming the absence of osteogenic differentiation within the PLA nodule. Interestingly, micro-mass culture of MSCs in CM did not result in the formation of nodules and was not examined. Taken together, the specific expression of CNII, aggrecan and CNX in induced PLA nodules, in addition to the presence of keratan- and chondroitin-4-sulfate within the ECM support the chondrogenic phenotype of these cells. Moreover, the chondrogenic capacity of PLA cells, together with their osteogenic and adipogenic potential, further supports the multi-lineage capacity of these putative stem cells.

PLA Cells Undergo Myogenic Differentiation:

RT-PCR analysis of PLA cells induced toward the myogenic lineage confirmed the expression of several myogenic genes, including the transcription factors MyoD1, myogenin and myf5, in addition to the muscle-specific protein, the myosin heavy chain. Determination of the myogenic lineage is thought to be controlled at the transcriptional level by MyoD1 and myf-5, which are expressed in proliferating myoblasts (Atchley, et al., Proc. Natl. Acad. Sci. 91:11522-11526; Lassar, et al., 1994 Curr. Opin. Cell Biol. 6:432-442; Weintraub, et al., 1994 Genes Dev. 15:2203-2211), whereas execution of the myogenic differentiation program is controlled by myogenin and MRF4 expression (emerson, et al., 1993 Curr. Opin. Genet. Dev. 3:265-274; Olson, et al., 1996 Cell 5:1-4). Finally, terminal differentiation of myoblasts can be confirmed through the expression of the myosin heavy chain. Consistent with these findings, the expression of myf5 was restricted to the first 3 weeks of myogenic PLA induction while increased MyoD1 expression was detected within the first week relative to the remainder of the differentiation period. Myo-induced PLA cells also expressed myogenin at relatively equivalent levels throughout the 6 week induction period. Finally, increased expression of the myosin heavy chain was detected at 6 weeks induction and suggests that PLA cells underwent of terminal differentiation. The expression of myf5 and myogenesis further supports this potential and, together with the osteogenic, adipogenic and chondrogenic capacity of PLA cells, indicates their potential for differentiation to multiple mesodermal lineages.

PLA Cells May Possess Neurogenic Potential:

True pluripotency of a stem cell is achieved upon differentiation to cells from distinct embryologic lineages. Recent reports have documented the differentiation of MSCs to neural cells (Deng, et al., 1994 Genes Devel. 8:3045-3057; Kopen, et al., 1999 Proc. Natl. Acad. Sci. USA 95:3908-3913; Sanchez-Ramos, et al. Exp. Neurol. 164:247-256; Woodbury, et al., 2000 J. Neurosci. Res. 61:364-370) and neural stem cells (NSCs) to haematopoietic cells (Bjornson, et al., 1999 Science 283:534-537), suggesting that stem cell populations may not be as restricted as previously thought. Based on these findings, we investigated if PLA cells could be induced beyond their putative multilineage mesodermal capacity. To this end, PLA cells were cultured in a medium known to induce neurogenic differentiation (Vescovi, et al., 1999 Exp. Neurol. 156:71-83; Woodbury, et al., 2000 J. Neurosci. Res. 61:364-370) and differentiation assessed by staining for neural markers, including NSE, trk-a and MAP-2 or for the expression of GFAP and GalC, markers of astrocytes and oligodendrocytes, respectively. The morphologic and histologic data suggest that PLA cells, like MSCs, possess neurogenic potential in vitro. Induction of PLA cells in NM for a minimum of 30 minutes resulted in a dramatic change in morphology with cells assuming a neuronal-like phenotype. NM-induced PLA cells underwent retraction, forming compact cells bodies with multiple extensions. Cell bodies became more spherical and cell processes exhibited secondary branches with increasing induction time. A time-dependent increase in the proportion of PLA cells with this phenotype was observed in all induced PLA cultures. Similar morphologic changes have been observed upon neurogenic induction of MSCs from both rodents and human (Woodbury, et al., 2000 J. Neurosci. Res. 61:364-370). Moreover, this PLA morphology was similar to that observed upon NGF stimulation of PC12 cells, a neuroendocrine cell line similar to primary sympathetic neurons.

The observed morphologic changes in neuro-induced PLA cells were accompanied by the increased expression of neuron-specific markers, such as NSE, trk-a and NeuN, and did not result in expression of markers for astrocytes and oligodendrocytes. Furthermore, expression of these markers was also observed in PC12 cultures, suggesting that PLA cells may be assuming a neuronal-like phenotype. In support of the PLA results, increased expression of NSE, a neuron-specific enolase, and trk-a has been observed upon induction of MSCs with β-ME, with approximately 100% of the neuronal-like MSCs positive for these markers (Woodbury, et al., 2000 J. Neurosci. Res. 61:364-370). Like the MSC studies, all PLA cells exhibiting a neuronal phenotype expressed significant levels of NSE and trk-a. In addition to NSE, expression of NeuN has also been used to identify neuronal development in neurogenic precursors and MSCs (Sanchez-Ramos, et al., 2000 Exp. Neurol. 164:247-256). Specifically, NeuN is expressed in post-mitotic neurons (Sarnat, et al., 1998 Brain Res. 20:88-94) and its appearance is thought to coincide with the withdrawl of the developing neuron from the cell cycle and/or the initiation of terminal differentiation (Mullen, et al., 1992 Development 116:210-211). The expression of NeuN within the neuronal-like PLA cells, together with the presence of NSE and trk-a, further supports the development of a neuronal phenotype in PLA cells. Moreover, the expression of NeuN may indicate the development of a post-mitotic neuronal phenotype. In contrast to NSE, trk-a and NeuN, expression of the mature neuronal markers, tau, MAP-2 and NF-70, was not observed, suggesting that induced PLA cells represent an early developmental stage. Consistent with this, MAP-2 expression in induced MSC cultures has not been observed by several groups and may reflect the induction conditions used or the need for prolonged induction time (Deng, et al., 2001 Biochem. Biophys. Res. Commun. 282: 148-152; Sanchez-Ramos, et al., 2000 Exp. Neurol. 164:247-256).

Finally, the putative neuronal potential of PLA cells was confirmed using RT-PCR. Consistent with the immunohistochemistry results, no expression of GFAP could be detected, supporting the restriction of induced PLA cells to the neuronal lineage. In addition, PLA cells were examined for the expression of the gene nestin. Nestin, an intermediate filament protein, has been detected in high amounts in CNS stem cells (Lendahl, et al., 1990 Cell 60:585-595), within the developing neural tubes of mice (Frederikson and McKay 1988 J. Neurosci. 8:1144-1151) and in MSCs induced toward the neurogenic lineage (Sanchez-Ramos, et al., 2000 Exp. Neurol. 164:247-256). Differentiation of neural precursors results in a decrease in nestin expression levels, indicating that this protein can be used as a marker of a progenitor phenotype (Johe, et al., 1996 Genes Dev. 10:3129-3140; Lendahl, et al., 1990 Cell 60:585-595). The expression of nestin in control PLA cultures is supportive of the presence of neurogenic precursors within the PLA. However, differentiation of PLA cells did not result in an appreciable decrease in nestin expression. This may be due to two possibilities: 1) the differentiation of PLA cells into a neurogenic progenitor population only or 2) the differentiation of PLA cells into an early neuronal-like cell that retains nestin expression. In support of the latter, nestin expression was also detected in NGF-treated PC12 controls. Based on this, together with the expression of NeuN, NSE and trk-a in induced PLA cells, leads us to favor the latter possibility and further studies are warranted. Like our IH results, RT-PCR analysis failed to detect expression of a mature neuronal marker (GAD65), a marker detected in PC12 controls and brain. It is possible that additional growth factors or a prolonged induction period may be required to induce PLA cells into a more mature stage. Finally, induction of PLA cells with NM appeared to restrict their development to cells characteristic of the CNS, as the cells did not express ChaT, a specific marker of peripheral nerves. Nestin expression has also been observed in non-induced MSCs, in addition to myogenic cells, newly formed endothelial cells, epithelial cells of the developing lens and hepatic stellate cells. This broad distribution indicates that nestin cannot be used as a neurogenic precursor marker per se. However, combined with the expression of additional neuronal markers, such as NeuN, the possibility that PLA cells are forming precursors of the neuroectodermal lineage is strengthened.

Figure 39:
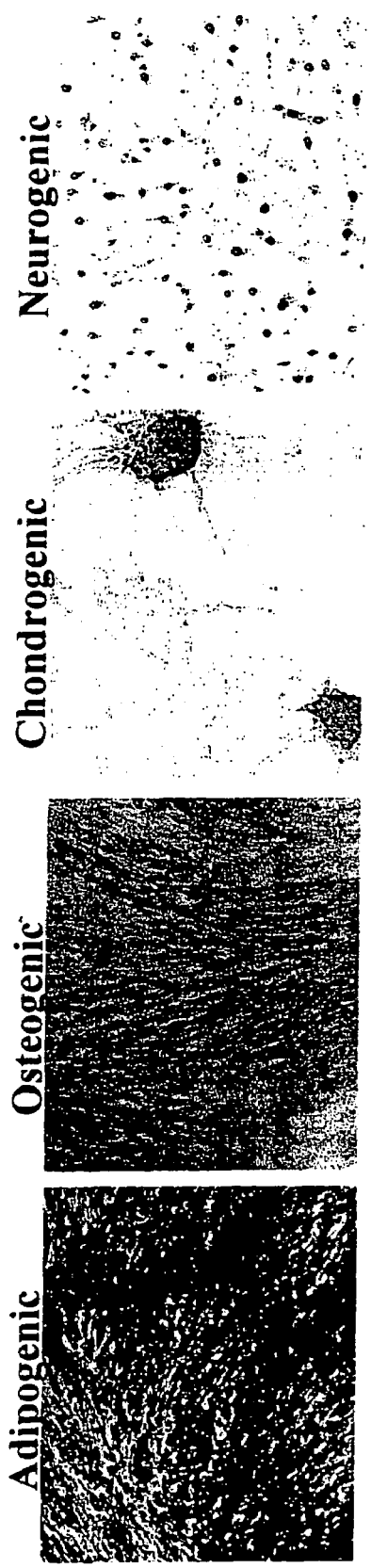
FIG. 39. Clones isolated from adipose-derived stem cell fractions exhibit neurogenic potential. Clones were examined using immunohistochemistry for adipogenic (oil red O stain), osteogenic (alkaline phosphotase), chondrogenic (Alcian blue stain), and neurogenic (anti-trka expression) differntiation.

ADSC Clonal Isolates Demonstrate Multi-lineage Capacity:

Multi-lineage differentiation by PLA cells may result from the commitment of multiple lineage-specific precursors rather than the presence of a pluripotent stem cell population within adipose tissue. Therefore, multi-lineage differentiation by clonal isolates derived from single PLA cells is critical to the classification of PLA cells as a source of stem cells. In support of, this, single PLA cell isolates expanded in culture exhibited multi-lineage capacity in vitro, staining positively for alkaline phosphatase (osteogenesis), Oil Red O (adipogenesis) and Alcian Blue (chondrogenesis). Clonal analysis resulted in the isolation of several lineage combinations, including tri-lineage (osteogenic, adipogenic and chondrogenic), dual-lineage (osteogenic/adipogenic, osteogenic/chondrogenic) and single lineage (adipogenic only). The tri-lineage clones were subsequently termed Adipose Derived Stem cells (ADSCs) and were analyzed for multilineage potential using RT-PCR. Consistent with multilineage capacity ADSCs expressed several genes characteristic of osteogenesis (OC, ON, OP, CNI and AP), adipogenesis (PPARγ2, aP2 and LPL) and chondrogenesis (AGG, CNX, decorin and biglycan). Furthermore, several tri-lineage ADSCs also expressed the neuronal marker trk-a using IH (FIG. 39). Based on these results, the expression of multiple lineage-specific mesodermal genes by ADSCs suggests that these isolated clones possess multipotentiality and may be considered stem cells.

EXAMPLE 12

The following provides a description of molecular and biochemical characterization of adipose-derived stem cells:

Materials and Methods

All materials were purchased from Sigma (St. Louis, Mo.), VWR (San Dimas, Calif.) and Fisher Scientific (Pittsburgh, Pa.) unless otherwise stated. All tissue culture reagents were purchased from Life Technologies (New York, N.Y.). Fetal Bovine Serum (FBS) and Horse Serum (HS) were purchased from Hyclone (Logan, Utah) and Life Technologies, respectively.

Antibodies:

Monoclonal antibodies to CD29, CD34, CD44, CD45, CD58, CD90, CD104, CD105 and CD140a were purchased from Pharmingen (Bedford, Mass.). Monoclonal antibodies to CD31 and CD71 were obtained from R&D Systems (Minneapolis, Mass.) and Zymed (S. San Francisco, Calif.), respectively. FITC and PE-conjugated anti-CD antibodies used for flow cytometry (FC) were purchased from Pharmingen. A monoclonal antibody to the SH3 antigen was produced from the SH3 hybridoma (ATCC). The Stro-1 hybridoma supernatant was the generous gift of Dr. John Fraser (UCLA). Monoclonal antibodies to the human collagens 1 (αCNI) and 4 (αCNIV) were purchased from Sigma. Monoclonal antibodies to human collagen 3 (αCNIII) and collagen 5 (αCNV) was purchased from Biogenesis (Kingston, N.H.).

Cell Harvest, Culture and Differentiation Conditions:

Processed lipoaspirate (PLA) cells were obtained from raw lipoaspirates and cultured as described previously (Zuk, P. et al., 2001 Tissue Engineering 7:209-226). PLA cells were maintained in non-inductive Control medium (Table 13) while MSCs were maintained in specialized Control medium (Clonetics). PLA cells were induced toward the desired mesenchymal lineages using the induction media outlined in Table 13. MSCs were induced using the commerical control medium supplemented with the same growth factors as outlined in Table 13.

PLA Clonal Isolation and Analysis: Adipose-Derived Stem Cells (ADSCs):

ADSC Isolation: PLA cells were plated at extremely low confluence in order to result in isolated single cells. Cultures were maintained in Control medium until proliferation of single PLA cells resulted in the formation of well-defined colonies. The single PLA-cell derived colonies were termed Adipose Derived Stem Cells (ADSCs). ADSCs were harvested using sterile cloning rings and 0.25% trypsin/EDTA. The harvested ADSCs were amplified in Cloning Medium (15% FBS, 1% antibiotic/antimycotic in F12/DMEM (1:1)).

Indirect Immunofluorescence:

Indirect Immunofluorescence (IF): PLA cells, ADSCs and MSCs were processed for IF as described previously (Zuk, P. et al., 2001, Tissue Engineering, 7:209-226) using the anti-CD marker antibodies outlined in Table 14. In addition, PLA cells were incubated with supernatants produced from the STRO-1 and SH3 hybridoma cell lines. To determine the cell characteristics of differentiated PLA cells and MSCs, cells were induced toward either the osteogenic lineage for 3 weeks or the adipogenic lineage for 2 weeks and incubated with anti-CD antibodies. The differentiated cells were also analyzed using antibodies to human collagens 1, 4 and 5.

Flow Cytometry:

PLA cells from multiple donors, in addition to MSCs, were cultured for 3 weeks in Control medium and analyzed for the expression of CD antigens by flow cytometry (FC) as described previously (Zuk, P. et al., 2001, Tissue Engineering, 7:209-226). PLA cells were also induced in either OM or AM for 2 weeks prior to analysis. Briefly, cells were harvested a 80% confluence with trypsin/EDTA, washed and resuspended in Flow Cytometry Buffer (FCB) at a concentration of $1 \times 10^6$ cells/ml. One hundred microliters of the cell preparation ($1 \times 10^5$ cells) were stained with saturating concentrations of FITC-conjugated (anti-CD 14, 44, 45 61, 71, 90 and 105) or PE-conjugated (anti-CD 13, 16, 31, 34, 44, 49d, 56, 62E and 106) antibodies for 1 hour at 4° C. Cells were also incubated with isotype-matched IgG's as a control to assess autofluorescence. After incubation, the cells were washed three times with FCB and resuspended for analysis. Flow cytometry was performed on a FACStar flow cytometer (Becton Dickson). The geometric means, calculated from the absolute numbers of cells per 10,000 events are shown in Table 12.

Results

PLA Cells Share Many Similarities with MSCs

The results described in this example demonstrate the mutli-lineage potential of adipose-derived stem cells and their clonal isolates. In order to characterize the PLA population further, cells were examined using indirect IF and FC and compared to a commercial population of human MSCs. MSCs have been shown to express a unique set of cell surface markers that can be used to help identify this stem cell population (Table 14) (Bruder, S. P. et al., 1998, Clin. Orthop., S247-256; Conget, P. A. et al., 1999, J. Cell Physiol, 181:67-73; Pittenger, M. F et al., 1999, Science, 284:143-147.) Like MSCs, PLA cells expressed several of these proteins (FIGS. 23 and 24), supporting the characterization of these cells as stem cells. Approximately 100% of the PLA and MSC cultures were positive for the expression of CD29, CD44, CD90 and CD105/SH2 with high expression levels for each of these markers being observed in both cell populations. Both cell populations also expressed the SH3 antigen, which, together with SH2, is considered a specific marker for MSCs (Haynesworth, S. E. et al., 1992, Bone, 13:69-80.) In addition, the majority of PLA cells and MSCs were also positive for the transferrin receptor, CD71, indicating that a fraction of these cell populations were replicating. PLA and MSCs did not express the haematopoietic lineage markers, CD31 and CD34. A small number of PLA samples did show negligible staining for CD45, although the number of CD45-positive cells did not exceed 5% of the total PLA cell number. Unlike MSCs, no staining for the adhesion molecule CD58 was observed in PLA cells. The IF results were subsequently confirmed by FC (FIG. 24, Panel B). Both MSC and PLA cells showed similar profiles, comprised mainly of a population of relatively small, agranular cells (FIG. 24, Panel A). However, a greater proportion of the PLA population did appear to contain larger, granular cells (see upper right corner), while a larger proportion of the MSC population contained smaller agranular cells. FC confirmed the expression of CD44, CD71, CD90 and CD105 on both PLA and MSCs and did not detect significant levels of CD31, CD34, CD45 and CD104. In addition to these markers, FC also measured expression of CD13, CD49d, SH3 and STRO-1 on PLA cells yet did not detect expression of CDs 4, 8, 11, 14, 16, 19, 33, 56, 62E and 106 (Table 12). Taken together, the immunofluorescent and flow results demonstrate several similarities in CD expression profiles between PLA populations and bone marrow-derived MSCs.

Figure 40:
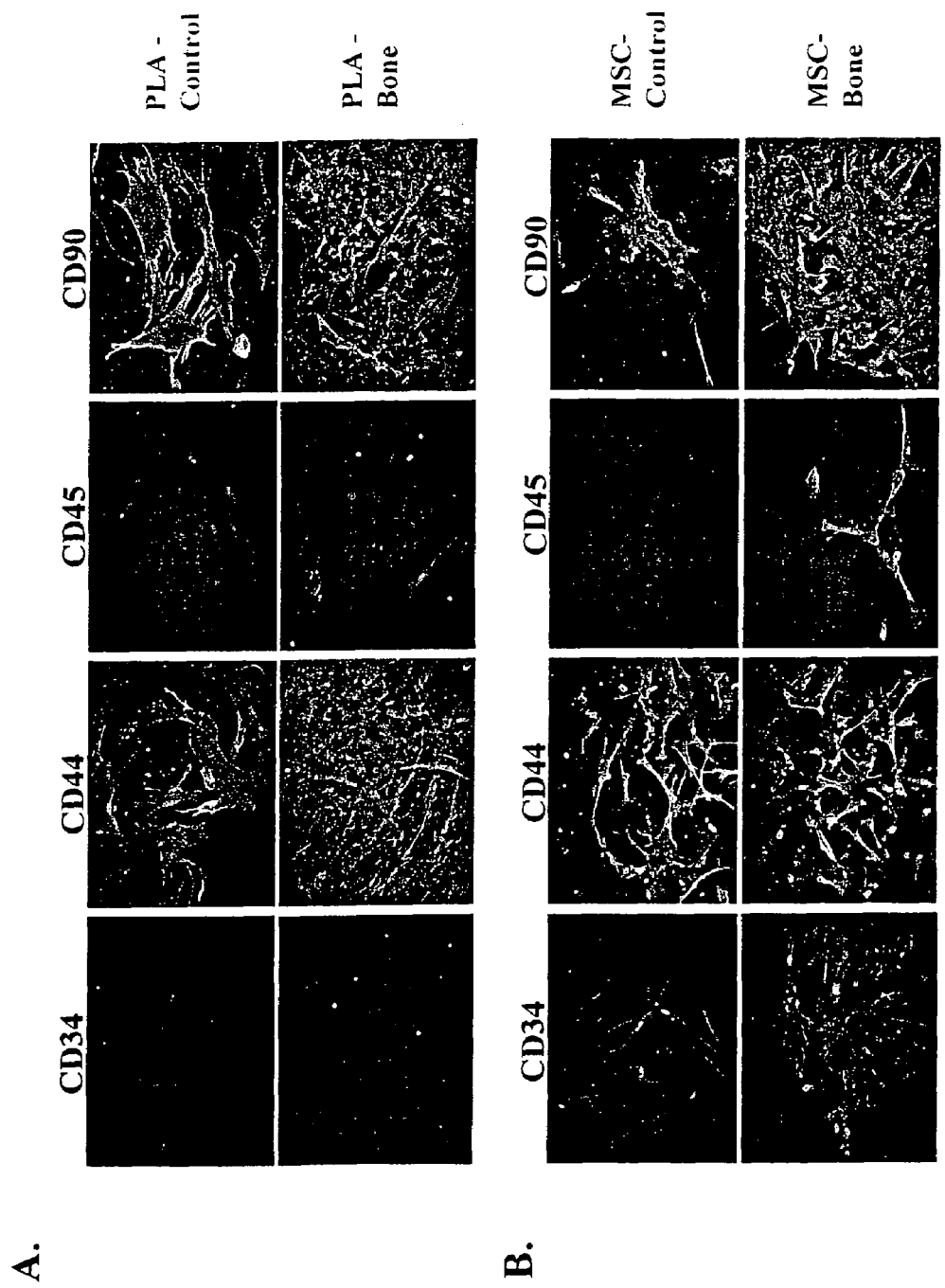
FIG. 40. Osteogenic differentiation of the adipose-derived stem cells (PLA) does not significantly alter CD marker expression. PLA cells (Panel A) and MSCs (Panel B) were induced in OM for 3 weeks (PLA-Bone, MSC-Bone respectively), or maintained in non-inductive Control medium (PLA-Control, MSC-Control). Cells were processed for IF for the expression of CD34, CD44, CD45 and CD90, co-stained with DAPI to visualize nuclei (blue) and the fluorescent images combined.

Phenotypic Characterization of Differentiated PLA Cells:

Differentiation of stem cells may alter the expression of several cell surface and intracellular proteins. In order to characterize differentiated PLA cells, cells from the same patient were maintained in non-inductive Control medium or were induced toward the osteogenic and adipogenic lineages. Control and differentiated PLA cells were subsequently analyzed by IF and compared to MSCs as a control. The results are presented in Table 15. PLA cells induced for 3 weeks in OM underwent increased proliferation and did not show any significant differences in CD marker profile when compared to undifferentiated PLA cells. Like control PLA cells, expression of CD45 was not observed in osteogenic PLA cells while significant expression of CD44 and CD90 was detected (FIG. 40, Panel A: PLA- Bone). However, in contrast to control cells, osteogenic differentiation resulted in localized areas of CD34 expression. Like PLA cells, the CD marker profile of control and osteo-induced MSCs was similar, with the exception of CD34 and CD45. As shown in FIG. 40, Panel B, expression of CD34 and CD45 was not observed in control MSCs. However, a slight increase in CD34 expression level was observed upon induction in OM while an increased number of CD45-positive cells were detected.

Figure 41:
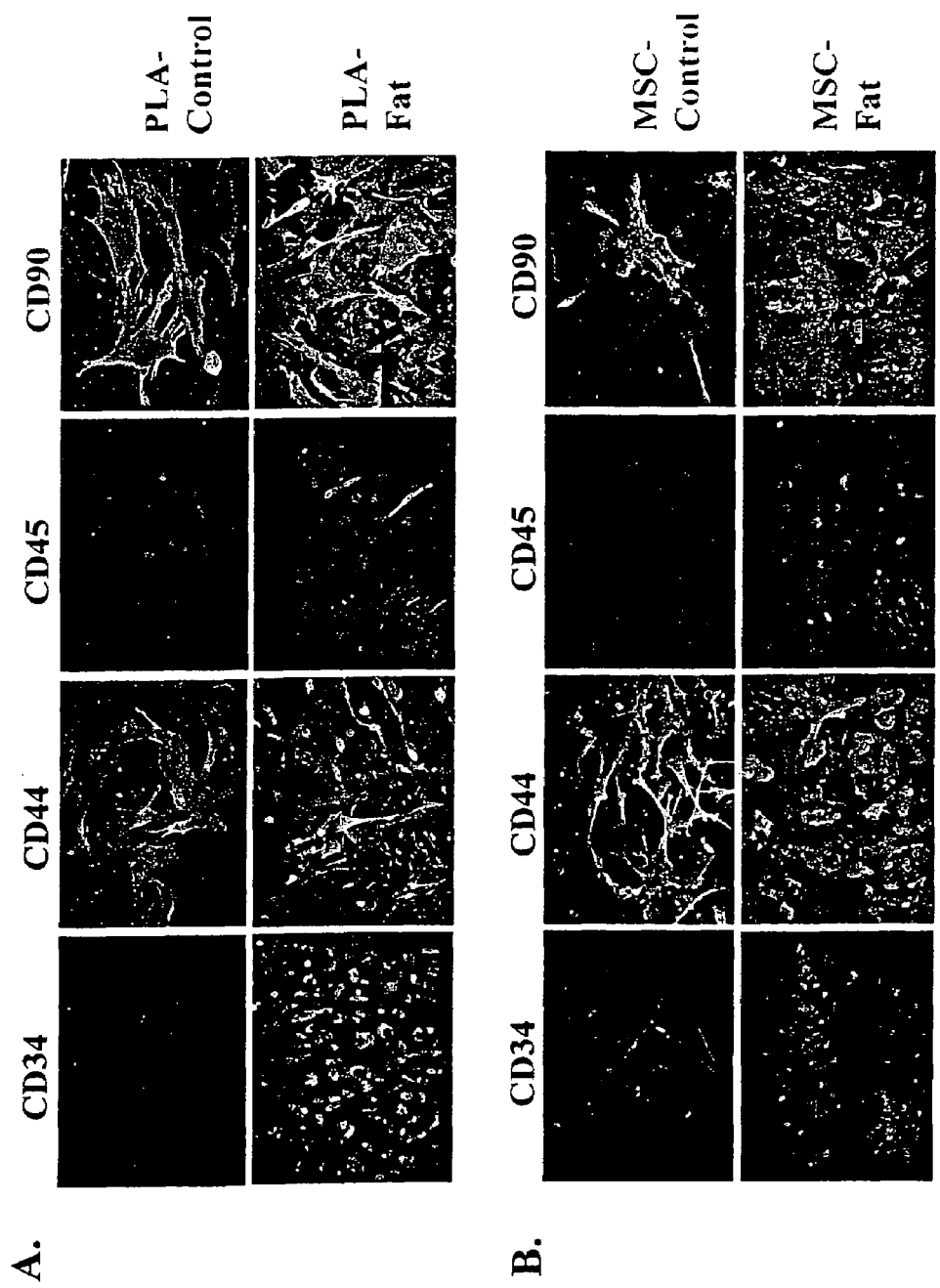
FIG. 41. Adipogenic differentiation results in subtle changes to the adipose-derived stem cells (PLA) CD marker profile. PLA cells (Panel A) and MSCs (Panel B) were induced in AM for 2 weeks (PLA-Fat, MSC-Fat, respectively) or maintained in non-inductive Control medium (PLA-Control, MSC-Control). Cells were processed for IF for the expression of CD34, CD44, CD45 and CD90, co-stained with DAPI to visualize nuclei (blue) and the fluorescent images combined. To visualize adipocytes and their staining pattern, fluorescent images were combined with light micrographs (inset). Lipid-filled cells (white arrows—fluorescent image; black arrows—inset) and fibroblasts (filled white arrows—fluorescent image; filled black arrows—inset) are indicated.

To induce adipogenic differentiation, PLA cells were maintained for a minimum of 2 weeks in AM. In order to correlate CD marker expression to cell morphology, fluorescent micrographs were overlaid with light micrographs (inset pictures). Induction of PLA cells with AM resulted in an expanded cellular morphology and the accumulation of multiple, intracellular lipid vacuoles, consistent with adipogenesis. These lipid-containing PLA cells were considered to be mature adipocytes (white arrows) (FIG. 41, Panel A: PLA-Fat). Like osteogenesis, adipogenic differentiation appeared to result in slightly increased CD34 levels in both fibroblastic and lipid-containing PLA cells (FIG. 41, Panel A). In addition, a negligible fraction of the adipogenic PLA cultures contained CD45-positive cells. However, these cells did not contain the lipid vacuoles characteristic of mature adipocytes (CD45-inset). A significant level of CD44 was also detected in adipogenic PLA cultures. However, lipid-filled PLA cells appeared to express lower levels of CD44 in comparison to their fibroblastic counterparts (open arrows—CD44-ve adipocytes, filled arrows—CD44+ve cell). Furthermore, CD44 staining levels varied among the fibroblasts, ranging from intense to little or no CD44 expression. A similar restriction was also observed for CD90 with all fibroblasts expressing this protein at comparable levels. Like PLA cells, adipo-induced MSCs expressed CD44 and CD90 and showed increased staining for CD34 and CD45 (FIG. 41, Panel B and Table 16). However, unlike adipo-induced PLA cells, both fibroblastic and lipid-filled MSCs (filled vs. open arrows, respectively) appeared to express CD44 and CD90 at similar levels.

Figure 42:
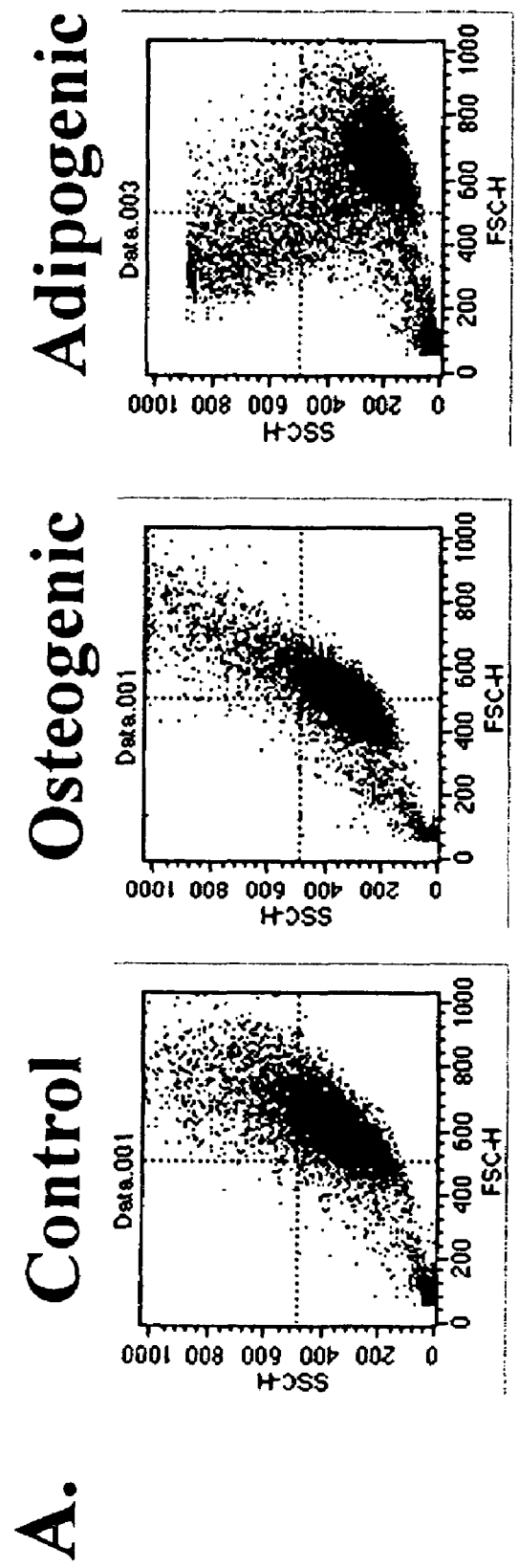
FIG. 42. Differentiation alters the expression of specific CD markers on adipose-derived stem cells (PLA): Flow cytometry. Panel A: PLA cells were maintained for 2 weeks in Control medium (Control), or in OM (Osteogenic) or AM (Adipogenic). Cells were analyzed by FC using forward and side scatter to assess cell size and granularity (FSC-H and SSC-H, respectively). Panels B and C: PLA cells were maintained for 2 weeks in Control medium (PLA-CM), or in OM (PLA-OM) or AM (PLA-AM). Cells were directly stained for the indicated CD markers using fluorochrome-conjugated primary antibodies and analyzed by FC. The adipose-derived stem cells, stained with fluorochrome-conjugated non-specific IgG, were examined as a negative control. All results were corrected for senescence and represent a total of $10^5$ events.
Figure 42:
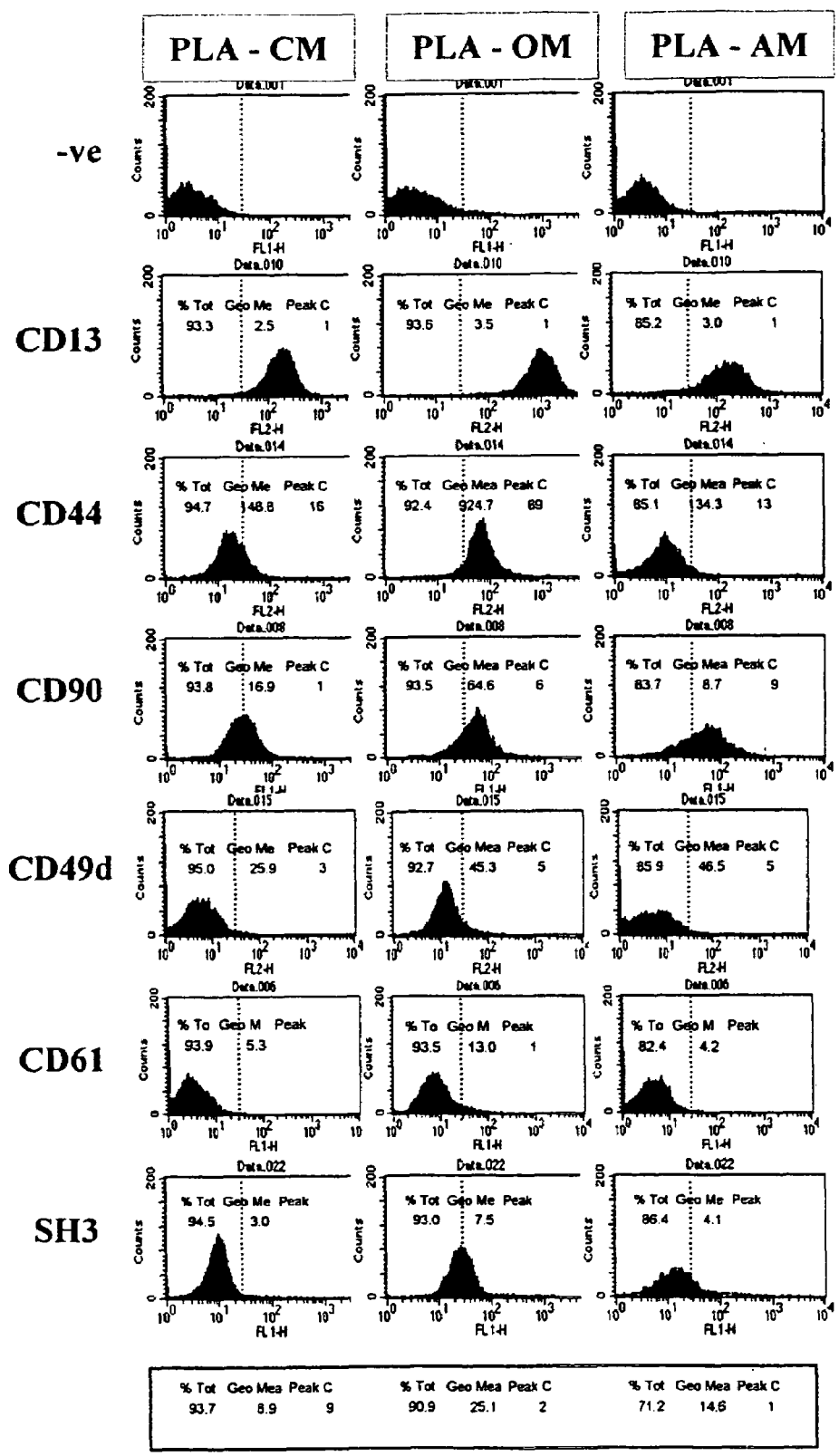
Figure 42:
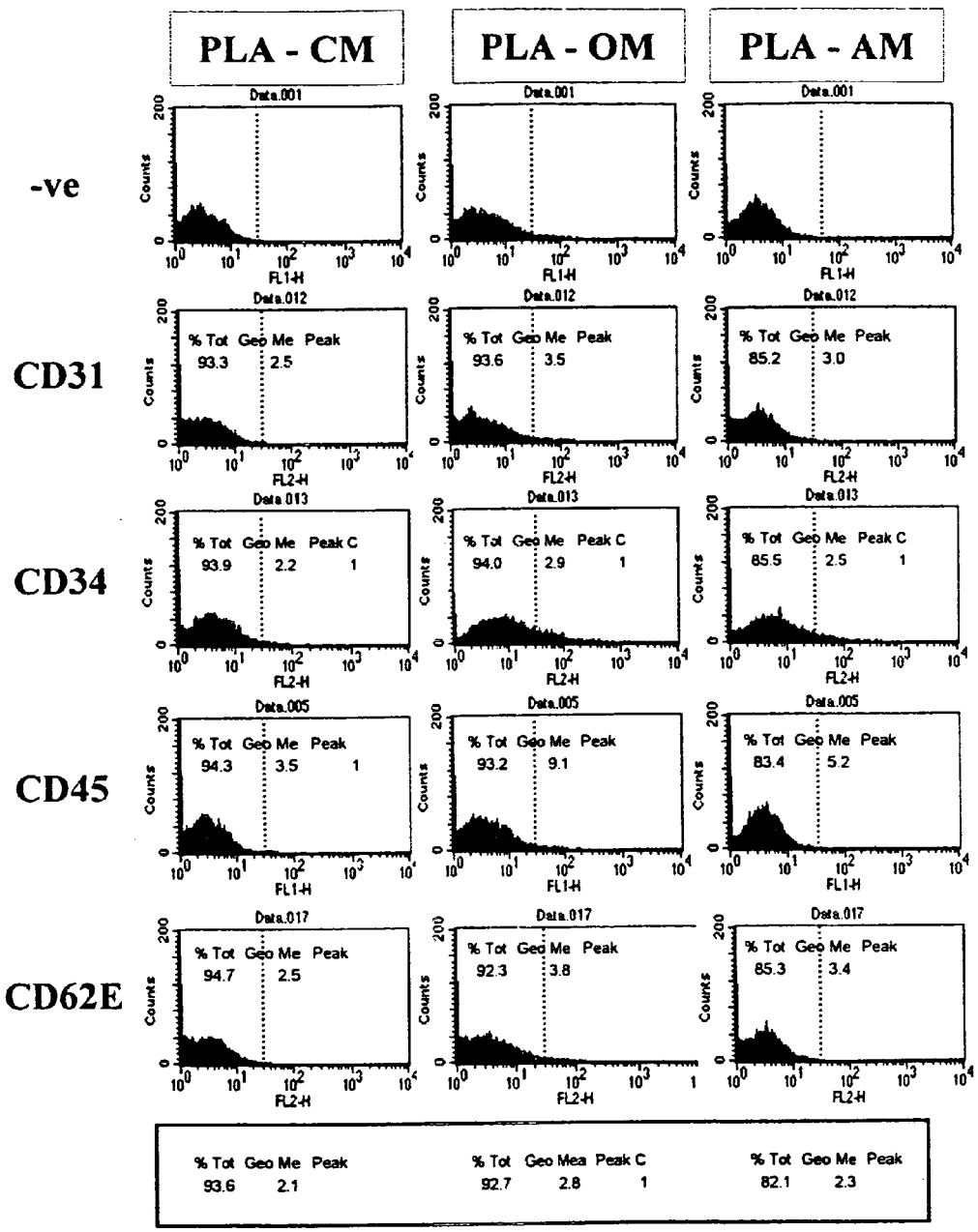

In order to confirm the immunofluorescent results, FC was performed on non-induced and differentiated PLA cells and the geometric means calculated for each CD marker protein (FIG. 42) (Table 16). Osteogenic differentiation did not appreciably change the size and granularity of the PLA populations (FIG. 42, Panel A). Adipogenesis, however, resulted in a significant increase in the size and granularity of the PLA population, likely a reflection of the expanded cellular morphology and the formation of intracellular lipid vacuoles. Consistent with the immunofluorescent results, control PLA cells were negative for CD34 and CD45 expression (Panel B), nor could expression of CD14, CD16, CD31, CD34, CD45, CD56, CD61, CD62, CD105 or CD106 be measured in these cells (Panel B). Differentiation appeared to increase CD34 and CD61 expression with a greater increase being observed upon osteogenic differentiation. The increased CD34 expression was consistent with the increased staining observed upon IF processing (FIG. 40). Slight increases in CD56 and CD49d were detected specifically in osteo-induced PLA cells. The expression of CD56 in adipo-induced PLA cells did not differ significantly from controls, while a decrease in CD49d expression was detected upon adipogenesis. FC also confirmed the expression of CD13, CD44 and CD90 in control cells (FIG. 42, Panel C). Osteogenesis significantly increased expression of these markers and a further increase in CD90 was measured in adipo-induced PLA cells. Finally, adipogenic differentiation resulted in a decreased expression of CD13 and CD44 to below that of undifferentiated PLA cells. The decrease in CD44 was consistent with the IF results, in which lower expression levels were seen in lipid-containing PLA cells.

Mesodermally-derived cells, such as adipocytes and osteoblasts are associated with extensive extracellular matrices (ECMs). To assess the expression of ECM proteins in differentiated PLA cells, adipogenic and osteogenic PLA cells were analyzed by IF for the expression of ECM collagens. The results are summarized in Table 17. The majority of undifferentiated PLA cells expressed collagen types 1 and 3 (CNI, CNIII) (FIG. 43, Panel A: PLA-Control). CNI and CNIII in fibroblastic PLA cells were restricted to a defined perinuclear concentration and was evenly distributed throughout while cells with an expanded morphology. Contrary to CNI and CNIII, the expression of collagen types 4 and 5 (CNIV, CNV) was restricted to defined culture regions of concentrated PLA cells and matrix formation. The expression patterns of CNIV and CNV were fibrillar in nature, consistent with the secretion of these proteins into the extracellular space surrounding these cells.

Figure 43:
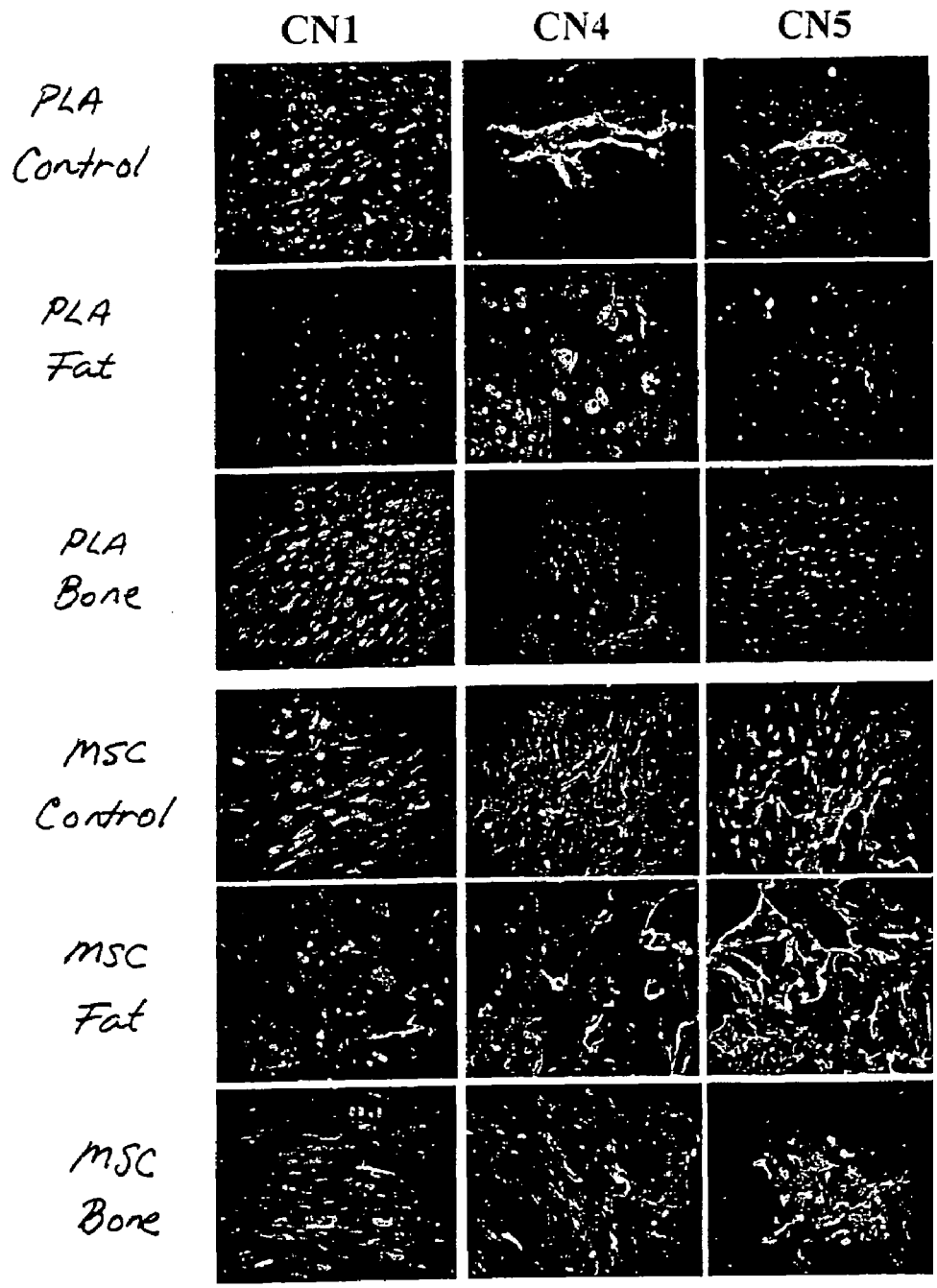
FIG. 43. Differentiation of the adipose-derived stem cells (PLA) results in a change in ECM composition. PLA cells were induced for either 3 weeks in OM (PLA-Bone), 2 weeks in AM (PLA-Fat) or maintained in Control medium (PLA-Control). Cells were processed for IF using antibodies to collagen type 1 (CNI), type 4 (CNIV) and type 5 (CNV). Cells were co-stained with DAPI to visualize nuclei (blue) and the fluorescent images combined. Fluorescent images were combined with light micrographs (inset). Lipid-filled PLA cells (white arrows—fluorescent image; black arrows—inset) are indicated. Osteo-induced MSCs (MSC-Bone), adipo-induced MSCs (MSC-Fat) and non-induced MSCs (MSC-Control) were also analyzed.

Adipogenic differentiation of PLA cells inhibited both CNI and CNV expression (FIG. 43, Panel A: PLA-Fat). Differentiation also appeared to alter the intracellular expression pattern of CNIII, redistributing it evenly throughout the mature PLA adipocyte. In addition, a lower level of CNIV expression was observed in adipogenic PLA samples, with the majority of the CNIV fluorescence observed in lipid-filled PLA cells (see arrows; inset). While an inhibition of CNV expression was also observed upon osteogenic induction, no significant difference in CNI expression pattern could be detected for this lineage (FIG. 43, Panel A; PLA-Bone). Finally, osteogenesis appeared to increase CNIV expression levels and resulted in a more widespread distribution of this collagen within the PLA culture. The expression patterns of CNI, CNIII, CNIV and CNV in control MSCs were found to be similar to control PLA cells (FIG. 43, Panel B: MSC-Control). Like PLA cultures, CNIII and CNIV were detected in adipo-induced MSC samples. However, CNIV appeared to be restricted to extracellular fibrils rather than an intracellular distribution (FIG. 43, Panel B: MSC-Fat, see arrows). In contrast to adipogenic PLA cultures, induction toward this lineage did not inhibit synthesis of CNI and CNV by MSCs. Rather, these collagens could be detected within extracellular fibrils and weak CNI expression could also be observed within lipid-filled MSCs. Finally, in contrast to osteo-induced PLA cells, osteogenic induction of MSCs did not alter the intracellular expression pattern of CNI or the synthesis and extracellular deposition of CNIV and CNV (FIG. 43, Panel B; MSC-Bone).Taken together, the immunofluorescent data suggests that both adipogenic and osteogenic differentiation of PLA cells leads to a remodeling of the associated ECM, resulting in a matrix that appears to be distinct from those of MSCs.

PLA Clonal Isolates (ADSCs) Express a Similar Complement of CD Marker Proteins

Multi-lineage differentiation by PLA cells may be the result of the commitment of multiple lineage-specific precursors rather than the presence of a pluripotent stem cell population within adipose tissue. Therefore, multi-lineage differentiation by clonal isolates derived from single PLA cells is critical to the classification of PLA cells as a source of stem cells. In support of this, single PLA cells colonies, termed Adipose-Derived Stem Cells (ADSCs), exhibited multi-lineage capacity in vitro (FIG. 35). Analysis of 500 ADSC isolates confirmed differentiation potential in approximately 6% of the total number of clones examined. Seven ADSC isolates exhibited tri-lineage potential, differentiating into cells of the osteogenic, adipogenic and chondrogenic lineages, approximately 24% of the total number of ADSCs positive for differentiation potential (Table 11). Furthermore, a qualitative increase in differentiation level, as measured by histologic staining, was also observed in these tri-lineage ADSC populations. In addition to tri-lineage ADSCs, several dual-lineage clones (O/A, O/C and A/O) and single adipogenic lineage clones were also isolated. Isolation and expansion of ADSCs did not alter the CD expression profile of the clones, as no difference in CD expression could be detected by IF. Furthermore, no difference was also observed between tri- and dual lineage ADSC isolates (FIG. 36). Like the heterogeneous PLA populations, ADSCs were positive for CD29, CD44, CD71 and CD90 expression, while no expression of CD31, 34, 45 and 104 was observed. Therefore, the presence of multi-lineage ADSC isolates within the heterogenous PLA cell population and their identical CD marker profile to PLA cells further supports the theory that the adipose compartment is a source of multi-potential stem cells.

TABLE 13

Lineage-specific differentiation induced by media supplementation

| Medium | Media | Serum | Supplementation |
|---|---|---|---|
| Control | DMEM | 10% FBS | None |
| Adipogenic (AM) | DMEM | 10% FBS | 0.5 mM isobutyl-methylxanthine (IBMX), 1 µM dexamethasone, 10 µM insulin, 200 µM indomethacin, 1% antibiotic/antimycotic |
| Osteogenic (OM) | DMEM | 10% FBS | 0.1 µM dexamethasone, 50 µM ascorbate-2-phosphate, 10 mM β-glycerophosphate, 1% antibiotic/antimycotic |

TABLE 14

Monoclonal antibodies to CD antigens: Reported cell specificity and distribution

| CD Antigen | | Clone | Cell Specificity |
|---|---|---|---|
| 29 | Integrin β1 | MAR4 | broad distribution - lymphocytes, monocytes, granulocytes NOT on erythrocytes |
| 31 | PECAM-1 | 9G11 | endothelial cells, platelets, monocytes, granulocytes, haematopoietic precursors |
| 34 | — | 581 | endothelial cells, some tissue fibroblasts, haematopoietic precursors |
| 44 | Pgp-1 | G44-26 | leucocytes, erythrocytes, epithelial cells, platelets |
| 45 | LCA | HI30 | leucocytes, haematopoietic cells |
| 58 | LFA-3 | L306.4 | wide distribution - haematopoietic cells, endothelial cells, fibroblasts |
| 71 | TfR | H68.4 | most dividing cells |
| 90 | Thy-1 | 5E10 | immature CD34+ cells, cells capable of long term culture, primitive progenitor cells |
| 104 | | | |
| 105 | Endoglin | — | endothelial cells, B cell precursors, MSCs |
| SH3 | — | — | mesenchymal stem cells |

TABLE 15

Immunofluorescent analysis of differentiated PLA and MSC populations

| CD marker | PLA | PLA-OM | PLA-AM | MSC | MSC-OM | MSC-AM |
|---|---|---|---|---|---|---|
| CD29 | +ve | +ve | +ve | +ve | +ve | +ve |
| CD31 | −ve | −ve | −ve | −ve | −ve | −ve |
| CD34 | −ve | +/−, restricted | +ve (weak) | −ve | +ve (weak) | +ve (weak) |
| CD44 | +ve | +ve | +ve, fibroblastic cells | +ve | +ve | +ve |
| CD45 | −ve | −ve | +/−, fibroblastic cells | −ve | +ve | +ve (weak) |
| CD58 | −ve | −ve | −ve | +ve | +ve | +ve |
| CD71 | +ve | +ve | +ve | +ve | +ve | +ve |
| CD90 | +ve | +ve | +ve, fibroblastic cells | +ve | +ve | +ve |
| CD105 | +ve | +ve | +ve | +ve | +ve | +ve |

−ve no staining observed
+/− minimal staining observed (less than 10% of the population)
+ve staining observed

TABLE 16

Flow cytometric analysis of CD marker expression in osteogenic, adipogenic and control PLA cells.

| CD Antigen | PLA-CM | PLA-OM | PLA-AM |
|---|---|---|---|
| CD13 | 148.88 | 924.79 | 134.34 |
| CD14 | 2.43 | 3.54 | 3.08 |
| CD16 | 2.38 | 3.43 | 2.70 |
| CD31 | 2.22 | 2.92 | 2.53 |
| CD34 | 3.55 | 9.10 | 5.27 |
| CD44 | 16.92 | 64.62 | 8.76 |
| CD45 | 2.52 | 3.85 | 3.47 |
| CD49d | 5.33 | 13.05 | 4.27 |
| CD56 | 2.66 | 4.86 | 2.72 |
| CD61 | 3.68 | 7.55 | 4.12 |
| CD62E | 2.30 | 2.89 | 2.38 |
| CD90 | 25.96 | 45.32 | 46.53 |
| CD105 | 8.39 | 16.70 | 11.53 |
| CD106 | 2.45 | 3.27 | 2.51 |
| SH3 | 8.95 | 25.15 | 14.65 |
| −ve | 2.59 | 3.57 | 3.08 | with MSCs (positive: CD29, CD44, CD71, CD90, CD105 SH3, negative: CD31, CD34, CD45), the expression of CD58, CD104 and CD140a differed on PLA cells when examined by immunofluorescence. Flow cytometry also confirmed the expression of CD13 and the absence of CD14, CD16, CD56 and CD62E. Subtle distinctions between non-induced and differentiation PLA cells could be determined using flow cytometry. Specifically, increases in CD13, CD44 and CD90 were observed upon osteogenic induction, whereas CD13 and CD44 levels in adipogenic cultures were found to be lower. Consistent with this, IF analysis indicated a lower level of CD44 expression within lipid-filled PLA cells (i.e. mature adipocytes). Osteogenic differentiation also resulted in slight increases in CD34, CD49d, CD56 and CD61. CD34 expression was confirmed using immunofluorescence, with CD34-positive regions being observed in osteogenic PLA cultures. ADSC clonal populations also expressed a similar complement of CD antigens to that observed in the heterogenous PLA population, suggesting that clonal isolation and

TABLE 17

Immunuofluorescent staining patterns of extracellular matrix collagens: Effect of differentiation.

| Collagen type | Immunofluorescent Staining Pattern | | | | | |
|---|---|---|---|---|---|---|
| | PLA | MSC | PLA-Fat | MSC-Fat | PLA-Bone | MSC-Bone |
| 1 | punctate + perinuclear concentration | punctate + perinuclear concentration | no expression | weak cellular expression + fibrillar pattern | punctate + perinuclear concentration | punctate + perinuclear concentration |
| 4 | fibrillar, localized to defined regions | fibrillar pattern | cellular distribution, lipid-filled cells only | fibrillar, decreased expression | fibrillar, weak expression | fibrillar pattern |
| 5 | fibrillar, localized to defined regions | fibrillar pattern | no expression | fibrillar pattern | no expression | cellular + fibrillar pattern |

Discussion

In this study, a more comprehensive characterization of the PLA and ADSC populations was performed using a combination of immunofluorescence and flow cytometry. While PLA cells expressed a similar complement of CD antigens expansion of these cells does not affect cell surface protein expression. Finally, differentiation of PLA cells also resulted in changes to the associated ECM and differences in the expression patterns and levels of collagen types 1, 4 and 5 were found between differentiated PLA and MSC cultures. Taken together, this data suggests that PLA cells may represent a stem cell population within adipose tissue but is a population that possesses subtle distinctions from MSCs.

While PLA cells expressed a similar complement of CD antigens with MSCs, an established mesenchymal stem cell population, PLA cells did show subtle differences in the expression of CD58, CD104 and CD140a. The CD marker profile on PLA cells was further confirmed using flow cytometry. Osteogenic and adipogenic differentiation did not significantly change the CD profile, but, as with control cells, subtle distinctions could be determined using flow cytometry. Differentiation also resulted in changes to the associated ECM. Finally, both ADSC clonal populations expressed a similar complement of CD antigens to that observed in the heterogenous PLA population, suggesting that clonal isolation of a multi-lineage population from the PLA does not affect the expression of cell surface proteins.

Characterization of a cell population can be performed through identification of unique proteins expressed on the cell surface. Several groups have subsequently characterized MSCs based on their expression of cell-specific proteins (e.g. STRO-1, SH2, SH3, SH4) and "cluster designation" (CD) marker profiles (Bruder, S. P. et al., 1998, Clin. Orthop., S247-256; Conget, P. A. et al., 1999, J. Cell Physiol, 181:67-73; Pittenger, M. F et al., 1999, Science, 284:143-147.) This study confirms that, like MSCs, a unique combination of cell surface proteins are expressed on PLA cells with the two populations showing similar expression profiles. Like MSCs, PLA cells expressed CD13, CD29, CD44, CD71, CD90, CD105/SH2 and SH3 as shown by a combination of IF and FC. In addition, PLA cells did not express CD14, CD16, CD31, CD34, CD45, CD56, and CD62E on the cell surface. The similarity in CD profiles to MSCs lends support to the theory that PLA cells are a stem cell population. However, the degree of similarity may indicate that PLA cells are simply an MSC population located within or contaminating the adipose compartment. Lipoplasty results in the rupture of multiple blood vessels and while vasoconstrictors are used to minimize blood loss, the processed PLA pellet may be MSCs obtained from the peripheral blood supply (Zvaifler, N. J. et al., 2000, Arthritis Res., 2:477-488.) However, there appear to be a few subtle distinctions between PLA and MSC populations. In contrast to MSCs, no expression of CD58 could be detected on PLA cells using IF, while expression was seen on MSCs (FIG. 23). Furthermore, MSCs have also been reported to express CD104, CD106 and CD140a (Bruder, S. P. et al., 1998, Clin. Orthop., S247-256; Conget, P. A. et al., 1999, J. Cell Physiol, 181:67-73; Pittenger, M. F et al., 1999, Science, 284:143-147.) No expression of these CD antigens were detected on PLA cells using IF or FC (FIGS. 23 and 24). These differences may indicate that the PLA population represents a distinct population of stem cells. However, the possibility that PLA cells are a clonal variation of MSCs cannot be completely ruled out.

Multi-lineage differentiation by PLA cells may result from the commitment of multiple lineage-specific precursors rather than the presence of a pluripotent stem cell population within adipose tissue. Therefore, multi-lineage differentiation by clonal isolates derived from single PLA cells is critical to the classification of PLA cells as a source of stem cells. In support of this, ADSC isolated exhibited multi-lineage capacity in vitro staining positively using the histologic assays alkaline phosphatase (osteogenesis), Oil Red O (adipogenesis) and Alcian Blue (chondrogenesis). Several lineage combinations were observed, including tri-lineage (osteogenic, adipogenic and chondrogenic), dual-lineage (osteogenic/adipogenic, osteogenic/chondrogenic) and single lineage (adipogenic only). Isolation and expansion of ADSCs did not alter the CD expression profile and no difference in CD expression could be detected between any tri-lineage and dual-lineage ADSC population. Therefore, the presence of multi-lineage ADSC isolates and their identical CD marker profile to heterogenous PLA cells further supports the theory that the adipose compartment is a source of multi-potential stem cells.

Differentiation of mesenchymal precursors and stem cells may lead to changes in the expression of several cell surface and intracellular proteins as these cells acquire a new fate and function. To assess this, undifferentiated PLA cells and cells induced toward the osteogenic and adipogenic lineages were examined by IF and FC for any changes in CD marker profile. Osteogenic differentiation did not significantly alter the CD profiles of PLA cells (FIG. 2 and Tables 16 and 17). Indirect IF confirmed the expression of CD44 and CD90 and did not detect expression of CD34 and CD45 in both osteogenic PLA and MSC cultures. In addition, both osteogenic PLA and MSC cultures were positive for CD29, CD71, CD105 and SH3 expression, whereas no expression of CD31 could be detected. However, further analysis of osteogenic PLA cultures by FC revealed subtle changes to the CD profile. Specifically, osteo-induction resulted in a 1.8-fold and 3.8-fold increase in CD90 and CD44 expression levels, respectively. The increased expression of CD44, the hyaluronan receptor, is likely the result of increased matrix synthesis and cell-matrix interaction by PLA cells upon osteogenesis. Recent work has also confirmed the expression of Thy-1/CD90 on osteoblasts and osteoblast-like cells derived from mice, rats and human. Expression of this protein increased markedly during the earliest stages of maturation (proliferative phase) and decreased as the osteoblasts matured. The increased expression of CD90 upon osteogenic induction of PLA cells may, therefore, reflect the increased expression of this protein as the osteogenic PLA cells proliferate during the earliest phases of differentiation. In addition to CD44 and CD90, a dramatic increase (6.2-fold) in the metalloprotease, CD13/aminopeptidaseN, was also observed in osteogenic PLA cells. In addition to its expression on committed progenitors of granulocytes and monocytes [Kishimoto, 1997 #1082], CD13 has also been identified on fibroblasts, bone marrow stromal cells and osteoclasts (Syrjala, M. et al., 1994, Br. J. Haematol., 88:679-684). Recent work has identified an increase in CD13 mRNA levels upon cell-cell contact (Kehlen, A. et al., 2000, J. Cell Biochem, 80:115-123; Reimann, D. et al., 1997, J. Immunol., 158:33425-3432.) The dramatic increase in CD13 on PLA cells may therefore be due to the increased cell to cell contact within osteogenic PLA cultures. Additionally, increased expression of proteases, such as CD13, on stem cells may also participate in differentiation by degrading regulatory peptides and proliferation agents that may affect the development of these cells (Young, H. E. et al, 1998, Wound Repair Regen, 6:66-75; Young, H. E. et al., 1999, Proc. Soc. Exp. Biol. Med., 221:63-71.)

Interestingly, FC measured slight increases in CD34, CD56, CD49d, CD61 and CD105 expression upon osteogenic induction. With the exception of CD105, these markers were not expressed on undifferentiated PLA cells and MSCs and their increase is likely the result of differentiation. A 2.6-fold increase in CD34 expression was detected in osteo-induced PLA cultures. This increase was consistent with the appearance of CD34-positive regions within osteogenic PLA cultures as shown by IF (FIG. 23). A slight increase in CD34 was also observed upon IF analysis of osteogenic MSCs (FIG. 40). However, this increase appeared to be the result of an overall enhanced expression level by all MSCs. Osteogenic induction also resulted in a 1.8-fold increase in CD56 expression. Identified as neural cell adhesion molecule (NCAM), CD56 is expressed on haematopoietic stem cells (Kishimoto, T. et al, 1997, *Leucocyte Typing VI. White Cell Differentiation Antigens*. (Hamden Conn.: Garland Publishing), mediating their adhesion with adjacent cells and the surrounding matrix (Lanier, L. L. et al, 1991, J. Immunol, 146:4421-4426; Lanier, L. L. et al., 1989, J. Exp. Med., 183:681-689.) Although its function has not been confirmed, CD56 may act in a similar manner in non-haematopoietic cells. In support of this, osteoblasts express NCAM, using this adhesion molecule to mediate cell and matrix interactions and leading to their differentiation (Lee, Y. A. et al., 1992, J. Bone Miner. Res., 7:1435:1466.) The osteogenic differentiation of PLA cells, therefore, may induce elevated levels of this CD protein in order to regulate the increasing cell-cell and cell-matrix interactions during differentiation. The same explanation can likely be applied to the observed 3-fold increase in the α4 integrin, CD49d. Finally, a small increase in CD105 expression was measured on osteogenic PLA cells. Classified as a type III TGFβ3 receptor (Cheifetz, S. et al., 1992, J. Biol. Chem., 267:19027-19030), CD105 is expressed on a wide variety of cells, including endothelial cells, B-lineage precursors, MSCs and a subset of $CD34^+$ cells isolated from peripheral blood (Rokhlin, O. W. et al., 1995, J. Immunol., 154:4456-4465; Majumdar, M. K. et al., 1998, J. Cell Physiol., 176:57-66; Barry, F. P. et al., 1999, Biochem. Biophys. Res. Commun., 265:134-139; Pierelli, L. et al., 2000, Br. J. Hematol., 108:610-620.) While little is know of this protein during bone development, expression of CD105 is thought to decrease as osteogenic precursors proceed toward terminal differentiation, disappearing on mature osteoblasts (Haynesworth, S. E. et al., 1992, Bone, 13:69-80.) Therefore, the expression of CD105 on osteogenic PLA and MSCs, as shown by IF, may indicate that these cells represent an early stage in differentiation and have not reached their final differentiation stage. Furthermore, the slight increase in CD105 expression on PLA cells, as measured by FC, correlates to the increase in CD34 and may reflect the increase in a $CD34^+$ subset within the osteogenic culture.

Adipogenic differentiation of PLA cells has been shown to result in an expanded morphology, together with the accumulation of multiple lipid-filled intracellular vacuoles (Zuk, P. et al., 2001, Tissue Engineering, 7:209-226.) As a result, adipo-induced PLA cultures are a heterogenous mixture of lipid-filled cells (i.e. mature PLA adipocytes) and more immature fibroblastic cells. Consistent with this, FC characterization of adipogenic PLA cultures demonstrated a shift toward a population of larger, more granular cells. IF analysis confirmed the expression of CD29, CD44, CD71, CD90 and CD105 on adipogenic PLAs and MSCs (FIG. 41). While equivalent levels of CD29, CD71 and CD105 were found on both fibroblastic and lipid-filled cells, lower levels of CD44 and CD90 were observed in the mature PLA adipocytes. Contrary to PLA cultures, no such restriction could be detected by IF in adipo-induced MSCs. While expression of CD90 appeared to be decreased in lipid-filled PLA cells, virtually 100% of the PLA fibroblasts stained brightly for CD90 and a 1.8-fold increase in this protein was measured using FC, a level comparable to that measured in osteogenic cultures (1.75-fold). Contrary to CD90, expression levels of the CD44-positive PLA fibroblasts appeared to vary, with cell staining ranging from intense to little or no CD44. In support of this, FC confirmed a 48% decrease in CD44 expression in adipogenic PLA samples. A decrease was also measured for CD13/aminopeptidase N and the decrease of these two proteins is likely a reflection of the remodeling of the ECM to one more consistent with adipogenic tissue.

Like osteogenic PLA cells, FC confirmed the absence of CD14, CD16, CD31, CD45, CD62E and CD106 in adipogenic PLA cultures while expression of CD34, CD49d and CD61 were slightly elevated in these cells. While FC did not detect a significant increase in CD45 upon adipogenic induction, a small percentage of PLA cells positive for this protein was observed upon IF analysis. The increased expression of CD34 on adipogenic PLA cells was not as large as that measured upon osteogenesis and IF analysis confirmed CD34 expression by all PLA morphologies. However, expression was restricted to cells with a fibroblastic morphology. Weak expression of both CD34 and CD45 were also detected upon IF analysis of adipogenic MSCs with expression observed in both fibroblastic and lipid-filled cells.

Differentiation of mesenchymal precursors to their lineage-committed cell types (i.e. osteoblasts, adipocytes) is accompanied by synthesis and remodelling of an ECM. Variation of ECM composition and organization gives each tissue its specific characteristics and participates in the differentiation and growth of the constituent cell types. For example, bone matrix consists of inorganic hydroxyapatite together with an organic fraction comprised of proteoglycans and collagens, with collagen type 1 making up the majority (approx. 90% of the organic fraction). Cartilage matrix consists mainly of collagens type 2 and 10 and multiple sulfated proteoglycans. Adipogenic ECMs are comprised of multiple collagen subtypes (1 through 6), laminin and fibronectin. Together, these collagens are a part of the unique extracellular environment of each tissue and are crucial to the survival and function of the component cells. Based on this, the expression of ECM collagens were examined in both control and induced PLA cells and MSCs.

Non-induced PLA cells and MSCs expressed CNI, CNIV and CNV (FIG. 43), in addition to CNIII. Both CNI and CNIII exhibited similar staining patterns in both cell populations and osteogenic induction did not alter the intracellular distribution of these collagens. Furthermore, a qualitative increase in CNI was observed in several PLA and MSC samples. A large volume of work confirms the role of collagen type 1 in osteogenic differentiation. For example, CNI levels increase during the early stages of rat calvarial osteoblast differentiation and inhibition of this collagen totally blocks osteogenic differentiation (Stein, G. S. et al., 1990, Faseb J., 4:3111-3123; Lynch, et al., 1995, Exp. Cell Res., 216:35-45.) Factors that are known to affect osteogenesis, such as dexamethasone, vitamin D and the parathyroid hormone, can directly affect levels of CNI. Furthermore, bone marrow stromal cells maintained on CNI matrices differentiate into osteoblasts in vitro and induce bone formation in vivo, an effect that is not seen on CNII, CNIII or CNV matrices. Therefore, the synthesis of CNI in pre-induced and osteo-induced PLA cultures in consistent with the role of this collagen in osteogenesis. Moreover, the similarities in CNI expression observed in both osteo-induced PLA cells and MSCs suggests that similar mechanisms may function in the osteogenic differentiation of these cell types.

In addition to CNI, expression of CNIV and CNV were also observed in both control PLA and MSC cultures, distributed in a fibrillar pattern consistent their secretion into the extracellular environment. The presence of these collagens is a vital component of the osteogenic ECM as expression of these collagens is observed in whole bone marrow stroma, the osteoblasts of newly forming bone and in STRO-1-positive colony derived stromal cell lines. In contrast to induced MSC cultures, osteogenic induction of PLA cells appeared to significantly decrease CNIV synthesis and completely inhibited CNV expression.

Adipogenic differentiation resulted in additional distinctions between PLA and MSC populations. Like osteogenic cultures, adipogenic induction of PLA cells resulted in an inhibition of CNV expression. Moreover, adipogenesis also resulted in the inhibition of CNI. No such inhibition was seen in adipo-induced MSCs. Rather, a reduced level of CNIV synthesis was observed in adipogenic MSC populations with all three collagen types (I, IV and V) exhibiting a fibrillar, extracellular expression pattern. While weak cellular expression of CNI was also observed in lipid-filled MSCs, the expression of CNIV and CNV appeared to remain extracellular. Like MSC samples, adipo-induced PLA cells also expressed CNIV. However, CNIV expression in these cells remained intracellular and appeared to be expressed exclusively in lipid-filled PLAs.

Like osteogenesis, several lines of evidence suggest that ECM components, such as collagens, participate in adipogenesis. First, changes in the ECM lead to morphologic and cytoskeletal alterations that are required for the expression of lipogenic enzymes (Kuri-Haruch, W. et al., 1984, Differentiation, 28; Spiegelman, B. M. et al., 1983, Cell, 357-666.) Second, expression of CNI, CNIII and CNIV varies dramatically upon differentiation of 3T3-L1 cells (Weiner, F. R. et al., 1989, Biochem., 28:4094-4099.) Lastly, the ECM of developing adipose tissue is organized during differentiation, an event thought to be mediated by the adipocytes themselves (Nakajima, I. et al., 1998, Differentiation, 63:193-200.) Fibroblasts and adipocyte precursors with a fibroblastic morphology synthesize and secrete type I and III collagens, in addition to small amounts of the basement membrane collagen, type IV (Goldberg, B., 1977, PNAS, 74:3322-3325; Alitano, K. et al., 1982, J. Cell Biol., 94:497-505; Cryer, A. et al., 1982, Eur. J. Clin., Invest., 12:235-238; Kuri-Harcuch, W. et al., 1984, Differentiation, 28; Liau, G. et al., 1985, J. Biol., Chem., 260:531-536.) As these cells begin to differentiate changes occur in cell morphology, cytoskeleton and the level and type of ECM secreted (Napolitano, L., 1963, J. Cell Biol., 18:663-679; Aratani, Y. et al., 1988, J. Biol. Chem., 263: 16163-16169; Weiner, F. R. et al., 1989, Biochem., 28:4094-4099.) These changes, in turn, may be a requirement for their terminal differentiation into adipocytes.

To study the synthesis and distribution of ECM components upon adipogenesis, several preadipocyte cell lines have been developed, including several 3T3 variants (Green, H. et al., 1974, Cell, 3:127-133) and a clonal preadipocyte cell line from Japanese cattle (BIP cells) (Aso, H. et al., 1995, Biochem. Biophys. Res. Commun., 213:369-374.) Adipose conversion of BIP cells results in production of an ECM similar to adipose tissue in which adipocytes are interconnected by a fibrillar network of collagens I, II, IV, V and VI together with an intracellular expression of CNIII (Nakajima, I. et al., 1998, Differentiation, 63:193-200.) Like BIP cells, adipo-induction of both PLA cells and MSCs resulted in a similar intracellular distribution of CNIII. Furthermore, fibrils of CNI, CNIV and CNV were also associated with adipogenic MSCs and appeared to be organized randomly. The expression of similar collagens and their random organization in adipogenic MSCs is consistent with that observed upon differentiation of preadipocytes and suggests that comparable ECM synthesis and remodeling may occur upon differentiation of these stem cells.

However, the adipegenic differentiation of PLA cells presents several differences to several preadipocyte cell lines and MSCs. Like preadipocyte cells, including BIP cells from cattle, and 3T3 cells from mice, pre-differentiated PLA cells synthesize CNI and CNV. However, these collagens are no longer observed upon differentiation. The disappearance of CNI and CNV in adipogenic PLA cultures may represent a specific remodelling pathway unique to these cells. In support of this, changes in the pericellular environment that occur during differentiation can change the intracellular environment and the secretion of MMPs that degrade the surrounding ECM. Low levels of CNIV are also produced by preadipocytes and a dramatic increase is observed upon adipogenesis (Aratani, Y. et al., 1988, J. Biol. Chem., 263:16163-16169; Nakajima, I. et al., 1998, Differentiation, 63:193-200.) While a qualitative increase in CNIV is observed in adipogenic PLA cultures, its fibrillar distribution is lost and the collagen is restricted to lipid-filled PLA cells. The change in CNIV expression pattern in comparison to preadipocytes and MSCs remains unclear.

While EM observations of mature fat cells have identified a CNIV-rich basement membrane associated with several other fibrillar collagens (Chase, W. H., 1959, J. Ultrastruc. Res., 2:283-287; Barnett, R. J., 1962, L. W. Kinsell ed. (Springfield, Ill.: Charles C. Thomas); Angel., A. et al., 1970, B. Jeanrenaud and Hepp. D., et ed. (Thiene, Stuttgard: Academic Press), mature fat cells do not synthesize collagens. Moreover, adipogenic precursors lose the capacity for collagen synthesis in vitro during the post-confluent differentiation stage. However, collagen synthesis is critical for terminal adipocyte differentiation and triacylglyerol accumulation indicating that the predifferentiation expression of an ECM determines their ultimate phenotype. Therefore, the predifferentiation expression of CNI, CNIII, CNIV and CNV by PLA cells and MSCs may serve to initiate their differentiation program. As differentiation proceeds and the appearance of lipid-filled cells (i.e. mature adipocytes) increases, the synthesis of these collagens ceases, resulting in a collagenous ECM unique to adipose tissue. This is likely the case with the MSC population. However, the absence of CNI and CNV in PLA cultures may be the result of a direct inhibition of synthesis or a dramatic remodeling of the ECM. The precise time of collagen inhibition upon PLA adipogenesis and/or the possible existence of agents involved in collagen degradation remains unknown.

What is claimed is:

1. An isolated population of stem cells, obtained from human adipose tissue having a CD marker profile comprising a combination of STRO-1+, CD29+, CD44+, CD71+, CD49D+, low or undetectable levels of CD 106, CD90+, and CD105+.

2. An isolated population of stem cells, obtained from human adipose tissue having a CD marker profile comprising
   (a) STRO-1,
   (b) CD49d,
   (c) low or undetectable levels of CD106, and
   (d) any one or more of CD29, CD44, CD71, CD90, SH3, and CD105, and
   wherein the CD marker profile further comprises CD31−, and CD45−.

3. An isolated population of stem cells, obtained from human adipose tissue having a CD marker profile comprising a combination of STRO-1+, CD29+, CD44+, CD49D+, low or undetectable levels of CD106, CD71+, CD90+, CD105+, CD31−, and CD45−.

* * * * *

UNITED STATES PATENT AND TRADEMARK OFFICE
CERTIFICATE OF CORRECTION

PATENT NO. : 7,470,537 B2
APPLICATION NO. : 11/740315
DATED : December 30, 2008
INVENTOR(S) : Marc H. Hedrick et al.

It is certified that error appears in the above-identified patent and that said Letters Patent is hereby corrected as shown below:

On the cover page item [73], should read,
-- Assignee: The Regents of the University of California, Oakland, CA --.

Signed and Sealed this

Twenty-sixth Day of October, 2010

David J. Kappos
*Director of the United States Patent and Trademark Office*

UNITED STATES PATENT AND TRADEMARK OFFICE
CERTIFICATE OF CORRECTION

| | | Page 1 of 1 |
|---|---|---|
| PATENT NO. | : 7,470,537 B2 | |
| APPLICATION NO. | : 10/740315 | |
| DATED | : December 30, 2008 | |
| INVENTOR(S) | : Marc H. Hedrick et al. | |

It is certified that error appears in the above-identified patent and that said Letters Patent is hereby corrected as shown below:

On the cover page item [73], should read,
        -- Assignee: The Regents of the University of California, Oakland, CA --.

This certificate supersedes the Certificate of Correction issued October 26, 2010.

Signed and Sealed this
Eighth Day of February, 2011

David J. Kappos
*Director of the United States Patent and Trademark Office*